US008580252B2

(12) United States Patent
Bookbinder et al.

(10) Patent No.: US 8,580,252 B2
(45) Date of Patent: *Nov. 12, 2013

(54) SOLUBLE GLYCOSAMINOGLYCANASES AND METHODS OF PREPARING AND USING SOLUBLE GLYCOSAMINOGLYCANASES

(75) Inventors: Louis H. Bookbinder, San Diego, CA (US); Anirban Kundu, San Diego, CA (US); Gregory I. Frost, Del Mar, CA (US)

(73) Assignee: Halozyme, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/507,540

(22) Filed: Jul. 6, 2012

(65) Prior Publication Data

US 2012/0294830 A1 Nov. 22, 2012

Related U.S. Application Data

(60) Division of application No. 13/374,248, filed on Dec. 15, 2011, now Pat. No. 8,257,699, which is a continuation of application No. 12/802,864, filed on Jun. 15, 2010, now Pat. No. 8,105,586, which is a division of application No. 11/065,716, filed on Feb. 23, 2005, now Pat. No. 7,871,607, and a continuation-in-part of application No. 10/795,095, filed on Mar. 5, 2004, now Pat. No. 7,767,429.

(51) Int. Cl.
*A61K 38/46* (2006.01)
*A61P 35/00* (2006.01)

(52) U.S. Cl.
USPC .................................. 424/94.62; 514/19.3

(58) Field of Classification Search
None
See application file for complete search history.

(56) References Cited

U.S. PATENT DOCUMENTS

| | | | |
|---|---|---|---|
| 3,536,809 A | 10/1970 | Applezweig | 424/28 |
| 3,598,123 A | 8/1971 | Zaffaroni | 424/435 |
| 3,630,200 A | 12/1971 | Higuchi | 424/427 |
| 3,710,795 A | 1/1973 | Higuchi et al. | 424/424 |
| 3,845,770 A | 11/1974 | Theeuwes et al. | 424/427 |
| 3,916,899 A | 11/1975 | Theeuwes et al. | 424/424 |
| RE28,819 E | 5/1976 | Thompson | 514/174 |
| 4,002,531 A | 1/1977 | Royer | 435/188 |
| 4,008,719 A | 2/1977 | Theeuwes et al. | 424/427 |
| 4,044,126 A | 8/1977 | Cook et al. | 514/180 |
| 4,179,337 A | 12/1979 | Davis et al. | 435/181 |
| 4,328,245 A | 5/1982 | Yu et al. | 514/530 |
| 4,358,603 A | 11/1982 | Yu | 560/2 |
| 4,364,923 A | 12/1982 | Cook et al. | 424/46 |
| 4,409,239 A | 10/1983 | Yu | 514/530 |
| 4,410,545 A | 10/1983 | Yu et al. | 514/530 |
| 4,414,209 A | 11/1983 | Cook et al. | 514/180 |
| 4,522,811 A | 6/1985 | Eppstein et al. | 514/2.4 |
| 4,769,027 A | 9/1988 | Baker et al. | 424/493 |
| 4,820,516 A | 4/1989 | Sawyer et al. | 424/94.62 |
| 4,952,496 A | 8/1990 | Studier et al. | 435/91.41 |
| 4,980,286 A | 12/1990 | Morgan et al. | 435/371 |
| 5,041,292 A | 8/1991 | Feijen | 424/484 |
| 5,052,558 A | 10/1991 | Carter | 206/439 |
| 5,059,595 A | 10/1991 | Le Grazie | 424/468 |
| 5,073,543 A | 12/1991 | Marshall et al. | 514/21 |
| 5,120,548 A | 6/1992 | McClelland et al. | 424/473 |
| 5,122,614 A | 6/1992 | Zalipsky | 548/520 |
| 5,215,899 A | 6/1993 | Dattagupta | 435/6.11 |
| 5,292,509 A | 3/1994 | Hageman | 424/94.61 |
| 5,323,907 A | 6/1994 | Kalvelage | 206/531 |
| 5,436,128 A | 7/1995 | Harpold et al. | 435/6.13 |
| 5,446,090 A | 8/1995 | Harris | 525/54.1 |
| 5,591,767 A | 1/1997 | Mohr et al. | 514/413 |
| 5,631,018 A | 5/1997 | Zalipsky et al. | 424/450 |
| 5,639,476 A | 6/1997 | Oshlack et al. | 424/468 |
| 5,672,662 A | 9/1997 | Harris et al. | 525/408 |
| 5,674,533 A | 10/1997 | Santus et al. | 424/493 |
| 5,714,166 A | 2/1998 | Tomalia et al. | 424/486 |
| 5,721,348 A | 2/1998 | Primakoff et al. | 536/22.1 |
| 5,723,147 A | 3/1998 | Kim et al. | 424/450 |
| 5,733,566 A | 3/1998 | Lewis | 424/426 |
| 5,747,027 A | 5/1998 | Stern et al. | 424/94.62 |
| 5,766,581 A | 6/1998 | Bartley et al. | 424/85.1 |
| 5,766,627 A | 6/1998 | Sankaram et al. | 424/450 |
| 5,795,569 A | 8/1998 | Bartley et al. | 424/85.1 |
| 5,827,721 A | 10/1998 | Stern et al. | 435/201 |

(Continued)

FOREIGN PATENT DOCUMENTS

| | | |
|---|---|---|
| CA | 2318356 | 7/2000 |
| EP | 0400472 | 12/1990 |

(Continued)

OTHER PUBLICATIONS

U.S. Appl. No. 13/507,263, filed Jun. 15, 2012.

(Continued)

*Primary Examiner* — Nashaat Nashed
(74) *Attorney, Agent, or Firm* — McKenna Long & Aldridge, LLP; Stephanie Seidman

(57) ABSTRACT

The invention relates to the discovery of novel soluble neutral active Hyaluronidase Glycoproteins (sHASEGPs), methods of manufacture, and their use to facilitate administration of other molecules or to alleviate glycosaminoglycan associated pathologies. Minimally active polypeptide domains of the soluble, neutral active sHASEGP domains are described that include asparagine-linked sugar moieties required for a functional neutral active hyaluronidase domain. Included are modified amino-terminal leader peptides that enhance secretion of sHASEGP. The invention further comprises sialated and pegylated form of a recombinant sHASEGP to enhance stability and serum pharmacokinetics over naturally occurring slaughterhouse enzymes. Further described are suitable formulations of a substantially purified recombinant sHASEGP glycoprotein derived from a eukaryotic cell that generate the proper glycosylation required for its optimal activity.

34 Claims, 1 Drawing Sheet

(56) References Cited

U.S. PATENT DOCUMENTS

| | | | |
|---|---|---|---|
| 5,854,046 A | 12/1998 | Au-Young et al. | 435/201 |
| 5,900,461 A | 5/1999 | Harris | 525/54.11 |
| 5,958,750 A | 9/1999 | Au-Young et al. | 435/201 |
| 5,990,237 A | 11/1999 | Bentley et al. | 525/54.2 |
| 6,057,110 A | 5/2000 | Au-Young et al. | 435/6 |
| 6,123,938 A | 9/2000 | Stern et al. | 424/94.62 |
| 6,184,023 B1 | 2/2001 | Hashimoto et al. | 435/232 |
| 6,193,963 B1 | 2/2001 | Stern et al. | 424/94.6 |
| 6,413,507 B1 | 7/2002 | Bentley et al. | 424/78 |
| 6,420,339 B1 | 7/2002 | Gegg et al. | 514/12 |
| 6,437,025 B1 | 8/2002 | Harris et al. | 523/406 |
| 6,448,369 B1 | 9/2002 | Bentley et al. | 528/425 |
| 6,492,560 B2 | 12/2002 | Wilbur et al. | 564/505 |
| 6,495,659 B2 | 12/2002 | Bentley et al. | 528/425 |
| 6,552,170 B1 | 4/2003 | Thompson et al. | 530/351 |
| 6,737,505 B2 | 5/2004 | Bentley et al. | 528/425 |
| 6,828,401 B2 | 12/2004 | Nho et al. | 526/333 |
| 6,858,736 B2 | 2/2005 | Nho et al. | 546/290 |
| 7,105,330 B2 | 9/2006 | Stern et al. | 435/200 |
| 7,148,201 B2 | 12/2006 | Stern et al. | 514/44 R |
| 7,544,499 B2 | 6/2009 | Frost et al. | 435/200 |
| 7,767,429 B2 | 8/2010 | Frost et al. | 435/201 |
| 7,781,397 B2 | 8/2010 | Stern et al. | 424/94.62 |
| 7,829,081 B2 | 11/2010 | Bookbinder et al. | 424/94.62 |
| 7,846,431 B2 | 12/2010 | Bookbinder et al. | 424/94.62 |
| 7,871,607 B2 | 1/2011 | Bookbinder et al. | 424/94.62 |
| 8,105,586 B2 | 1/2012 | Bookbinder et al. | 424/94.3 |
| 8,187,855 B2 | 5/2012 | Baker et al. | 435/201 |
| 8,202,517 B2 | 6/2012 | Bookbinder et al. | 424/94.62 |
| 8,257,699 B2 | 9/2012 | Bookbinder et al. | 424/94.62 |
| 8,318,154 B2 | 11/2012 | Frost et al. | 424/94.5 |
| 8,343,487 B2 | 1/2013 | Baker et al. | 424/94.62 |
| 2004/0013637 A1 | 1/2004 | Bentley et al. | 424/78.17 |
| 2004/0157787 A1 | 8/2004 | Or et al. | 514/28 |
| 2004/0224012 A1 | 11/2004 | Suvanprakorn et al. | 424/450 |
| 2004/0224023 A1 | 11/2004 | Hunter et al. | 424/486 |
| 2005/0002865 A1 | 1/2005 | Klaveness et al. | 424/9.52 |
| 2005/0004095 A1 | 1/2005 | Glinka et al. | 514/204 |
| 2005/0114037 A1 | 5/2005 | Desjarlais et al. | 702/19 |
| 2005/0171328 A1 | 8/2005 | Harris | 528/322 |
| 2005/0209416 A1 | 9/2005 | Harris | 525/523 |
| 2005/0287134 A1 | 12/2005 | Klein | 424/94.61 |
| 2006/0104968 A1 | 5/2006 | Bookbinder et al. | 424/94.61 |
| 2009/0123367 A1 | 5/2009 | Bookbinder et al. | 424/1.49 |
| 2009/0181032 A1 | 7/2009 | Bookbinder et al. | 424/141.1 |
| 2009/0214505 A1 | 8/2009 | Bookbinder et al. | 424/94.1 |
| 2009/0253175 A1 | 10/2009 | Bookbinder et al. | 435/69.1 |
| 2009/0304665 A1 | 12/2009 | Frost et al. | 424/94.5 |
| 2010/0003237 A1 | 1/2010 | Keller et al. | |
| 2010/0003238 A1 | 1/2010 | Frost et al. | 424/94.62 |
| 2010/0074885 A1 | 3/2010 | Schiff et al. | 424/130.1 |
| 2010/0143457 A1 | 6/2010 | Wei et al. | 424/450 |
| 2010/0172892 A1 | 7/2010 | Uvarkina et al. | 424/94.62 |
| 2010/0284995 A1 | 11/2010 | Bookbinder et al. | |
| 2011/0066111 A1 | 3/2011 | Teschner et al. | 514/183 |
| 2011/0152359 A1 | 6/2011 | Bookbinder et al. | 435/200 |
| 2012/0020951 A1 | 1/2012 | Shepard et al. | 424/130.1 |
| 2012/0093770 A1 | 4/2012 | Bookbinder et al. | 424/94.62 |
| 2012/0108455 A1 | 5/2012 | Kodandapani et al. | |
| 2012/0148555 A1 | 6/2012 | Bookbinder et al. | 435/200 |
| 2012/0171153 A1 | 7/2012 | Frost et al. | 424/94.62 |
| 2012/0196348 A1 | 8/2012 | Baker et al. | 424/94.62 |
| 2012/0213767 A1 | 8/2012 | Wei et al. | 424/450 |
| 2012/0251517 A1 | 10/2012 | Frost et al. | 424/94.62 |
| 2012/0251620 A1 | 10/2012 | Bookbinder et al. | 424/450 |
| 2013/0011378 A1 | 1/2013 | Yang et al. | 424/94.3 |
| 2013/0022588 A1 | 1/2013 | Yang et al. | 424/94.3 |
| 2013/0022592 A1 | 1/2013 | Vaughn et al. | 424/94.62 |
| 2013/0058893 A1 | 3/2013 | Bookbinder et al. | 435/200 |

FOREIGN PATENT DOCUMENTS

| | | |
|---|---|---|
| EP | 0822199 | 9/2004 |
| JP | 6-153947 | 3/1994 |
| JP | 6-503721 | 4/1994 |
| WO | WO 88/02261 | 4/1988 |
| WO | WO 88/09810 | 12/1988 |
| WO | WO 89/10134 | 11/1989 |
| WO | WO 90/11364 | 10/1990 |
| WO | WO 92/06180 | 4/1992 |
| WO | WO 92/16640 | 10/1992 |
| WO | WO 92/20316 | 11/1992 |
| WO | WO 92/22635 | 12/1992 |
| WO | WO 93/14188 | 7/1993 |
| WO | WO 93/20221 | 10/1993 |
| WO | WO 94/08598 | 4/1994 |
| WO | WO 99/32619 | 7/1999 |
| WO | WO 01/29058 | 11/2001 |
| WO | WO 2006/091871 | 8/2006 |

OTHER PUBLICATIONS

U.S. Appl. No. 13/507,262, filed Jun. 15, 2012.
U.S. Appl. No. 13/507,261, filed Jun. 15, 2012.
U.S. Appl. No. 13/573,472, filed Sep. 14, 2012.
Adams et al., "The c-myc oncogene driven by immunoglobulin enhancers induces lymphoid malignancy in transgenic mice," Nature 318:533-538 (1985).
Afify et al., "Purification and characterization of human serum hyaluronidases," Arch. Biochem. Biophys. 305:434-441, 1993.
Alberts, Molecular Biology of the Cell, Garland Publishing Inc. New York and London, 1983 3rd ed., p. 347.
Alexander et al., "Expression of the c-myc oncogene under control of an immunoglobulin enhancer in E mu-myc transgenic mice," Mol. Cell Biol. 7:1436-1444 (1987).
Altschul, S., "Basic local alignment search tool," J Molec Biol 215(3):403-410 (1990).
Antoszyk et al., "An experimental model of preretinal neovascularization in the rabbit," Invest Ophthalmol Vis Sci 32:(1) 46-51 (1991).
Arming et al., "In vitro mutagenesis of PH-20 hyaluronidase from human sperm," Eur J Biochem 247(3):810-814 (1997).
Ashwell and Harford, "Carbohydrate-specific receptors of the liver," Ann. Rev. Biochem. 51:531 (1982).
Bailey and Levine, "Optimization of the USP assay for hyaluronidase," Journal of Pharmaceutical & Biomedical Analysis 11(4/5):285-292 (1993).
Baumgartner et al., "Phase I study in chemoresistant loco-regional malignant disease with hyaluronidase," Reg. Cancer Treat. 1:55-58 (1988).
Beckenlehner et al., "Hyaluronidase enhances the activity of adriamycin in breast cancer models in vitro and in vivo," J. Cancer Res. Oncol. 118:591-596 (1992).
Benton and Davis, "Screening lambdagt recombinant clones by hybridization to single plaques in situ," Science 196:180 (1977).
Berger E., "Nutrition by hypodermoclysis," Am Geriatr Soc 32(3):199-203 (1984).
Bemoist, C. and P. Chambon, "In vivo sequence requirements of the SV40 early promotor region," Nature 290:304-310 (1981).
Bernstein et al., "Role for a bidentate ribonuclease in the initiation step of RNA interference," Nature 409:363-366 (2001).
Bertrand et al., "Hyaluronan (hyaluronic acid) and hyaluronectin in the extracellular matrix of human breast carcinomas: comparison between invasive and non-invasive areas," Int. J. Cancer 52:1-6 (1992).
Bianchi et al., "Synthetic depsipeptide substrates for the assay of human hepatitis C virus protease," Anal. Biochem. 237: 239-244 (1996).
Bitter et al., "Expression and secretion vectors for yeast," Methods in Enzymol 153:516-544 (1987).
Bjermer, "Hyaluronate and type III procollagen peptide concentrations in bronchoalveolar lavage fluid as markers of disease activity in farmer's lung," Br Med J Clin Res Ed. 295(6602):803-806 (1987).
Boesen et al., "Circumvention of chemotherapy-induced myelosuppression by transfer of the mdr1 gene," Biotherapy 6:291-302 (1994).
Bonner, W. and E. Cantey, "Colorimetric method for determination of serum hyaluronidase activity," Clin. Chim. Acta 13:746-752 (1966).

(56) References Cited

OTHER PUBLICATIONS

Bookbinder et al., "A recombinant human enzyme for enhanced interstitial transport of therapeutics," J Control Release, 114:230-241 (2006).
Borders et al. "Purification and Partial Characterization of Testicular Hyaluronidase," J. Biol. Chem 13:3756-3762 (1968).
Bordier C., "Phase separation of integral membrane proteins in Triton X-114 solution," J Biol Chem. 256(4):1604-1607 (1981).
Bouffard et al., "An in vitro assay for hepatitis C virus NS3 serine proteinase," Virology 209:52-59 (1995).
Bout et al., "Lung gene therapy: in vivo adenovirus-mediated gene transfer to rhesus monkey airway epithelium," Human Gene Therapy 5:3-10 (1994).
Bradbury, et al., "Chondroitinase ABC promotes functional recovery after spinal cord injury," Nature 416(6881):636-640 (2002).
Braunwald, E. and P. Maroko, "Effects of hyaluronidase and hydrocortisone on myocardial necrosis after coronary occlusion," Am. J. Cardiol 37:550-556 (1976).
Brinster et al., "Regulation of metallothionein—thymidine kinase fusion plasmids injected into mouse eggs," Nature 296:39-42 (1982).
Brown et al., "Cluster of diplopia cases after periocular anesthesia without hyaluronidase," J Cataract Refract Surg. 25(9):1245-1249 (1999).
Burket, L. and P. Gyorgy, "Clinical observations on the use of hyaluronidase," Pediatrics 3(1):56-63 (1949).
Callewaert et al., "Ultrasensitive profiling and sequencing of N-linked oligosaccharides using standard DNA-sequencing equipment," Glycobiology 11:275-281 (2001).
Capecchi, M., "Altering the genome by homologous recombination," Science 244:1288-1292 (1989).
Carrillo, H. and D. Lipman, "The multiple-sequence alignment problem in biology," SIAM J Applied Math 48:1073-1082 (1988).
Chain and Duthie "A Mucolytic Enzyme in Testis Extracts" Nature 144:977-978 (1939).
Chain, E and E Duthie, "Identity of Hyaluronidase and Spreading Factor," Brit. J. Exper. Path. 21:324-338 (1940).
Chapman et al., "Therapeutic antibody fragments with prolonged in vivo half-lives," Nature Biotech. 17:780-783 (1999).
Cheng et al., "Poly(ethylene glycol) modification of beta-glucuronidase-antibody conjugates for solid-tumor by targeted activation of glucuronide prodrugs." Cancer Immunology Immunother, 1997 44(6) pp. 305-315.
Cherr et al., "The dual functions of GPI-anchored PH-20: hyaluronidase and intracellular signaling," Matrix Biol., 20(8):515-525, 2001.
Cherr et al., "The PH-20 protein in cynomolgus macaque spermatozoa: identification of two different forms exhibiting hyaluronidase activity," Dev. Biol., 175:142-153, 1996.
Cho et al., "Construction of hepatitis C-SIN virus recombinants with replicative dependency on hepatitis C virus serine protease activity," J. Virol. Meth. (65):201-207 (1997).
Chuang, C. and E. Meyerowitz, "Specific and heritable genetic interference by double-stranded RNA in *Arabidopsis thaliana*," Proc. Natl. Acad. Sci. USA 97:4985 (2000).
Cline, M., "Perspectives for gene therapy: inserting new genetic information into mammalian cells by physical techniques and viral vectors," Pharmac. Ther. 29:69-92 (1985).
Clinical Trial: "Study of PEGPH2O with Initial Dexamethasone Premedication Given Intravenously to Patients with Advanced Solid Tumors" found at: www.clinicaltrials.gov/ct2/show?term=PEGPH20&rank=2 [accessed Jul. 27, 2010; ] [4 pages].
Clinical Trials.gov "HALO-109-102 Study of PEGPH2O with Dexamethasone (PEG2)" (accessed May 2, 2011).
Clowes et al., "Long-term biological response of injured rat carotid artery seeded with smooth muscle cells expressing retrovirally introduced human genes," J. Clin. Invest. 93:644-651 (1994).
Colbere-Garapin et al., "A new dominant hybrid selective marker for higher eukaryotic cells," J Mol Biol 150:1-14 (1981).
Cole, G. and C. McCabe, "Identification of a developmentally regulated keratan sulfate proteoglycan that inhibits cell adhesion and neurite outgrowth," Neuron 7(6):1007-1018 (1991).
Conserved domain search from U.S. Appl. No. 10/795,095 of SEQ ID No. 6, Primakoff et al. US 5,721,348, performed on the NCBI website on Aug. 5, 2008.
Cotten et al., "Receptor-mediated transport of DNA into eukaryotic cells," Meth. Enzymol. 217:618-644 (1993).
Csoka et al., "Hyaluronidases in tissue invasion," Invasion Metastasis 17:297-311 (1997).
Csoka et al., "Purification and microsequencing of hyaluronidase isozymes from human urine," FEBS Lett., 417(3):307-310 (1997).
Csoka et al., "The six hyaluronidase-like genes in the human and mouse genomes," Matrix Biol. 20:499-508 (2001).
Cummings, R., "Use of lectins in analysis of glycoconjugates," Methods in Enzymol. 230:66-86 (1994).
Czejka et al., "Influence of hyaluronidase on the blood plasma levels of 5-fluorouracil in patients," Pharmazie 45:H.9 (1990).
Danilkovitch-Miagkova, et al., "Hyaluronidase 2 negatively regulates RON receptor tyrosine kinase and mediates transformation of epithelial cells by jaagsiekte sheep retrovirus," Proc Natl Acad Sci US A. 100(8):4580-4585 (2003).
De Maeyer et al., "The growth rate of two transplantable murine tumors, 3LL lung carcinoma and B16F10 melanoma, is influenced by Hyal-1, a locus determining hyaluronidase levels and polymorphism," Int. J. Cancer 51:657-660 (1992).
De Sa Earp, "Hemiplegia secondary to cerebromeningeal hemorrhage treated with hyaluronidase with complete recovery,"Arq. Braz. Med. 44:217-220 (1954). [in Portugese].
De Sa Earp, "Hemiplegia secondary to cerebromeningeal hemorrhage treated with hyaluronidase with complete recovery,"Arq. Braz. Med. 44:217-220 (1954). [Certified English language translation].
De Salegui et al., "A Comparison of Serum and Testicular Hyaluronidase," Arch. Biochem. Biophys. 121:548-554 (1967).
DeBoer et al., "The tac promoter: a functional hybrid derived from the trp and lac promoters," Proc. Natl. Acad. Sci. USA 80:21-25 (1983).
Derwent Abstract for WO 1988002261. Inventor: Baumgarme et al., WPI Acc No. 1988-105412/198815, Abstract published 1988, 2 pages.
Devereux, J., et al, "A comprehensive set of sequence analysis programs for the VAX," Nucleic Acids Research 12:387-395 (1984).
Dexter et al., "Conditions controlling the proliferation of haemopoietic stem cells in vitro," J. Cell Physiol. 91(3):335-344 (1977).
Dillon, N., "Regulating gene expression in gene therapy," TIBTECH 11(5):167-173 (1993).
Dodet, B., "Commercial prospects for gene therapy," TIBTECH 11(5):182-189 (1993).
Dorfman, A. and M. Ott, "A turbidimetric method for the assay of hyaluronidase," J. Biol. Chem. 172:367-375 (1948).
Dorfman, A., "The kinetics of the enzymatic hydrolysis of hyaluronic acid," J. Biol. Chem. 172:377-387 (1948).
Drug Shortage Bulletin: Hyaluronidase Injection—Discontinued, published Jan. 18, 2005, American Society of Health-System Pharmacist, www.ashp.org/shortage/hyaluronidase.cfm?cfid=11944667&CFToken=9426953%2, last accessed Mar. 21, 2006.
Drugs R&D, "Hyaluronidase (Vitrase®)—ISTA," 4(3):194-197 (2003).
D'Souza et al., "In vitro cleavage of hepatitis C virus polyprotein substrates by purified recombinant NS3 protease," J. Gen. Virol. 76:1729-1736 (1995).
Dubensky et al., "Direct transfection of viral and plasmid DNA into the liver or spleen of mice," Proc Natl Acad Sci U S A 81(23):7529-7533 (1984).
Dunn et al., "Transcription of the human and rodent SPAM1/PH-20 genes initiates within an ancient endogenous retrovirus," BMC Genomics, 6:47 (2005).
Duran-Reynals, F., "Exaltation de l' Activite du Virus Vaccinal par les Extraits de Certains Organes," Comptes Rendus Hebdomadaires de Seances et Memoires de la Societe de Biologie 99: 6-7 (1928) [in French].

(56) References Cited

OTHER PUBLICATIONS

Duran-Reynals, F., "Exaltation de l'Activite du Virus Vaccinal par les Extraits de Certains Organes," Comptes Rendus Hebdomadaires de Seances et Memoires de la Societe de Biologie 99: 6-7 (1928) [Certified English translation].
Dzau et al., "Gene therapy for a cardiovascular disease," TIBTECH 11(5):205-210 (1993).
Edelson, E., "Wydase shortage creates alert; task force seeks new source," Opthamology Times, Jan. 1, 2001.
Egberts et al. "Dexamethasone reduces tumor recurrence and metastasis after pancreatic tumor resection in SCID mice," Cancer Biol Ther 7(7):1044-50 (2008).
Elbashir et al., "Duplexes of 21-nucleotide RNAs mediate RNA interference in cultured mammalian cells," Nature 41(1):494-498 (2001).
Elbashir et al., "RNA interference is mediated by 21- and 22-nucleotide RNAs," Genes Dev. 15:188-200 (2001).
Elder et. al, "Intra-arterial hyaluronidase in severe peripheral arterial disease," Lancet 648-649 (1980).
Ernst et al., "Enzymatic degradation of glycosaminoglycans," Critical Reviews in Biochemistry and Molecular Biology 30(5):387-444 (1995).
European Medicines Agency (EMEA) guideline 3AB1a, "Production and Quality Control of Medicinal Products Derived by Recombinant DNA Technology," published Jul. 1995.
European Medicines Agency (EMEA) guideline CPMP/BWP/268/95 3AB8a, "Virus Validation Studies: The Design, Contribution and Interpretation of Studies Validating the Inactivation and Removal of Viruses," published Feb. 1996.
European Medicines Agency (EMEA) guideline CPMP/ICH/295/95 ICH Topic 5QA (R1), "Quality of Biotechnological Products: Viral Safety Evaluation of Biotechnology Products Derived from Cell Lines of Human or Animal Origin," published Mar. 1997.
European Medicines Agency (EMEA) guideline CPMP/ICH/365/96 ICH Topic Q6B, "Specifications: Test Procedures and Acceptance Criteria for Biotechnical/Biological Products," published Mar. 1999.
Favre et al, "Hyaluronidase enhances recombinant adeno-associated virus (rAAV)-mediated gene transfer in the rat skeletal muscle," Gene Ther 7(16):1417-1420 (2000).
Federal Register Sep. 23, 1970 (35 FR 14800); Wydase NDA 6-343.
Few, B., "Hyaluronidase for treating intravenous extravasations," MCN Amer. J. Matern. Child Nurs. 12(1):23-26 (1987).
Filocamo et al., "Chimeric Sindbis viruses dependent on the NS3 protease of hepatitis C virus," J.Virology 71:1417-1427 (1997).
Findeis et al., "Targeted delivery of DNA for gene therapy via receptors," TIBTECH 11(5):202-205 (1993).
Fire et al., "Potent and specific genetic interference by double-stranded RNA in *Caenorhabditis elegans*," Nature (39)1:806-811 (1998).
Fire, A., "RNA-triggered gene silencing," Trends Genet. 15:358-363 (1999).
Fiszer-Szafarz et al., "Human hyaluronidases: electrophoretic multiple forms in somatic tissues and body fluids evidence for conserved hyaluronidase potential N-glycosylation sites in different mammalian species," J. Biochem. Biophys. Methods 45:103-116, 2000.
Fletcher et al., "Antinociceptive effect of bupivacaine encapsulated in poly(D,L)-lactide-co-glycolide microspheres in the acute inflammatory pain model of carrageenin-injected rats," Anesth. Analg. 84:90-94 (1997).
Friedmann, T. and H. Jinnah, "Gene therapy for disorders of the nervous system," TIBTECH 11(5):192-197 (1993).
Friedmann, T., "Gene therapy—a new kind of medicine," TIBTECH 11(5) 156-159 (1993).
Frost et al., "Purification, cloning, and expression of human plasma hyaluronidase," Biochem. Biophys. Res. Commun. 236(1):10-15 (1997).
Frost, G. and R. Stern, "A microtiter-based assay for hyaluronidase activity not requiring specialized reagents," Anal. Biochem. 251:263-269 (1997).

Frost, G., "Recombinant human hyaluronidase (rHuPH2O): an enabling platform for subcutaneous drug and fluid administration," Expert Opin. Drug. Deliv. 4:427-440 (2007).
Furuya et al., "Biochemical characterization of glycyrrhizin as an effective inhibitor for hyaluronidases from bovine testis," Biol. Pharm. Bull. 20(9):973-977 (1997).
Gacesa et al., "Effect of ionic strength and serum on the activity profile of bovine testicular hyaluronidase [proceedings]," Biochem. Soc. Trans. 7:1287-1289 (1979).
Gardner et al., "The complete nucleotide sequence of an infectious clone of cauliflower mosaic virus by M13mp7 shotgun sequencing," Nucleic Acids Res. 9:2871-2888 (1981).
Gautier et al., "Alpha-DNA. IV: Alpha-anomeric and beta-anomeric tetrathymidylates covalently linked to intercalating oxazolopyridocarbazole. Synthesis, physicochemical properties and poly (rA) binding," Nucl. Acids Res. 15:6625-6641 (1987).
Geisert, E. and D. Bidanset, "A central nervous system keratan sulfate proteoglycan: localization to boundaries in the neonatal rat brain," Brain Res Dev Brain Res. 75(2):163-173 (1993).
Genbank Accession No. L13780 [online], *Macaca fascicularis* sperm surface protein PH-20 mRNA sequence, Published on Jan. 31, 1994 [retrieved on Apr. 29, 2011] [retrieved from the Internet<URL: ncbi.nlm.nih.gov/nuccore/L13780], 1 page.
Genbank Accession No. NP-003108, "*Homo sapiens* sperm adhesion molecule 1 Isoform 1," Published on Feb. 10, 2008 [online][retrieved on May 1, 2008] [retrieved from the Internet<URL:ncbi.nlm.nih.gov/protein/21314606], 5 pages.
Genbank Accession No. P38567 [online], "RecName: Full=Hyaluronidase PH-20; Short=Hyal-PH20; AltName: Full=Hyaluronoglucosaminidase PH-20; AltName: Full=Sperm adhesion molecule 1; AltName: Full=Sperm surface protein PH-20; Flags: Precursor," [retrieved on Apr. 18, 2011] [retrieved from the Internet:<URL:ncbi.nlm.nih.gov/protein/P38567.1], 8 pages.
Genbank Accession No. P48794 [online], RecName: Full=Hyaluronidase PH-20; Short=Hyal-PH20; AltName: Full=Hyaluronoglucosaminidase PH-20; AltName: Full=Sperm adhesion molecule 1; AltName: Full=Sperm surface protein PH-20; Flags: Precursor, Published on Mar. 8, 2011 [retrieved on Apr. 29, 2011] [retrieved from the Internet:<URL:ncbi.nlm.nih.gov/protein/P48794], 4 pages.
Genbank Accession No. BC021102 "*Homo sapiens* zinc finger CCCH-type containing 15, mRNA (cDNA clone)" http://www.ncbi.nlm.nih.gov/entrez/viewer.fcgi?db=nucleotide&val= 18088891 (accessed May 1, 2008), 4 pages.
Gerber et al., "Phosphatidylinositol Glycan (P1-G) Anchored Membrane Proteins" J. Biol. Chem. 267(17):12168-12178 (1992).
Gilbert, W. and L. Villa-Komaroff, "Useful Proteins from Recombinant Bacteria," Scientific American 242(4):74-94 (1980).
Gmachl et al., "The human sperm protein PH-20 has hyaluronidase activity," FEBS 336(3):545-548 (1993).
Gohlke et al., "Analysis of site-specific N-glycosylation of recombinant Desmodus rotundus salivary plasminogen activator rDSPalpha1 expressed in Chinese hampster ovary cells." Glycobiology 7(1):67-77 (1997).
Gold, E., "Purification and properties of hyaluronidase from human liver. Differences from and similarities to the testicular enzyme," Biochem. J. 205:69-74 (1982).
Goldspiel et al., "Human gene therapy," Clinical Pharmacy 12:488-505 (1993).
Goochee et al., "The oligosaccharides of glycoproteins: bioprocess factors affecting oligosaccharide structure and their effect on glycoprotein properties," BioTechnology 9:1347-1355 (1991).
Gottleib et al., "The safety of intravitreal hyaluronidase. A clinical and histologic study," Invest Ophthalmol Vis Sci 31:(1 1)2345-2352 (1990).
Gribskov et al., "Sigma factors from *E. coli, B. subtilis*, phage SP01, and phage T4 are homologous proteins," Nucl. Acids Res. 14(16):6745-6763 (1986).
Grosschedl et al., "Introduction of a mu immunoglobulin gene into the mouse germ line: specific expression in lymphoid cells and synthesis of functional antibody," Cell 38:647-658 (1984).
Grossman, M. and J. Wilson, "Retroviruses: delivery vehicle to the liver," Curr. Opin. in Genetics and Devel. 3:110-114 (1993).

(56) References Cited

OTHER PUBLICATIONS

Grunstein, M. and D. Hogness, "Colony hybridization: a method for the isolation of cloned DNAs that contain a specific gene," Proc. Natl. Acad. Sci. U. S. A. 72: 3961 (1975).

Guiotto et al., "An improved procedure for the synthesis of branched polyethylene glycols (PEGs) with the reporter dipeptide Met-betaAla for protein conjugation," Bioorg. Med. Chem. Lett. 12: 177-180 (2002).

Guntenhoner et al., "A substrate-gel assay for hyaluronidase activity," Matrix 12:388-396 (1992).

Guo et al., "Protein tolerance to random amino acid change," Proc. Nat'l. Acad. Sci. USA, 101:9205-9210, 2004.

Hahm et al., "Generation of a novel poliovirus with a requirement of hepatitis C virus protease NS3 activity," Virology 226:318-326 (1996).

Haller et al., "Escaping the Interstitial Matrix With Enzyme-Mediated Drug Delivery," Drug Delivery Technology, 5(5):1-6, (2005).

Haller, "Converting Intravenous Dosing to Subcutaneous Dosing with Recombinant Human Hyaluronidase," Pharmaceut Tech. 31(12):118-132 (2007).

Hallgren et al, "Accumulation of hyaluronan (hyaluronic acid) in myocardial interstitial tissue parallels development of transplantation edema in heart allografts in rats," J Clin Invest 85:668-673 (1990).

Hallgren et al, "Hyaluronic acid accumulation and redistribution in rejecting rat kidney graft. Relationship to the transplantation edema," J Exp Med. 171:2063-2076 (1990).

Hallgren et al., "Accumulation of hyaluronan (hyaluronic acid) in the lung in adult respiratory distress syndrome," Am Rev Respzr Dis. 139(3):682-687 (1989).

Halozyme Therapeutics Clinical Trial Informed Consent Form, "A Phase 1, multicenter, open-label, dose escalation, safety, tolerability, pharmacokinetic and pharmacodynamic study of PEGPH2O (PEGylated recombinant human hyaluronidase) with intitial dexamethasone premedication given intravenously to patients with advanced solid tumors." Signed Jul. 16, 2010, 13 pages.

Hamatake et al., "Establishment of an in vitro assay to characterize hepatitis C virus NS3-4A protease trans-processing activity," Intervirology 39:249-258 (1996).

Hamilton et al., "A species of small antisense RNA in post-transcriptional gene silencing in plants," Science 286:950-952 (1999).

Hammer et al., "Diversity of alpha-fetoprotein gene expression in mice is generated by a combination of separate enhancer elements," Science 235:53-58 (1987).

Hammond et al., "An RNA-directed nuclease mediates post-transcriptional gene silencing in *Drosophila* cells," Nature 404:293-296 (2000).

Hammond et al., "Post-transcriptional gene silencing by double-stranded RNA," Nature Rev Genet. 2:110-119 (2001).

Hanahan, D., "Heritable formation of pancreatic beta-cell tumours in transgenic mice expressing recombinant insulin/simian virus 40 oncogenes," Nature (3)15:115-122 (1985).

Harris, J. and R Chess, "Effect of pegylation on pharmaceuticals," Nat Rev Drug Discov 2(3):214-221 (2003).

Harrison, R., "Hyaluronidase in Ram Semen," Biochem. J. 252:865-874 (1988).

Hartman S. and R. Mulligan, "Two dominant-acting selectable markers for gene transfer studies in mammalian cells," Proc Natl Acad Sci 85:8047-8051 (1988).

Haselbeck, et al., "Immunological detection of glycoproteins on blots based on labeling with digoxigenin," Methods in Mol. Biol. 14:161-173 (1993).

Herrera-Estrella et al., "Expression of chimaeric genes transferred into plant cells using a ti-plasmid-derived vector,"Nature 303:209-213 (1984).

Herrera-Estrella et al., "Light-inducible and chloroplast-associated expression of a chimaeric gene introduced into *Nicotiana tabacum* using a Ti plamid vector," Nature 310(5973):115-120 (1984).

Hiyama, K. and S. Okada, "Action of chondroitinases. I. The mode of action of two chondroitinase-AC preparations of different origin," J. Biochem. (Tokyo) 80:1201 (1976).

Hiyama, K. and S. Okada, "Crystallization and some properties of chondroitinase from Arthrobacter aurescens," J. Biol. Chem. 250:1824-1828 (1975).

Hooper et al., "Determination of glycosyl-phosphatidylinositol membrane protein anchorage" Proteomics 1:748-755 (2001).

Horn et al., "Intravesical chemotherapy of superficial bladder tumors in a controlled trial with cis-platinum versus cis-platinum plus hyaluronidase," J. Surg. Oncol. 28:304-307 (1985).

Hunkapiller et al, "A microchemical facility for the analysis and synthesis of genes and proteins," Nature 310:105-111 (1984).

Hunnicut et al., "Structural relationship of sperm soluble hyaluronidase to the sperm membrane protein PH-20," Biol Reprod. 54(6):1343-1349 (1996).

Hutchison et al., "Mutagenesis at a specific position in a DNA sequence," J. Biol. Chem. 253:6551-6560 (1978).

ICSI Cumulase, "Human hyaluronidase for human oocytes" Medicult Product information Jun. 16, 2009, 2 pages [accessed on Mar. 30, 2010].

Inoue et al., "Sequence-dependent hydrolysis of RNA using modified oligonucleotide splints and RNase H," FEBS Lett. 215: 327-330 (1987).

Inoue et al., "Synthesis and hybridization studies on two complementary nona(2'-O-methyl)ribonucleotides," Nucl. Acids Res. 15:6131-6148 (1987).

Ishikawa et al., "Action of chondroitinase ABC on epidurally transplanted nucleus pulposus in the rabbit," Spine. 24(11):1071-1076 (1999).

Ito et al., "Cultivation of hepatitis C virus in primary hepatocyte culture from patients with chronic hepatitis C results in release of high titre infectious virus," J. Gen. Virol. 77:1043- 1054 (1996).

IUPAC-IUB Commission on Biochemical Nomenclature Biochem. 11:942-944 (1972).

Kaiser, K. and N. Murray, "Combination and packaging," in: Glover, D., Ed., 1985, DNA Cloning : A Practical Approach, MRL Press, Ltd., Oxford, U. K. vol. 1 pp. 11-12 (1985).

Kanamori et al., "Deaminated neuraminic acid-rich glycoprotein of rainbow trout egg vitelline envelope. Occurrence of a novel alpha-2,8-linked oligo(deaminated neuraminic acid) structure in O-linked glycan chains," J. Biol. Chem. 265:21811-21819 (1990).

Kelsey et al., "Species- and tissue-specific expression of human alpha 1-antitrypsin in transgenic mice," Genes and Devel. 1:161-171 (1987).

Kiem et al., "Retrovirus-mediated gene transduction into canine peripheral blood repopulating cells," Blood 83:1467-1473 (1994).

Kimata et al., "Increased synthesis of hyaluronic acid by mouse mammary carcinoma cell variants with high metastatic potential," Cancer Res. 43: 1347-1354 (1983).

Klocker et al., "Combined Application of Cisplatin, Vindesine, Hyaluronidase and Radiation for Treatment of Advanced Squamous Cell Carcinoma of the Head and Neck" Am. J. Clin. Oncol. 18: 425-428 (1995).

Knudson et al, "Hyaliironan-binding proteins in development, tissue homeostasis, and disease," FASEB J. 7:1233-1241 (1993).

Kodo et al., "Antibody synthesis by bone marrow cells in vitro following primary and booster tetanus toxoid immunization in humans," J. Clin. Invest. 73:1377-1384 (1984).

Kodukula et al., "Biosynthesis of Phosphatidylinositol Glycan-anchored Membrane Proteins" J. Biol. Chem. 266:4464-4470 (1991).

Kohler, G. and C. Milstein, "Continuous cultures of fused cells secreting antibody of predefined specificity," Nature 256:495-497 (1975).

Kohno et al., "Effects of hyaluronidase on doxorubicin penetration into squamous carcinoma multicellular tumor spheroids and its cell lethality," J. Cancer Res. Oncol. 120:293-297 (1994).

Koller, B. and O. Smithies, "Inactivating the beta 2-microglobulin locus in mouse embryonic stem cells by homologous recombination," Proc. Natl. Acad. Sci. USA 86:8932-8935 (1989).

Kollias et al., "Regulated expression of human a gamma-, beta-, and hybrid gamma beta-globin genes in transgenic mice: manipulation of the developmental expression patterns," Cell 46:89-94 (1986).

(56) References Cited

OTHER PUBLICATIONS

Kolodgie et al, "Differential accumulation of proteoglycans and hyaluronan in culprit lesions: insights into plaque erosion," Arterioscler Thromb Vasc Biol. 22(10):1642-1648 (2002).
Kozak et al., "The effect of recombinant human hyaluronidase on dexamethasone penetration into the posterior segment of the eye after sub-tenon's injection," Journal of Ocular Pharmacology and Therapeutics, 22 (5): 362-369, 2006.
Kozak J., "Structural features in eukaryotic mRNAs that modulate the initiation of translation," J Biol. Chem. 266:19867-19870 (1991).
Kozarsky, K. and J. Wilson, "Gene therapy: adenovirus vectors," Current Opinion in Genetics and Development 3:499-503 (1993).
Kriel, K., "Hyaluronidases—a group of neglected enzymes," Protein Sci. 4(9):1666-1669 (1995).
Krol et al., "Modulation of eukaryotic gene expression by complementary RNA or DNA sequences," BioTechniques 6:958-976 (1988).
Kroll et al., "A multifunctional prokaryotic protein expression system: overproduction, affinity purification, and selective detection," DNA Cell Biol 12:441-453 (1993).
Krumlauf et al., Developmental regulation of alpha-fetoprotein genes in transgenic mice, Mol. Cell. Biol. 5:1639-1648 (1985).
Krupers et al., "Complexation of poly(ethylene oxide) with poly(acrylic acid-co-hydroxyethyl methacrylate)s," Eur. Polym J. 32:785-790, 1996).
Kudawara et al., "In vivo inhibition of tumour growth by dexamethasone." European Journal of Cancer, 37:1703-1708 (2001).
Kyte et al., "A Simple Method for Displaying the Hydropathic Character of a Protein" J. Mol. Biol. 157:105-132 (1982).
Lalancette et al, "Characterization of an 80-kilodalton bull sperm protein identified as PH-20," Biol Reprod. 65(2):628-636 (2001).
Larsson et al., "Hyaluronic acid (hyaluronan) in BAL fluid distinguishes farmers with allergic alveolitis from farmers with asymptomatic alveolitis," Chest. 101(1):109-114 (1992).
Lathrop et al., "cDNA cloning reveals the molecular structure of a sperm surface protein, PH-20, involved in sperm-egg adhesion and the wide distribution of its gene among mammals," J Cell Biol. 111(6 Pt 2):2939-2949 (1990).
Laurent et al, "Hyaluronan in human cerebrospinal fluid," Acta Neurol Scand 94(3):194-206 (1996).
Laurent, T. and J. Fraser, "Hyaluronan," FASEB J 6:2397-2404 (1992).
Leder et al., "Consequences of widespread deregulation of the c-myc gene in transgenic mice: multiple neoplasms and normal development," Cell 45:485-495 (1986).
Lemaitre et al., "Specific antiviral activity of a poly(L-lysine)-conjugated oligodeoxyribonucleotide sequence complementary to vesicular stomatitis virus N protein mRNA initiation site," Proc. Natl. Acad. Sci. USA 84:648-652 (1987).
Letsinger et al., "Cholesteryl-conjugated oligonucleotides: synthesis, properties, and activity as inhibitors of replication of human immunodeficiency virus in cell culture," Proc. Natl. Acad. Sci. USA 86:6553-6556 (1989).
Levine, J., "Increased expression of the NG2 chondroitin-sulfate proteoglycan after brain injury," J Neurosci. 14(8):4716-4730 (1994).
Li et al., "Importance of Glycosylation and Disulfide Bonds in Hyaluronidase Activity of Macaque Sperm Surface PH-20." J. Androl. 23:211-219 (2002).
Lin et al., "A hyaluronidase activity of the sperm plasma membrane protein PH-20 enables sperm to penetrate the cumulus cell layer surrounding the egg," J Cell Biol. 125(5):1157-1163 (1994).
Lin et al., "Molecular cloning of the human and monkey sperm surface protein PH-20," Proc. Natl. Acad. Sci. USA 90:10071-10075 (1993).
Loeffler, J. and J. Behr, "Gene transfer into primary and established mammalian cell lines with lipopolyamine-coated DNA," Meth. Enzymol. 217:599-618 (1993).
Low et al., "Biochemistry of the glycosyl-phosphatidylinositol membrane protein anchors," Biochem. J. 224:1-13 (1987).
Lowy et al., "Isolation of transforming DNA: cloning the hamster aprt gene," Cell 22:817-823 (1980).
Lu, H. and E. Wimmer., "Poliovirus chimeras replicating under the translational control of genetic elements of hepatitis C virus reveal unusual properties of the internal ribosomal entry site of hepatitis C virus," Proc. Natl. Acad. Sci. USA 93:1412-1417 (1996).
MacDonald, R., "Expression of the pancreatic elastase I gene in transgenic mice," Hepatology 7:425-515(1987).
Maclean, et. al., "Hyaluronidase-induced reductions in myocardial infarct size," Science 194(4261):199-200 (1976).
Maeyama et al., "Chondroitinase AC—a unique illegible structure of ABC," Seikagaku 57:1189 (1985). [in Japanese].
Magram et al., "Developmental regulation of a cloned adult beta-globin gene in transgenic mice," Nature 315:338-340 (1985).
Mammalian Gene Collection (MGC) Program Team, "Generation and initial analysis of more than 15,000 full-length human and mouse cDNA sequences," Proc. Natl. Acad. Sci. USA 99:16899-16903 (2002).
Mantovani et al., "Efficacy of varying concentrations of hyaluronidase in peribulbar anaesthesia," British J. Anaesthesia 86:876-878 (2001).
Mantyh et al., "Inhibition of hyperalgesia by ablation of lamina I spinal neurons expressing the substance P receptor," Science 278:275-279 (1997).
Maroko et al., "Reduction by hyaluronidase of myocardial necrosis following coronary occlusion," Circulation 46:430-437 (1972).
Mason et al., "The hypogonadal mouse: reproductive functions restored by gene therapy," Science 234:1372-1378 (1986).
Mastrangeli et al., "Diversity of airway epithelial cell targets for in vivo recombinant adenovirus-mediated gene transfer," J. Clin. Invest. 91:225-234 (1993).
Matousek et al., "Effect of hyaluronidase and PEG chain conjugation on the biologic and antitumor activity of RNase A," J Control Release 94(2-3):401-410 (Feb. 2004).
McKeon et al., "Reduction of neurite outgrowth in a model of glial scarring following CNS injury is correlated with the expression of inhibitory molecules on reactive astrocytes," J Neurosci. 11(11):3398-3411 (1991).
Mehvar et al., "Modulation of the pharmacokinetics and pharmacodynamics of proteins by polyethylene glycol conjugation," J. Pharm. Pharmaceut. Sci. 3(1):125-136 (2000).
Menzel, E. and C. Farr, "Hyaluronidase and its substrate hyaluronan: biochemistry, biological activities and therapeutic uses," Cancer Lett., 131:3-11 (2003).
Merrifield, J., "Solid phase peptide synthesis. I. The synthesis of a tetrapeptide," J Am Chem Soc 85:2149-2154 (1963).
Meyer et al. Hyaluronidases, In:Boyer P.D. (Ed.), The Enzymes. Academic Press, New York (1971):307-320.
Meyer et al., "The soluble hyaluronidase from bull testes is a fragment of the membrane-bound PH-20 enzyme." FEBS Letters 413(2):385-388 (1997).
Michelacci, Y. and C. Dietrich, "Isolation and partial characterization of an induced chondroitinase B from Flavobacterium heparinum," Biochem. Biophys. Res. Commun. 56:973-980 (1974).
Michelacci, Y. and C. Dietrich, "A comparative study between a chondroitinase B and a chondroitinase AC from Flavobacterium heparinum: Isolation of a chondroitinase AC-susceptible dodecasaccharide from chondroitin sulphate B," Biochem. J. 151:121-129 (1975).
Milev et al., "Interactions of the chondroitin sulfate proteoglycan phosphacan, the extracellular domain of a receptor-type protein tyrosine phosphatase, with neurons, glia, and neural cell adhesion molecules," J Cell Biol. 127(6 Pt 1):1703-1715 (1994).
Miller et al., "Use of retroviral vectors for gene transfer and expression," Meth. Enzymol. 217:581-599 (1993).
Mitani, K. and C. Caskey, "Delivering therapeutic genes—matching approach and application," TIBTECH 11(5):162-166 (1993).
Miyazono et al., "A structural analysis of the sugar chain (II)," Seikagaku 61:1023 (1989). [in Japanese].
Miyazono et al., "A structural analysis of the sugar chain (II)," Seikagaku 61:1023 (1989). [Certified English language translation].

(56) References Cited

OTHER PUBLICATIONS

Mizutani et al., Characterization of hepatitis C virus replication in cloned cells obtained from a human T-cell leukemia virus type 1-infected cell line, MT-2, J.Virol. 70:7219-7223 (1996).
Mizutani et al., "Inhibition of hepatitis C virus replication by antisense oligonucleotide in culture cells," Biochem. Biophys. Res. Commun. 212:906-911 (1995).
Mizutani et al., "Long-term human T-cell culture system supporting hepatitis C virus replication," Biochem. Biophys. Res. Commun. 227:822-826 (1996).
Modena et al., "Hyaluronidase-injectable microparticles intended for the treatment of extravasation," J. Microencapsulation, 15(I):85-92 (1998).
Monfardini et al, "A branched monomethoxypoly(ethylene glycol) for protein modification," Bioconjugate Chem. 6: 62-69 (1995).
Morgan, R. and W. Anderson, "Human gene therapy," An. Rev. Biochem. 62:191-217 (1993).
Mulligan, R., "The basic science of gene therapy," Science 260:926-932 (1993).
Nabel et al., "Direct gene transfer for immunotherapy and immunization," TIBTECH 11:211-215 (1993).
Nadano et al., "A naturally occurring deaminated neuraminic acid, 3-deoxy-D-glycero-D-galacto-nonulosonic acid (KDN). Its unique occurrence at the nonreducing ends of oligosialyl chains in polysialoglycoprotein of rainbow trout eggs," J. Biol. Chem. 261:11550-11557 (1986).
Needleman, S. and C. Wunsch "A general method applicable to the search for similarities in the amino acid sequence of two proteins," J Mol Biol. 48:443-453 (1970).
Nettelbladt et al, "Accumulation of hyaluronic acid in the alveolar interstitial tissue in bleomycin-induced alveolitis," Am Rev Resp Dis 139:759-762 (1989).
Nogrady, Medicinal Chemistry A Biochemical Approach, Oxford University Press, New York, pp. 388-392 (1985).
O'Reilly, M., "The preclinical evaluation of angiogenesis inhibitors," Invest New Drugs 15(1): 5-13 (1997).
Oettl et al. "Comparative characterization of bovine testicular hyaluronidase and a hyaluronate lyase from Streptococcus agalactiae in pharmaceutical preparations," Eur. J. Pharm. Sci. 18:267-277 (2003).
Ornitz et al., "Elastase 1 promoter directs expression of human growth hormone and SV40 T antigen genes to pancreatic acinar cells in transgenic mice," Cold Spring Harbor Symp. Quant. Biol. 50:399-409 (1986).
Ozzello et al., "Growth-promoting activity of acid mucopolysaccharides on a strain of human mammary carcinoma cells," Cancer Res. 20:600-604 (1960).
Paul, A. and D. Sochart, "Improving the results of ganglion aspiration by the use of hyaluronidase," J Hand Surg 22(2):219-221 (1997).
Pawlowski et al., "The effects of hyalurodinase upon tumor formation in BALB/c mice painted with 7,12-dimethylbenz-(a)anthracene," Int: J. Cancer 23:105-109 (1979).
Pearson, W. and D. Lipman "Improved tools for biological sequence comparison," Proc. Natl. Acad. Sci. USA 85:2444 (1988).
Phelps et al., "Restricted lateral diffusion of Ph-20, a PI-anchored sperm membrane protein," Science 240:1780-1782 (1988).
Pinkert et al., "An albumin enhancer located 10 kb upstream functions along with its promoter to direct efficient, liver-specific expression in transgenic mice," Genes and Devel. 1:268- 276 (1987).
Pirrello et al., "Initial experiences with subcutaneous recombinant human hyaluronidase," J Palliat Med. Aug. 2007;10(4):861-864.
Pittelkow, M. and R. Scott, "New techniques for the in vitro culture of human skin keratinocytes and perspectives on their use for grafting of patients with extensive burns," Clinic Proc. 61:771-777 (1986).
Porath, J., "Immobilized metal ion affinity chromatography," Protein Expression and Purification 3:263-281 (1992).
Porteous et al., "How relevant are mouse models for human diseases to somatic gene therapy?" TIBTECH 11:173-181 (1993).
Powell et al., "Mechanisms of astrocyte-directed neurite guidance," Cell Tissue Res. 290(2):385-393 (1997).
Powell, E. and H. Geller, "Dissection of astrocyte-mediated cues in neuronal guidance and process extension," Glia. 26(1):73-83 (1999).
Readhead et al., "Expression of a myelin basic protein gene in transgenic shiverer mice: correction of the dysmyelinating phenotype," Cell 48:703-712 (1987).
Rheinwald, J., "Serial cultivation of normal human epidermal keratinocytes," Meth. Cell Bio. 21A:229-254 (1980).
Rhodes et al., "Transformation of maize by electroporation of embryos," Methods Mol Biol 55:121-131 (1995).
Roberts et al., "Chemistry for peptide and protein PEGylation," Advanced Drug Delivery Review 54:459-476 (2002).
Roberts et al., "Heparan sulphate bound growth factors: a mechanism for stromal cell mediated haemopoiesis," Nature 332(6162):376-378 (1988).
Robinson, C., "Gene therapy—proceeding from laboratory to clinic," TIBTECH 11:155 (1993).
Rodbard et al., "Statistical characterization of the random errors in the radioimmunoassay dose—response variable," Clin. Chem. 22:350-358 (1976).
Rosenfeld et al., "Adenovirus-mediated transfer of a recombinant alpha 1-antitrypsin gene to the lung epithelium in vivo," Science 252:431-434 (1991).
Rosenfeld et al., "In vivo transfer of the human cystic fibrosis transmembrane conductance regulator gene to the airway epithelium," Cell 68:143-155 (1992).
Ruoslahti, E. and Y. Yamaguchi, "Proteoglycans as modulators of growth factor activities," Cell 64(5):867-869 (1991).
Salmons, B. and W. Gunzberg, "Targeting of retroviral vectors for gene therapy," Human Gene Therapy 4:129-141 (1993).
Saltus R, "Shortages of Drugs Have Hospitals Scrambling," The Boston Globe, Jan. 9, 2001.
Sambrook, E. F. Fritsch, T. Maniatis, in: Molecular Cloning, A Laboratory Manual, Cold spring Harbor Laboratory Press 1989 vol. 3, p. B. 13.
Sarin et al., "Inhibition of acquired immunodeficiency syndrome virus by oligodeoxynucleoside methylphosphonates," Proc. Natl. Acad. Sci. USA 85:7448-7451 (1988).
Sarver et al., "Ribozymes as potential anti-HIV-1 therapeutic agents," Science 247:1222-1225 (1990).
Sasaki et al., "Effects of chondroitinase ABC on intradiscal pressure in sheep: an in vivo study," Spine 26(5):463-468 (2001).
Sato, H., "Enzymatic procedure for site-specific pegylation of proteins," Adv. Drug Deliv. Rev. 54:487-504 (2002).
Sawhney et al., "Bioerodible hydrogels based on photopolymerized poly(ethylene glycol)-co poly(hydroxyl acid) Diacrylate Macromers," Macromolecules 26:581-587 (1993).
Scharf et al., "Heat stress promoters and transcription factors," Results Probl Cell Differ 20:125-162 (1994).
Scheithauer et al., "In vitro evaluation of the anticancer drug modulatory effect of hyaluronidase in human gastrointestinal cell lines," Anticancer Res. 8:391-396 (1988).
Schuller et al., "Pharmacokinetics of intrahepatic 5-fluorouracil + preinjected hyaluronidase," Proc. Amer. Assoc. Cancer Res. 32:173, abstract No. 1034 (1991).
Schwartz, R. and M. Dayhoff, eds., "Matrices for detecting distant relationships," Atlas of Protein Sequence and Structure, National Biomedical Research Foundation, pp. 353-358 (1979).
Schwartzman, J., "Hyaluronidase: A Review in Its Therapeutic Use in Pediatrics," J. Pediat. 39:491-502 (1951).
Seaton et al., "Rat sperm 2B1 glycoprotein (PH2O) contains a C-terminal sequence motif for attachment of a glycosyl phosphatidylinositol anchor. Effects of endoproteolytic cleavage on hyaluronidase activity," Biol Reprod. 62(6):1667-1676 (2000).
Sequence alignments from U.S. Appl. No. 10/795,095 search of SEQ ID No. 1 in the Issued Patents database, performed on Sep. 25, 2007, 13 pages.
Shani, M., "Tissue-specific expression of rat myosin light-chain," Nature 314:283-286 (1985).
Sharp, P., "RNA interference—2001," Genes Dev. 15:485-490 (2001).
Shilo, B. and R. Weinberg, "DNA sequences homologous to vertebrate oncogenes are conserved in *Drosophila melanogaster*," Proc. Natl. Acad Sci USA 78:6789-6792 (1981).

(56) References Cited

OTHER PUBLICATIONS

Shimizu, Y. and H. Yoshikura, "Multicycle infection of hepatitis C virus in cell culture and inhibition by alpha and beta interferons," J. Virol. 68:8406-8408 (1994).
Shuster et al., "Hyaluronidase reduces human breast cancer xenografts in SCID mice," Int. J. Cancer 102:192-197 (2002).
Sikora, K. "Gene therapy for cancer," TIBTECH 11(5):197-201 (1993).
Smith, D. and K. Johnson, "Single-step purification of polypeptides expressed in *Escherichia coli* as fusions with glutathione S-transferase," Gene 7:31-40 (1988).
Smith, T. and M. Waterman, "Comparison of biosequences," Advances in Applied Mathematics 2:482-489 (1981).
Snow et al., "Immunolocalization of heparan sulfate proteoglycans to the prion protein amyloid plaques of Gerstmann-Straussler syndrome, Creutzfeldt-Jakob disease and scrapie," Lab Invest. 63(5):601-611 (1990).
Snow, D. and P. Letourneau, "Neurite outgrowth on a step gradient of chondroitin sulfate proteoglycan (CS-PG," J Neurobiol. 23(3):322-336 (1992).
Spatola, A., "Peptide backbone modifications," pp. 267-357 in Chemistry and Biochemistry of Amino Acids, Peptides, and Proteins, Weistein, Ed. vol. 7, Marcel Dekker:New York (1983).
Specification Sheet, Phosphate Buffered Saline[online][retrieved on Sep. 1, 2010 from: <URL:sigmaaldrich.com/catalog/DataSheetPage.do?brandKey=SIGMA&symbol=P4417], 1 page.
St Croix et al., "Reversal of intrinsic and acquired forms of drug resistance by hyaluronidase treatment of solid tumors," Cancer Lett 131(1):35-44 (1998).
Stein et al., "Physicochemical properties of phosphorothioate oligodeoxynucleotides," Nucl. Acids Res. 16:3209 (1988).
Steinkuhler et al., "Design of selective eglin inhibitors of HCV NS3 proteinase," Biochem. 37(33):11459-11468(1998).
Stemple, D. and D. Anderson, "Isolation of a stem cell for neurons and glia from the mammalian neural crest," Cell 71:973-985 (1992).
Stern, R., "Devising a pathway for hyaluronan catabolism: are we there yet?" Glycobiology 13:105R-115R (2003).
Stryer Biochemistry, Third Edition, ed. W.H. Freeman and Company, NY, 1988 pp. 18-20.
Stuhlmeier et al. "Glucocorticoids inhibit induced and non-induced mRNA accumulation of genes encoding hyaluronan synthases (HAS): hydrocortisone inhibits HAS1 activation by blocking the p38 mitogen-activated protein kinase signalling pathway," Rheumatology (Oxford) 43:164-169 (2004).
Sudo et al., "Establishment of an in vitro assay system for screening hepatitis C virus protease inhibitors using high performance liquid chromatography," Antiviral Res. 32:9-18 (1996).
Suzuki et al., "Formation of three types of disulfated disaccharides from chondroitin sulfates by chondroitinase digestion," J. Biol. Chem. 243:1543 (1968).
Swift et al., "Tissue-specific expression of the rat pancreatic elastase I gene in transgenic mice," Cell 38(3):639-646 (1984).
Takeshita et al., "An enzyme-linked immunosorbent assay for detecting proteolytic activity of hepatitis C virus proteinase," (1997) Anal. Biochem. 247:242-246.
Takeuchi et al., "Variation in glycosaminoglycan components of breast tumors," Cancer Res. 36:2133-2139 (1976).
Taliani et al., "A continuous assay of hepatitis C virus protease based on resonance energy transfer depsipeptide substrates," Anal. Biochem. 240:60-67 (1996).
Thompson et al., "Enzymatic Depletion of Tumor Hyaluronan Induces Antitumor Responses in Preclinical Animal Models" Molecular Cancer Therapeutics 9(1 1):3052-3064 (2010).
Tolstoshev, P., "Gene therapy, concepts, current trials and future directions," an. Rev. Phmacol. Toxicol. 32:573-596 (1993).
Tomita, M., "Background of Paroxysmal Nocturnal Hemoglobinuria," BiochemicalBiochim. Biophys. Acta 1455:269-286 (1997).
Toole, B., "Proteoglycans and hyaluronan in morphogenesis and differentiation," in Cell Biol. Extracell. Matrix, Hay (ed), Plenum Press:New York pp. 305-341 (1991).
Townsend et al., "Separation of branched sialylated oligosaccharides using high-pH anion-exchange chromatography with pulsed amperometric detection," Anal. Biochem. 182:1-8 (1989).
Townsend et al, "Analysis of glycoconjugates using high-ph anion-exchange chromatography," in Carbohydrate Analysis: High-perfonnance liquid chromatography and capillary electrophoresis (Z. El Rassi ed.). pp. 181-209 (1995).
Tsubery et al., "Prolonging the action of protein and peptide drugs by a novel approach of reversible polyethylene glycol modification.," J Biol. Chem 279(37):38118-38124 (2004).
Tuschl, T., "RNA interference and small interfering RNAs," Chem. Biochem. 2:239-245 (2001).
Tyle, P., "Iontophoretic devices for drug delivery," Pharmaceutical Research 3(6):318-326 (1986).
Tyndel, M., "Hyaluronidase as an adjuvant in insulin shock therapy" J Am Med Assoc,162(1):32-34 (1956).
UniProt Murine PH20 sequence at uniprot.org/uniprot/P48794.
Van Halbeek, H., "1H nuclear magnetic resonance spectroscopy of carbohydrate chains of glycoproteins," Methods Enzymol 230:132-168 (1994).
Varki, A., "Diversity in the sialic acids," Glycobiology 2: 25-40; Sialic Acids: Chemistry, Metabolism and Function, R. Schauer, Ed. (Springer-Verlag, N.Y. (1992)).
Veronese et al., "Branched and Linear Poly(Ethylene Glycol): Influence of the Polymer Structure on Enzymological, Pharmacokinetic, and Immunological Properties of Protein Conjugates," J. Bioactive Compatible Polymers 12:197-207 (1997).
Villa-Kamaroff et al., "A bacterial clone synthesizing proinsulin," Proc. Natl. Acad. Sci. USA 75:3727-3731 (1978).
Waeghe et al., "Determination, by methylation analysis, of the glycol-syl-linkage compositions of microgram quantities of complex carbohydrates," Carbohydr Res. 123:281-304 (1983).
Wagner et al., "Nucleotide sequence of the thymidine kinase gene of herpes simplex virus type 1," Proc. Natl. Acad. Sci. USA 78:1441-1445 (1981).
Waldenstrom et al, "Accumulation of hyaluronan and tissue edema in experimental myocardial infarction," J Clin Invest 88(5):1622-1628 (1991).
Waldenstrom et al, "Coxsackie B3 myocarditis induces a decrease in energy charge and accumulation of hyaluronan in the mouse heart," Eur J Clin Invest 23:277-282 (1993).
Wallander et al, "Intestinal distribution of hyaluronan in small bowel allografting in the rat," Transplant Int 6:133-137 (1993).
Walsh et al., "Gene therapy for human hemoglobinopathies," Proc. Soc. Exp. Biol. Med. 204:289-300 (1993).
Watson et al., Molecular Biology of the Gene, 4th Edition, The Benjamin/Cummings Pub. Co., p. 224 (1987).
Weitzhandler et al, "Monosaccharide and oligosaccharide analysis of proteins transferred to polyvinylidene fluoride membranes after sodium dodecyl sulfate-polyacrylamide gel electrophoresis," J. Biol. Chem. 268:5121-5130 (1993).
Wells et al, "The localization of hyaluronan in normal and rejected human kidneys," Transplantation 1990; 50: 240-243 (1990).
West et al., "The effect of hyaluronate and its oligosaccharides on endothelial cell proliferation and monolayer integrity," Exp. Cell. Res. 183:179-196 (1989).
Whitlock, C. and O. Witte, "Long-term culture of B lymphocytes and their precursors from murine bone marrow," Proc. Natl. Acad. Sci. USA 79:3608-3612 (1982).
Wigler et al., "Transfer of purified herpes virus thymidine kinase gene to cultured mouse cells," Cell 11:223-232 (1977).
Wigler et al., "Transformation of mammalian cells with an amplifiable dominant-acting gene," Proc Natl Acad Sci. USA 77:3567-3570 (1980).
Williams, R., "The Effects of Continuous Local Injection of Hyaluronidase on Skin and Subcutaneous Tissue in Rats," Anat. Rec. 122:349-361 (1955).
Williamson, R., "From genome mapping to gene therapy," TIBTECH 11(5):159-161 (1993).

(56) References Cited

OTHER PUBLICATIONS

Wivel, N., "Regulatory considerations for gene-therapy strategies and products," TIBTECH 11(5):189-191 (1993).
Wolf, et. al., "The serum kinetics of bovine testicular hyaluronidase in dogs, rats and humans," J Pharmacol Exp Ther 222(2):331-337 (1982).
World Health Organization (WHO) guideline: cf. D21, WHO Technical Report Series, No. 814 "Guidelines for assuring the quality of pharmaceutical and biological products prepared by recombinant DNA technology," (1991).
Wu, G. and C. Wu, "Receptor-mediated in vitro gene transformation by a soluble DNA carrier system," J. Biol. Chem, 262:4429-4432 (1987).
Wu, G. and C. Wu, "Delivery systems for gene therapy," Biotherapy 3:87-95 (1991).
Yamagata et al., "Purification and properties of bacterial chondroitinases and chondrosulfatases," J. Biol. Chem. 243: 1523-1535 (1968).
Yamamoto et al., "Identification of a functional promoter in the long terminal repeat of Rous sarcoma virus," Cell 22:787-797 (1980).
Yudin et al., "Characterization of the active site of monkey sperm hyaluronidase," Reproduction. • 121(5):735-743 (2001).
Zalipsky, S. and C. Lee, "Poly(ethyl ene glycol) Chemistry: Biotechnical and Biomedical Applications," J.M. Hams, ed., Plenum, NY, chapter 21, pp. 347-370 (1992).
Zalipsky, S., "Chemistry of polyethylene glycol conjugates with biologically active molecules," Adv. Drug Del. Rev. 16:157-182 (1995).
Zamore et al., "RNAi: double-stranded RNA directs the ATP-dependent cleavage of mRNA at 21 to 23 nucleotide intervals," Cell 101:25-33 (2000).
Zanker et al., "Induction of response in previous chemotherapy resistant patients by hyaluronidase," Proc. Amer. Assoc. Cancer Res. 27:390 Abstract 1550 (1986).
Zhang et al., "Glucocorticoids induce a near-total suppression of hyaluronan synthase mRNA in dermal fibroblasts and in osteoblasts: a molecular mechanism contributing to organ atrophy," Biochem. J. 349: 91-97 (2000).
Zhao, X. and J. Harris, "Novel degradable poly(ethylene glycol) esters for delivery," in Poly(ethylene glycol), Chemistry and Biological Applications, ACS Symposium Series 680, Hams, J. and S. Zalipsky, (eds), 458-472 (1997).
Zijlstra et al., "Germ-line transmission of a disrupted beta 2-microglobulin gene produced by homologous recombination in embryonic stem cells," Nature 342:435-438 (1989).
Zon, G., "Oligonucleotide analogues as potential chemotherapeutic agents," Pharm. Res. 5:539-549 (1988).
Bookbinder et al., "Enhancing Drug Transport Through Temporary Matrix Depolymerization," Keystone Symposium 2005, 1 page. Abstract, 1 page.
Bookbinder et al., "EnhanzeTM Technology for Antibody Dispersion," Strategic Research Institute Antibody World Summit, Jul. 24, 2005, Jersey City, NJ. Presentation, 40 pages.
Bookbinder et al., "EnhanzeTM Technology for Antibody Dispersion," Strategic Research Institute Antibody World Summit, Jul. 24-27, 2005, Jersey City, NJ. Abstract, 1 page.
Bookbinder et al., "Evaluation of the compatibility and pharmacokinetics of co-formulated biologics with recombinant human hyaluronidase: Dose Response," American Association of Pharmaceutical Scientists Conference, Nov. 2006. Abstract, 2 pages.
Bookbinder et al., "Evaluation of the compatibility and pharmacokinetics of co-formulated biologics with recombinant human hyaluronidase: Dose Response," American Association of Pharmaceutical Scientists Conference, Nov. 2006. Poster, 1 page.
Haberman et al., 1981, Proceedings of the 17th Annual Meeting of the American Society of Clinical Oncology, Washington, D.C., 22: 105, abstract No. 415).
Haller et al., "Enhanze Technology—A Revolution in Drug Dispersion," Biotechnology Industry Organization (B1O) Annual Meeting, Jun. 19-22, 2005, Philadelphia, PA. Abstract, 3 pages.

Haller et al., "Recombinant Human Hyaluronidase for the Interstitial Transport of Therapeutics," American Association of Pharmaceutical Scientists Conference, Jun. 2006, San Antonio, TX. Abstract, 2 pages.
Haller et al., "Recombinant Human Hyaluronidase for the Interstitial Transport of Therapeutics," Controlled Release Society Conference, Vienna, Austria, 2006, Poster, 1 page.
Haller et al., "Recombinant Human Hyaluronidase for the Interstitial Transport of Therapeutics," Controlled Release Society Conference, Vienna, Austria, 2006, Abstract, 1 page.
Haller et al., "Revolutionizing Drug Dispersion with Enhanze Technology," American Association of Pharmaceutical Scientists Annual Meeting, Nov. 6-10, 2005, Nashville, TN, Poster 1 page.
Haller et al., "Revolutionizing Drug Dispersion with Enhanze Technology," Biotechnology Industry Organization (B10) Annual Meeting, Jun. 19-22, 2005, Philadelphia, PA. Poster, 1 page.
Haller et al., "The Effects of Recombinant Human Hyaluronidase on Drug Dispersion," American Association of Pharmaceutical Scientists Annual Meeting, Nashville, TN, Abstract in AAPS Journal 7(S2) May 5, 2005; 3 pages.
Haller, "Enhanze Technology—An Enzymatic Drug Delivery System (DDS)," Japanese Export Trade Organization, Nov. 2005, Santa Clara, CA. Abstract, 2 pages.
Haller, "Focus on Enhanced and Innovative Recombinant Human Enzymes," Japanese Export Trade Organization, Sep. 2004, Chicago, IL. Presentation, 16 pages.
Haller, "Halozyme's Enhanze Technology for the Enhanced Dispersion of Co-Injected Pharmaceuticals," Japanese Export Trade Organization, Sep. 2004, Chicago, IL. Abstract, 1 page.
Haller, M., "Enzyme-facilitated Parenteral Drug Transport." Strategic Research Institute's 10$^{th}$ Anniversary Drug Delivery Technology and Deal-making Summit, 2005 New Brunswick, NJ. Presentation, 24 pages.
Hofer, "Human Recombinant Hyaluronidase Increases the Convection of Molecules up to 0.2 μm in Athymic Nude Mice," American Association for Laboratory Animal Science, 2006, Salt Lake City, UT. Abstract published in J. Am. Assoc. Lab. Animal Sci., 45:120, 2006. Poster P97, 1 page.
Jiang et al., "Effects of Recombinant Human PH20 (rHuPH20) on Interstitial Matrices: Creating a Favorable Environment for the Delivery of Cytostatic Agents," American Association for Cancer Research Annual Meeting, 2005, Anaheim, CA, 1 page. (vol. 46 Apr. 2005 p. 1198 XP001525054).
Jiang et al., "Reduction of ischemic stroke mortality with chronic intravenous recombinant human hyaluronidase (rHuPH20): effects of pharmacokinetic optimization," American Neurological Association Annual Meeting, Sep. 25-28, 2005, San Diego, CA, 2 pages.
Kozak et al., "Recombinant human hyaluronidase facilitates dexamethasone penetration into the posterior ocular segment after sub-Tenon's injection," Association for Research in Vision and Ophthalmology Annual Meeting (ARVO) Meeting Abstracts May 1, 2005 46:478. Abstract, 2 pages.
Kozak et al., "Recombinant human hyaluronidase facilitates dexamethasone penetration into the posterior ocular segment after sub-Tenon's injection," Association for Research in Vision and Ophthalmology Annual Meeting, May 1-5, 2005, Fort Lauderdale, FL. Poster, 1 page.
Kundu et al., "Dispersion of the Cumulus Matrix with a Highly Purified Recombinant Human Hyaluronidase (rHuPH20)," Hyaluronan Meeting, 2003, Cleveland, OH. Oct. 11-16, 2003 (together 2 pages).
Kundu et al., "Dispersion of the Cumulus Matrix with a Highly Purified Recombinant Human Hyaluronidase (rHuPH20)," Hyaluronan Meeting, 2003, Cleveland, OH. POSTER Oct. 11-16, 2003.
Li et al, "PEGylated human recombinant hyaluronidase (PEGPH20) removes peritumoral hyaluronan and increases the efficacy of chemotherapy and radiotherapy in an experimental brain metastisis model" 2009 ASCR Apr. 19, 2009. Abstract #262, 2 pages.
Li et al, "PEGylated human recombinant hyaluronidase (PEGPH20) removes peritumoral hyaluronan and increases the efficacy of chemotherapy and radiotherapy in an experimental brain metastisis model" Poster #262 2009 ASCR Apr. 19, 2009 [1 page].

(56) References Cited

OTHER PUBLICATIONS

Li et al., "Combinatorial treatment of PEGylated human recombinant hyaluronidase (PEGPH20) and the mTOR inhibitor everolimus demonstrate additive antitumor activity in hyaluronan-rich PC3 hormone refractory prostate cancer xenografts," AACR meeting Apr. 2011. Abstract (published Mar. 2011).

Pinkstaff et al., "Reduction of Ischemic Stroke Mortality Following Intravenous Recombinant Human Hyaluronidase (rHuPH20): Effects of Pharmacokinetic Optimization," American Neurological Association, Sep. 25-28, 2005, San Diego, CA. Poster #33, 1 page.

Pinkstaff et al., "Enhancing Drug Transport Through Temporary Matrix Depolymerization," Keystone Symposium 2005. Poster, 12 pages.

Pinkstaff et al., "Evaluation of the Compatibility and Pharmacokinetics of Co-formulated Biologics with Recombinant Human Hyaluronidase: Dose Response," American Association of Pharmaceutical Scientists Conference, Nov. 2006, San Antonio, TX. Abstract, 2 pages.

Pinkstaff et al., "Evaluation of the Compatibility and Pharmacokinetics of Co-formulated Biologics with Recombinant Human Hyaluronidase: Dose Response," American Association of Pharmaceutical Scientists Conference, Nov. 2006, San Antonio, TX. Poster, 1 page.

Pinkstaff et al., "Recombinant Human Hyaluronidase for Drug and Fluid Dispersion," American Association of Pharmaceutical Scientists Annual Meeting, Nov. 2006, Boston, MA, Abstract, 1 page.

Pinkstaff et al., "Recombinant Human Hyaluronidase for Drug and Fluid Dispersion," American Association of Pharmaceutical Scientists Annual Meeting, Nov. 2006, Boston, MA, Poster, 1 page.

Wasserman et al., "Pharmacokinetics of Recombinant Human Hyaluronidase (rHuPH20)-Facilitated Subcutaneous Infusion of Immune Globulin (Human), 10% (IGHy) in Patients with Primary Immunodeficiency Disease (P1)" American College of Allergy, Asthma, & Immunology Meeting, Boston, MA, Nov. 5, 2011. Poster, 1 page.

Wei et al., "Functions of N-linked glycans on human hyaluronidase PH20," presented at San Diego Glycobiology Symposium 2009. Poster 83, 1 page.

Wei et al., "Structure function analysis of the human hyaluronidase enzymes," Matrix Biology 27 (Supplement 1):S41, Dec. 2008, American Society for Matrix Biology Biennial Meeting, San Diego, CA, (available on-line Nov. 17, 2008), Abstract 132/B4, 1 page.

Wei et al., "Structure function analysis of the human hyaluronidase enzymes," Presented at American Society for Matrix Biology Biennial Meeting, San Diego, CA, Dec. 9, 2008. Poster B4, 1 page.

Wilson MS, "Enhanze Technology—An Enzymatic Drug Delivery System (DDS)," Japanese Export Trade Organization, Nov. 2005, Santa Clara, CA. Oral presentation, 22 pages.

Yang et al., "An Alternative Approach for Delivering High Dose Biologics Subcutaneously" presented at PEP TALK, Jan. 11, 2011 (oral presentation) [28 pages].

Halozyme Therapeutics Investor Presentation, "Company Overview," Feb. 1, 2006, 34 pages.

Halozyme Therapeutics Investor Presentation, "Company Overview," Feb. 12, 2008, 37 pages.

Halozyme Therapeutics Investor Presentation, "Company Overview," Feb. 22, 2007, 25 pages.

Halozyme Therapeutics Investor Presentation, "Company Overview," Jun. 28, 2006, 28 pages.

Halozyme Therapeutics Investor Presentation, "Company Overview," May 15, 2008, 15 pages.

Halozyme Therapeutics Investor Presentation, "Company Overview," Nov. 29, 2005, 34 pages.

Halozyme Therapeutics Investor Presentation, "Focus on enhanced and innovative recombinant human enzymes," Jan. 28, 2005, 28 pages.

Halozyme Therapeutics Investor Presentation, "Focus on enhanced and innovative recombinant human enzymes," Mar. 12, 2004, 32 pages.

Halozyme Therapeutics, "Exclusive Distribution Agreement," Aug. 13, 2004, 13 pages.

Halozyme Therapeutics, "Non-Exclusive Distribution Agreement," Apr. 13, 2004, 22 pages.

Halozyme Therapeutics, "Non-Exclusive Distribution Agreement," Feb. 9, 2004, 21 pages.

Halozyme Therapeutics, "Non-Exclusive Distribution Agreement," Jan. 30, 2004, 19 pages.

Halozyme Therapeutics, "Securities and Exchange Comission Amendment No. 1 to Form SB-2," Jun. 21, 2004, 108 pages. (cumulase enhanze).

Halozyme Therapeutics, "Securities and Exchange Comission Form 10-QSB," Nov. 12, 2004, 34 pages.

Halozyme Therapeutics, "Securities and Exchange Comission Form S-3," Nov. 12, 2004, 30 pages.

Halozyme Therapeutics, "Securities and Exchange Comission Form SB-2," Mar. 23, 2004, 102 pages. (cumulase and enhanze).

Halozyme Therapeutics, Securities and Exchange Commission form 10K, Mar. 11, 2011.

Halozyme Website, "Products & pipeline-PEGPH20," [online][retrieved on Nov. 17, 2011] Retrieved from:<URL:halozyme.com/Products-And-Pipeline/Pipeline/PEGPH20/default.aspx [2 pages].

News Release, "Halozyme Therapeutics Announces Implementation of Development Focused Strategy," San Diego, CA Oct. 11, 2010, http://phx.corporate-ir.net/phoenix.zhtml?c=175436&p=irol-newsArticle&ID=1481205&highlight= (accessed Nov. 19, 2010), 3 pages.

News Release, "Halozyme Therapeutics Awarded Four Qualifying Therapeutic Discovery Project Grants," San Diego, CA Nov. 4, 2010, http://phx.corporate-ir.net/phoenix.zhtml?c=175436&p=irol-newsArticle&ID=1491739&highlight= (accessed Nov. 19, 2010), 2 pages.

News Release, "Halozyme Therapeutics Inc., Second Quarter 2010 Financial Results Conference Call Transcript" Aug. 6, 2010, [retrieved on Sep. 3, 2010].

News Release, "Halozyme Therapeutics Reports Second Quarter 2010 Financial Results" Aug. 6, 2010, retrieved from: phx.corporate-ir.net/phoenix.zhtml?c=175436&p=irol-newsArticle—print&ID=1457558&highlight= [retrieved on Sep. 1, 2010].

News Release, "Halzoyme Therapeutics Reports Third Quarter 2010 Financial Results." San Diego, CA Nov. 5, 2010, http://phx.corporate-ir.net/phoenix.zhtml?c=175436&p=irol-newsArticle&ID=1492590&highlight= (accessed Nov. 19, 2010), 5 pages.

News Release, Halozyme Therapeutics Inc., "Halozyme Therapeutics and Baxter Healthcare Corporation Sign Exclusive Sales and Marketing Agreement for Halozyme's Investigational Therapeutic, Enhanze SC," Aug. 16, 2004, retrieved from the Internet<URL: sec.gov/Archives/edgar/data/1159036/000095013704006885/a01296exv99wl.txt, [retrieved on Mar. 29, 2010] [2 pages].

News Release, Halozyme Therapeutics Inc., "Halozyme therapeutics presents rHuPH20 hyaluronidase preclinical data at the 2005 association for research in vision and ophthalmology annual meeting," retrieved from: http://www2.prnewswire.com/cgi-bin/stories.pl?ACCT=104&STORY=/www/story/05-02-2005/0003536239&EDATE= (May 2, 2005) [retrieved on 06.23.09] [2 pages].

News Release, Halozyme Therapeutics, Inc., "Fourth quarter and full year 2010 conference call transcript," Published on Mar. 11, 2011[online][retrieved on Apr. 7, 2011] Retrieved from:<URL:phx.corporate-ir.net/Extental.File?item=UGFyZW5OSUQ9NDE5Mj UyfENoaWxkSUQ9NDMyNDcwfFR5cGU9MQ==&t=1 [18 pages].

News Release, Halozyme Therapeutics, Inc., "Halozyme and Baxter announce availability of hylenex for subcutaneous delivery of medications and fluids," Published on Jun. 27, 2006[online][retrieved on Jan. 6, 2009] Retrieved from:<URL:phx.corporate-ir.net/phoenix.zhtml?c=175436&p=irol-newsArticle—Print&ID=876530&highlight= [3 pages].

News Release, Halozyme Therapeutics, Inc., "Halozyme therapeutics and Baxter Healthcare Corporation announce FDA approval of hylenex," Published on Dec. 5, 2005[online][retrieved on Jan. 6,

(56) References Cited

OTHER PUBLICATIONS

2009] Retrieved from:<URL:phx.corporate-ir.net/phoenix. zhtml?c=175436&p=irol-newsArticle—Print&ID=792608&highlight= [3 pages].
News Release, Halozyme Therapeutics, Inc., "Halozyme therapeutics announces FDA acceptance of hylenex NDA," Published on May 26, 2005[online][retrieved on Jan. 6, 2009] Retrieved from:<URL:phx.corporate-ir.net/phoenix.zhtml?c=175436&p=irol-newsArticle_Print&ID=714327&highlight= [2 pages].
News Release, Halozyme Therapeutics, Inc., "Halozyme Therapeutics announces submission of investigational new drug application for chemophase," Published on Jun. 30, 2005[online][retrieved on Jan. 6, 2009] Retrieved from:<URL:phx.corporate-ir.net/phoenix. zhtml?c=175436&p=irol-newsArticle_Print&ID=725295&highlight= [2 pages].
News Release, Halozyme Therapeutics, Inc., "Halozyme therapeutics files NDA for Enhanze SC," Published on Mar. 28, 2005[online][retrieved on Jan. 6, 2009] Retrieved from:<URL:phx. corporate-ir.net/phoenix.zhtml?c=175436&p=irol-newsArticle_ Print&ID=689194&highlight= [2 pages].
News Release, Halozyme Therapeutics, Inc., "Halozyme Therapeutics initiates chemophase phase I clinical trial for superficial bladder cancer—first patients treated," Published on Oct. 27, 2005[online][retrieved on Jan. 6, 2009] Retrieved from:<URL:phx. corporate-ir.net/phoenix.zhtml?c=175436&virol-newsArticle_ Print&ID=774533&highlight= [2 pages].
News Release, Halozyme Therapeutics, Inc., "Halozyme Therapeutics initiates hylenex clinical trial of subcutaneous hydration," Published on Dec. 15, 2005[online][retrieved on Jan. 6, 2009] Retrieved from:<URL:phx.corporate-ir.net/phoenix.zhtml?c=175436&p=irol-newsArticle_Print&ID=796125&highlight= [2 pages].
News Release, Halozyme Therapeutics, Inc., "Halozyme Therapeutics receives FDA clearance to initiate chemophase clinical trial," Published on Aug. 11, 2005[online][retrieved on Jan. 6, 2009] Retrieved from:<URL:phx.corporate-ir.net/phoenix. zhtml?c=175436&p=irol-newsArticle_Print&ID=742261 &highlight= [2 pages].
Examination Report, issued Apr. 9, 2008, in connection with related New Zealand Patent Application No. 567053, 5 pages.
Office Action, issued Aug. 20, 2008, in connection with related U.S. Appl. No. 10/795,095, 23 pages.
Office Action, issued Sep. 15, 2008, in connection with related U.S. Appl. No. 11/238,171, 13 pages.
Examination Report, issued Apr. 6, 2009, in connection with related Japanese Patent Application No. 2006-509139, 5 pages.
Final Office Action, issued Apr. 14, 2009, in connection with related U.S. Appl. No. 10/795,095, 15 pages.
Office Action, issued May 7, 2009, in connection with related U.S. Appl. No. 11/238,171, 11 pages.
Office Action, issued Sep. 30, 2009, in connection with corresponding U.S. Appl. No. 11/065,716, 11 pages.
Notice of Opposition, submitted Aug. 10, 2010, in connection with related European Patent No. EP1603541, 32 pages.
Office Action, issued Nov. 19, 2010, in connection with corresponding U.S. Appl. No. 12/802,864, 6 pages.
Examination Report, issued Dec. 1, 2010, in connection with corresponding New Zealand Patent Application No. 589500, 3 pages.
Exam Report and Notice of Acceptance, issued Jan. 6, 2011, in connection corresponding with New Zealand Patent Application No. 581233, 2 pages.
Response of Mar. 24, 2011 to Notice of Opposition, issued Aug. 10, 2010, for related European Patent No. EP 1 603 541, 42 pages.
Response to Office Action, issued Nov. 19, 2010, in connection with corresponding U.S. Appl. No. 12/802,864, 19 pages.

Final Rejection, issued Jun. 8, 2011, for corresponding U.S. Appl. No. 12/802,864, 5 pages.
Preliminary Opinion and Summons to attend Oral Proceedings, issued Jul. 28, 2011, in connection with related European Patent No. 1603541, 6 pages.
Response to Final Office Action, issued Jun. 8, 2011, in connection with corresponding U.S. Appl. No. 12/802,864, 7 pages.
Extended European Search Report, issued Feb. 8, 2012, in connection with related European Patent Application No. 10183410.9, 15 pages.
Withdrawal of Opposition, mailed Mar. 5, 2012, in connection with related European Patent No. 1603541, 1 page.
Response to Summons to Attend Oral Proceedings, dated Jul. 28, 2011, in connection with related European Patent No. 1603541, including enclosures: Main Request and Auxiliary Request Claims and Annexes A, 1-12, 471 pages.
Notice of Allowance, issued Apr. 2, 2012, in connection with corresponding U.S. Appl. No. 13/374,248, 11 pages.
European Patent Office Communication Pursuant to Article 101(1) and Rule 81(2) to (3) EPC, issued Apr. 5, 2012, in connection with Oral Proceedings for related European Patent No. 1603541, 3 pages.
U.S. Appl. No. 13/694,071, filed Oct. 24, 2012.
U.S. Appl. No. 13/684,731, filed Dec. 28, 2012.
U.S. Appl. No. 13/815,311, filed Feb. 19, 2013.
U.S. Appl. No. 13/815,553, filed Mar. 8, 2013.
U.S. Appl. No. 13/815,804, filed Mar. 15, 2013.
Letter/Written Disclosure of the Supplemental Information Disclosure Statement for the above-referenced application, mailed on Apr. 10, 2013, 2 pages.
Bertelli et al., "Hyaluronidase as Hyaluronidase as an antidote to extravasation of Vinca alkaloids: clinical results," J Cancer Res Clin Oncol. 120(8):505-506 (1994).
Bertelli et al., "Skin skin ulceration potential of paclitaxel in a mouse skin model in vivo," Cancer. 79(11):2266-2269 (1997).
Halozyme, Inc. Information and Consent Form, "A Phase 2, randomized, multicenter study of PEGPH20 (PEGylated Recombinant Human Hyaluronidase) combined with nab-paclitaxel plus gemcitabine compared with nab-paclitaxel plus gemcitabine in subjects with stage IV previously untreated pancreatic cancer," Study # HALO-109-202. Approved Feb. 14, 2013, 1 page.
Halozyme Therapeutics, "Hylenex(R) recombinant (hyaluronidase human injection) and infiltration and extravasion," [online][retrieved on Apr. 3, 2013] Retrieved from:<URL:.hylenex.com/files/resources_docs/Infiltration-Extravasation/documentation/ Hylenex%20recombinant%20and%20Infiltration-Extravasation. pdf, 7 pages.
Frost, G., "Halozyme Therapeutics, Inc. Thinking outside the cell," presented at J. P. Morgan Healthcare Conference on Jan. 10, 2013. Presentation. 23 pages.
Osgood et al, "Pegylated recombinant human hyaluronidase PH20 (PEGPH20) enhances Nab-Paclitaxel efficacy in BxPC-3 human pancreatic cancer xenografts," Available on-line Mar. 2012 [online][retrieved on Mar. 26, 2012] Retrieved from:<URL:ncbi. nlm.nih.gov/nuccore/AF177422, 1 page.
Osgood et al., "Pegylated recombinant human hyaluronidase PH20 (PEGPH20) enhances Nab-Paclitaxel efficacy in BxPC-3 human pancreatic cancer xenografts," AACR Annual Meeting 2012. Chicago, IL, Presented Apr. 4, 2012. Poster #5635, 1 page.
Osgood et al., "Pegylated recombinant human hyaluronidase PH20 (PEGPH20) enhances Nab-Paclitaxel efficacy in BxPC-3 human pancreatic cancer xenografts," Cancer Research 72(8):Suppl 1 (2012). 2 pages.
Thompson et al., "Pegylated recombinant human hyaluronidase PH20 (PEGPH20) increases tumor perfusion in mouse xenografts and phase 1 cancer patients," AACR Annual Meeting 2013 Apr. 6-10, 2013, Washington, D.C., Abstract #4955 [Retrieved from the internet Apr. 5, 2013], 1 page.
News Release, "Halozyme Therapeutics to present at the 31st Annual J.P. Morgan Healthcare Conference," Published Jan. 3, 2013 [online][Retrieved Jan. 17, 2013] Retrieved from:<URL:halozyme. com/Investors/News-Releases/News-Release-Details/2013/ Halozyme-Therapeutics-to-Present-at-the-31st-Annual-JP-Morgan-Healthcare-Conference1132508/default.aspx, 2 pages.

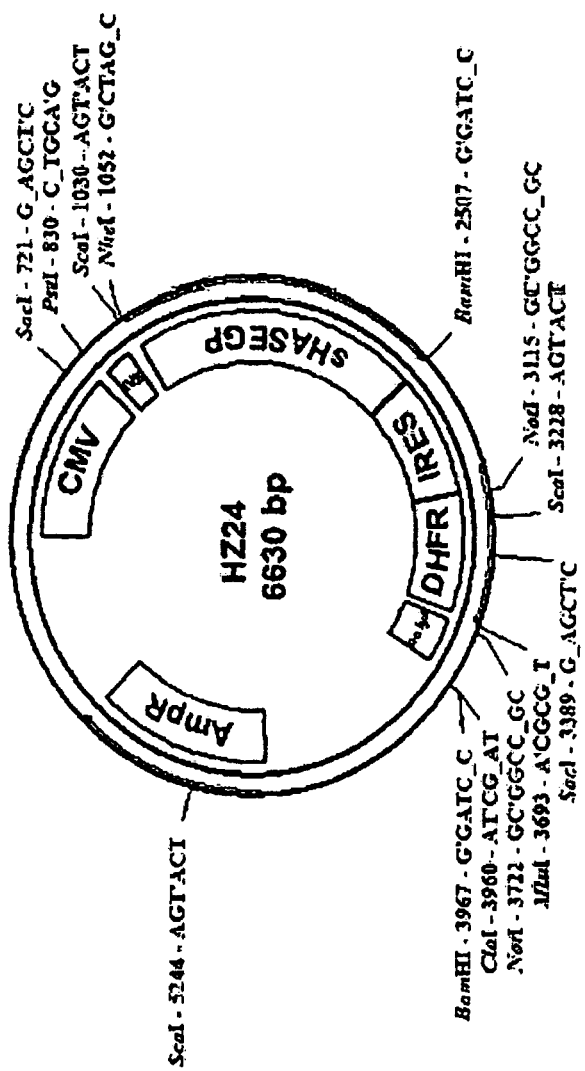
VECTOR MAP of sHASEGP VECTOR HZ24

SOLUBLE GLYCOSAMINOGLYCANASES AND METHODS OF PREPARING AND USING SOLUBLE GLYCOSAMINOGLYCANASES

CROSS REFERENCE TO RELATED APPLICATION(S)

This application is a divisional of U.S. application Ser. No. 13/374,248, filed Dec. 15, 2011 now U.S. Pat. No. 8,257,699, to Louis H. Bookbinder, Anirban Kundu and Gregory I. Frost, which is a continuation of U.S. application Ser. No. 12/802,864, filed Jun. 15, 2010, to Louis H. Bookbinder, Anirban Kundu and Gregory 1. Frost, now issued as U.S. Pat. No. 8,105,586, which is a divisional of U.S. application Ser. No. 11/065,716, filed Feb. 23, 2005, to Louis H. Bookbinder, Anirban Kundu, Gregory I. Frost, Michael F. Haller, Gilbert A. Keller and Tyler M. Dylan, as filed and now issued as U.S. Pat. No. 7,871,607 to Louis H. Bookbinder, Anirban Kundu and Gregory I. Frost. U.S. application Ser. No. 12/802,864 also is a continuation-in-part of U.S. application Ser. No. 10/795,095, filed Mar. 5, 2004, and now issued as U.S. Pat. No. 7,767,429 to Louis H. Bookbinder, Anirban Kundu and Gregory I. Frost. Each of U.S. application Ser. Nos. 11/065,716 and 12/802,864 is herein incorporated by reference in its entirety.

This application is related to U.S. Ser. No. 10/795,095, filed Mar. 5, 2004, which claims priority under 35 U.S.C. §119(e) to U.S. Ser. No. 60/452,360, filed Mar. 5, 2003, each of which is herein incorporated by reference in its entirety.

BACKGROUND OF THE INVENTION

1. Field of the Invention

The present invention is generally related to Glycosaminoglycanase enzymes, including Neutral-Active, Soluble Hyaluronidase Glycoproteins (sHASEGPs), and portions thereof, particularly Hyaluronidase domains. More specifically, the invention is related to chemical modifications, pharmaceutical compositions, expression plasmids, methods for manufacture and therapeutic methods using the Glycosaminoglycanases (and domains thereof and the encoding nucleic acid molecules) for the therapeutic modification of glycosaminoglycans in the treatment of disease and for use to increase diffusion of other molecules such as injected molecules in an animal.

2. Background Information

Glycosaminoglycans (GAGs) are complex linear polysaccharides of the extracellular matrix (ECM). GAGs are characterized by repeating disaccharide structures of an N-substituted hexosamine and an uronic acid, (in the case of hyaluronan (HA), chondroitin sulfate (CS), chondroitin (C), dermatan sulfate (DS), heparan sulfate (HS), and heparin (H)), or a galactose, (in the case of keratan sulfate (KS)). Except for HA, all exist covalently bound to core proteins. The GAGs with their core proteins are structurally referred to as proteoglycans (PGs).

Hyaluronan (HA) is found in mammals predominantly in connective tissues, skin, cartilage, and in synovial fluid. Hyaluronan is also the main constituent of the vitreous of the eye. In connective tissue, the water of hydration associated with hyaluronan creates hydrated matrices between tissues. Hyaluronan plays a key role in biological phenomena associated with cell motility including rapid development, regeneration, repair, embryogenesis, embryological development, wound healing, angiogenesis, and tumorigenesis (Toole 1991 Cell Biol. Extracell. Matrix, Hay (ed), Plenum Press, New York, 305-341; Bertrand et al. 1992 Int. J. Cancer 52:1-6; Knudson et al., 1993 FASEB J. 7:1233-1241). In addition, hyaluronan levels correlate with tumor aggressiveness (Ozello et al. 1960 Cancer Res. 20:600-604; Takeuchi et al. 1976, Cancer Res. 36:2133-2139; Kimata et al. 1983 Cancer Res. 43:1347-1354).

HA is found in the extracellular matrix of many cells, especially in soft connective tissues. HA has been assigned various physiological functions, such as in water and plasma protein homeostasis (Laurent T C et al (1992) FASEB J 6: 2397-2404). HA production increases in proliferating cells and may play a role in mitosis. It has also been implicated in locomotion and cell migration. HA seems to play important roles in cell regulation, development, and differentiation (Laurent et al., supra).

HA has been used in clinical medicine. Its tissue protective and rheological properties have proved useful in ophthalmic surgery (e.g. to protect the corneal endothelium during cataract surgery). Serum HA is diagnostic of liver disease and various inflammatory conditions, such as rheumatoid arthritis. Interstitial edema caused by accumulation of HA may cause dysfunction in various organs (Laurent et al., supra).

Hyaluronan protein interactions also are involved in the structure of the extracellular matrix or "ground substance".

Hyaluronidases are a group of generally neutral- or acid-active enzymes found throughout the animal kingdom. Hyaluronidases vary with respect to substrate specificity, and mechanism of action.

There are three general classes of hyaluronidases:

1. Mammalian-type hyaluronidases, (EC 3.2.1.35) which are endo-beta-N-acetylhexosaminidases with tetrasaccharides and hexasaccharides as the major end products. They have both hydrolytic and transglycosidase activities, and can degrade hyaluronan and chondroitin sulfates (CS), generally C4-S and C6-S.

2. Bacterial hyaluronidases (EC 4.2.99.1) degrade hyaluronan and, and to various extents, CS and DS. They are endo-beta-N-acetylhexosaminidases that operate by a beta elimination reaction that yields primarily disaccharide end products.

3. Hyaluronidases (EC 3.2.1.36) from leeches, other parasites, and crustaceans are endo-beta-glucuronidases that generate tetrasaccharide and hexasaccharide end products through hydrolysis of the beta 1-3 linkage.

Mammalian hyaluronidases can be further divided into two groups: neutral-active and acid-active enzymes. There are six hyaluronidase-like genes in the human genome, HYAL1, HYAL2, HYAL3 HYAL4 HYALP1 and PH20/SPAM1. HYALP1 is a pseudogene, and HYAL3 has not been shown to possess enzyme activity toward any known substrates. HYAL4 is a chondroitinase and exhibits little activity towards hyaluronan. HYAL1 is the prototypical acid-active enzyme and PH20 is the prototypical neutral-active enzyme. Acid active hyaluronidases, such as HYAL1 and HYAL2 generally lack catalytic activity at neutral pH (i.e. pH 7). For example, HYAL1 has little catalytic activity in vitro over pH 4.5 (Frost et al Anal Biochemistry, 1997). HYAL2 is an acid-active enzyme with a very low specific activity in vitro.

The hyaluronidase-like enzymes can also be characterized by those which are generally locked to the plasma membrane via a glycosylphosphatidyl inositol anchor such as human HYAL2 and human PH20 (Danilkovitch-Miagkova et al., Proc Natl Acad Sci USA. 2003 Apr. 15; 100(8):4580-5, Phelps et al., Science 1988), and those which are generally soluble such as human HYAL1 (Frost et al., Biochem Biophys Res Commun. 1997 Jul. 9; 236(1):10-5). However, there are variations from species to species: bovine, PH20 for example is very loosely attached to the plasma membrane and is not anchored via a phospholipase sensitive anchor (Lalancette et al., *Biol Reprod.* 2001 August; 65(2):628-36.). This unique feature of bovine hyaluronidase has permitted the use of the soluble bovine testes hyaluronidase enzyme as an extract for clinical use (Wydase™, Hyalase™). Other PH20 species are lipid anchored enzymes that are generally not soluble without the use of detergents or lipases. For example, human PH20 is anchored to the plasma membrane via a GPI anchor. Attempts to make human PH20 DNA constructs that would not introduce a lipid anchor into the polypeptide resulted in either a catalytically inactive enzyme, or an insoluble enzyme (Arming et al *Eur J. Biochem.* 1997 Aug. 1; 247(3):810-4). Naturally occurring macaque sperm hyaluronidase is found in both a soluble and membrane bound form. While the 64 kDa membrane bound form possesses enzyme activity at pH 7.0, the 54 kDa form is only active at pH 4.0 (Chem et al., Dev Biol. 1996 Apr. 10; 175(1):142-53.). Thus, soluble forms of PH20 are often lacking enzyme activity under neutral conditions.

Chondroitinases are enzymes found throughout the animal kingdom. These enzymes degrade glycosaminoglycans through an endoglycosidase reaction. Specific examples of known Chondroitinases include Chondroitinase ABC (derived from *Proteus vulgaris*; Japanese Patent Application Laid-open No 6-153947, T. Yamagata, H. Saito, O. Habuchi, and S. Suzuki, J. Biol. Chem., 243, 1523 (1968), S. Suzuki, H. Saito, T. Yamagata, K. Anno, N. Seno, Y. Kawai, and T. Furuhashi, J. Biol. Chem., 243, 1543 (1968)); Chondroitinase AC (derived from *Flavobacterium heparinum*; T. Yamagata, H. Saito, O. Habuchi, and S. Suzuki, J. Biol. Chem., 243, 1523 (1968)); Chondroitinase AC II (derived from *Arthrobacter aurescens*; K. Hiyama, and S. Okada, J. Biol. Chem., 250, 1824 (1975), K. Hiyama and S. Okada, J. Biochem. (Tokyo), 80, 1201 (1976)); Hyaluronidase ACIII (derived from *Flavobacterium* sp. Hp102; Hirofumi Miyazono, Hiroshi Kikuchi, Keiichi Yoshida, Kiyoshi Morikawa, and Kiyochika Tokuyasu, Seikagaku, 61, 1023 (1989)); Chondroitinase B (derived from *Flavobacterium heparinum*; Y. M. Michelacci and C. P. Dietrich, Biochem. Biophys. Res. Commun., 56, 973 (1974), Y. M. Michelacci and C. P. Dietrich, Biochem. J., 151, 121 (1975), Kenichi Maeyama, Akira Tawada, Akiko Ueno, and Keiichi Yoshida, Seikagaku, 57, 1189 (1985)); Chondroitinase C (derived from *Flavobacterium* sp. Hp102; Hirofumi Miyazono, Hiroshi Kikuchi, Keliichi Yoshida, Kiyoshi Morikawa, and Kiyochika Tokuyasu, Seikagaku, 61, 1023 (1989)); and the like.

Glycoproteins are composed of a polypeptide chain covalently bound to one or more carbohydrate moieties. There are two broad categories of glycoproteins that possess carbohydrates coupled though either N-glycosidic or O-glycosidic linkages to their constituent protein. The N- and O-linked glycans are attached to polypeptides through asparagine-N-acetyl-D-glucosamine and serine (threonine)-N-acetyl-D-galactosamine linkages, respectively. Complex N-linked oligosaccharides do not contain terminal mannose residues. They contain only terminal N-acetylglucosamine, galactose, and/or sialic acid residues. Hybrid oligosaccharides contain terminal mannose residues as well as terminal N-acetylglucosamine, galactose, and/or sialic acid residues.

With N-linked glycoproteins, an oligosaccharide precursor is attached to the amino group of asparagine during peptide synthesis in the endoplasmic reticulum. The oligosaccharide moiety is then sequentially processed by a series of specific enzymes that delete and add sugar moieties. The processing occurs in the endoplasmic reticulum and continues with passage through the cis-, medial- and trans-Golgi apparatus.

SUMMARY OF THE INVENTION

Provided herein are soluble glycosaminoglycanase enzymes particularly members of the soluble neutral-active Hyaluronidase Glycoprotein family (also referred to herein as sHASEGPs), preferred members being human soluble neutral-active Hyaluronidase Glycoproteins, particularly the human soluble PH-20 Hyaluronidase Glycoproteins (also referred to herein as rHuPH20s). The soluble neutral-active Hyaluronidases provided herein are each a sHASEGP family member, designated herein as a sHASEGP. The soluble Hyaluronidase domain, and uses thereof are also provided. While a number of uses and applications of soluble glycosaminoglycanases (sometimes referred to herein as GAG Enzymes) are illustrated herein using rHuPH20 as an exemplary glycosaminoglycanase (e.g. in promoting the delivery of pharmacologics and other agents within tissues of the mammalian body), it will be appreciated by those of skill in the art that other glycosaminoglycanases such as those described herein or others known in the art can be applied to a number of such applications. Presently preferred soluble glycosaminoglycanases, such as sHASEGPs, exhibit some hyaluronidase activity and can exhibit other glycosaminoglycanase activities as well. Human soluble glycosaminoglycanases are presently preferred for applications in which the enzyme is to be employed within the human body, including many medical applications as described and illustrated herein.

One aspect of the invention is based upon the discovery that a soluble, neutral-active hyaluronidase activity can be produced with high yield in a mammalian expression system by introducing nucleic acids that lack a narrow region encoding amino acids in the carboxy terminus of the human PH20 cDNA. Additional modifications of the sHASEGP to enhance secretion by use of non-native leader peptides are also provided. Further provided are methods to modify the sHASEGP to prolong its half life by way of masking the protein with polyethylene glycol (PEG) and/or post-translational modifications to native glycosylation. Previous attempts to generate soluble neutral-active human hyaluronidase glycoproteins were unsuccessful. It was concluded that truncations of the human hyaluronidase polypeptide resulted in both a loss of neutral enzymatic activity, and an inability of cells to secrete the recombinant protein in mammalian expression systems (Arming, et al Eur J Biochem 1997 Aug. 1; 247 (3):810-4). It is critical to generate neutral-acting secreted sHASEGP for commercial production and therapeutic utility as a hyaluronidase. The invention, disclosed herein, overcomes these and other challenges.

The invention further comprises a catalytically active human sHASEGP glycoprotein wherein the sHASEGP possesses at least one N-linked sugar moiety. The studies shown herein demonstrate that human PH20 requires N-linked glycans for catalytic activity, whereas bovine and bee venom hyaluronidases remain active without such N-linked glycans. A human hyaluronidase PH20 domain devoid of N-linked moieties is catalytically inactive. Thus classic recombinant DNA technology does not permit the production of a catalytically active human sHASEGP, unlike bee venom hyaluronidase, which can be produced in *E. coli*.

The invention includes methods and cells for generation of an N-linked sHASEGP glycoprotein polypeptide, by using of a cell capable of introducing said N-linked sugar moieties or by introduction of said N-linked moieties on a sHASEGP polypeptide. Methods of identifying properly glycosylated sHASEGPs are further disclosed.

Catalytically active PEGylated and/or super-Sialated sHASEGP glycoproteins are also provided. PEGylated and/or super-sialated sHASEGPs possess greater serum half-lives compared to naturally occurring non-sialated bovine and ovine testes sHASEGPs, and are thus preferable for both enzyme stability and use as drugs or adjuvants in circumstances in which prolonged half-lives are desirable (such as is commonly the case with intravenous delivery). The invention provides methods for the preparation of PEGylated and/or super-Sialated sHASEGPs, compositions and uses thereof. Without being restricted to a particular application or mechanism of action, it is generally considered that the attachment of PEG moieties to sHASEGPs and other glycosaminoglycanases can be used to effectively shield the molecules, decreasing its relative sensitivity to proteases and potentially also decreasing the extent and rate of its clearance and elimination from the body. Applying these principles and techniques to other glycosaminoglycanases, PEGylated, super-Sialated and/or otherwise modified versions of such other glycosaminoglycanases can likewise be generated and used in the context of methods and techniques as described and illustrated herein (e.g. techniques for promoting the dispersion of pharmacologics and other agents within tissues of the body).

Proteins encoded by naturally GPI anchor deficient sHASEGP splice variants are also provided.

Further provided are compositions of the sHASEGP comprising, a soluble sHASEGP glycoprotein with a metal ion, wherein the metal ion is Calcium, Magnesium or Sodium. sHASEGPs are generally optimally active in the presence of said metals. Formulations consisting of sHASEGP in the presence of said metal ions are also provided.

Modifications of sHASEGPs and other glycosaminoglycanases to further prolong their half life are provided. Chemical modifications of a sHASEGPs and other glycosaminoglycanases with polymers such as polyethylene glycol and dextran are provided. Such modifications shield sHASEGPs and other glycosaminoglycanases from removal from circulation and the immune system as well as glycosylation receptors for mannose and asialoglycoprotein. Further provide are methods to link to specific functional groups such as glycosylation sites, positively charged amino acids and cysteines.

Assays for identifying effectors, such as compounds, including small molecules, and conditions, such as pH, temperature and ionic strength, that modulate the activation, expression or activity of sHASEGPs, are also provided herein. In exemplary assays, the effects of test compounds on the ability of a Hyaluronidase domain of sHASEGP to cleave a known substrate, typically a glycosaminoglycan or proteoglycan, are assessed. Agents, generally compounds, particularly small molecules, that modulate the activity of the Hyaluronidase domain are candidate compounds for modulating the activity of the sHASEGP. The Hyaluronidase domains can also be used to produce Hyaluronidase-specific antibodies with function-perturbing activity. The Hyaluronidase domains provided herein include, but are not limited to, the N-terminal glycsoyl-hydrolase domain with C-terminal truncated portions thereof that exhibit catalytic activity in vitro.

Nucleic acid molecules encoding the proteins and Hyaluronidase domains are also provided. Nucleic acid molecules that encode a soluble Hyaluronidase domain or catalytically active portions thereof and also those that encode the full-length sHASEGP are provided. Nucleic acid encoding an exemplary Hyaluronidase domain and downstream nucleic acid is set forth in SEQ ID No. 6; and the Hyaluronidase domain of an exemplary sHASEGP is set forth in SEQ ID No. 1 (amino acids 35-464). The protein sequence and encoding nucleic acid sequence of an exemplary full-length sHASEGP are set forth in SEQ ID Nos. 1 and 6.

Also provided are nucleic acid molecules that hybridize to such sHASEGP-encoding nucleic acid along their full-length or along at least about 70%, 80% or 90% of the full-length and encode the Hyaluronidase domain or portion thereof are provided. Hybridization is generally effected under conditions of at least low, generally at least moderate, and often high stringency.

The isolated nucleic acid fragment is DNA, including genomic or cDNA, or is RNA, or can include other components, such as protein nucleic acid or other nucleotide analogs. The isolated nucleic acid may include additional components, such as heterologous or native promoters, enhancers and other transcriptional and translational regulatory sequences, these genes may be linked to other genes, such as reporter genes or other indicator genes or genes that encode indicators.

Also provided is an isolated nucleic acid molecule that includes the sequence of molecules that is complementary to the nucleotide sequence encoding sHASEGP or the portion thereof.

Also provided are fragments thereof or oligonucleotides that can be used as probes or primers and that contain at least about 10 to 16 nucleotides, typically at least about 20 nucleotides, and generally less than 1000, typically less than about 100 nucleotides, set forth in SEQ ID NO. 6 (or the complement thereof); or contain at least about 30 nucleotides (or the complement thereof) or contain oligonucleotides that hybridize along their full-length (or at least about 70, 80 or 90% thereof) to any such fragments or oligonucleotides. The length of the fragments are a function of the purpose for which they are used and/or the complexity of the genome of interest. Generally probes and primers contain less than about 50, 150 or 500 nucleotides.

Also provided are plasmids containing any of the nucleic acid molecules provided herein. Cells containing the plasmids are also provided. Such cells include, but are not limited to, bacterial cells, yeast cells, fungal cells, plant cells, insect cells and animal cells.

Also provided are enhanced mammalian expression systems using signal leaders capable of efficient secretion of sHASEGPs. An example of such efficient secretory leader peptide amino acid sequence and fusion protein with a sHASEGP is found in SEQ ID Nos. 43 and 46.

Also provided is a method of producing sHASEGPs by growing the above-described cells under conditions whereby the sHASEGP is expressed by the cells, and recovering the expressed sHASEGP polypeptide or glycoprotein. Methods for isolating nucleic acid encoding other sHASEGPs are also provided.

Also provided are cells, generally eukaryotic cells, such as mammalian cells and yeast cells, in which a sHASEGP polypeptide is expressed on the surface of the cells. Such cells can be used in drug screening assays to identify compounds that modulate the activity of the sHASEGP polypeptide. These assays, including in vitro binding assays, and transcription based assays in which signal transduction mediated directly or indirectly, such as via activation of pro-growth factors, by the sHASEGP is assessed.

Also provided are peptides encoded by such nucleic acid molecules. Included among those polypeptides is the sHASEGP Hyaluronidase domain or a polypeptide with amino acid changes such that the specificity and/or Hyaluronidase activity remains substantially unchanged. In particular, a substantially purified mammalian sHASEGP glycoprotein is provided that comprises a secreted neutral-active enzyme.

The invention also includes a Hyaluronidase catalytic domain and may additionally include other domains. The sHASEGP may form homodimers and can also form heterodimers with some other protein, such as a membrane-bound protein. Also provided is a substantially purified glycoprotein including a sequence of amino acids that has at least 60%, 70%, 80%, 81%, 82%, 83%, 84%, 85%, 86%, 87%, 88%, 89%, 90%, 91%, 92%, 93%, 94%, 95%, 96%, 97%, 98%, or 99% identity to an exemplary sHASEGP where the percentage identity is determined using standard algorithms and gap penalties that maximize the percentage identity.

Splice variants of sHASEGPs, particularly those with a catalytically active Hyaluronidase domains, are contemplated herein.

In other embodiments, substantially purified polypeptides that include a Hyaluronidase domain of a sHASEGP polypeptide or a catalytically active portion thereof, but that do not include the entire sequence of amino acids set forth in SEQ ID No. 1 are provided. Among these are polypeptides that include a sequence of amino acids that has at least 70%, 80%, 85%, 90%, 95% or 100% sequence identity to SEQ ID No. 1 or 3.

In a specific embodiment, a nucleic acid that encodes a eukaryotic Hyaluronidase glycoprotein, designated a eukaryotic sHASEGP is provided. In particular, the nucleic acid includes the sequence of nucleotides set forth in SEQ ID No. 6, particularly set forth as nucleotides 106-1446 of SEQ ID NO. 6, or a portion thereof that encodes a catalytically active polypeptide.

Also provided are nucleic acid molecules that hybridize under conditions of at least low stringency, generally moderate stringency, more typically high stringency to the SEQ ID NO. 6 or degenerates thereof.

In one embodiment, the isolated nucleic acid fragment hybridizes to a nucleic acid molecule containing the nucleotide sequence set forth in SEQ ID No: 6 (or degenerates thereof) under high stringency conditions. A full-length sHASEGP is set forth in SEQ ID No. 1 and is encoded by SEQ ID NO. 6 or degenerates thereof.

Also provided are muteins of the Hyaluronidase domain of sHASEGPs, particularly muteins in which one or more Cys residues in the Hyaluronidase domain that are free (i.e., do not form disulfide linkages with any other Cys residue in the Hyaluronidase domain) are substituted with another amino acid, typically, although not necessarily, with a conservative amino acid substitution or a substitution that does not eliminate the activity, and muteins in which a specific glycosylation site (or sites) is eliminated.

sHASEGP polypeptides, including, but not limited to splice variants thereof, and nucleic acids encoding sHASEGPs, and domains, derivatives and analogs thereof are provided herein. Single chain secreted Hyaluronidase glycoproteins that have an N-terminus functionally equivalent to that generated by activation of a signal peptidase to form sHASEGP are also provided. There are seven potential N-linked glycosylation sites at N82, N166, N235, N254, N368, N393, N490 of the human PH20 sHASEGP exemplified in SEQ ID NO: 1. Disulfide bonds form between the Cys residues C60-C351 and Cys residues C224 to C238 to form the core Hyaluronidase domain. However, additional cysteines are required in the carboxy terminus for neutral enzyme catalytic activity such that the sHASEGP domain from amino acids 36 to Cys 464 in SEQ ID No. 1 comprises the minimally active human PH20 sHASEGP hyaluronidase domain. Thus, N-linked glycosylation site N-490 is not required for proper sHASEGP activity. As will be appreciated by those of skill in the art, minor changes can be made to such compositions as described and illustrated herein without substantially eliminating or in some cases without substantially reducing (or potentially even improving) their useful activity, and can thus be similarly employed in various applications as described herein.

N-linked glycosylation of some sHASEGPs (such as the sHASEGP comprising the amino acid sequence of SEQ ID No. 1) can be very important for their catalytic activity and stability. While altering the type of glycan modifying a glycoprotein can have dramatic affects on a protein's antigenicity, structural folding, solubility, and stability, most enzymes are not thought to require glycosylation for optimal enzyme activity. Such sHASEGPs are thus unique in this regard, in that removal of N-linked glycosylation can result in near complete inactivation of the Hyaluronidase activity. For such sHASEGPs, the presence of N-linked glycans is critical for generating an active enzyme. Protein expression systems suitable for the introduction of critical N-linked glycosylation residues on sHASEGPs are included. Additionally, the introduction of deglycosylated sHASEGP polypeptide in the presence of extracts capable of introducing N-linked glycans are included. In one aspect of the invention, complex glycosylation capped with sialation is described whereas others capped with free mannose residues are contemplated as well. Preferably, sialic acid residues are found in the terminal residues of N-linked glycosylation on sHASEGPs.

N-linked oligosaccharides fall into several major types (oligomannose, complex, hybrid, sulfated), all of which have (Man) 3-GlcNAc-GlcNAc-cores attached via the amide nitrogen of Asn residues that fall within -Asn-Xaa-Thr/Ser-sequences (where Xaa is not Pro). Glycosylation at an -Asn-Xaa-Cys-site has been reported for coagulation protein C. N-linked sites are often indirectly assigned by the appearance of a "blank" cycle during sequencing. Positive identification can be made after release of the oligosaccharide by PNGase F, which converts the glycosylated Asn to Asp. After PNGase F release, N-linked oligosaccharides can be purified, for example by using Bio-Gel P-6 chromatography, with the oligosaccharide pool subjected to preparative high pH anion exchange chromatography (HPAEC) (Townsend et al., (1989) Anal. Biochem. 182, 1-8). Certain oligosaccharide isomers can be resolved using HPAEC. Fucose residues will shift elution positions earlier in the HPAEC chromatogram, while additional sialic acid residues will increase the retention time. Concurrent treatment of glycoproteins whose oligosaccharide structures are known (e.g., bovine fetuin, a-1 acid glycoprotein, ovalbumin, RNAse B, transferrin) can facilitate assignment of the oligosaccharide peaks. The collected oligosaccharides can be characterized by a combination of compositional and methylation linkage analyses (Waeghe et al., (1983) Carbohydr Res. 123, 281-304.), with anomeric configurations assigned by NMR spectroscopy (Van Halbeek (1993) in Methods Enzymol 230).

In the case of some sHASEGPs, exemplified by the human sHASEGP rHuPH20 described herein, the sHASEGP can comprise both N-glycosidic and O-glycosidic linkages. For example, rHuPH20 (as produced in the DG44 CHO line 3D3, as described in the Examples below) has been discovered to have O-linked oligosaccharides as well as N-linked oligosaccharides. Glycosidic modifications of such sHASEGPs (for example, modifications comprising one or more additions, removals or alterations of such N-linked and/or O-linked oligosaccharides can be used to generate glycosidic variant sHASEGPs exhibiting altered pharmacokinetic and/or pharmacodynamic profiles that make them desirable for particular applications. By way of illustration, but without being restricted to a particular mechanism of action, removal or alteration of (such as by capping or otherwise de-exposing) one or more N-linked and/or O-linked oligosaccharides that are involved in binding to cellular or other receptors can be used to alter the extent and/or rate at which a sHASEGP binds to or is taken up by a particular tissue, which can in turn be used to alter for example its pharmacokinetic profile (e.g., by increasing its serum half life or otherwise altering its bioabsorption).

Formulations of sHASEGPs are also provided. sHASEGPs may be formulated in lyophilized forms and stabilized solutions for example. Formulations containing specific metal ions, such as calcium, magnesium, or sodium, are useful for optimal activity at neutral pH. In addition to stabilized solution formulations, slow release formulations are contemplated herein for extended removal of glycosaminoglycans or extended promotion of spreading or diffusion of agents such as pharmacologics. Also provided herein are kits providing for pre-packaged syringes of sHASEGPs for the administration of small volumes of sHASEGP for intraocular surgical procedures and other small volume procedures. Balanced salt formulations for ex vivo use in artificial reproductive technology procedures are also provided.

Methods for the use of glycosaminoglycanases including sHASEGPs in the removal of glycosaminoglycans are also provided. Glycosaminoglycanases including sHASEGPs open channels in the interstitial space through degradation of glycosaminoglycans that generally permit the diffusion of molecules less than about 500 nm in size. These channels can remain relatively open for a period of 24-48 hours depending on dose and formulation. Such channels can be used to facilitate the diffusion of exogenously added molecules such as fluids, small molecules, proteins, nucleic acids and gene therapy vectors and other molecules less than about 500 nm in size. In addition, without being restricted to a particular theory or mechanism of action, it is believed that the formation of such channels can facilitate bulk fluid flow within an interstitial space, which can in turn promote the dispersion or movement of a solute (such as a detectable molecule or other diagnostic agent, an anesthetic or other tissue-modifying agent, a pharmacologic or pharmaceutically effective agent, or a cosmetic or other esthetic agent) that is effectively carried by the fluid in a process sometimes referred to herein as "convective transport" or simply convection. Such convective transport can substantially exceed the rate and cumulative effects of molecular diffusion and can thus cause the therapeutic or other administered molecule to more rapidly and effectively perfuse a tissue. Furthermore, when a molecule such as a therapeutic or other agent (such as a small molecule drug or a larger molecule or complex) is co-formulated or co-administered with a sHASEGP (or other glycosaminoglycanase) and both are injected into a relatively confined local site, such as a site of non-intravenous parenteral administration (e.g., intradermal, subcutaneous, intramuscular, or into or around other internal tissues, organs or other relatively confined spaces within the body), then the fluid associated with the administered dose can both provide a local driving force (i.e. hydrostatic pressure) as well as lower impedance to flow (by opening channels within the interstitial matrix)—both of which would tend to increase fluid flow, and with it convective transport of the therapeutic agent or other molecule contained within the fluid. As discussed and illustrated in more detail herein, and as will be appreciated by those of skill in the art, these aspects of the use of sHASEGPs and other glycosaminoglycanases can have substantial utility for improving the bioavailability as well as manipulating other pharmacokinetic and/or pharmacodynamic characteristics of co-formulated or co-administered agents.

sHASEGPs and other glycosaminoglycanases can also be used to remove excess glycosaminoglycans such as those that occur following ischemia reperfusion, inflammation, arteriosclerosis, edema, cancer, spinal cord injury and other forms of scarring. In some instances, sHASEGPs and other glycosaminoglycanases can be delivered systemically by intravenous infusion. This can be helpful when local access is not readily available such as the heart or brain or in the case of disseminated neoplasm wherein the disease is through the body. For such intravenous or other intravascular applications, Super-Sialated sHASEGPs are often preferable to increase serum half-life and distribution over native hyaluronidase enzymes that lack terminal sialic acids.

In some circumstances, such as spinal cord injury and other nervous system disorders, glaucoma and certain other disorders of the eye, as well as various autoimmune, inflammatory conditions, cancers and other chronically progressive diseases and conditions, and cosmetic treatments, sustained delivery is preferred. As will be appreciated by those of skill in the art, a number of different compositions and techniques have been developed to provide slow-release or sustained-release formulations or depots of molecules of interest.

In other indications, a single short acting dose is preferable. Temporary removal of glycosaminoglycans can be used to enhance the delivery of solutions and drugs into and/or through interstitial spaces. This can be useful for the diffusion of anesthesia and for the administration of therapeutic fluids, molecules and proteins. Subcutaneous, intradermal and intramuscular administration of molecules in the presence of sHASEGPs (and/or other glycosaminoglycanases) also facilitate their systemic distribution more rapidly. Such methods are very useful when intravenous access is not available or where more rapid systemic delivery of molecules is needed. By way of illustration, delivery of other large molecules such as Factor VIII, that are poorly bioavailable upon subcutaneous administration, may be injected with sHASEGPs to increase their availability.

Uses of sHASEGPs for enzymatic removal of the cumulus matrix surrounding oocytes are also provided. The removal of the cumulus matrix using a purified sHASEGP without the toxic contaminants of extract derived hyaluronidase permits more gentle recover of the oocyte with greater viabilities. Moreover, sHASEGPs can be manufactured without the use of cattle extracts or other organisms that carry viruses and other pathogens such as transmissible spongiform encephalopathies.

Injections of small volumes of sHASEGP for intraocular use may also be used for small spaces. For example, sHASEGPs and/or other glycosaminoglycanases may be injected into the anterior chamber of the eye to remove excess viscoelastic substrates that are administered during surgery. Intraocular injection of sHASEGPs can also be used to reduce intraocular pressure in glaucoma, to dissolve vitreous aggregates, or "floaters", to clear vitreous hemorrhage, for the treatment of macular degeneration, to promote vitreo retinal detachment in diabetic retinopathy and to be mixed with other enzymes to promote reshaping of the cornea along with corrective lenses. As described herein, sHASEGPs and/or other glycosaminoglycanases can also be injected into the eye or into surrounding periorbital spaces as a form of "spreading agent," i.e. to promote the delivery of diagnostic, anesthetic or pharmacologic agents to sites within and/or around the target tissue. For example, injection of a sHASEGP concomitant with or in temporal proximity to injection of diagnostic, anesthetic or pharmacologic agents into the sub-Tenon's or episcleral space can be used to promote transcleral delivery of the pharmacologic to interior portions of the eye (such as the choroid, retina and vitreous body). The episcleral space is a lymph-containing space between the Fascia Bulbi (capsule of Tenon) and the sclera which is a relatively tough protective tissue surrounding the choroid and retina and the interior of the eye. The Sub-Tenon's or episcleral space, which is sometimes referred to as the periscleral lymph space, is generally also continuous with the subdural and subarachnoid cavities and is traversed by bands of connective tissue extending from the fascia to the sclera. As will be appreciated by those of skill in the art, the ability to promote delivery of compositions across the protective scleral layer covering the eye allows for a great variety of pharmacologic and other agents to be conveniently and efficiently delivered to underlying tissues within the eye, such as the choroid, retina or vitreous humor. By applying compositions of the present invention to such in vivo delivery routes even relatively difficult to reach tissues, such as those at the back of the eye, can be treated by minimally invasive means. It will be recognized that in some instances, the use of a longer lasting sHASEGP such as a pegylated-sHASEGP will be desirable.

It is important to note that while animal-derived hyaluronidases can and have been applied to treat certain conditions of the eye, and as a spreading factor to promote the delivery of anesthetics and other therapeutic or pharmacologic agents, several important considerations apply to the use of animal-derived enzymes and potentially either limit their use or introduce safety concerns or additional risks when they are used for treating humans. Among these considerations is the concern that proteins and other impurities present in the formulations can lead to immunogenic and/or other problems when applied to human tissues in vivo. In addition, to the extent that non-human animal enzymes are employed, even purified enzymes can themselves further contribute to immunogenicity since they are of non-human origin. Further in that regard, the potential for degradative enzymes such as hyaluronidases to effectively promote their own dispersal (as described herein), could increase the probability that immunogenic versions or formulations of such animal-derived products are contacted by the immune system.

Concerns with animal-derived and/or impure factors are also of increased significance in a number of situations; for example, situations in which the target tissue has already been subjected to surgical or other procedures, situations in which the agent is being introduced into a relatively immune-privileged space (such as portions of the eye, the heart, the nervous system and many other tissues and organs that are not typically exposed to the external environment), and/or situations in which the patient is immuno-compromised or otherwise at elevated risk associated with infection. Use of such animal-derived formulations may thus be avoided in a number of applications in which the risk of infection or other complications undercut their potential utility. In those situations and in others, the use of recombinantly-prepared sHASEGPs of the present invention can provide applications that are both highly effective and have favorable safety profiles, and thus improve and expand the conditions and situations in which these enzymes are beneficially used.

In the context of non-intravenous parenteral injections (such as intradermal, subcutaneous, intramuscular and other injections into spaces other than the vasculature), a sHASEGP (and/or another glycosaminoglycanase) and another agent (e.g. a co-formulation or a mixture comprising a sHASEGP and another agent such as a diagnostic agent, an anesthetic agent, a pharmacologic agent, an esthetic agent, or combinations therefo) in a volume of liquid (e.g. a pharmaceutical excipient or other solution) can be introduced into a site or sites within the body by injection or infusion. Without wishing to be bound by theory, it is believed that several forces can be brought into motion to enhance delivery of the pharmacologic or other agent (the extent of which depends in part on the particular composition, volume and site of administration for example). These driving forces can include an increase in hydrostatic pressure as a volume of fluid is effectively forced into a contained space (such as the sub-Tenon's space referred to above, or a site of intradermal, subcutaneous, intramuscular or other non-IV parenteral injection), a subsequent increase in convective transport of solutes (or convection) as fluid flow is increased down its pressure gradient (and dissolved molecules or macromolecular complexes are carried with it), as well as an increase in diffusion and/or permeation mediated by degradation of glycosaminoglycans and concomitant channel formation within the downstream intercellular matrix or interstitial space.

In the case of sHASEGPs being injected into the anterior chamber of the eye to remove excess viscoelastic substrates such as glycosaminoglycan-containing formulations (which are commonly used as opthalmosurgical aids in a variety of anterior segment procedures), it will be appreciated by those of skill, in view of the teachings of the present application, that sHASEGP can be used to supplement or to obviate the need for post-surgical procedures such as irrigation and aspiration, which are commonly used to reduce the amount of applied viscoelastic remaining in the eye after surgery is completed. Viscoelastics are commonly used during anterior segment surgeries to maintain a deep anterior chamber allowing for more efficient manipulations and potentially protecting the corneal endothelium and other tissues during surgery. A variety of viscoelastics containing hyaluronate and/or chondroitin sulfate are used in surgeries such as anterior eye segment procedures (see, e.g., Provisc™, Viscoat™ and Duovisc™ (available from Alcon Laboratories, Inc., alconlabs. com); Healon™ Healon 5™ and Healon GV™ (available from Advanced Medical Optics, healon.com); Amvisc™ and Amvisc™ Plus (available from Bausch & Lomb, bausch.com); I-Visc™., I-Visc™ Plus, IVisc™ 18, and I-Visc™ Phaco (available from I-MED Pharma, imedpharma.com); LA LON™ (available from General Innovations, generaltrade.net)). However, as is known in the art, retained viscoelastic in the anterior chamber following surgical procedures such as cataract surgery can lead to compromised outflow from the anterior chamber (potentially by reducing outflow through the trabecular meshwork) which can cause elevations in intraocular pressure (IOP spikes) that can lead to glaucoma.

Thus sHASEGPs of the present invention can be introduced, for example, by injection into the anterior chamber of the eye as a "viscoelastic antidote" for previously-applied viscoelastic formulations containing glycosaminglycans such as hyaluronan. For use as such a viscoelastic antidote, the sHASEGP will generally be introduced by post-surgical injection into the anterior chamber (with or without prior irrigation or aspiration to remove some portion of the previously applied viscoelastic) following anterior segment procedures such as cataract surgery and intraocular lens implantation (e.g. by phacoemulsification or extracapsular surgery), glaucoma filtration surgery (trabeculectomy), corneal transplant surgery (e.g. penetrating keratoplasty), post-traumatic eye surgery, and the like. As will be appreciated by those of skill in the art, the amount of a sHASEGP applied in such a context will depend, inter alia, on its specific activity as well as the amount of viscoelastic used and whether or not some of the viscoelastic is first physically removed (e.g. by irrigation and aspiration). Each application will thus generally be optimized for the particular circumstances, as will be appreciated by those of skill in the art in view of the descriptions and illustrations provided herein.

Some viscoelastics, such as Viscoat™ and Duovisc™ (available from Alcon Labs) comprise both hyaluronate and chondroitin sulfate. Advantageously, many sHASEGPs of the present invention are enzymatically active both as hyaluronidases and as chondroitinases, making them particularly suitable for such dual formulation viscoelastics.

Hyaluronidases including sHASEGPs can also be combined with one or more additional glycosaminoglycanases (such as chondroitinases) for applications such as the foregoing or to further open channels within interstitial spaces for other applications such as those described and illustrated herein.

To the extent that viscoelastics are also used in other procedures, sHASEGPs of the present invention can likewise be used in conjunction with or as replacement of techniques for reducing or eliminating amounts of applied viscoelastic, i.e. as a viscoelastic antidote.

In applications of sHASEGPs as spreading agents in tissues such as those of the eye, a formulation comprising one or more sHASEGPs as described herein is typically applied to a target tissue prior to or concomitant with application of an anesthetic, diagnostic, pharmacologic or other agent that is desired to be delivered into or to the vicinity of the target tissue. In some contexts, sHASEGPs can be used to promote delivery of a pharmacologic or other agent across a first tissue to target one or more tissues distal to the first. By way of illustration, introduction of sHASEGPs into the episcleral space surrounding the eye prior to or concomitantly with introduction of a pharmacologic or other agent into the episcleral space can be used to promote delivery of the agent across the protective scleral tissue and into the choroid, the retina and the vitreous body. In this manner, a number of pharmacologic and/or other agents which are useful for treating conditions of the choroid, retina and/or vitreous can be delivered relatively locally to the target tissues but at the same time using a relatively non-invasive approach such as a Sub-Tenon's injection. Analogous situations exist in other situations in which sHASEGPs can be applied to one tissue or location in the body in order to facilitate the delivery of a pharmacologic or other agent within that tissue or location and/or to distal sites, as described and illustrated herein.

While the extent and rate of dispersal of a co-formulated or co-administered agent depends in part on the tissue and agent involved, such disperal can generally be increased by, inter alia, increasing the amount of sHASEGP applied, employing a sHASEGP having higher specific activity, employing a sHASEGP that is more resistant to degradation or other inactivation (such as a PEGylated, super-sialated or other such modified sHASEGP), providing a sustained release or depot formulation of the sHASEGP, and other such approaches to increasing the effective activity and/or duration of the applied sHASEGP. In addition, where it is desired that the sHASEGP faciliate the dispersion of an agent into a tissue or location distal to, e.g., a site of injection, then providing the sHASEGP and/or agent in a significant volume of liquid (such as would partially fill or even slightly distend the site of injection), can be used to further promote dispersion through a process of convective transport, as described and illustrated herein.

As will be appreciated by those of skill in the art, sHASEGPs can thus be used to effectively promote delivery of a number of anesthetics, diagnostics, pharmacologics and/or other agents to the posterior segments of the eye for treating conditions such as retinal detachments, retinal vein occlusions, proliferative retinopathies, diabetic retinopathies, inflammatory conditions (such as uveitis, choroiditis, retinitis and the like), as well as degenerative diseases, vascular diseases and various tumors. Again as will be appreciated by those of skill in the art, a variety of pharmacologic or pharmaceutically effective agents can be usefully applied to treating such posterior segment conditions and diseases, including, by way of illustration, anesthetic and pharmacologic agents such as those described and illustrated below.

Co-formulations or co-administrations of sHASEGP with other substances may also be envisioned for injectable pens for small volume or rapid subcutaneous administration. Examples such as Epipen™, insulin, and other fluids can be formulated. The methods of the invention include administration of the sHASEGP polypeptide or pharmaceutical compositions containing sHASEGP prior to, simultaneously with or following administration of other therapeutic molecules. The sHASEGP may be administered at a site different from the site of administration of the therapeutic molecule or the sHASEGP may be administered at a site the same as the site of administration of the therapeutic molecule.

Without wishing to be bound by theory, it is believed that the ability of sHASEGPs and other glycosaminoglycanases to cause the degradation of a portion of the glycosaminoglycans in the interstitial spaces between cells results in a temporary opening up of channels within the interstitium, which in turn tends to increase interstitial fluid flow and to concomitantly facilitate the diffusion and/or convective solute transport (convection) of dissolved components within the interstitial fluid (such as anesthetics, drugs and other pharmacologic agents, labels and diagnostic agents, and the like). As will be appreciated by those of skill in the art, sHASEGPs of the present invention can be applied to enhance the bioavailability (and potentially improve other pharmacokinetic and/or pharmacodynamic properties) of a number of pharmacologic and other agents that are useful for treating or diagnosing various disease conditions or otherwise modifying one or more tissues in vivo. Illustrative categories of such agents include: anti-cancer agents, anti-infectives, anesthetics, anti-inflammatories, cytokines, antibodies and other proteins, nucleic acids, macromolecular complexes, and numerous other molecules and pharmacologic agents which modify cellular or other physiologic activities, including various categories of agents (and exemplary members thereof) described herein and in the art.

While the diffusion and convective transport of even small molecules can be enhanced by opening interstitial channels and increasing fluid flow, in the case of larger pharmacologic or other agents, such as many biotherapeutics (including antibodies and other proteins, large nucleic acids, macromolecular complexes (such as liposomes and other macromolecular carriers), as well as gene therapy vectors and the like)), the size of the molecules and the presence of interstitial components such as glycosaminoglycans substantially impairs the diffusion and/or convection of the agents. Several consequences potentially limiting the agent's usefulness can result. For example, the pharmacokinetics of the agent can be effectively impaired by a slowing of absorption and thus distribution of the agent. In addition, trapping of a portion of the agent at or near the site of administration both limits its bioavailability and can also cause toxicity as a result of a potentially sustained and high local dose. In the latter regard, local toxicity that may be associated with painful or other side effects is a problem with many large biomolecules that are administered by non-intravenous injection, such as by subcutaneous, intradermal or intramuscuular injection. As a result, a number of pharmacologic agents have pharacokinetic (PK) and/or pharmacodynamic (PD) profiles that can be enhanced by co-formulating the agent with a sHASEGP (or other glycosaminoglycanase) and/or co-administering the agent with a sHASEGP (or other glycosaminoglycanase), which may be provided before, coincident with or after the agent, and administered at the same or a different site, which parameters would be the subject of optimization in standard models (such as animal models typically used to assess the pharmacokinetics and pharmacodynamics of the agent). Any of a variety of therapeutics and pharmacologics as well as other agents (such as cosmetic or esthetic formulations) that are typically administered by parenteral administration can thus be enhanced using sHASEGPs.

While intravascular administration, particularly by intravenous (IV) injection, can generally provide for rapid bioavailability, IV injections are often inconvenient, associated with risks or inapplicable (and even where practicable can be associated with less than optimal overall PK/PD profiles). Since sHASEGPs can be applied to enhance the bioavailability of agents administered by non-IV parenteral routes (such as subcutaneous, intradermal, intramuscular and other routes delivering agents into the interstitium), agents that have been delivered by IV injection can be reformulated for delivery by non-IV parenteral routes. Such reformulations can provide substantial benefits such as allowing use of agents in which IV administration is inconvenient, inapplicable, unsafe, too expensive or otherwise limited. The reformulation of IV agents as non-IV parenterals can also allow patients to self-administer the agents, and can allow dosing to be optimized (e.g. better tailored to the agent's PK/PD parameters) by avoiding the need for administration by intravenous injection.

As will be appreciated by those of skill in the art, PK/PD parameters that can be improved by using sHASEGPs (and/or other glycosaminoglycanases) include such measures as Cmax (the maximal concentration of agent achieved following absorption in, e.g., the bloodstream), Tmax (the time required to achieve maximal concentration), T1/2 (the time required for the concentration to fall by half), Cmin (the minimal concentration of agent following metabolism and excretion), AUC (area under the curve of concentration versus time, a measure of the overall amount of bioavailability), concentrations in various tissues of interest (including, e.g., the rate of achieving desired concentrations, the overall levels, and the duration of maintaining desired levels), and Emax (the maximal effect achieved). By way of illustration, reformulating a drug or other pharmacologic agent with a sHASEGP or co-administering the agent with a sHASEGP (which can be introduced locally or systemically, and before, together with or after the agent) can be used for example to increase an agent's Cmax, decrease its Tmax, decrease its T1/2, increase its AUC and/or increase its Emax. As will be appreciated, the ability to readily and proportionately manipulate such key PK and PD parameters (e.g. by applying more or less units of sHASEGP and altering the timing and/or location of administration) enables the improvement of a number of a pharmacologic and other agents. Evaluating the levels of these parameters can be performed in models such as animal models used for PK/PD measurements of the agent, and co-formulations and/or co-administrations that enhance the relative efficacy to safety profile thus selected for a particular application.

Among non-IV parenterals, sHASEGPs (and/or other glycosaminoglycanases) can also be used to allow the agents to be administered by more convenient routes, and/or with greater efficiency. By way of illustration (and without limitation), by reformulating and/or co-administering agents with sHASEGP (either local or systemic and either before, coincident with or after administration of the agent) agents that are typically administered by subcutaneous injection can instead be administered by intradermal injection, and agents that are typically administered by intramuscular injection can instead be administered by subcutaneous or intradermal injection. Alternatively, agents can be administered by the same route, but with improved pharmacokinetics and/or pharmacodynamics using sHASEGPs.

The use of sHASEGPs (and/or other glycosaminoglycanases) to reformulate IV drugs and other agents as non-IV parenterals also enables delivery of the agents using any of a variety of new injection devices designed to ease and/or speed delivery, and to facilitate self-administration. Such devices include, for example, ultra-sharp and microneedle devices (such as those being developed by Becton Dickinson and others) as well as needle-free injection devices (such as Biojector™ and other devices available from Bioject; IntraJect™. and other devices available from Aradigm; Medijector™ devices and the like). A number of devices (such as the Biojector) are particularly useful for facilitating intradermal injections which tend to require more experience when using standard needles (due to the potential for penetrating the dermis during needle placement, and delivering the agent to an underlying tissue site such as the subcutaneous layer). For some pharmacologic agents, such as vaccines for example (e.g. a DNA-based or other vaccine), it can be particularly advantageous to deliver the agent into the dermal as opposed to sub-dermal layers since there tends to be a relatively high concentration of antigen-presenting cells (APCs) localized within the dermis.

In the context of those agents that are typically delivered by intradermal injection (whether by standard needles or other newer devices), or those many other agents which are not currently but could be delivered by intradermal injection, the local co-introduction of a sHASEGP (and/or other glycosaminoglycanase) can be used to enhance delivery of the pharmacologic or other agent delivered and to promote its dispersal or spreading within the dermis. In the case of a vaccine, where the dermis may be the primary target tissue, given the local abundance of APCs, the sHASEGP (and/or other glycosaminoglycanase) can thus facilitate dispersal of the vaccine within the target tissue, thereby increasing the probability and extent of interactions between a vaccine and APCs (which can significantly potentiate the generation of an immunomodulatory response). In the case of other agents, the dermis may not be the primary target tissue but is rather a tissue into which a dose of the agent is introduced from which it is desired that the agent be absorbed into another tissue, typically the bloodstream. In the latter case, the bloodstream may itself be the target tissue of interest (e.g. for blood-modulatory factors as described herein and in the art), or the bloodstream may itself be a delivery tissue by which the agent is transported to a distal target tissue (e.g. a tissue in the body supplied by the bloodstream). In either of these latter cases (in which delivery is intradermal but it is desired that the agent be delivered to the bloodstream), the sHASEGP (and potentially a volume of liquid in which it is injected) can facilitate dispersal of the agent first within the dermis and thence into the vasculature draining the dermis and eventually into the larger blood supply), as described and illustrated herein.

The use of sHASEGPs to enhance the pharmacokinetics and/or pharmacodynamics of other therapeutic or pharmacologic agents can also be applied to agents delivered by routes other than non-IV parenteral administration. For example, without wishing to be bound by theory, it is believed that the presence of sHASEGPs in interstitial spaces within the body (which can be achieved by local and/or systemic administration of sHASEGPs) tends to promote interstitial channels and an increase in fluid flow within the interstitial space that in turn facilitates both diffusion and convective transport of agents dissolved with the interstitial fluid (such as pharmacologic and other agents). By way of illustration, agents that are administered directly into the bloodstream (e.g. by intravenous injection), or orally (and thus enter the bloodstream after uptake from the gastrointestinal tract for example), can still be subject to constraints in the post-absorption i.e. distribution phase of their pharmacokinetics. Without wishing to be bound by theory, it is believed that sHASEGPs can enhance delivery to target cells by increasing interstitial permeability and fluid flow and thus increasing the diffusion and/or convection of agents within the interstitial space (which effectively forms the intermedium between almost all pharmacologic delivery routes and the target cells).

In addition, it is believed that changes in oncotic pressure brought about by the administration of sHASEGPs can contribute to enhancing the delivery of pharmacologic agents. Again, without wishing to be bound by theory, the presence of sHASEGP and concomitant degradation along the interstitial side of a vascularized tissue, would tend to decrease the oncotic pressure within the interstitial space which in turn would enhance fluid filtration from the vasculature into the interstitial space.

The potential to decrease interstitial pressure is considered to be particularly important in the context of many cancers in which interstitial pressure within the tumor (tumor interstitial pressure of TIF) is elevated. High TIF can result in relative impedance to fluid flow from the vasculature toward the center of a tumor, thereby limiting the amount of an anti-cancer agent that effectively reaches a tumor, particularly sites that are deeper within a tumor mass. The introduction of sHASEGPs to tumor interstitia would thus tend to enhance the delivery of locally delivered as well as systemically available anti-cancer agents which can more readily penetrate the tumor when interstitial oncotic pressure is reduced and diffusion and/or convective transport increased. Measurements of TIF and hydraulic conductivity (K) within tumors (e.g. using tagged molecules such as albumin labeled with Evan's Blue dye) can be used to quantitatively assess the effect of various concentrations of sHASEGPs on the fluid dynamics of tumors in vivo, as illustrated herein and/or in the art.

Further exacerbating the reduced fluid dynamics within many tumors, and highlighting an additional potential benefit of applying sHASEGPs to tumors, is the fact that many tumors exhibit accumulation of glycosaminoglycans, particularly hyaluronan (which may be due to the fact that lymphatics, which are the predomint route for hyaluronan catabolism, are impaired or lacking in many tumors). Such excess hyaluronan can contribute to impeding hydraulic conductivity. The introduction of sHASEGPs can thus be used to counteract the accumulation of glycosaminoglycans in many tumors, improving hydraulic conductivity within the tumor and effectively rendering them more susceptible to anti-tumor agents (whether locally or systemically delivered).

As will be appreciated by those of skill in the art, the principles described herein can also be applied to numerous other pharmacologics and other agents that are desired to be delivered to sites within the body, such as for the prevention, diagnosis and/or treatment of disease or to otherwise modulate physiological functions. Illustrative classes of such agents (and exemplary members thereof) are provided herein, and many more are known in the art or under development.

In addition to their use in potential improvements and/or reformulations of a variety of parenterally-administered pharmacologics and/or agents, sHASEGPs can also be usefully employed in connection with non-parenteral agents (such as agents formulated as pills, liquids or other forms for ingestion and typical absorption through the gastrointestinal tract). For example, since most non-parenteral drugs must ultimately reach cells within the interstitium in order to exert their desired effects, the use of sHASEGPs to enhance diffusion and/or convective transport within the interstitium (either systemically or locally (e.g., by local or targeted administration of sHASEGP)) can be applied to improve the extent and/or rate at which non-parenterals (as well as parenterals) reach desired target cells.

In addition, a number of agents that are typically administered non-parenterally (e.g. orally) may be reformulated, or their active ingredients reformulated, for use in parenteral administrations that are rendered more effective and/or safe in combination with sHASEGPs. To illustrate this broadly applicable approach, the ability of sHASEGPs to facilitate targeted delivery to particular tissues (such as the ability of sHASEGPs to provide for transcleral delivery to tissues within the posterior of the eye) can be used to deliver any of a variety of agents (including agents previously administered systemically) directly and preferentially to a localized site of interest within the body. This can not only provide for more desirable and/or more rapidly achieved concentrations at the site of interest, but can substantially reduce potential problems and limitations associated with systemic administration in which concentrations at undesired sites may equal or even exceed concentrations at the desired target site (potentially triggering undesired side effects as well as wasting agent). In some cases, agents that are not widely used or are not used for certain indications or in certain patients, for example, may be effectively applied to benefit additional patients by being co-formulated or co-administered with sHASEGPs as described and illustrated herein.

As will be appreciated by those of skill in the art, the ability to employ sHASEGPs to enhance, speed and/or target biodistribution of co-formulated and/or co-administered agents, and to manipulate other aspects of their pharmacokinetics or pharmacodynamics (e.g. in order to improve their risk:benefit profile or facilitate their use by patients, family or health care professionals), provides a major opportunity for improving drugs and other agents that are used treat, diagnose or prevent diseases.

Without being limited to a particular set of applications, glycosaminoglycanases, including sHASEGPs as described herein (as well as other hyaluronidases and other glycosaminoglycanases) can be used to effectively achieve bolus or bolus-like delivery of any number of pharmacologic and other agents by non-intravenous parenteral routes, as well as by other routes of administration (e.g. by enhancing the delivery of agents into and/or through a target tissue after they leave the bloodstream (whether they were introduced into the bloodstream directly (such as by IV administration) or indirectly (such as by oral or non-IV parenteral administration)).

Without being restricted to a specific mechanism of action or aspect thereof, it is believed that the ability of these enzymes to temporarily degrade components of the interstitial matrix between cells (which accounts for a substantial portion of the fluid space in the body and a correspondingly large space that must be traversed in order for pharmacologics and other agents to reach most target cells) can significantly promote the delivery of agents to target cells by one or more of several potentially synergistic means. First, while the bulk of the interstitial fluid exhibits some degree of flow, that flow is often restrained or impeded by glycosaminoglycans such as hyaluronan and other interstitial components. The ability of glycosaminoglycanases including sHASEGPs (as well as other hyaluronidases and other glycosaminoglycanases) to open channels within such interstitial spaces, as described and illustrated herein, can be used to decrease impedance and increase the extent and rate of "downstream" flow resulting from any given "upstream" pressure. Second, in the case of non-IV parenteral injections of sHASEGPs (or other glycosaminoglycanase) and another pharmacologic or other agent, the volume of the non-IV parenteral injection can be used to increase the upstream driving pressure or pressure head (e.g. by increasing the hydrostatic pressure within a confined space), which can further promote flow. Third, since the volume of fluid comprising the introduced sHASEGP (or other glycosaminoglycanase) and other agent is effectively driven down the increased pressure gradient (i.e. the increased gradient created by elevating the hydrostatic pressure associated within the injected "bolus" and simultaneously decreasing the interstitial pressure within the surrounding tissue), solutes within the bolus can be effectively carried (e.g. by convective transport) into the adjacent tissue. This injected fluid or bolus can thus be efficiently and relatively quickly moved into the adjacent tissue and deliver whatever pharmacologic or other agent was introduced at or near the same site of introduction (e.g. by co-formulating or co-administering the agent in combination with the sHASEGP or other glycosaminoglycanase).

By way of illustration, using glycosaminoglycanases such as sHASEGPs to open channels within interstitial spaces, as described and illustrated herein, can be used to increase interstitial flow into and through tissues such as tumors and others in which flow is typically impeded and interstitial pressures elevated. Illustrative examples of these principles as described herein include the use of sHASEGPs to reduce the interstitial pressure within a tumor in vivo.

Increased flow can likewise be applied to normal tissue to, e.g., allow an anesthetic, diagnostic, cosmetic or other esthetic, or a pharmacologic or other agent to be delivered into a tissue (e.g. to modify the tissue or introduce a depot formulation into a tissue). Increased flow can likewise be applied to a first or proximal tissue to promote delivery of an agent through the tissue of introduction to a distal tissue, which distal tissue may itself by the desired target tissue or a route to the desired target tissue. Illustrative examples of these principles as described herein include, for example: (i) the use of sHASEGPs introduced into the episcleral space surrounding the eye to promote the delivery of agents across the sclera in order to target distal target tissues within the interior of the eye such as the retina and choroid; and (ii) the use of sHASEGPs introduced intradermally to promote the delivery of agents through the subdermal layers and into the bloodstream, which can itself be the target tissue (e.g. for blood-modifying agents) or a route by which the agent(s) can be delivered to other target tissues within the body By way of further illustration of these techniques and compositions for promoting delivery of pharmacologics and other agents to desired tissues within the body, the following additional examples are provided. By means such as described and illustrated herein, the pharmacokinetic and/or pharmacodynamic profiles of pharmacologic agents, and the absorption, distribution and/or effectiveness profiles of other agents, can be enhanced or otherwise modified. In addition, agents that were essentially or practically limited to delivery by one route (such as by IV injection) can be delivered by other safer, less intrusive, less costly, and/or more convenient routes.

By way of further illustration and without being limited to a particular type of application, a volume (V) of liquid (L) comprising a sHASEGP or other glycosaminoglycanase (GAG Enzyme) can be introduced into a tissue site in the body (a Dosing Tissue). By means as described and illustrated herein, the GAG Enzyme can be delivered into and to some extent through the Dosing Tissue. Without being restricted to a particular mechanism of action, the GAG Enzyme can be effectively carried into the Dosing Tissue by convective transport by the volume of liquid (L). The convective transport can in turn be promoted in part by the hydrostatic pressure associated with L (which can provide a driving pressure) and in part by the ability of the GAG Enzyme to open channels within the interstitial spaces of the Dosing Tissue (which can reduce downstream impedance to flow and thereby lower the resisting pressure). A fluid-driving pressure differential can thus be created and to the extent desired it can be increased, for example, by one or both of the following: (i) introducing and if desired increasing a driving hydrostatic pressure (e.g. by introducing L into a confined space and if desired increasing V); and (ii) reducing the downstream impedance to flow (e.g. by introducing GAG Enzyme, and if desired increasing its effectiveness by for example increasing its concentration, increasing its resistance to degradation (e.g. by PEGylation, super-sialation or other modification), and/or increasing its delivery by convective transport (e.g. by increasing V)).

In certain embodiments (e.g. in which increased extent or rate of delivery is desired), V is a volume sufficient to temporarily distend the site within the Dosing Tissue at which the GAG Enzyme is introduced. As will be appreciated by those of skill in the art, the volume (V) that can be accommodated and the resulting extent of distension (D) depends on the particular tissue. For purposes of illustration and not limitation, the extent to which distention occurs varies, for example, from situations in which (i) the Dosing Tissue is a relatively large and/or rapidly moving fluid-filled space (such as the bloodstream in connection with intravenous or intraarterial delivery), in which case L can be large (e.g. many ml if desired) but D tends to be relatively minimal; (ii) the Dosing Tissue is a relatively smaller and/or less rapidly moving fluid-filled space (such as cerebrospinal fluid in connection with intrathecal delivery), in which case L can still be relatively large but D may be more than minimal depending on the precise site and volume of injection); (iii) the Dosing Tissue is a relatively smaller but somewhat distensible space (such as the episcleral space surrounding the eye for purposes of illustration); or (iv) the Dosing Tissue is a relatively more dense and/or more confined space with higher resisting pressure (such as the dermis in connection with intradermal delivery for purposes of illustration).

As will be appreciated by those of skill in the art, V can range from volumes of less than 0.1 ml to volumes of greater than 100 ml, for many applications being in the range of about 0.5 ml to 20 ml, and for many in the range of 1 ml to 10 ml, frequently from 2 to 5 ml; but can be varied for particular situations as illustrated herein. V can also be specifically optimized within such ranges for a particular application as desired; e.g. by comparing standard pharmacokinetic and/or pharmacodynamic profiles over a range of test volumes.

As will be appreciated by those of skill in the art in view of these teachings, by combining the rapidly acting and reinitiating channel-opening activity of the GAG Enzyme (which both promotes and is promoted by its own delivery), together with a delivery system that both promotes and is promoted by the catalytic activity, a multiply synergistic drug delivery system can thus be generated; as further described and illustrated herein.

In a first illustrative aspect, a volume of liquid (V) comprising a sHASEGP or other glycosaminoglycanase (GAG Enzyme) and one or more pharmacologic or other agents (Agent(s) (such as detectable molecules or other diagnostic agents, anesthetics or other tissue-modifying agents, pharmacologics or pharmaceutically effective agents, cosmetics or other esthetic agents, and other agents desired to be introduced into one or more tissues within the body) is introduced into a first tissue site in the body (a Dosing Tissue) which is itself a desired target tissue (a Target Tissue) for the agent. By means as described and illustrated herein, the Agent(s) are delivered into and throughout the Target Tissue to a greater extent and/or rate than would occur in the absence of the GAG Enzyme.

As will be appreciated by those of skill in the art in connection with this and the other illustrative aspects herein, the Dosing Tissue can be any of a variety of tissues that can be readily reached from outside of the body (e.g. using various routes of administration as described and illustrated herein and/or as known in the art) or from inside the body (e.g. in connection with surgery or using any of a variety of non-surgical or minimally-invasive approaches and devices to reach tissues within the body). Such Dosing Tissues include those described and illustrated herein as well as others known in the art.

As will likewise be appreciated by those of skill in the art in connection with this and the other illustrative aspects herein, the Target Tissue can be any of a variety of tissues to which it is desired that a GAG Enzyme and potentially other Agent(s) are delivered (e.g. (i) tissues that are the subject of efforts to diagnose, prevent or treat a disease condition (whether intrinsically caused such as an inherited or developed disease condition or extrinsically caused such as an infection); (ii) tissues that are desired to be anesthetized or otherwise modulated (e.g. in the context of surgery and/or other procedures); (iii) tissues in which it is desired to trigger an immune response (such as associated with vaccination); (iv) tissues which are to serve as a depot site for releasing agent(s) to other tissues; (v) tissues to be modified for esthetic or cosmetic purposes; and (vi) tissue or sites in the body to be modified for other purposes). Such Target Tissues include those described and illustrated herein as well as others known in the art.

As will likewise be appreciated by those of skill in the art in connection with the forgoing and with other illustrative aspects herein, the Agent(s) can be any of a variety of molecules, macromolecules and macromolecular complexes, that are or can be used for altering or modulating conditions within the body (e.g. (i) for purposes of diagnosing, preventing or treating a disease condition (whether intrinsically caused such as an inherited or developed disease condition or extrinsically caused such as an infection) affecting the Target Tissue and/or adjacent tissues; (ii) for purposes of anesthetizing or otherwise modulating the physiology of the Target Tissue; (iii) for purposes of triggering an immune response as associated with vaccination; (iv) for purposes of using the Target Tissue as a depot site for releasing agent(s) to other tissues; (v) for esthetic or cosmetic purposes; and/or (vi) for other purposes served by delivering a GAG Enzyme and potentially other Agent(s) to a tissue or other site in the body). Such Agents include the various classes of agents and members thereof described and illustrated herein, as well as other members of such classes of agents, and other classes of agents (and members thereof) known in the art.

In a second illustrative aspect, a volume of liquid (V) comprising a sHASEGP or other glycosaminoglycanase (GAG Enzyme) and one or more pharmacologic or other agents (Agent(s)) is introduced into a tissue site in the body (Dosing Tissue) which is adjacent or proximal to a tissue (Tissue B) which is itself a desired target tissue. By means as described and illustrated herein, the Agent(s) are delivered from Tissue A to the target Tissue B to a greater extent and/or rate than would occur in the absence of the GAG Enzyme.

In a third illustrative aspect, a volume of liquid (V) comprising a sHASEGP (or other glycosaminoglycanase) (GAG Enzyme) and one or more pharmacologic or other agents (Agent(s)) is introduced into a tissue site in the body (Dosing Tissue) which is proximal to one or more tissues (Intervening Tissues) located between Tissues A and another tissue or tissues (Distal Tissues) which are themselves desired target tissues or include a desired target tissue (Target Tissues). By means as described and illustrated herein, the Agent(s) are delivered from Tissue A and through one or more Intervening Tissues to reach one or more Target Tissues to a greater extent and/or rate than would occur in the absence of the GAG Enzyme(s).

In a fourth illustrative aspect, a volume of liquid (V) comprising a sHASEGP (or other glycosaminoglycanase) (GAG Enzyme) and one or more pharmacologic or other agents (Agent(s)) is introduced into a tissue site in the body (Dosing Tissue) which is proximal to one or more delivery tissues, such as the bloodstream, lymph or cerebrospinal fluid (Delivery Tissues), which are desired target tissues or include a desired target tissue. By means as described and illustrated herein, the Agent(s) are delivered from Tissue A to one or more Delivery Tissues to a greater extent and/or rate than would occur in the absence of the GAG Enzyme(s).

In a fifth illustrative aspect, a volume of liquid (V) comprising a sHASEGP (or other glycosaminoglycanase) (GAG Enzyme) and one or more pharmacologic or other agents (Agent(s)) is introduced into a tissue site in the body (Dosing Tissue) which is proximal to one or more delivery tissues, such as the bloodstream, lymph or cerebrospinal fluid (Delivery Tissues), which deliver fluid to one or more desired target tissues (Target Tissues) within the body. By means as described and illustrated herein, the Agent(s) are delivered from Tissue A to one or more Delivery Tissues and from there to one or more downstream Target Tissues to a greater extent and/or rate than would occur in the absence of the GAG Enzyme(s).

In a sixth illustrative aspect, a volume of liquid (V) comprising a sHASEGP (or other glycosaminoglycanase) (GAG Enzyme) together with one or more pharmacologic or other agents (Agent(s)) is introduced into one or more delivery tissues, such as the bloodstream, lymph or cerebrospinal fluid (Delivery Tissues) which supplies fluid to one or more desired Target Tissues (e.g. via the bloodstream supplying a Target Tissue). By means as described and illustrated herein, the Agent(s) permeate the Target Tissue to a greater extent and/or rate than would occur in the absence of the GAG Enzyme(s).

In a seventh illustrative aspect, a volume of liquid (V) comprising a sHASEGP (or other glycosaminoglycanase) (GAG Enzyme) is introduced into a tissue site in the body (Tissue A) which is a desired target tissue or near a desired target tissue (Target Tissue), and one or more pharmacologic or other agents (Agent(s)) are introduced into the body by another route of administration (such as by oral delivery or intravenous injection) which allows the Agent(s) to reach the Target Tissue (e.g. via the bloodstream supplying the Target Tissue, following absorption or injection into the blood). By means as described and illustrated herein, the Agent(s) permeate the Target Tissue to a greater extent and/or rate than would occur in the absence of the GAG Enzyme(s).

In an eighth illustrative aspect, a volume of liquid (V) comprising a sHASEGP (or other glycosaminoglycanase) (GAG Enzyme) is introduced into a tissue site or sites within the body (Tissue Site(s)) which has an elevated interstitial pressure. By means as described and illustrated herein, the interstitial pressure within the Tissue Site(s) is reduced by the degradative activity of the GAG Enzyme(s).

In a ninth illustrative aspect, a volume of liquid (V) comprising a sHASEGP (or other glycosaminoglycanase) (GAG Enzyme) is introduced into a tissue site or sites within the body (Tissue Site(s)) which has an excess of hyaluronan or other glycosaminoglycan. By means as described and illustrated herein, the excess of hyaluronan or other glycosaminoglycan within the Tissue Site(s) is reduced by the degradative activity of the GAG Enzyme(s).

In an tenth illustrative aspect, a volume of liquid (V) comprising a sHASEGP (or other glycosaminoglycanase) (GAG Enzyme) is introduced into a tissue site or sites within the body (Tissue Site(s)) which are at or near a desired access point for hypodermoclysis (a Clysis Site). By means as described and illustrated herein, fluids can then be delivered into and through the Clysis Site(s) to a greater extent and/or rate than would occur in the absence of the GAG Enzyme(s).

As will be appreciated by those of skill in view of the detailed descriptions and illustrative embodiments provided herein, any of a large variety of agents can be co-introduced (e.g. by co-formulation or co-administration with the GAG Enzyme) and any of a variety of GAG Enzymes can be employed at concentrations in ranges such as those provided herein but typically optimized for the particular tissue and objective involved. The volume of liquid (V) applied in the above illustrative aspects will generally depend on the nature of the site of introduction and will likewise typically be optimized for the particular tissue and objective involved. As described and illustrated herein, in the case of non-IV parenteral administrations, V can be increased (within the particular constraints of the tissue site) in order to provide an enhanced hydrostatic driving pressure which, coupled with decreased impedance associated with degradation of hyaluronan or other glycosaminoglycan, can effectively cause the volume of liquid to function as a bolus—carrying any solute it contains into the downstream interstitial space and potentially beyond.

Hence, provided herein are a variety of techniques employing hyaluronidases (and/or other glycosaminoglycanases) to promote the delivery of pharmacologic and other agents to sites within the body, as well as a family of eukaryotic secreted neutral active hyaluronidase glycoproteins designated sHASEGPs, and functional domains thereof, especially Hyaluronidase (or catalytic) domains thereof, muteins and other derivatives and analogs thereof. Also provided herein are nucleic acids encoding the sHASEGPs. Additionally provided are formulations, co-formulations and therapeutic uses of said sHASEGPs (including by co-administration with other agents) to treat, prevent or diagnose disease, and for use as tissue modifying enzymes.

BRIEF DESCRIPTION OF THE DRAWINGS

FIG. 1 is a vector map of sHASEGP Vector HZ24.

DETAILED DESCRIPTION OF THE INVENTION

A. Definitions: Unless defined otherwise, all technical and scientific terms used herein have the same meaning as is commonly understood by one of skill in the art to which the invention (s) belong. All patents, patent applications, published applications and publications, Genbank sequences, websites and other published materials referred to throughout the entire disclosure herein, unless noted otherwise, are incorporated by reference in their entirety. In the event that there is a plurality of definitions for terms herein, those in this section prevail.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) Biochem. 11: 942-944).

As used herein, eukaryotic Hyaluronidase refers to a diverse family of glycosaminoglycan endoglucosaminidases, wherein a glutamate residue in the Hyaluronidase hydrolyzes the beta 1,4 linkages of hyaluronan and chondroitin sulfates through an acid-base catalytic mechanism.

Of particular interest are soluble neutral-active hyaluronidases or sHASEGPs of mammalian, including human, origin. Those of skill in this art recognize that, in general, single amino acid substitutions in non-essential regions of a polypeptide do not substantially alter biological activity (see, e.g., Watson et al., (1987) Molecular Biology of the Gene, 4th Edition, The Benjamin/Cummings Pub. Co., p. 224).

As used herein, membrane anchored HASEGP, refers to a family of membrane anchored Hyaluronidases that share common structural features as described herein. As described and illustrated herein, hyaluronidases (i.e. glycosaminoglycanases capable of breaking down hyaluronan, preferably those exhibiting at least some activity in the ranges of neutral pH) that are normally membrane anchored can be converted to soluble HASEGPs or sHASEGPs by removing or otherwise modifying one or more of the regions that are associated with anchoring the hyaluronidase in the membrane.

As used herein, soluble hyaluronidase refers to a polypeptide characterized by its solubility under physiologic conditions. Soluble HASEGP can be distinguished for example by its partitioning into the aqueous phase of a Triton X-114 solution warmed to 37° C. (Bordier et al J. Biol. Chem. 1981 Feb. 25; 256(4):1604-7). Lipid anchored HASEGP on the other hand will partition into the detergent rich phase, but will partition into the detergent poor or aqueous phase following treatment with Phospholipase-C.

Thus, reference, for example, to "sHASEGP" encompasses all glycoproteins encoded by the sHASEGP gene family, including but not limited to: Human sHASEGP, mouse sHASEGP, or an equivalent molecule obtained from any other source or that has been prepared synthetically or that exhibits the same activity. Sequences of encoding nucleic acid molecules and the encoded amino acid sequences of exemplary sHASEGPs and/or domains thereof are set forth, for example in SEQ ID NO: 4. The term also encompasses sHASEGP with amino acid substitutions that do not substantially alter activity of each member and also encompasses splice variants thereof. Suitable substitutions, including, although not necessarily, conservative substitutions of amino acids, are known to those of skill in this art and can be made without eliminating the biological activity, such as the catalytic activity, of the resulting molecule.

As used herein, a sHASEGP, whenever referenced herein, includes at least one or all of or any combination of: a polypeptide encoded by the sequence of nucleotides set forth in SEQ ID NO. 6 or by a sequence of nucleotides that includes nucleotides that encode amino acids 1-509 of SEQ ID No. 1; a polypeptide encoded by a sequence of nucleotides that hybridizes under conditions of low, moderate or high stringency to the sequence of nucleotides set forth in SEQ ID NO. 6; a polypeptide that includes the sequence of amino acids set forth as amino acids 1-509 of SEQ ID No. 1; a polypeptide that includes a sequence of amino acids having at least about 60%, 70%, 75%, 80%, 81%, 82%, 83%, 84%, 85%, 86%, 87%, 88%, 89%, 90%, 91%, 92%, 93%, 94%, 95%, 96%, 97%, 98% or 99% sequence identity with the sequence of amino acids set forth in SEQ ID No. 1 or as amino acids 1-448 of SEQ ID No. 4.

In particular, the sHASEGP polypeptide, with the Hyaluronidase domains as indicated in SEQ ID No. 4 is provided. The polypeptide is a single or two chain polypeptide. Smaller portions thereof that retain Hyaluronidase activity are also provided. The Hyaluronidase domains from sHASEGPs vary in size and constitution, including insertions and deletions in surface loops. Thus, for purposes herein, the catalytic domain is a portion of a sHASEGP, as defined herein, and is homologous to a domain of other hyaluronidase like sequences, such as HYAL1, HYAL2, HYAL3, which have been previously identified; it was not recognized, however, that an isolated single chain form of the human Hyaluronidase domain could function in in vitro assays. The Aspartate and Glutamate residues necessary for activity are present in conserved motifs.

As used herein, a "neutral hyaluronidase domain of a soluble sHASEGP" refers to a beta 1,4 endoglucosaminidase domain of a sHASEGP that exhibits Hyaluronidase activity at neutral pH, is soluble under conditions as described and shares homology and structural features with the hyaluronidase glycosyl-hydrolase family domains but contains additional sequences in the carboxy terminus that are required for neutral activity. Hence it is at least the minimal portion of the domain that exhibits Hyaluronidase activity as assessed by standard in vitro assays and remains soluble. Contemplated herein are such Hyaluronidase domains and catalytically active portions thereof. Also provided are truncated forms of the Hyaluronidase domain that include the smallest fragment thereof that acts catalytically as a single chain form. As used herein and in the art, neutral or neutral-active refers to a protein exhibiting activity at neutral pH (e.g. exhibiting activity at about pH 7) and which is therefore active at a pH range characteristic of many physiological tissues. As will also be appreciated by those of skill in the art, a protein generally exhibits a range of activity around its pH optimum. The pH optimum of a neutral active protein will typically be within one to several pH units above or below pH 7, but its range of activity may extend over many pH units.

A Hyaluronidase domain of an sHASEGP, whenever referenced herein, includes at least one or all of or any combination of or a catalytically active portion of: an N-linked glycoprotein polypeptide that includes the sequence of amino acids set forth in SEQ ID No. 1; a polypeptide encoded by a sequence of nucleotides that hybridizes under conditions of low, moderate or high stringency to the sequence of nucleotides set forth in SEQ ID NO. 6; a polypeptide that includes the sequence of amino acids set forth in SEQ ID No. 1; a polypeptide that includes a sequence of amino acids having at least about 70%, 75%, 80%, 81%, 82%, 83%, 84%, 85%, 86%, 87%, 88%, 89%, 90%, 91%, 92%, 93%, 94%, 95%, 96%, 97%, 98% or 99% sequence identity with the sequence of amino acids set forth in SEQ ID No. 1; and/or a Hyaluronidase domain of a polypeptide encoded by a splice variant of the sHASEGP.

Thus, for purposes herein, the Hyaluronidase domain is a portion of a sHASEGP, as defined herein, and is homologous to a domain of other sHASEGPs. As with the larger class of enzymes of the hyaluronidase family, the sHASEGP catalytic domains share a high degree of amino acid sequence identity. The Asp and Glu residues necessary for activity are present in conserved motifs.

By active form is meant a form active in vivo and/or in vitro. As described herein, the Hyaluronidase domain also can exist as a soluble secreted glycoprotein. It is shown herein that, at least in vitro, the single chain forms of the sHASEGPs and the catalytic domains or enzymatically active portions thereof (typically C-terminal truncations) exhibit Hyaluronidase activity. Hence provided herein are isolated forms of the Hyaluronidase domains of sHASEGPs and their use in in vitro drug screening assays for identification of agents that modulate the activity thereof.

As used herein, the catalytically active domain of a sHASEGP refers to the neutral active endoglucosaminidase domain as defined by activity in vitro towards a glycosaminoglycan substrate.

sHASEGPs of interest include those that are active against chondroitin sulfates and chondroitin sulfate proteoglycans (CSPG's) in vivo and in vitro; and those that are active against hyaluronan. As used herein, a human sHASEGP is one encoded by nucleic acid, such as DNA, present in the genome of a human, including all allelic variants and conservative variations as long as they are not variants found in other mammals.

As used herein, nucleic acid encoding a Hyaluronidase domain or catalytically active portion of a sHASEGP™ shall be construed as referring to a nucleic acid encoding only the recited single chain Hyaluronidase domain or active portion thereof, and not the other contiguous portions of the sHASEGP as a continuous sequence.

As used herein, "disease" or "disorder" refers to a pathological condition in an organism resulting from, e.g., infection or genetic defect, and characterized by identifiable symptoms.

As used herein, a splice variant refers to a variant produced by differential processing of a primary transcript of genomic nucleic acid, such as DNA, that results in more than one type of mRNA. Splice variants of sHASEGPs are provided herein.

As used herein, the Hyaluronidase domain of a sHASEGP protein refers to the Hyaluronidase domain of a sHASEGP that exhibits neutral endoglucosaminidase activity. Hence it is at least the minimal portion of the protein that exhibits endoglucosaminidase activity as assessed by standard assays in vitro. Exemplary human Hyaluronidase domains include at least a sufficient portion of sequences of amino acids set forth in SEQ ID No. 4 to exhibit endoglucosaminidase activity.

Also contemplated are nucleic acid molecules that encode a polypeptide that has endoglucosaminidase activity in an in vitro Hyaluronidase assay and that have at least 70%, 75%, 80%, 81%, 82%, 83%, 84%, 85%, 86%, 87%, 88%, 89%, 90%, 91%, 92%, 93%, 94%, 95%, 96%, 97%, 98% or 99% sequence identity with the full-length of a Hyaluronidase domain of an sHASEGP polypeptide, or that hybridize along their full-length or along at least about 70%, 80% or 90% of the full-length to a nucleic acids that encode a Hyaluronidase domain, particularly under conditions of moderate, generally high, stringency.

For the Hyaluronidase domains of PH20 for example, residues within the N-terminal region can be critical yet not sufficient for activity. By application of techniques such as shown herein one can generate Hyaluronidase domains of the sHASEGP that are catalytically active. By way of illustration, while the Hyaluronidase domain of human PH20 generally requires the N-terminal amino acids thereof for activity; the C-terminus portion can be truncated until the last Cysteine residue, yet requires additional amino acids to be optimally active. The amount that can be removed can be determined empirically by testing the polypeptide for Hyaluronidase activity in an in vitro assay that assesses catalytic cleavage.

Hence smaller portions of the Hyaluronidase domains, particularly the single chain domains, thereof that retain Hyaluronidase activity are contemplated. Such smaller versions generally are C-terminal truncated versions of the Hyaluronidase domains. The Hyaluronidase domains vary in size and constitution, including insertions and deletions in surface loops. Such domains exhibit conserved structure, including at least one structural feature, such as the proton donor, and/or other features of Hyaluronidase domains of endoglucosaminidases. Thus, for purposes herein, the Hyaluronidase domain is a single chain portion of a sHASEGP, as defined herein, but is homologous in its structural features and retention of sequence of similarity or homology the Hyaluronidase domain of other hyaluronidase-like sequences. The glycoprotein exhibits Hyaluronidase activity as a single chain.

As used herein, by homologous means about greater than 25% nucleic acid sequence identity, such as 25% 40%, 60%, 70%, 80%, 90% or 95%. If necessary the percentage homology will be specified. The terms "homology" and "identity" are often used interchangeably. In general, sequences are aligned so that the highest order match is obtained (see, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part/, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; Carrillo et al. (1988), Slam J Applied Math 48:1073-1082).

By sequence identity, the numbers of conserved amino acids is determined by standard alignment algorithms programs, and are used with default gap penalties established by each supplier. Substantially homologous nucleic acid molecules would hybridize typically at moderate stringency or at high stringency all along the length of the nucleic acid or along at least about 70%, 80% or 90% of the full-length nucleic acid molecule of interest. Also contemplated are nucleic acid molecules that contain degenerate codons in place of codons in the hybridizing nucleic acid molecule.

Whether any two nucleic acid molecules have nucleotide sequences that are at least, for example, 80%, 85%, 90%, 95%, 96%, 97%, 98% or 99% "identical" can be determined using known computer algorithms such as the "FASTA" program, using for example, the default parameters as in Pearson et al (1988) Proc. Natl. Acad. Sci. USA 85: 2444 (other programs include the GCG program package (Devereux, J. et al., Nucleic Acids Research 12: 387 (1984)), BLASTP, BLASTN, FASTA (Altschul, S. F. et al., J Molec Biol 215: 403-410 (1990); Guide to Huge Computers, Martin J. Bishop, Ed., Academic Press, San Diego, 1994, and Carrillo et al. (1988) SIAM J Applied Math 48:1073-1082). For example, the BLAST function of the National Center for Biotechnology Information database can be used to determine identity. Other commercially or publicly available programs include, DNASTAR "MEGALIGN" PROGRAM (Madison, Wis.) and the University of Wisconsin Genetics Computer Group (UWG) "Gap" program (Madison Wis.)). Percent homology or identity of proteins and/or nucleic acid molecules can be determined, for example, by comparing sequence information using a GAP computer program e.g. Needleman et al. (1970), J. Mol. Biol. 48: 443, as revised by Smith and Waterman Adv. Appl. Math (1981) 2:482). Briefly, the GAP program defines similarity as the number of aligned symbols (i.e., nucleotides or amino acids) that are similar, divided by the total number of symbols in the shorter of the two sequences. Default parameters for the GAP program can include: (1) a unary comparison matrix (containing a value of 1 for identities and 0 for non-identities) and the weighted comparison matrix of Gribskov et al (1986) Nucl. Acids Res. 14:6745-6763, as described by Schwartz and Dayhoff, eds., Atlas Of Protein Sequence And Structure, National Biomedical Research Foundation, pp. 353-358 (1979); (2) a penalty of 3.0 for each gap and an additional 0.10 penalty for each symbol in each gap; and (3) no penalty for end gaps. Therefore, as used herein, the term "identity" represents a comparison between a test and a reference polypeptide or polynucleotide.

As used herein, the term at least "90% identical to" refers to percent identities from 90 to 99.99 relative to the reference polypeptides. Identity at a level of 90% or more is indicative of the fact that, assuming for exemplification purposes a test and reference polynucleotide length of 100 amino acids are compared. No more than 10% (i.e., 10 out of 100) amino acids in the test polypeptide differ from that of the reference polypeptides. Similar comparisons can be made between a test and reference polynucleotides. Such differences can be represented as point mutations randomly distributed over the entire length of an amino acid sequence or they can be clustered in one or more locations of varying length up to the maximum allowable, e.g. 10/100 amino acid difference (approximately 90% identity). Differences are defined as nucleic acid or amino acid substitutions, or deletions. At the level of homologies or identities above about 85-90%, the result should be independent of the program and gap parameters set; such high levels of identity can be assessed readily, often without relying on software.

As used herein, primer refers to an oligonucleotide containing two or more deoxyribonucleotides or ribonucleotides, typically more than three, from which synthesis of a primer extension product can be initiated. Experimental conditions conducive to synthesis include the presence of nucleoside triphosphates and an agent for polymerization and extension, such as DNA polymerase, and a suitable buffer, temperature and pH.

As used herein, animals include any animal, such as, but are not limited to, goats, cows, deer, sheep, rodents, pigs and humans. Non-human animals, exclude humans as the contemplated animal. The sHASEGPs provided herein are from any source, animal, plant, prokaryotic and fungal. Preferred sHASEGPs are of animal origin, including mammalian origin, and more preferably are of human origin in the case of their use in humans.

As used herein, genetic therapy involves the transfer of heterologous nucleic acid, such as DNA, into certain cells, target cells, of a mammal, particularly a human, with a disorder or conditions for which such therapy is sought. The nucleic acid, such as DNA, is introduced into the selected target cells in a manner such that the heterologous nucleic acid, such as DNA, is expressed and a therapeutic product encoded thereby is produced.

Alternatively, the heterologous nucleic acid, such as DNA, can in some manner mediate expression of DNA that encodes the therapeutic product, or it can encode a product, such as a peptide or RNA that in some manner mediates, directly or indirectly, expression of a therapeutic product. Genetic therapy can also be used to deliver nucleic acid encoding a gene product that replaces a defective gene or supplements a gene product produced by the mammal or the cell in which it is introduced. The introduced nucleic acid can encode a therapeutic compound, such as a growth factor inhibitor thereof, or a tumor necrosis factor or inhibitor thereof, such as a receptor therefore, that is not normally produced in the mammalian host or that is not produced in therapeutically effective amounts or at a therapeutically useful time. The heterologous nucleic acid, such as DNA, encoding the therapeutic product can be modified prior to introduction into the cells of the afflicted host in order to enhance or otherwise alter the product or expression thereof. Genetic therapy can also involve delivery of an inhibitor or repressor or other modulator of gene expression.

As used herein, heterologous nucleic acid is nucleic acid that encodes proteins (or, if DNA, encodes RNA that encodes proteins) that are not normally produced in vivo by the cell in which it is expressed or that mediates or encodes mediators that alter expression of endogenous nucleic acid, such as DNA, by affecting transcription, translation, or other regulatable biochemical processes. Heterologous nucleic acid, such as DNA, can also be referred to as foreign nucleic acid, such as DNA. Any nucleic acid, such as DNA, that one of skill in the art would recognize or consider as heterologous or foreign to the cell in which is expressed is herein encompassed by heterologous nucleic acid; heterologous nucleic acid includes exogenously added nucleic acid that is also expressed endogenously. Examples of heterologous nucleic acid include, but are not limited to, nucleic acid that encodes traceable marker proteins, such as a protein that confers drug resistance, nucleic acid that encodes therapeutically effective substances, such as anti-cancer agents, enzymes and hormones, and nucleic acids (such as DNA and RNA), that indirectly or directly encode other types of proteins, such as antibodies. Antibodies that are encoded by heterologous nucleic acid can be secreted or expressed on the surface of the cell in which the heterologous nucleic acid has been introduced.

Heterologous nucleic acid is generally not endogenous to the cell into which it is introduced, but has been obtained from another cell or prepared synthetically.

Generally, although not necessarily, such nucleic acid encodes RNA and/or proteins that are not normally produced by the cell in which it is expressed.

As used herein, a therapeutically effective product is a product that is encoded by heterologous nucleic acid, typically DNA, that, upon introduction of the nucleic acid into a host, a product is expressed that ameliorates or eliminates the symptoms, manifestations of an inherited or acquired disease or that cures the disease.

As used herein, recitation that a glycoprotein consists essentially of the Hyaluronidase domain means that the only sHASEGP portion of the polypeptide is a Hyaluronidase domain or a catalytically active portion thereof. The polypeptide can optionally, and generally will, include additional non-sHASEGP-derived sequences of amino acids.

As used herein, domain refers to a portion of a molecule, e.g., glycoproteins or the encoding nucleic acids that is structurally and/or functionally distinct from other portions of the molecule.

As used herein, Hyaluronidase refers to an enzyme catalyzing hydrolysis of glycosaminoglycans including hyaluronans.

For clarity reference to Hyaluronidase refers to all forms, and particular forms will be specifically designated. For purposes herein, the Hyaluronidase domain includes the membrane bound and soluble forms of a sHASEGP protein.

As used herein, nucleic acids include DNA, RNA and analogs thereof, including protein nucleic acids (PNA) and mixture thereof. Nucleic acids can be single or double-stranded. When referring to probes or primers, optionally labeled with a detectable label, such as a fluorescent dye or radiolabel, single-stranded molecules are generally contemplated. Such molecules are typically of a length such that their target is statistically unique or of low copy number (typically less than 5, generally less than 3) for probing or priming a library. As is known in the art, generally a probe or primer contains at least 14, 16, 20 or 30 residues of contiguous or nearly-contiguous sequence complementary to or identical a gene of interest. Probes and primers can be 10, 20, 30, 50, 100 or more nucleic acids long.

As used herein, nucleic acid encoding a fragment or portion of a sHASEGP refers to a nucleic acid encoding only the recited fragment or portion of sHASEGP, and not the other contiguous portions of the sHASEGP.

As used herein, operative linkage of heterologous nucleic to regulatory and effector sequences of nucleotides, such as promoters, enhancers, transcriptional and translational stop sites, and other signal sequences refers to the relationship between such nucleic acid, such as DNA, and such sequences of nucleotides. For example, operative linkage of heterologous DNA to a promoter refers to the functional (and typically physical) relationship between the DNA and the promoter such that the transcription of such DNA is initiated from the promoter by an RNA polymerase that specifically recognizes, binds to and transcribes the DNA in reading frame. Thus, operatively linked or operationally associated refers to the functional relationship of nucleic acid, such as DNA, with regulatory and effector sequences of nucleotides, such as promoters, enhancers, transcriptional and translational stop sites, and other signal sequences. In order to optimize expression and/or in vitro transcription, it can be necessary to remove, add or alter 5' Untranslated portions of the clones to eliminate extra, potential inappropriate alternative translation initiation i.e. start) codons or other sequences that can interfere with or reduce expression, either at the level of transcription or translation. Alternatively, consensus ribosome binding sites (see, e.g., Kozak J. Biol. Chem. 266: 19867-19870 (1991) can be inserted immediately 5' of the start codon and can enhance expression. The desirability of (or need for) such modification can be empirically determined.

As used herein, a sequence complementary to at least a portion of an RNA, with reference to antisense oligonucleotides, means a sequence having sufficient complementarity to be able to hybridize with the RNA, generally under moderate or high stringency conditions, forming a stable duplex; in the case of double-stranded sHASEGP antisense nucleic acids, a single strand of the duplex DNA (or dsRNA) can thus be tested, or triplex formation can be assayed. The ability to hybridize depends on the degree of complementarity and the length of the antisense nucleic acid. Generally, the longer the hybridizing nucleic acid, the more base mismatches with a sHASEGP encoding RNA it can contain and still form a stable duplex (or triplex, as the case can be). One skilled in the art can ascertain a tolerable degree of mismatch by use of standard procedures to determine the melting point of the hybridized complex.

For purposes herein, amino acid substitutions can be made in any of sHASEGPs and Hyaluronidase domains thereof provided that the resulting protein exhibits Hyaluronidase activity. Amino acid substitutions contemplated include conservative substitutions, such as those set forth in Table 1, and other modifications that do not eliminate proteolytic activity. As described herein, substitutions that alter properties of the proteins, such as removal of cleavage sites and other such sites are also contemplated; such substitutions are generally non-conservative, but can be readily effected by those of skill in the art.

Suitable conservative substitutions of amino acids are known to those of skill in this art and can be made generally without eliminating (and preferably without substantially altering) the biological activity, for example enzymatic activity, of the resulting molecule. Those of skill in this art recognize that, in general, single amino acid substitutions in non-essential regions of a polypeptide do not substantially alter biological activity (see, e.g., Watson et al. Molecular Biology of the Gene, 4th Edition, 1987, The Benjamin/Cummings Pub. co., p. 224). Also included within the definition, is the catalytically active fragment of a sHASEGP, particularly a single chain Hyaluronidase portion. Conservative amino acid substitutions are made, for example, in accordance with those set forth in TABLE 1 as follows:

TABLE 1 Original residue Conservative substitution Ala (A) Gly; Ser, Abu Arg (R) Lys, Orn Asn (N) Gln; His Cys (C) Ser Gln (O) Asn Glu (E) ASP Gly (G) Ala; Pro His (H) Asn; Gln Ile (I) Leu; Val; Met; Nle; Nva Leu (L); Val; Met; Nle; Nva Lys (K) Arg; Gln; Glu Met (M) Leu; Tyr; Ile; NLe Val Orn Lys; Arg Phe (F) Met; Leu; Tyr Ser (S) Thr Thr (T) Ser Trp (W) Tyr Tyr (Y) Trp; Phe Val (V) ILE; Leu; Met; Nle; Nva. Other substitutions are also permissible and can be determined empirically or in accord with known conservative substitutions.

As used herein, Abu is 2-aminobutyric acid; Nle is norleucine; Nva is norvaline; Orn is ornithine. As used herein, the amino acids, which occur in the various amino acid sequences appearing herein, are identified according to their well-known, three-letter or one-letter abbreviations. The nucleotides, which occur in the various DNA fragments, are designated with the standard single-letter designations used routinely in the art.

As used herein, a probe or primer based on a nucleotide sequence disclosed herein, includes at least 10, 14, typically at least 16 contiguous sequence of nucleotides of SEQ ID NO. 6, and even more preferably at least 20, 30, 50 or 100 contiguous sequence of nucleotides of SEQ ID NO. 6. The length of the probe or primer for unique hybridization is a function of the complexity of the genome of interest.

As used herein, amelioration of the symptoms of a particular disorder by administration of a particular pharmaceutical composition refers to any lessening, whether permanent or temporary, lasting or transient that can be attributed to or associated with administration of the composition.

As used herein, antisense polynucleotides refer to synthetic sequences of nucleotide bases complementary to mRNA or the sense strand of double-stranded DNA. Admixture of sense and antisense polynucleotides under appropriate conditions leads to the binding of the two molecules, or hybridization. When these polynucleotides bind to (hybridize with) mRNA, inhibition of protein synthesis (translation) occurs. When these polynucleotides bind to double-stranded DNA, inhibition of RNA synthesis (transcription) occurs.

The resulting inhibition of translation and/or transcription leads to an inhibition of the synthesis of the protein encoded by the sense strand. Antisense nucleic acid molecule typically contain a sufficient number of nucleotides to Specifically bind to a target nucleic acid, generally at least 5 contiguous nucleotides, often at least 14 or 16 or 30 contiguous nucleotides or modified nucleotides complementary to the coding portion of a nucleic acid molecule that encodes a gene of interest, for example, nucleic acid encoding a single chain Hyaluronidase domain of an sHASEGP.

As used herein, an array refers to a collection of elements, such as antibodies, containing three or more members. An addressable array is one in which the members of the array are identifiable, typically by position on a solid phase support. Hence, in general the members of the array are immobilized on discrete identifiable loci on the surface of a solid phase.

As used herein, antibody refers to an immunoglobulin, whether natural or partially or wholly synthetically produced, including any derivative thereof that retains the specific binding ability the antibody. Hence antibody includes any protein having a binding domain that is homologous or substantially homologous to an immunoglobulin-binding domain. Antibodies include members of any immunoglobulin claims, including IgG, IgM, IgA, IgD and IgE.

As used herein, antibody fragment refers to any derivative of an antibody that is less then full-length, retaining at least a portion of the full-length antibody's specific binding ability. Examples of antibody fragments include, but are not limited to Fab, Fab', $F(AB)_2$, single chain Fvs (scFV), FV, dsFV diabody and Fd fragments. The fragment can include multiple chains linked together, such as by disulfide bridges. An antibody fragment generally contains at least about 50 amino acids and typically at least 200 amino acids.

As used herein, an Fv antibody fragment is composed of one variable heavy domain (VH) and one variable light domain linked by noncovalent interactions.

As used herein, a dsFV refers to an Fv with an engineered intermolecular disulfide bond.

As used herein, an $F(AB)_2$ fragment is an antibody fragment that results from digestion of an immunoglobulin with pepsin at pH 4.0-4.5; it can be recombinantly expressed to produce the equivalent fragment.

As used herein, Fab fragments are antibody fragments that result from digestion of an immunoglobulin with papain; they can be recombinantly expressed to produce the equivalent fragment.

As used herein, scFVs refer to antibody fragments that contain a variable light chain V, and variable heavy chain (VH) covalently connected by a polypeptide linker in any order. The linker is of a length such that the two variable domains are bridged without substantial interference. Included linkers are (Gly-Ser) n residues with some Glu or Lys residues dispersed throughout to increase solubility.

As used herein, humanized antibodies refer to antibodies that are modified to include human sequences of amino acids so that administration to a human does not provoke an immune response. Methods for preparation of such antibodies are known. For example, to produce such antibodies, the hybridoma or other prokaryotic or eukaryotic cell, such as an *E. coli* or a CHO cell, that expresses the monoclonal antibody are altered by recombinant DNA techniques to express an antibody in which the amino acid composition of the non-variable region is based on human antibodies. Computer programs have been designed to identify such regions.

As used herein, diabodies are dimeric scFV; diabodies typically have shorter peptide linkers than ScFVs, and they generally dimerize.

As used herein, production by recombinant means by using recombinant DNA methods means the use of the well known methods of molecular biology for expressing proteins encoded by cloned DNA.

As used herein the term assessing is intended to include quantitative and qualitative determination in the sense of obtaining an absolute value for the activity of an sHASEGP, or a domain thereof, present in the sample, and also of obtaining an index, ratio, percentage, visual or other value indicative of the level of the activity. Assessment can be direct or indirect and the chemical species actually detected need not of course be the proteolysis product itself but can for example be a derivative thereof or some further substance.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures. Biological activities can be observed in in vitro systems designed to test or use such activities. Thus, for purposes herein the biological activity of a luciferase is its oxygenase activity whereby, upon oxidation of a substrate, light is produced.

As used herein, functional activity refers to a polypeptide or portion thereof that displays one or more activities associated with a full-length protein.

Functional activities include, but are not limited to, biological activity, catalytic or enzymatic activity, antigenicity (ability to bind to or compete with a polypeptide for binding to an anti-polypeptide antibody), immunogenicity, ability to form multimers, the ability to Specifically bind to a receptor or ligand for the polypeptide.

As used herein, a conjugate refers to the compounds provided herein that includes one or more sHASEGPs, including a sHASEGP, particularly single chain Hyaluronidase domains thereof, and one or more targeting agents. These conjugates include those produced by recombinant means as fusion proteins, those produced by chemical means, such as by chemical coupling, through, for example, coupling to sulfhydryl groups, and those produced by any other method whereby at least one sHASEGP, or a domain thereof, is linked, directly or indirectly via linker (s) to a targeting agent.

As used herein, a targeting agent is any moiety, such as a protein or effective portion thereof, that provides specific binding of the conjugate to a cell surface receptor, which, can internalize the conjugate or sHASEGP portion thereof. A targeting agent can also be one that promotes or facilitates, for example, affinity isolation or purification of the conjugate; attachment of the conjugate to a surface; or detection of the conjugate or complexes containing the conjugate.

As used herein, an antibody conjugate refers to a conjugate in which the targeting agent is an antibody.

As used herein, derivative or analog of a molecule refers to a portion derived from or a modified version of the molecule.

As used herein, an effective amount of a compound for treating a particular disease is an amount that is sufficient to ameliorate, or in some manner reduce the symptoms associated with the disease. Such amount can be administered as a single dosage or can be administered according to a regimen, whereby it is effective. The amount can cure the disease but, typically, is administered in order to ameliorate the symptoms of the disease. Repeated administration can be required to achieve the desired amelioration of symptoms.

As used herein equivalent, when referring to two sequences of nucleic acids means that the two sequences in question encode the same sequence of amino acids or equivalent proteins. When equivalent is used in referring to two proteins or peptides, it means that the two proteins or peptides have substantially the same amino acid sequence with only amino acid substitutions (such, as but not limited to, conservative changes such as those set forth in Table 1, above) that do not substantially alter the activity or function of the protein or peptide. When equivalent refers to a property, the property does not need to be present to the same extent (e.g., two peptides can exhibit different rates of the same type of enzymatic activity), but the activities are usually substantially same. Complementary, when referring to two nucleotide sequences, means that the two sequences of nucleotides are capable of hybridizing, typically with less than 25%, 15%, 5% or 0% mismatches between opposed nucleotides. If necessary the percentage of complimentarily will be specified. Typically the two molecules are selected such that they will hybridize under conditions of high stringency.

As used herein, an agent that modulates the activity of a protein or expression of a gene or nucleic acid either decreases or increases or otherwise alters the activity of the protein or, in some manner up- or down-regulates or otherwise alters expression of the nucleic acid in a cell.

As used herein, inhibitor of the activity of an sHASEGP encompasses any substance that prohibits or decrease production, post-translational modification (s), maturation, or membrane localization of the sHASEGP or any substance that interferes with or decreases the proteolytic efficacy of thereof, particularly of a single chain form in an in vitro screening assay.

As used herein, a method for treating or preventing neoplastic disease means that any of the symptoms, such as the tumor, metastasis thereof, the vascularization of the tumors or other parameters by which the disease is characterized are reduced, ameliorated, prevented, placed in a state of remission, or maintained in a state of remission. It also means that the hallmarks of neoplastic disease and metastasis can be eliminated, reduced or prevented by the treatment. Non-limiting examples of the hallmarks include uncontrolled degradation of the basement membrane and proximal extracellular matrix, migration, division, and organization of the endothelial cells into new functioning capillaries, and the persistence of such functioning capillaries.

As used herein, pharmaceutically acceptable salts, esters or other derivatives of the conjugates include any salts, esters or derivatives that can be readily prepared by those of skill in this art using known methods for such derivatization and that produce compounds that can be administered to animals or humans without substantial toxic effects and that either are pharmaceutical active or are prodrugs.

As used herein, a prodrug is a compound that, upon in vivo administration, is metabolized or otherwise converted to the biologically, pharmaceutically or therapeutically active form of the compound. To produce a prodrug, the pharmaceutical active compound is modified such that the active compound is regenerated by metabolic processes. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

As used herein, a drug identified by the screening methods provided herein refers to any compound that is a candidate for use as a therapeutic or as a lead compound for the design of a therapeutic. Such compounds can be small molecules, including small organic molecules, peptides, peptide mimetics, antisense molecules or dsRNA, such as RNAi, antibodies, fragments of antibodies, recombinant antibodies and other such compounds that can serve as drug candidates or lead compounds.

As used herein, a peptidomimetic is a compound that mimics the conformation and certain stereochemical features of the biologically active form of a particular peptide. In general, peptidomimetics are designed to mimic certain desirable properties of a compound, but not the undesirable properties, such as flexibility, that lead to a loss of a biologically active conformation and bond breakdown. Peptidomimetics may be prepared from biologically active compounds by replacing certain groups or bonds that contribute to the undesirable properties with bioisosteres. Bioisosteres are known to those of skill in the art. For example the methylene bioisostere CH2S has been used as an amide replacement in enkephalin analogs (see, e.g. Spatola (1983) pp. 267-357 in Chemistry and Biochemistry of Amino Acids, Peptides, and Proteins, Weistein, Ed. volume 7, Marcel Dekker, New York). Morphine, which can be administered orally, is a compound that is a peptidomimetic of the peptide endorphin. For purposes herein, cyclic peptides are included among pepidomimetics.

As used herein, a promoter region or promoter element refers to a segment of DNA or RNA that controls transcription of the DNA or RNA to which it is operatively linked. The promoter region includes specific sequences that are sufficient for RNA polymerase recognition, binding and transcription initiation.

This portion of the promoter region is referred to as the promoter. In addition, the promoter region includes sequences that modulate this recognition, binding and transcription initiation activity of RNA polymerase. These sequences can be cis acting or can be responsive to trans acting factors. Promoters, depending upon the nature of the regulation, can be constitutive or regulated. Exemplary promoters contemplated for use in prokaryotes include the bacteriophage T7 and T3 promoters.

As used herein, a receptor refers to a molecule that has an affinity for a given ligand. Receptors can be naturally occurring or synthetic molecules. Receptors can also be referred to in the art as anti-ligands. As used herein, the receptor and anti-ligand are interchangeable. Receptors can be used in their unaltered state or as aggregates with other species. Receptors can be attached, covalently or noncovalently, or in physical contact with, to a binding member, either directly or indirectly via a specific binding substance or linker. Examples of receptors, include, but are not limited to: antibodies, cell membrane receptors surface receptors and internalizing receptors, monoclonal antibodies and antisera reactive with specific antigenic determinants such as on viruses, cells, or other materials], drugs, polynucleotides, nucleic acids, peptides, factors, lectins, sugars, polysaccharides, cells, cellular membranes, and organelles.

Examples of receptors and applications using such receptors, include but are not restricted to: a) enzymes: specific transport proteins or enzymes essential to survival of microorganisms, which could serve as targets for antibiotic [ligand] selection; b) antibodies: identification of a ligand-binding site on the antibody molecule that combines with the epitope of an antigen of interest can be investigated; determination of a sequence that mimics an antigenic epitope can lead to the development of vaccines of which the immunogen is based on one or more of such sequences or lead to the development of related diagnostic agents or compounds useful in therapeutic treatments such as for auto-immune diseases c) nucleic acids: identification of ligand, such as protein or RNA, binding sites; d) catalytic polypeptides: polymers, including polypeptides, that are capable of promoting a chemical reaction involving the conversion of one or more reactants to one or more products; such polypeptides generally include a binding site specific for at least one reactant or reaction intermediate and an active functionality proximate to the binding site, in which the functionality is capable of chemically modifying the bound reactant (see, e.g., U.S. Pat. No. 5,215,899); e) hormone receptors: determination of the ligands that bind with high affinity to a receptor is useful in the development of hormone replacement therapies; for example, identification of ligands that bind to such receptors can lead to the development of drugs to control blood pressure; and f) opiate receptors: determination of ligands that bind to the opiate receptors in the brain is useful in the development of less-addictive replacements for morphine and related drugs.

As used herein, sample refers to anything that can contain an analyte for which an analyte assay is desired. The sample can be a biological sample, such as a biological fluid or a biological tissue. Examples of biological fluids include urine, blood, plasma, serum, saliva, semen, stool, sputum, cerebral spinal fluid, tears, mucus, sperm, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cells.

As used herein: stringency of hybridization in determining percentage mismatch is as follows: 1) high stringency: 0.1× SSPE, 0.1% SDS, 65° C. 2) medium stringency: 0.2×SspE, 0.1% SDS, 50° C. 3 low stringency: 1.0×SspE, 0.1% SDS, 50° C. Those of skill in this art know that the washing step selects for stable hybrids and also know the ingredients of SspE (see, e.g., Sambrook, E. F. Fritsch, T. Maniatis, in: Molecular Cloning, A Laboratory Manual, Cold spring Harbor Laboratory Press 1989 Vol 3, p. B. 13, see, also, numerous catalogs that describe commonly used laboratory solutions). SspE is pH 7.4 phosphate-buffered 0.18 NaCl. Further, those of skill in the art recognize that the stability of hybrids is determined by TmT which is a function of the sodium ion concentration and temperature (Tm=81.5° C.−16.6+0.41(% G+C)−600/L)) so that the only parameters in the wash conditions critical to hybrid stability are sodium ion concentration in the SspE (or SSC) and temperature.

It is understood that equivalent stringencies can be achieved using alternative buffers, salts and temperatures. By way of example and not limitation, procedures using conditions of low stringency are as follows (see also Shilo and Weinberg, Proc. Natl. Acad Sci USA 78: 6789-6792 (1981)): Filters containing DNA are pretreated for 6 hours at 40° C. in a solution containing 35% formamide, 5×SSC, 50 mM Tris-HCl (pH 7.5), 5 mM EDTA, 0.1% PVP, 0.1% Ficoll 1% BSA, and 500 ug/ml Denatured Salmon sperm DNA (10×) SSC is 1.5 M sodium chloride, and 0.15 M sodium citrate, adjusted to a pH of 7).

Hybridizations are carried out in the same solution with the following modifications: 0.02% PVP, 0.02% Ficoll 0.2% BSA, 100 VG/M sperm DNA, 10% (wt/vol) dextran sulfate, and 5-20×10$^6$ cpm 32P-labeled probe is used. Filters are incubated in hybridization mixture for 18-20 hours at 40° C. and then washed for 1.5 hours at 55° C. in a solution containing 2×SSC, 25 mM Tris-HCl (pH 7.4), 5 mM EDTA, and 0.1% SDS. The wash solution is replaced with fresh solution and incubated an additional 1.5 hours at 60° C. Filters are blotted dry and exposed for autoradiography. If necessary, filters are washed for a third time at 65-68° C. and reexposed to film. Other conditions of low stringency which can be used are well known in the art (e.g. as employed for cross-species hybridizations).

By way of example and not way of limitation, procedures using conditions of moderate stringency include, for example, but are not limited to, procedures using such conditions of moderate stringency are as follows: Filters containing DNA are pretreated for 6 hours at 55° C. in a solution containing 6×SSC, 5×Denhardt's solution, 0.5% SDS and 100 ug/ml denatured salmon sperm DNA. Hybridizations are carried out in the same solution and 5-20×10$^6$ $^{32}$P labeled probe is used. Filters are incubated in hybridization mixture for 18-20 hours at 55° C. and then washed twice for 30 minutes at 60° C. in a solution containing 1×SSC and 0.1% SDS. Filters are blotted dry and exposed for autoradiography. Other conditions of moderate stringency that can be used are well known in the art. Washing of filters is done at 37° C. for 1 hour in a solution containing 2×SSC, 0.1% SDS.

By way of example and not way of limitation, procedures using conditions of high stringency are as follows: Prehybridization of filters containing DNA is carried out for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 ug/ml denatured salmon sperm DNA. Filters are hybridized for 48 hours at 65° C. in prehybridization mixture containing 100 ug/ml denatured salmon sperm DNA and 5-20×10$^6$ CPM $^{32}$P labeled probe. Washing of filters is done at 37° C. for 1 hour in a solution containing 2×SSC, 0.01% PVP, 0.01% Ficoll, and 0.01% BSA. This is followed by a wash in 0.1×SSC at 50° C. for 45 minutes before autoradiography. Other conditions of high stringency that can be used are well known in the art.

The term substantially identical or substantially homologous or similar varies with the context as understood by those skilled in the relevant art and generally means at least 60% or 70%, preferably means at least 80%, 85% or more preferably at least 90%, and most preferably at least 95% identity.

As used herein, substantially identical to a product means sufficiently similar so that the property of interest is sufficiently unchanged so that the substantially identical product can be used in place of the product.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound can, however, be a mixture of stereoisomers or isomers. In such instances, further purification might increase the specific activity of the compound.

As used herein, target cell refers to a cell that expresses a sHASEGP (in the context of sHASEGP production as described herein), or to a cell that is targeted by a sHASEGP or co-formulated or co-administered agent in vivo (in the context of using sHASEGPs to promote the delivery of pharmacologics and other agents to target cells as described herein).

As used herein, test substance (or test compound) refers to a chemically defined compound (e.g., organic molecules, inorganic molecules, organic/inorganic molecules, proteins, peptides, nucleic acids, oligonucleotides, lipids, polysaccharides, saccharides, or hybrids among these molecules such as glycoproteins, etc.) or mixtures of compounds (e.g., a library of test compounds, natural extracts or culture supernatants, etc.) whose effect on an sHASEGP, particularly a single chain form that includes the Hyaluronidase domain or a sufficient portion thereof for activity, as determined by an in vitro method, such as the assays provided herein.

As used herein, the terms a therapeutic agent, therapeutic regimen, radioprotectant or chemotherapeutic mean conventional drugs and drug therapies, including vaccines, which are known to those skilled in the art. Radiotherapeutic agents are well known in the art.

As used herein, treatment means any manner in which the symptoms of a condition, disorder or disease are ameliorated or otherwise beneficially altered.

Treatment also encompasses any pharmaceutical use of the compositions herein.

As used herein, vector (or plasmid) refers to discrete elements that are used to introduce heterologous nucleic acid into cells for either expression or replication thereof. The vectors typically remain episomal, but can be designed to effect integration of a gene or portion thereof into a chromosome of the genome. Also contemplated are vectors that are artificial chromosomes, such as yeast artificial chromosomes and mammalian artificial chromosomes. Selection and use of such vehicles are well known to those of skill in the art. An expression vector includes vectors capable of expressing DNA that is operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, protein binding sequence refers to a protein or peptide sequence that is capable of specific binding to other protein or peptide sequences generally, to a set of protein or peptide sequences or to a particular protein or peptide sequence.

As used herein, epitope tag refers to a short stretch of amino acid residues corresponding to an epitope to facilitate subsequent biochemical and immunological analysis of the epitope tagged protein or peptide. Epitope tagging is achieved by including the sequence of the epitope tag to the protein-encoding sequence in an appropriate expression vector. Epitope tagged proteins can be affinity purified using highly specific antibodies raised against the tags.

As used herein, metal binding sequence refers to a protein or peptide sequence that is capable of specific binding to metal ions generally, to a set of metal ions or to a particular metal ion.

As used herein, a combination refers to any association between two or among more items.

As used herein, a composition refers to any mixture. It can be a solution, a suspension, liquid, powder, a paste, aqueous, non-aqueous or any combination thereof.

As used herein, fluid refers to any composition that can flow. Fluids thus encompass compositions that are in the form of semi-solids, pastes, solutions, aqueous mixtures, gels, lotions, creams and other such compositions.

As used herein, a cellular extract refers to a preparation or fraction which is made from a lysed or disrupted cell.

As used herein, an agent is said to be randomly selected when the agent is chosen randomly without considering the specific sequences involved in the association of a protein alone or with its associated substrates, binding partners, etc. An example of randomly selected agents is the use a chemical library or a peptide combinatorial library, or a growth broth of an organism or conditioned medium.

As used herein, an agent is said to be rationally selected or designed when the agent is chosen on a non-random basis that takes into account the sequence of the target site and/or its conformation in connection with the agent's action. As described in the Examples, there are proposed binding sites for Hyaluronidase and (catalytic) sites in the glycoprotein having SEQ ID NO: 1 or SEQ ID NO: 4. Agents can be rationally selected or rationally designed by utilizing the peptide sequences that make up these sites. For example, a rationally selected peptide agent can be a peptide whose amino acid sequence is identical to the ATP or calmodulin binding sites or domains.

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right. All oligosaccharides described herein are described with the name or abbreviation for the non-reducing saccharide (e.g., Gal), followed by the configuration of the glycosidic bond (.alpha. or beta.), the ring bond, the ring position of the reducing saccharide involved in the bond, and then the name or abbreviation of the reducing saccharide (e.g., GlcNAc). The linkage between two sugars may be expressed, for example, as 2,3, 2.fw darw.3, or (2,3). Each saccharide is a pyranose.

As used herein, N-linked sugar moiety refers to an oligosaccharide attached to a sHASEGP via the amide nitrogen of Asn residues. N-linked oligosaccharides fall into several major types (oligomannose, complex, hybrid, sulfated), all of which have (Man) 3-GlcNAc-GlcNAc-cores attached via the amide nitrogen of Asn residues that fall within -Asn-Xaa-Thr/Ser-sequences (where Xaa is not Pro). N-linked sites are often indirectly assigned by the appearance of a "blank" cycle during sequencing. Positive identification can be made after release of the oligosaccharide by PNGase F, which converts the glycosylated Asn to Asp. After PNGase F release, N-linked oligosaccharides can be purified using Bio-Gel P-6 chromatography, with the oligosaccharide pool subjected to preparative high pH anion exchange chromatography (HPAEC) (Townsend et al., (1989) Anal. Biochem. 182, 1-8). Certain oligosaccharide isomers can be resolved using HPAEC. Fucose residues will shift elution positions earlier in the HPAEC chromatogram, while additional sialic acid residues will increase the retention time. Concurrent treatment of glycoproteins whose oligosaccharide structures are known (e.g., bovine fetuin, a-1 acid glycoprotein, ovalin, RNAse B, transferrin) can facilitate assignment of the oligosaccharide peaks. The collected oligosaccharides can be characterized by a combination of compositional and methylation linkage analyses (Waeghe et al., (1983) Carbohydr Res. 123, 281-304.), with anomeric configurations assigned by NMR spectroscopy (Van Halbeek (1993) in Methods Enzymol 230).

Alternatively, oligosaccharides can be identified by fluorescence assisted carbohydrate electrophoresis (FACE) Callewaert et al. (2001) Glycobiology 11, 275-281.

As used herein, the term "sialic acid" refers to any member of a family of nine-carbon carboxylated sugars. The most common member of the sialic acid family is N-acetylneuraminic acid (2-keto-5-acetamindo-3,5-di-deoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) J. Biol. Chem. 261: 11550-11557; Kanamori et al. (1990) J. Biol. Chem. 265: 21811-21819. Also included are 9-substituted sialic acids such as a 9-O—$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki (1992) Glycobiology 2: 25-40; Sialic Acids: Chemistry, Metabolism and Function, R. Schauer, Ed. (Springer-Verlag, N.Y. (1992)). The synthesis and use of sialic acid compounds in a sialation procedure is disclosed in international application WO 92/16640, published Oct. 1, 1992.

As used herein, PNGase refers to an Asparagine Peptide specific N-glycosidase F such as the *Flavobacterium maningoseptum* peptide-N-glycosidase F. PNGASE enzymes are characterized by their specificity towards N-linked rather than O-linked oligosaccharides. Characterization of PNGASE efficacy can be defined by both SDS PAGE electrophoresis, or fluorescent assisted carbohydrate electrophoresis.

As used herein substantially terminated Sialation refers to N-linked oligosaccharides terminating with sialic acid residue as a terminal sugar. Terminal sialic acids can be identified by FACE analysis of released carbohydrates following treatment with neuraminidase.

The circulatory lifetime of glycoproteins in the blood is highly dependent on the composition and structure of its N-linked carbohydrate groups. This fact is of direct relevance for therapeutic glycoproteins that are intended to be administered parenterally. In general, maximal circulatory half-life of a glycoprotein requires that its N-linked carbohydrate groups terminate in the sequence NeuAc-Gal-GlcNAc. Without the terminal sialic acid (NeuAc), the glycoprotein is rapidly cleared from the blood by a mechanism involving the recognition of the underlying N-acetylgalactosamine (GalNAc) or galactose (Gal) residues (Goochee et al. (1991) Biol/Technology 9: 1347-1355). For this reason, ensuring the presence of terminal sialic acid on N-linked carbohydrate groups of therapeutic glycoproteins is an important consideration for their commercial development.

Circulating glycoproteins are exposed to sialidase(s) (or neuraminidase) which can remove terminal sialic acid residues. Typically the removal of the sialic acid exposes galactose residues, and these residues are recognized and bound by galactose-specific receptors in hepatocytes (reviewed in Ashwell and Harford (1982) Ann. Rev. Biochem. 51:531). Liver also contains other sugar-specific receptors which mediate removal of glycoproteins from circulation. Specificities of such receptors also include N-acetylglucosamine, mannose, fucose and phosphomannose. Glycoproteins cleared by the galactose receptors of hepatocytes undergo substantial degradation and then enter the bile; glycoproteins cleared by the mannose receptor of Kupffer cells enter the reticuloendothelial system (reviewed in Ashwell and Harford (1982) Ann. Rev. Biochem. 51:53).

As used herein Neutral Active refers to a sHASEGP glycoprotein with catalytic activity towards a glycosaminoglycan substrate in vitro at a PH between 5 and 8 under conditions of salt less than 150 mM and buffering strength less than 50 mM.

As used herein, a stabilized solution refers to a sHASEGP that retains greater than 60% of its initial activity after storage at room temperature for 30 days.

As used herein unless otherwise specified, a unit is expressed in turbidity reducing units (TRU). One TRU is defined as the amount of hyaluronidase activity required to reduce the turbidity of an acidified solution of hyaluronic acid and is equivalent to the U.S.P./National Formulary (NF XIII) units (NFU). The ELISA-like enzyme assay described herein can be related to the TRU, the NFU, and U.S.P. unit through a standard curve of a sample of hyaluronidase (e.g., USP or WHO standard) standardized through the U.S.P. Therefore, the enzyme activities determined by the ELISA-like enzyme assay are actually relative TRU, since enzyme activity is not actually measured using the turbidometric assay (Dorfman et al., 1948, J. Biol. Chem. 172:367).

As used herein, potency is defined by the amount of sHASEGP protein required to degrade substrate in vitro based upon a Turbidity Reducing Unit or Relative Turbidity Reducing Unit.

As used herein, specific activity refers to Units of activity per mg protein. The amount of sHASEGP protein is defined by the absorption of a solution of sHASEGP at 280 nm assuming a molar extinction coefficient of approximately 1.7, in units of $M^{-1}$ $cm^{-1}$.

Polyethylene glycol (PEG) has been widely used in biomaterials, biotechnology and medicine primarily because PEG is a biocompatible, nontoxic, nonimmunogenic and water-soluble polymer (Zhao and Harris, ACS Symposium Series 680: 458-72, 1997). In the area of drug delivery, PEG derivatives have been widely used in covalent attachment (i.e., "PEGylation") to proteins to reduce immunogenicity, proteolysis and kidney clearance and to enhance solubility (Zalipsky, Adv. Drug Del. Rev. 16:157-82, 1995). Similarly, PEG has been attached to low molecular weight, relatively hydrophobic drugs to enhance solubility, reduce toxicity and alter biodistribution. Typically, PEGylated drugs are injected as solutions.

A closely related application is synthesis of crosslinked degradable PEG networks or formulations for use in drug delivery since much of the same chemistry used in design of degradable, soluble drug carriers can also be used in design of degradable gels (Sawhney et al., Macromolecules 26: 581-87, 1993). It is also known that intermacromolecular complexes can be formed by mixing solutions of two complementary polymers. Such complexes are generally stabilized by electrostatic interactions (polyanion-polycation) and/or hydrogen bonds (polyacid-polybase) between the polymers involved, and/or by hydrophobic interactions between the polymers in an aqueous surrounding (Krupers et al., Eur. Polym J. 32:785-790, 1996). For example, mixing solutions of polyacrylic acid (PAAc) and polyethylene oxide (PEO) under the proper conditions results in the formation of complexes based mostly on hydrogen bonding. Dissociation of these complexes at physiologic conditions has been used for delivery of free drugs (i.e., non-PEGylated). In addition, complexes of complementary polymers have been formed from both homopolymers and copolymers.

In one aspect, the polyethylene glycol has a molecular weight ranging from about 3 kD to about 50 kD, and preferably from about 5 kD to about 30 kD. Covalent attachment of the PEG to the drug (known as "PEGylation") may be accomplished by known chemical synthesis techniques. For example, in one aspect of the present invention, the PEGylation of protein may be accomplished by reacting NHS-activated PEG with the protein under suitable reaction conditions.

While numerous reactions have been described for PEGylation, those that are most generally applicable confer directionality, utilize mild reaction conditions, and do not necessitate extensive downstream processing to remove toxic catalysts or bi-products. For instance, monomethoxy PEG (mPEG) has only one reactive terminal hydroxyl, and thus its use limits some of the heterogeneity of the resulting PEG-protein product mixture. Activation of the hydroxyl group at the end of the polymer opposite to the terminal methoxy group is generally necessary to accomplish efficient protein PEGylation, with the aim being to make the derivatised PEG more susceptible to nucleophilic attack. The attacking nucleophile is usually the epsilon-amino group of a lysyl residue, but other amines can also react (e.g. the N-terminal alpha-amine or the ring amines of histidine) if local conditions are favorable. A more directed attachment is possible in proteins containing a single lysine or cysteine. The latter residue can be targeted by PEG-maleimide for thiol-specific modification. Alternatively, PEG hydrazide can be reacted with periodate oxidized sHASEGP and reduced in the presence of $NaCNBH_3$ More specifically, PEGylated CMP sugars can be reacted with sHASEGP in the presence of appropriate glycosyl-transferases. One technique is the "PEGylation" technique where a number of polymeric molecules are coupled to the polypeptide in question. When using this technique the immune system has difficulties in recognizing the epitopes on the polypeptide's surface responsible for the formation of antibodies, thereby reducing the immune response. For polypeptides introduced directly into the circulatory system of the human body to give a particular physiological effect (i.e. pharmaceuticals) the typical potential immune response is an IgG and/or IgM response, while polypeptides which are inhaled through the respiratory system (i.e. industrial polypeptide) potentially may cause an IgE response (i.e. allergic response). One of the theories explaining the reduced immune response is that the polymeric molecule(s) shield(s) epitope(s) on the surface of the polypeptide responsible for the immune response leading to antibody formation. Another theory or at least a partial factor is that the heavier the conjugate is, the more reduced immune response is obtained.

In the case of human sHASEGPs being used in the human body, a preferred combination as described herein, the tendency for the sSHASEGP to elicit an immune response can be significantly reduced as compared to, for example, non-human animal-derived enzymes such as bovine or ovine hyaluronidases (i.e. even if those animal-derived enzymes could be completely purified away from other animal-derived proteins, which is difficult to impossible to achieve in practice). Although human sHASEGPs thus represent a substantial and very important improvement over animal-derived products, they can for many uses be improved still further by post-translational modifications (PTMs) such as PEGylation to enhance their resistance to degradation or elimination and/or to improve other properties making them even more beneficial for particular applications.

For example, although preferred compositions for humans (such as the human sHASEGPs) exhibit reduced immunogenicity compared to animal-derived hyaluronidases or non-human sHASEGPs, PEGylation of such human sHASEGPs can be used for example to extend their half life in the bloodstream and/or in other tissues within the body. Without being restricted to a particular mechanism of action, it is generally considered that the attachment of PEG moieties to sHASEGPs can be used to effectively shield the molecule, decreasing its relative sensitivity to proteases and potentially also decreasing the extent and rate of its clearance and elimination from the body.

The polymeric molecules coupled to the polypeptide may be any suitable polymeric molecule with a molecular weight as defined according to the invention, including natural and synthetic homopolymers, such as polyols (i.e. poly-OH), polyamines (i.e. poly-$NH_2$) and polycarboxyl acids (i.e. poly-COOH), and further heteropolymers i.e. polymers comprising one or more different coupling groups e.g. a hydroxyl group and amine groups.

Examples of suitable polymeric molecules include polymeric molecules selected from the group comprising poly-alkylene oxides (PAO), such as polyalkylene glycols (PAG), including polypropylene glycols (PEG), methoxypolyethylene glycols (mPEG) and polypropylene glycols, PEG-glycidyl ethers (Epox-PEG), PEG-oxycarbonylimidazole (CDI-PEG) branched polyethylene glycols (PEGs), polyvinyl alcohol (PVA), polycarboxylates, polyvinylpyrrolidone, poly-D,L-amino acids, polyethylene-co-maleic acid anhydride, polystyrene-co-maleic acid anhydride, dextrans including carboxymethyl-dextrans, heparin, homologous albumin, celluloses, including methylcellulose, carboxymethylcellulose, ethylcellulose, hydroxyethylcellulose carboxyethylcellulose and hydroxypropylcellulose, hydrolysates of chitosan, starches such as hydroxyethyl-starches and hydroxypropyl-starches, glycogen, agaroses and derivatives thereof, guar gum, pullulan, inulin, xanthan gum, carrageenan, pectin, alginic acid hydrolysates and bio-polymers.

Preferred polymeric molecules are non-toxic polymeric molecules such as (m)polyethylene glycol (mPEG) which further requires a relatively simple chemistry for its covalent coupling to attachment groups on the enzyme's surface.

Generally seen polyalkylene oxides (PAO), such as polyethylene oxides, such as PEG and especially mPEG, are the preferred polymeric molecules, as these polymeric molecules, in comparison to polysaccharides such as dextran, pullulan and the like, have few reactive groups capable of cross-linking, which is undesirable.

Improvements in PEGylation and other types of post-translational modifications (PTMs) have been extensive and there are now a large number of PTM techniques and reagents known in the art, and new ones are regularly being developed. Techniques and reagents for PEGylation include, for example: (i) specialized linkers and coupling chemistries (see, e.g., the reagents and technologies reviewed by Roberts et al., Adv. Drug Deliv. Rev. 54: 459-476 (2002) and the primary references reviewed therein); (ii) branched PEGs which effectively allow additional PEG groups to be attached to a single conjugation site (see, e.g., Guiotto et al., Bioorg. Med. Chem. Lett. 12: 177-180 (2002)); (iii) site-specific PEGylation, including site-specific monoPEGylation (see, e.g., Chapman, A. P. et al., Nature Biotech. 17: 780-783 (1999); and (iv) site-directed enzymatic PEGylation (e.g. using a transglutaminase reaction as described by Sato, H., Adv. Drug Deliv. Rev. 54: 487-504 (2002)). There are also additional technologies and reagents available from an increasing number of commercial suppliers (see, e.g., Nektar/Shearwater (nektar.com), Sunbio (sunbio.com and sunbio.com/peg-shop), Celares GmbH (celares.com), and others).

B. Tissue Expression Profiles Shasegp

While previously thought to be testis specific, human sHASEGP is expressed in multiple tissues in humans when using more sensitive techniques such as RT-PCR. The sHASEGP transcript is found in medulla (brain), microvascular endothelium, prostate, breast, retina, pooled human melanocyte, fetal heart, and pregnant uterus. sHASEGP is also expressed in germ cell tumors. RT-PCR based detection of sHASEGP transcripts is generally required to detect levels in tissues other than testis.

C. Assays for sHASEGP Enzyme Activity

Turbidometric Microtiter Assay for Hyaluronidase Activity

Hyaluronidase activity can be detected by way of a modified turbidometric assay in acidified serum solution. The reagents required are as follows:

| UV sterilized 2X-deionized water or sterile water for irrigation | Braun | R5000-01 |
| Hylumed Medical - Sodium Hyaluronate, High Molecular Weight HA | Genzyme Advanced Biomaterials | 4876 |
| Hyaluronidase Reference Standard | USP | 31200 |
| Potassium Acetate, Granular, USP, ACS | JTBaker | 2914-01 |
| Acetic Acid, Glacial, 99+% | Sigma | A-6283 |
| Sodium Phosphate Monobasic Monohydrate, USP Granular | Mallinkrodt | 7774 |
| Sodium Phosphate Dibasic Anhydrous, USP | Mallinkrodt | 7771 |
| Sodium Chloride, Crystals, GR, ACS | EMScience | SX0420-5 |
| Gelatin Hydrolysate Enzymatic | Sigma | G-0262 |
| Horse Serum, Donor Herd, cell culture tested, Hybridoma culture tested, USA Origin | Sigma | H-1270 |
| Human Serum Albumin 20% | Griffols | |
| Hydrochloric Acid, ACS Reagent | Sigma | H-7020 |
| Calcium Chloride, Dihydrate, Granular, USP, -FCC | JTBaker | 1336-01 |

The following reagents are prepared: Acetate Buffer Solution—14.0 g of potassium acetate and 25.0 mL of glacial acetic acid in water to make 1000 mL. Phosphate Buffer Solution—2.5 g of sodium phosphate monobasic, 1.0 g of anhydrous sodium phosphate dibasic, and 8.2 g of sodium chloride in water to make 1000 mL. Enzyme Diluent Stock Solution—500 mL of Phosphate Buffer Solution with 500 mL of water. Enzyme Diluent Working Solution—33 mg of hydrolyzed gelatin in 50 mL of Enzyme Diluent Stock Solution-prepared within 2 hours of use. Sample Stabilization Buffer Solution ("SSB" Soln.)—125 microliters (μL) of a 20% Human Serum Albumin Solution and 50 μl of a 1 M Calcium Chloride solution in 50 mL of Enzyme Diluent Working Solution, and mix thoroughly. Serum Stock Solution—Dilute 1 volume of Horse Serum with 9 volumes of Acetate Buffer Solution. Adjust with 4 N hydrochloric acid to a pH of 3.1 and allow the solution to stand at room temperature for 18 to 24 hrs. Store the solution at 4° C., and use within 30 days. Serum Working Solution—10 mL of the Serum Stock Solution in 30 mL of the Acetate Buffer Solution, adjusted to room temperature. Hyaluronic Acid Stock Solution—Sodium Hyaluronic Acid to a concentration 5.0 mg/mL in water. Hyaluronic Acid Working Solution—0.75 mL of the Hyaluronic Acid Stock Solution in 4.25 mL of the Phosphate Buffer Solution. Standard Stock Solution—One container of USP Reference Standard Hyaluronidase to a concentration 1000 Units/mL in water, aliquoted into 50 μL portions, and stored at −20° C. Standard Working Solution—40 μL of Standard Stock Solution in 960 uL of cold Enzyme Diluent Working Solution to obtain a solution having a known concentration of 40 Units/mL, prepared immediately before use in the assay.

All enzyme samples are diluted in a "Low Protein Binding" 96-well plate according to the following guidelines:

a) The range of maximum sensitivity of this assay is between 10-30 Units/mL. To minimize the number of times an assay must be repeated in order to get results that are within range, first determine the approximate number of total units/mL for the sample, and then choose a (whole number) dilution such that the final concentration is approximately 20 Units/ml.

b) Minimum Sample volumes needed to perform assay are as follows: FPLC Fractions=50 μL, Tissue Culture Supernatants=1 mL, Purified/Concentrated/Final Step Material=10 μL.

c) For samples with serial dilutions, 1:10 dilutions in the "Low Protein Binding" 96-well plate are made in triplicate by pipetting 360 μL of the "SSB" Solution and 40 μL of Sample into each well.

For preparation of USP Standard prepare the USP Standard Curve in the "Low Protein Binding" 96-well plate as follows:

| | | USP Standard Curve: | | |
|---|---|---|---|---|
| Wells: | Standard: | Enzyme Diluent Soln.(in µL): | Standard Working Soln.(in µL): | Final Conc.(in Units/mL): |
| A1-A3 | St01 | 0 | 100 | 40 |
| B1-B3 | St02 | 20 | 80 | 32 |
| C1-C3 | St03 | 40 | 60 | 24 |
| D1-D3 | St04 | 60 | 40 | 16 |
| E1-E3 | St05 | 80 | 20 | 8 |
| F1-F3 | St06 | 90 | 10 | 4 |
| G1-G3 | St07 | 100 | 0 | 0 |

For preparation of the Hyaluronic Acid Control in columns 1-3, prepare the H.A. Control in the "Flat Bottom" 96-well plate is prepared as follows:

| | | H.A. Controls: | |
|---|---|---|---|
| Wells: | Control: | Hyaluronic Acid Working Soln.(in µL): | Enzyme Diluent Working Soln.(in µL): |
| H1-H3 | Co01 | 0 | 60 |

The Reaction Plate: 30 µL per well of Hyaluronic Acid Working Solution is pipetted using a 50 µL 8-channel transfer pipette into a "Flat Bottom" 96-well microtiter plate leaving wells H1-H3 empty. 60 µL/well of Enzyme Diluent Working Solution is pipetted into wells H1-H3 of the same plate as the HA control.

Serum Working Solution: 40 mL of Serum Working Solution is dispensed into a transfer basin and next to the Heat Block.

Pre-warming stage: Once both plates have been prepared, the Low Protein Binding 96-Well plate containing the diluted samples, standards, controls and the Flat Bottom 96-well plate containing the Hyaluronic Acid Working Solution are placed onto a heat block and allow them to warm for 5 min. at 37° C.

The Reaction is initiated by the addition of Enzyme to Substrate: 30 µL from the enzyme plate into all of the wells in column #1 of the 96-Well flat bottom plate (containing the substrate) using a 5-50 µL 8-channel pipette. The Enzyme/Substrate reaction mixture is aspirated 5 times (drawing the solution up and down with the transfer during the first 15 seconds to ensure complete sample mixing. After mixing the enzyme and substrate, the tips are ejected and a new set of tips loaded on the transfer pipettor for the next column. A timer is restarted, and at time (t)=0:30, this process is repeated for column 2. At the next 30 second interval (t)=1:00, this is repeated process for column 3. This process is repeated moving from left to right across the plate, every 30 seconds until all of the wells contain both enzyme and substrate.

Stopping the reaction: When timer reaches 6 minutes (t)=6:00, 240 µL of the Serum Working Solution is pippetted into each well, using a 50-300 µL 8-channel transfer pipette, into column 1 of the 96-well flat bottom plate from the adjacent 50 mL Reagent Reservoir. The mixture is aspirated 3 times (drawing the solution up and down with the transfer Pipettor) during the first 10 seconds to ensure complete mixing. The process is repeated every 30 seconds, proceeding from column's 1 to 12. Upon completion of the last column (column 12), the reaction plate is removed from the heat block and place the plate onto the read tray of the plate reader at 640 nM. A linear curve fit is generated from the standard curve that permits extrapolation of test samples.

Alternative Assays for Hyaluronidase

Biotinylated Hyaluronan Microtiter Assay

The free carboxyl groups on glucuronic acid residues of Hyaluronan are biotinylated in a one step reaction using biotin-hydrazide (Pierce), Sulfo NHS (Pierce) and 1-Ethyl dimethylaminopropyl-carbodiimide (Sigma). This biotinylated HA substrate is covalently coupled to a 96 well microtiter plate in a second reaction. At the completion of the enzyme reaction, residual substrate is detected with an avidin-peroxidase reaction that can be read in a standard ELISA plate reader. As the substrate is covalently bound to the microtiter plate, artifacts such as pH-dependent displacement of the biotinylated substrate does not occur. The sensitivity permits rapid measurement of Hyaluronidase activity from cultured cells and biological samples with an inter-assay variation of less than 10%.

The specific activity of hyaluronidase is expressed in turbidity reducing units (TRU). One TRU is defined as the amount of hyaluronidase activity required to reduce the turbidity of an acidified solution of hyaluronic acid and is equivalent to the U.S.P./National Formulary (NF XIII) units (NFU). The ELISA-like enzyme assay used for purification is related to the TRU, the NFU, and U.S.P. unit through a standard curve of a sample of hyaluronidase (e.g., USP) standardized through the U.S.P. Therefore, the enzyme activities determined by the ELISA-like enzyme assay are actually relative TRU, since enzyme activity is not actually measured using the turbidometric assay (Dorfman et al., 1948, J. Biol. Chem. 172:367).

Many Hyaluronidase assays have been based upon the measurement of the generation of new reducing N-acetylamino groups (Bonner and Cantey, Clin. Chim. Acta 13:746-752, 1966), or loss of viscosity (De Salegui et al., Arch. Biochem. Biophys. 121:548-554, 1967) or turbidity (Dorfman and Ott, J. Biol. Chem. 172:367, 1948). With purified substrates all of these methods suffice for determination of the presence or absence of endoglucosamidic activity.

Substantially purified glycosaminoglycan substrates can also be used for in a Gel Shift Assay. Glycosaminoglycans are mixed with recombinant sHASEGP to test for endoglucosidase activity that results in a shift in substrate mobility within the gel. Chondroitin-4 and 6 sulfate, dermatan sulfate, heparan-sulfate can be obtained from Sigma Chemical. Human umbilical cord Hyaluronan can be obtained from ICN. Each test substrate is diluted to 0.1 mg/ml in a buffer range from pH 3.5-7.5. 10 ul samples of purified sHASEGP or conditioned media from sHASEGP expressing cells as well as are mixed with 90 ul of test substrate in desired buffer and incubated for 3 hours at 37 C. Following incubation samples are neutralized with sample buffer (Tris EDTA PH 8.0, Bromophenol Blue and glycerol) followed by electrophoresis. Glycosaminoglycans are detected by staining the gels in 0.5% Alcian Blue in 3% Glacial Acetic Acid overnight followed by destaining in 7% Glacial Acetic Acid. Degradation is determined by comparison substrate mobility in the presence and absence of enzyme.

Hyaluronidase activity can also be detected by substrate gel zymography (Guentenhoner et al., 1992, Matrix 388-396). In this assay a sample is applied to a SDS-PAGE gel containing hyaluronic acid and the proteins in the sample separated by electrophoresis. The gel is then incubated in an enzyme assay buffer and subsequently stained to detect the hyaluronic acid in the gel. Hyaluronidase activity is visualized as a cleared zone in the substrate gel.

D. Identification and Isolation of sHASEGP Polypeptide Genes

The sHASEGP polypeptide gene and/or domains thereof, can be obtained by methods well known in the art for DNA isolation. Any method known to those of skill in the art for identification of nucleic acids that encode desired genes can be used. Any method available in the art can be used to obtain a full-length (i.e., encompassing the entire coding region) cDNA or genomic DNA clone encoding a sHASEGP polypeptide. For example, the polymerase chain reaction (PCR) can be used to amplify a sequence that is expressed in normal tissues, e.g., nucleic acids encoding a sHASEGP polypeptide (SEQ. Nos: 1 and 2), in a genomic or cDNA library. Oligonucleotide primers that hybridize to sequences at the 3' and 5' termini of the identified sequences can be used as primers to amplify by PCR sequences from a nucleic acid sample (RNA or DNA generally a cDNA library, from an appropriate source (e. testis, prostate, breast).

PCR can be carried out, e.g., by use of a Perkin-Elmer Cetus thermal cycler and Taq polymerase (Gene Amp). The DNA being amplified can include mRNA or cDNA or genomic DNA from any eukaryotic species. One can choose to synthesize several different degenerate primers, for use in the PCR reactions.

It is also possible to vary the stringency of hybridization conditions used in priming the PCR reactions, to amplify nucleic acid homologs (e.g., to obtain sHASEGP polypeptide sequences from species other than humans or to obtain human sequences with homology to sHASEGP polypeptide) by allowing for greater or lesser degrees of nucleotide sequence similarity between the known nucleotide sequence and the nucleic acid homolog being isolated. For cross-species hybridization, low stringency to moderate stringency conditions are used. For same species hybridization, moderately stringent to highly stringent conditions are used. The conditions can be empirically determined.

After successful amplification of the nucleic acid containing all or a portion of the identified sHASEGP polypeptide sequence or of a nucleic acid encoding all or a portion of a sHASEGP polypeptide homolog, that segment can be molecularly cloned and sequenced, and used as a probe to isolate a complete cDNA or genomic clone. This, in turn, permits the determination of the gene's complete nucleotide sequence, the analysis of its expression, and the production of its protein product for functional analysis. Once the nucleotide sequence is determined, an open reading frame encoding the sHASEGP polypeptide gene protein product can be determined by any method well known in the art for determining open reading frames, for example, using publicly available computer programs for nucleotide sequence analysis. Once an open reading frame is defined, it is routine to determine the amino acid sequence of the protein encoded by the open reading frame. In this way, the nucleotide sequences of the entire sHASEGP polypeptide genes as well as the amino acid sequences of sHASEGP polypeptide proteins and analogs can be identified.

Any eukaryotic cell potentially can serve as the nucleic acid source for the molecular cloning of the sHASEGP polypeptide gene. The nucleic acids can be isolated from vertebrate, mammalian, human, porcine, bovine, feline, avian, equine, canine, as well as additional primate sources, insects, plants and other organisms. The DNA can be obtained by standard procedures known in the art from cloned DNA (e.g., a DNA "library"), by chemical synthesis, by cDNA cloning, or by the cloning of genomic DNA, or fragments thereof, purified from the desired cell (see, e.g., Sambrook et al. 1989, Molecular Cloning, A Laboratory Manual, 2d Ed., Cold Spring Harbor Laboratory Press, Cold Spring Harbor, N.Y.; Kaiser, K. and N. Murray, "The use of phage lambda replacement vectors in the construction of representative genomic DNA libraries." In DNA Cloning: A Practical Approach (Ed. D. Glover). 1985, MRL Press, Ltd., Oxford, U. K., 1985. Vol. 1 pp. 11-12). Clones derived from genomic DNA can contain regulatory and intron DNA regions in addition to coding regions; clones derived from cDNA will contain only exon sequences. For any source, the gene is cloned into a suitable vector for propagation thereof.

In the molecular cloning of the gene from genomic DNA, DNA fragments are generated, some of which will encode the desired gene.

The DNA can be cleaved at specific sites using various restriction enzymes.

Alternatively, one can use DNAse in the presence of manganese to fragment the DNA, or the DNA can be physically sheared, for example, by sonication. The linear DNA fragments then can be separated according to size by standard techniques, including but not limited to, agarose and polyacrylamide gel electrophoresis and column chromatography.

Once the DNA fragments are generated, identification of the specific DNA fragment containing the desired gene can be accomplished in a number of ways.

For example, a portion of the sHASEGP polypeptide (of any species) gene (e.g., a PCR amplification product obtained as described above or an oligonucleotide having a sequence of a portion of the known nucleotide sequence) or its specific RNA, or a fragment thereof be purified and labeled, and the generated DNA fragments can be screened by nucleic acid hybridization to the labeled probe (Benton and Davis, Science 196: 180 (1977); Grunstein and Hogness, Proc. Natl. Acad. Sci. U.S.A. 72: 3961 (1975)). Those DNA fragments with substantial homology to the probe will hybridize. It is also possible to identify the appropriate fragment by restriction enzyme digestion (s) and comparison of fragment sizes with those expected according to a known restriction map if such is available or by DNA sequence analysis and comparison to the known nucleotide sequence of sHASEGP polypeptide. Further selection can be carried out on the basis of the properties of the gene. Alternatively, the presence of the gene can be detected by assays based on the physical, chemical, or—immunological properties of its expressed product. For example, cDNA clones, or DNA clones which hybrid-select the proper mRNA can be selected which produce a protein that, e.g., has similar or identical electrophoretic migration, isoelectric focusing behavior, proteolytic digestion maps, antigenic properties, Hyaluronidase activity. If an anti-sHASEGP polypeptide antibody is available, the protein can be identified by binding of labeled antibody to the putatively sHASEGP polypeptide synthesizing clones, in an ELISA (enzyme-linked immunosorbent assay)-type procedure.

Alternatives to isolating the sHASEGP polypeptide genomic DNA include, but are not limited to, chemically synthesizing the gene sequence from a known sequence or making cDNA to the mRNA that encodes the sHASEGP polypeptide.

For example, RNA for cDNA cloning of the sHASEGP polypeptide gene can be isolated from cells expressing the protein. The identified and isolated nucleic acids then can be inserted into an appropriate cloning vector. A large number of vector-host systems known in the art can be used. Possible vectors include, but are not limited to, plasmids or modified viruses, but the vector system must be compatible with the host cell used. Such vectors include, but are not limited to, bacteriophages such as lambda derivatives, or plasmids such as pBR322 or pUC plasmid derivatives or the Bluescript vector (Stratagene, La Jolla, Calif.). The insertion into a cloning vector can, for example, be accomplished by ligating the DNA fragment into a cloning vector that has complementary cohesive termini.

If the complementary restriction sites used to fragment the DNA are not present in the cloning vector, the ends of the DNA molecules can be enzymatically modified. Alternatively, any site desired can be produced by ligating nucleotide sequences (linkers) onto the DNA termini; these ligated linkers can include specific chemically synthesized oligonucleotides encoding restriction endonuclease recognition sequences. In an alternative method, the cleaved vector and sHASEGP polypeptide gene can be modified by homopolymeric tailing.

Recombinant molecules can be introduced into host cells via transformation, transfection, infection, electroporation, calcium precipitation and other methods, so that many copies of the gene sequence are generated.

In specific embodiments, transformation of host cells with recombinant DNA molecules that incorporate the isolated sHASEGP polypeptide gene, cDNA, or synthesized DNA sequence enables generation of multiple copies of the gene.

Thus, the gene can be obtained in large quantities by growing transformants, isolating the recombinant DNA molecules from the transformants and, when necessary, retrieving the inserted gene from the isolated recombinant DNA.

E. Vectors, Plasmids and Cells that Contain Nucleic Acids Encoding a sHASEGP Polypeptide or Hyaluronidase Domain Thereof and Expression of sHASEGP Polypeptides Vectors and Cells For recombinant expression of one or more of the sHASEGP polypeptides, the nucleic acid containing all or a portion of the nucleotide sequence encoding the sHASEGP polypeptide can be inserted into an appropriate expression vector i.e., a vector that contains the necessary elements for the transcription and translation of the inserted protein coding sequence. The necessary transcriptional and translational signals can also be supplied by the native promoter for sHASEGP genes, and/or their flanking regions.

Also provided are vectors that contain nucleic acid encoding the sHASEGPs that can be introduced into an expression system capable of producing a soluble neutral active sHASEGP.

Cells containing the vectors are also provided. The cells include eukaryotic and prokaryotic cells, and the vectors suitable for use therein.

Eukaryotic cells, including dihydrofolate reductase deficient Chinese Hamster Ovary Cells (DG44), containing the vectors are provided. Suitable cells include yeast cells, fungal cells, plant cells, insect cells and animal cells. The cells are used to produce a sHASEGP polypeptide or Hyaluronidase domain thereof by (a) growing the above-described cells under conditions whereby the encoded sHASEGP polypeptide or Hyaluronidase domain of the sHASEGP polypeptide is expressed by the cell, and then (b) recovering the expressed Hyaluronidase domain protein. In the exemplified embodiments, the Hyaluronidase domain is secreted into the medium.

In one embodiment, the vectors include a sequence of nucleotides that encodes a polypeptide that has Hyaluronidase activity and contains all or a portion of only the Hyaluronidase domain, or multiple copies thereof, of a sHASEGP protein are provided. Also provided are vectors that comprise a sequence of nucleotides that encodes the Hyaluronidase domain and additional portions of a sHASEGP protein up to and including a full-length sHASEGP protein, as well as multiple copies thereof, are also provided. The vectors can be selected for expression of the sHASEGP protein or Hyaluronidase domain thereof in the cell or such that the sHASEGP protein is expressed as a secreted protein. Alternatively, the vectors can include signals necessary for secretion of encoded proteins. When the Hyaluronidase domain is expressed the nucleic acid is linked to nucleic acid encoding a secretion signal, such as the *Saccharomyces cerevisiae* a mating factor signal sequence or a portion thereof, or the native signal sequence.

In order to generate a soluble, neutral active sHASEGP, cells capable of introducing N-linked glycosylation are required. In the preferred embodiment, mammalian Chinese Hamster Ovary cells deficient in dihydrofolate reductase such as DG44, are electroporated with a plasmid encoding a strong mammalian promoter, such as CMV, nucleic acid encoding a sHASEGP followed by an internal ribosomal entry site, the mouse dihydrofolate reductase gene and the SV40 polyadenylation sequence as shown in SEQ ID NO 51. Such cells are then cultured in chemically defined medium in the absence of hypoxanthine and thymidine, followed by further gene amplification with increasing concentrations of methotrexate.

A variety of host-vector systems can be used to express the protein coding sequence. These include but are not limited to mammalian cell systems infected with virus e.g. vaccinia virus, adenovirus, etc.; insect cell systems infected with virus (e.g. baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system used, any one of a number of suitable transcription and translation elements can be used. Note that bacterial expression of sHASEGP DNA will not result in a catalytically active sHASEGP per se, but when combined with proper glycosylation machinery can be artificially glycosylated as such.

Any methods known to those of skill in the art for the insertion of nucleic acid fragments into a vector can be used to construct expression vectors containing a chimeric gene containing appropriate transcriptional/translational control signals and protein coding sequences. These methods can include in vitro recombinant DNA and synthetic techniques and in vivo recombinants (genetic recombination). Expression of nucleic acid sequences encoding sHASEGP polypeptide, or domains, derivatives, fragments or homologs thereof, can be regulated by a second nucleic acid sequence so that the genes or fragments thereof are expressed in a host transformed with the recombinant DNA molecule (s). For example, expression of the proteins can be controlled by any promoter/enhancer known in the art. In a specific embodiment, the promoter is not native to the genes for sHASEGP polypeptide. Promoters which can be used include but are not limited to the SV40 early promoter (Benoist and Chambon, Nature 290: 304-310 (1981) the promoter contained in the 3' long terminal repeat of Rous sarcoma virus (Yamamoto et al., Cell 22: 787-797 (1980) the herpes thymidine kinase promoter (Wagner et al. Proc. Natl. Acad. Sci. USA 78: 1441-1445 (1981) the regulatory sequences of the metallothionein gene (Brinster et al., Nature 296: 39-42 (1982)); prokaryotic expression vectors such as the β-Lactamase promoter (Villa-Kamaroff et al., Proc. Natl. Acad. Sci. USA 75: 3727-3731 1978)) Or The TAC Promoter Deboer et al., Proc. Natl. Acad. Sci. USA 80: 21-25 (1983)); see also "Useful Proteins from Recombinant Bacteria": in Scientific American 242: 79-94 (1980)); plant expression vectors containing the opaline synthetase promoter (Herrar-Estrella et al., Nature 303: 209-213

(1984)) or the cauliflower mosaic virus 35S RNA promoter (Gardner et al., Nucleic Acids RES. 9: 2871 (1981)), and the promoter of the photosynthetic enzyme ribulose bisphosphate carboxylase (Herrera-Estrella et al., Nature 310: 115-120 (1984)); promoter elements from yeast and other fungi such as the Gal4 promoter, the alcohol dehydrogenase promoter, the phosphoglycerol kinase promoter, the alkaline phosphatase promoter, and the following animal transcriptional control regions that exhibit tissue specificity and have been used in transgenic animals: elastase I gene control region which is active in pancreatic acinar cells (Swift Et Al., Cell 38: 639-646 (1984); Ornitz Et Al., Cold Spring Harbor Symp. Quant. Biol. 50: 399-409 (1986); Macdonald, Hepatology 7: 425-515 (1987)); insulin gene control region which is active in pancreatic beta cells (Hanahan et al., Nature 315: 115-122 (1985)), immunoglobulin gene control region which is active in lymphoid cells (Grosschedl et al., Cell 38: 647-658 (1984); Adams et al., Nature 318: 533-538 (1985); Alexander et al., Mol. Cell. Biol. 7: 1436-1444 (1987)), mouse mammary tumor virus control region which is active in testicular, breast, lymphoid and mast cells (Leder et al., CELL 45: 485-495 (1986)), albumin gene control region which is active in liver (Pinkert et al., Genes and Devel. 1: 268-276 (1987)), alpha-fetoprotein gene control region which is active in liver (Krumlauf et al., Mol. Cell. Biol. 5: 1639-1648 (1985); Hammer et al., Science 235: 53-58 1987)), alpha-1 antitrypsin gene control region which is active in liver (Kelsey et al., Genes And Devel. 1: 161-171 (1987)), beta globin gene control region which is active in myeloid cells (Mogram et al., Nature 315: 338-340 (1985); Kollias et al., CE//46: 89-94 (1986)), myelin basic protein gene control region which is active in oligodendrocyte cells of the brain (Readhead et al., Cell 48: 703-712 (1987)), myosin light chain-2 gene control region which is active in skeletal muscle (Sani, Nature 314: 283-286 (1985)), and gonadotrophic releasing hormone gene control region which is active in gonadotrophs of the hypothalamus (Mason et al., Science 234: 1372-1378 (1986)).

In a specific embodiment, a vector is used that contains a promoter operably linked to nucleic acids encoding a sHASEGP polypeptide, or a domain, fragment, derivative or homolog, thereof, one or more origins of replication, and optionally, one or more selectable markers (e. G., an antibiotic resistance gene).

Specific initiation signals may also be required for efficient translation of a sHASEGP sequence. These signals include the ATG initiation codon and adjacent sequences. In cases where sHASEGP, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al (1994) Results Probl Cell Differ 20:125-62; Bittner et al (1987) Methods in Enzymol 153:516-544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO (DG44, DXB11 CHO-K1), HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines that stably express sHASEGP may be transformed using expression vectors which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M et al (1977) Cell 11:223-32) and adenine phosphoribosyltransferase (Lowy I et al (1980) Cell 22:817-23) genes which can be employed in TK- or APRT-cells, respectively. Also, antimetabolite, antibiotic or herbicide resistance can be used as the basis for selection; for example, DHFR which confers resistance to methotrexate (Wigler M et al (1980) Proc Natl Acad Sci 77:3567-70); npt, which confers resistance to the aminoglycosides neomycin and G-418 (Colbere-Garapin F et al (1981) J Mol Biol 150:1-14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S C and R C Mulligan (1988) Proc Natl Acad Sci 85:8047-51). Recently, the use of visible markers has gained popularity with such markers as anthocyanins, beta glucuronidase and its substrate, GUS, and luciferase and its substrate, luciferin, being widely used not only to identify transformants, but also to quantify the amount of transient or stable protein expression attributable to a specific vector system (Rhodes C A et al (1995) Methods Mol Biol 55:121-131).

Identification of Transformants Containing the Polynucleotide Sequence

Although the presence/absence of marker gene expression suggests that the gene of interest is also present, the presence and expression of an active sHASEGP should be confirmed. For example, if the sHASEGP is inserted within a marker gene sequence, recombinant cells containing sHASEGP can be identified by the absence of marker gene function. Alternatively, a marker gene can be placed in tandem with a sHASEGP sequence under the control of a single promoter. Expression of the marker gene in response to induction or selection usually indicates expression of the tandem sHASEGP as well. Detection of a properly glycosylated neutral active sHASEGP can be determined by way of testing the conditioned media for sHASEGP enzyme activity under appropriate conditions.

Purification of sHASEGP

Host cells transformed with a sHASEGP nucleotide sequence may be cultured under conditions suitable for the expression and recovery of the encoded protein from cell culture. The protein produced by a recombinant cell is preferably secreted but may be contained intracellularly depending on the sequence and/or the vector used. As will be understood by those of skill in the art, expression vectors containing sHASEGP can be designed with signal sequences that facilitate direct secretion of sHASEGP through a prokaryotic or eukaryotic cell membrane. Other recombinant constructions may join sHASEGP to nucleotide sequence encoding a polypeptide domain which will facilitate purification of soluble proteins (Kroll D J et al (1993) DNA Cell Biol 12:441-53; cf discussion of vectors infra containing fusion proteins).

sHASEGP may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor XA or enterokinase (Invitrogen, San Diego Calif.) between the purification domain and sHASEGP is useful to facilitate purification. One such expression vector provides for expression of a fusion protein compromising a sHASEGP and contains nucleic acid encoding 6 histidine residues followed by thioredoxin and an enterokinase cleavage site. The histidine residues facilitate purification on IMIAC (immobilized metal ion affinity chromatography as described in Porath et al (1992) Protein Expression and Purification 3: 263-281) while the enterokinase cleavage site provides a means for purifying the chemokine from the fusion protein.

In addition to recombinant production, fragments of sHASEGP may be produced by direct peptide synthesis using solid-phase techniques (see, e.g., Stewart et al (1969) Solid-Phase Peptide Synthesis, W H Freeman Co, San Francisco; Merrifield J (1963) J Am Chem Soc 85:2149-2154). In vitro protein synthesis may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various fragments of sHASEGP may be chemically synthesized separately and combined using chemical methods to produce the full-length molecule.

Expression vectors containing the coding sequences, or portions thereof, of a sHASEGP polypeptide, is made, for example, by subcloning the coding portions into the EcoRI restriction site of each of the three PGEX vectors (glutathione S-transferase expression vectors (Smith and Johnson, Gene 7: 31-40 (1988)). This allows for the expression of products in the correct reading frame. Exemplary vectors and systems for expression of the Hyaluronidase domains of the sHASEGP polypeptides include the well-known *Pichia* vectors (available, for example, from Invitrogen, San Diego, Calif.), particularly those designed for secretion of the encoded proteins. The protein can also be expressed cytoplasmically, such as in the inclusion bodies. One exemplary vector is described in the examples.

Plasmids for transformation of *E. coli* cells, include, for example, the pET expression vectors (see, U.S. Pat. No. 4,952,496; available from Novagen, Madison, Wis.; see, also literature published by Novagen describing the system).

Such plasmids include pET 11a, which contains the T71ac promoter, T7 terminator, the inducible *E. coli* lac operator, and the lac repressor gene; pET 12A-C, which contains the T7 promoter, T7 terminator, and the *E. coli* OMPT secretion signal; and pET 15B and PET19B (Novagen, Madison, Wis.), which contain a His-Tag leader sequence for use in purification with a His column and a thrombin cleavage site that permits cleavage following purification over the column; the T7-lac promoter region and the T7 terminator.

The vectors are introduced into host cells, such as *Pichia* cells and bacterial cells, such as *E. coli*, and the proteins expressed therein. Exemplary *Pichia* strains include, for example, GS115. Exemplary bacterial hosts contain chromosomal copies of DNA encoding T7 RNA polymerase operably linked to an inducible promoter, such as the LACUV promoter (see, U.S. Pat. No. 4,952,496). Such hosts include, but are not limited to, the lysogenic *E. coli* strain BL21 (DE3).

The sHASEGP domains, derivatives and analogs can be produced by various methods known in the art. For example, once a recombinant cell expressing a sHASEGP polypeptide, or a domain, fragment or derivative thereof, is identified, the individual gene product can be isolated and analyzed. This is achieved by assays based on the physical and/or functional properties of the protein, including, but not limited to, radioactive labeling of the product followed by analysis by gel electrophoresis, immunoassay, cross-linking to marker-labeled product, and assays of proteolytic activity.

The sHASEGP polypeptides can be isolated and purified by standard methods known in the art (either from natural sources or recombinant host cells expressing the complexes or proteins), including but not restricted to column chromatography (E. g., ion exchange, affinity, gel exclusion, reversed-phase high pressure and fast protein liquid), differential centrifugation, differential solubility, or by any other standard technique used for the purification of proteins.

In one embodiment, a sHASEGP can be purified to homogeneity from the chemically defined conditioned media of HZ24 transfected and methotrexate amplified DG44 cells by 1) tangential flow diafiltration, 2) binding and elution from anion exchange chromatography, 3) flow through phenyl sepharose chromatography, 4) binding and elution from phenylboronate chromatography and 4) binding and elution with hydroxyapatite chromatography.

Functional properties can be evaluated using any suitable assay known in the art.

Alternatively, once a sHASEGP polypeptide or its domain or derivative is identified, the amino acid sequence of the protein can be deduced from the nucleotide sequence of the gene that encodes it. As a result, the protein or its domain or derivative can be synthesized by standard chemical methods known in the art (e. G. see Hunkapiller et al., Nature 310: 105-111 (1984)) followed by glycosylation in vitro.

Manipulations of sHASEGP polypeptide sequences can be made at the protein level. Also contemplated herein are sHASEGP polypeptide proteins, domains thereof, derivatives or analogs or fragments thereof, which are differentially modified during or after translation, e.g., by glycosylation, acetylation, phosphorylation, amidation, pegylation, derivatization by known protecting/blocking groups, proteolytic cleavage, linkage to an antibody molecule or other cellular ligand.

Any of numerous chemical modifications can be carried out by known techniques, including but not limited to specific chemical cleavage by cyanogen bromide, trypsin, chymotrypsin, papain, V8, NABH4, acetylation, formylation, oxidation, reduction, metabolic synthesis in the presence of tunicamycin and other such agents.

In addition, domains, analogs and derivatives of a sHASEGP polypeptide can be chemically synthesized. For example, a peptide corresponding to a portion of a sHASEGP polypeptide, which includes the desired domain or which mediates the desired activity in vitro can be synthesized by use of a peptide synthesizer.

Furthermore, if desired, nonclassical amino acids or chemical amino acid analogs can be introduced as a substitution or addition into the sHASEGP polypeptide sequence. Non-classical amino acids include but are not limited to the D-isomers of the common amino acids, a-amino isobutyric acid, 4-aminobutyric acid, Abu, 2-aminobutyric acid, E-ABU, e-Ahx, 6-amino hexanoic acid, Aib, 2-amino isobutyric acid, 3-amino propionoic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, ca-methyl amino acids, na-methyl amino acids, and amino acid analogs in general. Furthermore, the amino acid can be d (dextrorotary) or l (levorotary).

In cases where natural products are suspected of being mutant or are isolated from new species, the amino acid sequence of the sHASEGP polypeptide isolated from the natural source, as well as those expressed in vitro, or from synthesized expression vectors in vivo or in vitro, can be determined from analysis of the DNA sequence, or alternatively, by direct sequencing of the isolated protein. Such analysis can be performed by manual sequencing or through use of an automated amino acid sequenator.

Modifications—A variety of modifications of the sHASEGP polypeptides and domains are contemplated herein. A sHASEGP-encoding nucleic acid molecule can be modified by any of numerous strategies known in the art (Sambrook ET A/. (1990), Molecular Cloning, A Laboratory Manual, 2d ed., Cold Spring Harbor Laboratory, Cold Spring Harbor, N.Y.). The sequences can be cleaved at appropriate sites with restriction endonuclease (s), followed by further enzymatic modification if desired, isolated, and ligated in vitro. In the production of the gene encoding a domain, derivative or analog of sHASEGP, care should be taken to ensure that the modified gene retains the original translational reading frame, uninterrupted by translational stop signals, in the gene region where the desired activity is encoded.

Additionally, the sHASEGP-encoding nucleic acid molecules can be mutated in vitro or in vivo, to create and/or destroy translation, initiation, and/or termination sequences, or to create variations in coding regions and/or form new restriction endonuclease sites or destroy pre-existing ones, to facilitate further in vitro modification. Also, as described herein muteins with primary sequence alterations, such as replacements of Cys residues and elimination or addition of glycosylation sites are contemplated; the sHASEGP of SEQ ID No. 1 has seven potential glycosylation sites. Such mutations can be effected by any technique for mutagenesis known in the art, including, but not limited to, chemical mutagenesis and in vitro site-directed mutagenesis (Hutchinson et al., j. Biol. Chem. 253: 6551-6558 (1978)), use of TABE Linkers (Pharmacia). In one embodiment, for example, a sHASEGP polypeptide or domain thereof is modified to include a fluorescent label. In other specific embodiments, the sHASEGP polypeptide is modified to have a heterobifunctional reagent, such heterobifunctional reagents can be used to crosslink the members of the complex.

In addition, domains, analogs and derivatives of a sHASEGP can be chemically synthesized. For example, a peptide corresponding to a portion of a sHASEGP, which includes the desired domain or which mediates the desired activity in vitro can be synthesized by use of a peptide synthesizer. Furthermore, if desired, nonclassical amino acids or chemical amino acid analogs can be introduced as a substitution or addition into the sHASEGP sequence. Non-classical amino acids include but are not limited to the D-isomers of the common amino acids, a-amino isobutyric acid, 4-aminobutyric acid, Abu, 2-aminobutyric acid, S-ABU, e-Ahx, 6-amino hexanoic acid, Aib, 2-amino isobutyric acid, 3-amino propionoic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as ti-methyl amino acids, ca-methyl amino acids, na-methyl amino acids, and amino acid analogs in general. Furthermore, the amino acid can be d (dextrorotary) or l (levorotary).

F. Generation of a Functionally Active Glycosylated sHASEGP with N-Linked Sugar Moieties Properly N-glycosylated human sHASEGP is required to generate a catalytically stable protein. N-linked glycosylation of sHASEGP can be achieved through various techniques. Glycosylation of sHASEGP can be achieved by introducing nucleic acids encoding sHASEGP into cells of eukaryotic origin capable of proper N-linked glycosylation or alternatively, by contacting sHASEGP polypeptide with cell free extracts or purified enzymes capable of introducing the desired N-linked sugar moieties.

Selection of an Expression System

Eukaryotic cell expression systems vary in the extent and type of glycosylation they introduce into an ectopically expressed polypeptide. CHO cells are, for example, highly efficient at the introduction of N-linked glycosylation into an active sHASEGP polypeptide.

Additional eukaryotic expression systems that introduce N-linked glycosylation to generate a functional sHASEGP product can be tested by introducing a human sHASEGP expression plasmid into said cells and testing for neutral activity. Proper N-linked glycosylation can be determined by way of FACE analysis of PNGASE released oligosaccharides. Glycosylation profiles of catalytically active sHASEGPs are further provided herein. Verification of glycosylation can also be made by treatment of sHASEGP from said cells with PNGASE-F or by growth of such cells in tunicamycin following introduction of sHASEGP encoding nucleic acids.

N-glycosylation of sHASEGP polypeptide in vitro. The sHASEGP polypeptide can be N-glycosylated by contact of sHASEGP polypeptide with cell-free extracts containing activity capable of transferring N-linked sugars to sHASEGP polypeptide such as canine microsomal membranes or through coupled transcription and translation as is commercially available (Promega Madison Wis.).

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right. All oligosaccharides described herein are described with the name or abbreviation for the non-reducing saccharide (e.g., Gal), followed by the configuration of the glycosidic bond (.alpha. or beta.), the ring bond, the ring position of the reducing saccharide involved in the bond, and then the name or abbreviation of the reducing saccharide (e.g., GlcNAc). The linkage between two sugars may be expressed, for example, as 2,3, 2.fw darw.3, or (2,3). Each saccharide is a pyranose.

As used herein, N-linked sugar moiety refers to an oligosaccharide attached to a sHASEGP via the amide nitrogen of Asn residues. N-linked oligosaccharides fall into several major types (oligomannose, complex, hybrid, sulfated), all of which have (Man) 3-GlcNAc-GlcNAc-cores attached via the amide nitrogen of Asn residues that fall within -Asn-Xaa-Thr/Ser-sequences (where Xaa is not Pro). N-linked sites are often indirectly assigned by the appearance of a "blank" cycle during sequencing. Positive identification can be made after release of the oligosaccharide by PNGase F, which converts the glycosylated Asn to Asp. After PNGase F release, N-linked oligosaccharides can be purified using Bio-Gel P-6 chromatography, with the oligosaccharide pool subjected to preparative high pH anion exchange chromatography (HPAEC) (Townsend et al., (1989) Anal. Biochem. 182, 1-8). Certain oligosaccharide isomers can be resolved using HPAEC. Fucose residues will shift elution positions earlier in the HPAEC chromatogram, while additional sialic acid residues will increase the retention time. Concurrent treatment of glycoproteins whose oligosaccharide structures are known (e.g., bovine fetuin, a-1 acid glycoprotein, ovalbumin, RNAse B, transferrin) can facilitate assignment of the oligosaccharide peaks. The collected oligosaccharides can be characterized by a combination of compositional and methylation linkage analyses (Waeghe et al., (1983) Carbohydr Res. 123, 281-304.), with anomeric configurations assigned by NMR spectroscopy (Van Halbeek (1993) in Methods Enzymol 230).

Alternatively, oligosaccharides can be identified by fluorescence assisted carbohydrate electrophoresis (FACE) Callewaert et al. (2001) Glycobiology 11, 275-281.

G. Detection and Characterization of N-Linked Sugar Moieties on sHASEGP

Determining whether a protein is in fact glycosylated is the initial step in glycoprotein glycan analysis. Polyacrylamide gel electrophoresis in the presence of sodium dodecyl sulfate (SDS-PAGE) has become the method of choice as the final step prior to protein sequencing. Glycosylated proteins often migrate as diffuse bands by SDS-PAGE. A marked decrease in bandwidth and change in migration position after treatment with peptide-N4-(N-acetyl-D-glucosaminyl) asparagine amidase (PNGase F) is considered diagnostic of N-linked glycosylation. If the other types of glycosylation are predominant other approaches must be used. Lectin blotting methods provide an approach that is independent of the class of glycosylation (N versus O). Lectins, carbohydrate-binding proteins from various plant tissues, have both high affinity and narrow specificity for a wide range of defined sugar epitopes found on glycoprotein glycans (Cummings, R. D. (1994) Methods in Enzymol. 230, 66-86.). When conjugated with biotin or digoxigenin, they can be easily identified on membrane blots through a colorimetric reaction utilizing avidin or anti-digoxigenin antibodies conjugated with alkaline phosphatase (Haselbeck et al., (1993) Methods in Mol. Biol. 14, 161-173.), analogous to secondary antibody-alkaline phosphatase reactions employed in Western blotting. Screening with a panel of lectins with well-defined specificity can provide considerable information about a glycoprotein's carbohydrate complement. Importantly, the color development amplification is sufficiently high that 10-50 ng of a glycoprotein can easily be seen on a membrane blot of an SDS-PAGE. Although lectins exhibit very high affinity for their cognate ligands, some do reveal significant avidity for structurally related epitopes. Thus, it is important to carefully note the possibility of cross-reactivity when choosing a panel of lectins, and apply those with the highest probability of individually distinguishing complex, hybrid and high mannose N-linked glycans from O-linked structures.

Monosaccharide analysis can also be used to determine whether sHASEGP is glycosylated and as in the case of lectin analysis provides additional information on structural features. Quantitative monosaccharide composition analysis i) identifies glycosylated proteins, ii) gives the molar ratio of individual sugars to protein, iii) suggests, in some cases, the presence of oligosaccharide classes, iv) is the first step in designing a structural elucidation strategy, and v) provides a measure of production consistency for recombinant glycoprotein therapeutics. In recent years high-pH anion-exchange chromatography with pulsed amperometric detection (HPAEC-PAD) has been extensively used to determine monosaccharide composition (Townsend et al., (1995) in Carbohydrate Analysis: High-performance liquid chromatography and capillary electrophoresis (Z. El Rassi ed.). pp. 181-209.). More recently, fluorophore-based labeling methods have been introduced and many are available in kit form. A distinct advantage of fluorescent methods is an increase in sensitivity (50-fold). One potential disadvantage is that different monosaccharides may demonstrate different selectivity for the fluorophore during the coupling reaction, either in the hydrolysate or in the external standard mixture. However, the increase in sensitivity and the ability to identify which monosaccharides are present from a small portion of the total amount of available glycoprotein, as well as the potential for greater sensitivity using laser induced fluorescence makes this approach attractive.

Monosaccharide composition analysis of small amounts of sHASEGP is best performed on PVDF (PSQ) membranes, after either electroblotting (Weitzhandler et al., (1993) J. Biol. Chem. 268, 5121-5130.) or if smaller aliquots are to be analyzed on dot blots. PVDF is an ideal matrix for carbohydrate analysis since neither mono- or oligosaccharides bind to the membrane, once released by either acid or enzymatic hydrolysis.

FACE analysis is an efficient means of detecting glycosylation profiles of sHASEGPs. FACE® N-Linked Oligosaccharide Profiling (Prozyme) with 30% oligosaccharide gels is one such mechanism. Oligosaccharides cleaved from 100 μg of glycoproteins by enzymatic digestion with N-Glycanase (a.k.a PNGase), labeled using the fluorophore ANTS, and separated by electrophoresis can be used for detection of sHASEGP glycosylation profiles. The relative positions of the oligosaccharide bands are determined by running the sample and dilutions of the sample alongside an oligosaccharide standard ladder which designated the migration distance in Degree of Polymerization (DP) units.

H. Screening Methods to Identify Compounds that Modulate sHASEGP Activity

Several types of assays are exemplified and described herein. It is understood that the Hyaluronidase domains can be used in other assays. It is shown here, however, that the Hyaluronidase domains exhibit catalytic activity.

As such they are ideal for in vitro screening assays.

They can also be used in binding assays.

The sHASEGP full length zymogens, activated enzymes, and Hyaluronidase domains are contemplated for use in any screening assay known to those of skill in the art, including those provided herein. Hence the following description, if directed to Hyaluronidase assays is intended to apply to use of a single chain Hyaluronidase domain or a catalytically active portion thereof of any Hyaluronidase, including a sHASEGP. Other assays, such as binding assays are provided herein, particularly for use with a sHASEGP, including any variants, such as splice variants thereof.

1. Catalytic Assays for identification of agents that modulate the Hyaluronidase activity of a sHASEGP protein. Methods for identifying a modulator of the catalytic activity of a sHASEGP, particularly a single chain Hyaluronidase domain or catalytically active portion thereof, are provided herein. The methods can be practiced by: contacting the sHASEGP, a full-length zymogen or activated form, and particularly a single-chain domain thereof, with a substrate of the sHA- SEGP in the presence of a test substance, and detecting the proteolysis of the substrate, whereby the activity of the sHASEGP is assessed, and comparing the activity to a control. For example, a control can be the activity of the sHASEGP assessed by contacting a sHASEGP, including a full-length zymogen or activated form, and particularly a single-chain domain thereof, particularly a single-chain domain thereof, with a substrate of the sHASEGP, and detecting the proteolysis of the substrate, whereby the activity of the sHASEGP is assessed. The results in the presence and absence of the test compounds are compared. A difference in the activity indicates that the test substance modulates the activity of the sHASEGP. Activators of sHASEGP activation cleavage are also contemplated; such assays are discussed below.

In one embodiment a plurality of the test substances are screened simultaneously in the above screening method. In another embodiment, the sHASEGP is isolated from a target cell as a means for then identifying agents that are potentially specific for the target cell.

In another embodiment, a test substance is a therapeutic compound, and whereby a difference of the sHASEGP activity measured in the presence and in the absence of the test substance indicates that the target cell responds to the therapeutic compound.

One method includes the steps of (a) contacting the sHASEGP polypeptide or Hyaluronidase domain thereof with one or a plurality of test compounds under conditions conducive to interaction between the ligand and the compounds; and (b) identifying one or more compounds in the plurality that specifically binds to the ligand.

Another method provided herein includes the steps of a) contacting a sHASEGP polypeptide or Hyaluronidase domain thereof with a substrate of the sHASEGP polypeptide, and detecting the degradation of substrate, whereby the activity of the sHASEGP polypeptide is assessed; b) contacting the sHASEGP polypeptide with a substrate of the sHASEGP polypeptide in the presence of a test substance, and detecting the degradation of the substrate, whereby the activity of the sHASEGP polypeptide is assessed; and c) comparing the activity of the sHASEGP polypeptide assessed in steps a) and b), whereby the activity measured in step a) differs from the activity measured in step b) indicates that the test substance modulates the activity of the sHASEGP polypeptide.

In another embodiment, a plurality of the test substances is screened simultaneously. In comparing the activity of a sHASEGP polypeptide in the presence and absence of a test substance to assess whether the test substance is a modulator of the sHASEGP polypeptide, it is unnecessary to assay the activity in parallel, although such parallel measurement is typical. It is possible to measure the activity of the sHASEGP polypeptide at one time point and compare the measured activity to a historical value of the activity of the sHASEGP polypeptide.

For instance, one can measure the activity of the sHASEGP polypeptide in the presence of a test substance and compare with historical value of the activity of the sHASEGP polypeptide measured previously in the absence of the test substance, and vice versa. This can be accomplished, for example, by providing the activity of the sHASEGP polypeptide on an insert or pamphlet provided with a kit for conducting the assay.

Methods for selecting substrates for a particular sHASEGP are described in the EXAMPLES, and particular Hyaluronidase assays are exemplified.

Combinations and kits containing the combinations optionally including instructions for performing the assays are provided. The combinations include a sHASEGP polypeptide and a substrate of the sHASEGP polypeptide to be assayed; and, optionally reagents for detecting proteolysis of the substrate. The substrates, which can be chromogenic or fluorogenic molecules, including glycosaminoglycans, subject to proteolysis by a particular sHASEGP polypeptide, can be identified empirically by testing the ability of the sHASEGP polypeptide to cleave the test substrate. Substrates that are cleaved most effectively i.e. at the lowest concentrations and/or fastest rate or under desirable conditions), are identified.

Additionally provided herein is a kit containing the above-described combination. The kit optionally includes instructions for identifying a modulator of the activity of a sHASEGP polypeptide. Any sHASEGP polypeptide is contemplated as target for identifying modulators of the activity thereof.

2. Binding assays. Also provided herein are methods for identification and isolation of agents, particularly compounds that bind to sHASEGPs. The assays are designed to identify agents that bind to the isolated Hyaluronidase domain (or a protein, other than a sHASEGP polypeptide, that contains the Hyaluronidase domain of a sHASEGP polypeptide), and to the activated form, including the activated form derived from the full-length zymogen or from an extended Hyaluronidase domain. The identified compounds are candidates or leads for identification of compounds for treatments of disorders and diseases involving aberrant Hyaluronidase activity. The sHASEGP polypeptides used in the methods include any sHASEGP polypeptide as defined herein, including the sHASEGP single chain Hyaluronidase domain or proteolytically active portion thereof.

A variety of methods are provided herein. These methods can be performed in solution or in solid phase reactions in which the sHASEGP polypeptide (s) or Hyaluronidase domain (s) thereof are linked, either directly or indirectly via a linker, to a solid support. Screening assays are described in the Examples, and these assays have been used to identify candidate compounds.

For purposes herein, all binding assays described above are provided for sHASEGP.

Methods for identifying an agent, such as a compound, that specifically binds to a sHASEGP single chain Hyaluronidase domain, a full-length activated sHASEGP or two chain Hyaluronidase domain thereof are provided herein. The method can be practiced by (a) contacting the sHASEGP with one or a plurality of test agents under conditions conducive to binding between the sHASEGP and an agent; and (b) identifying one or more agents within the plurality that specifically binds to the sHASEGP.

For example, in practicing such methods the sHASEGP polypeptide is mixed with a potential binding partner or an extract or fraction of a cell under conditions that allow the association of potential binding partners with the polypeptide. After mixing, peptides, polypeptides, proteins or other molecules that have become associated with a sHASEGP are separated from the mixture. The binding partner that bound to the sHASEGP can then be removed and further analyzed. To identify and isolate a binding partner, the entire protein, for instance the entire disclosed protein of SEQ ID No. 1 can be used. Alternatively, a fragment of the protein can be used.

A variety of methods can be used to obtain cell extracts or body fluids, such as blood, serum, urine, sweat, synovial fluid, CSF and other such fluids.

For example, cells can be disrupted using either physical or chemical disruption methods. Examples of physical disruption methods include, but are not limited to, sonication and mechanical shearing. Examples of chemical lysis methods include, but are not limited to, detergent lysis and enzyme lysis. A skilled artisan can readily adapt methods for preparing cellular extracts in order to obtain extracts for use in the present methods.

Once an extract of a cell is prepared, the extract is mixed with the sHASEGP under conditions in which association of the protein with the binding partner can occur. A variety of conditions can be used, including conditions that resemble conditions found in the cytoplasm of a human cell or in a body fluid, such as blood. Features, such as osmolarity pH, temperature, and the concentration of cellular extract used, can be varied to optimize the association of the protein with the binding partner. Similarly, methods for isolation of molecules of interest from body fluids are known.

After mixing under appropriate conditions, the bound complex is separated from the mixture. A variety of techniques can be used to separate the mixture. For example, antibodies specific to a sHASEGP can be used to immunoprecipitate the binding partner complex. Alternatively, standard chemical separation techniques such as chromatography and density/sediment centrifugation can be used.

After removing the non-associated cellular constituents in the extract, the binding partner can be dissociated from the complex using conventional methods. For example, dissociation can be accomplished by altering the salt concentration or pH of the mixture.

To aid in separating associated binding partner pairs from the mixed extract, the sHASEGP can be immobilized on a solid support. For example, the protein can be attached to a nitrocellulose matrix or acrylic beads. Attachment of the protein or a fragment thereof to a solid support aids in separating peptide/binding partner pairs from other constituents found in the extract. The identified binding partners can be either a single protein or a complex made up of two or more proteins.

Alternatively, the nucleic acid molecules encoding the single chain Hyaluronidases can be used in a yeast two-hybrid system. The yeast two-hybrid system has been used to identify other protein partner pairs and can readily be adapted to employ the nucleic acid molecules herein described.

Another in vitro binding assay, particularly for a sHASEGP, uses a mixture of a polypeptide that contains at least the catalytic domain of one of these proteins and one or more candidate binding targets or substrates. After incubating the mixture under appropriate conditions, the ability of the sHASEGP or a polypeptide fragment thereof containing the catalytic domain to bind to or interact with the candidate substrate is assessed. For cell-free binding assays, one of the components includes or is coupled to a detectable label. The label can provide for direct detection, such as radioactivity, luminescence, optical or electron density, etc., or indirect detection such as an epitope tag, an enzyme, etc. A variety of methods can be employed to detect the label depending on the nature of the label and other assay components. For example, the label can be detected bound to the solid substrate or a portion of the bound complex containing the label can be separated from the solid substrate, and the label thereafter detected.

3. Detection of signal transduction sHASEGP, which is a membrane anchored protein, can be involved directly or indirectly in signal transduction directly as a cell surface receptor or indirectly by activating proteins, such as pro-growth factors that can initiate signal transduction.

In addition, secreted sHASEGP, such as the soluble domain of sHASEGP as described in SEQ ID NO. 4, can be involved in signal transduction either directly by binding to or interacting with a cell surface receptor or indirectly by activating proteins, such as pro-growth factors that can initiate signal transduction. Assays for assessing signal transduction are well known to those of skill in the art, and can be adapted for use with the sHASEGP polypeptide.

Assays for identifying agents that affect or alter signal transduction mediated directly or indirectly, such as via activation of a pro-growth factor, by a sHASEGP, particularly the full length or a sufficient portion to anchor the extracellular domain or a functional portion thereof of a sHASEGP on the surface of a cell are provided. Such assays, include, for example, transcription based assays in which modulation of a transduced signal is assessed by detecting an effect on an expression from a reporter gene (see, e.g., U.S. Pat. No. 5,436,128).

4. Methods for Identifying Agents that Modulate the Expression a Nucleic Acid encoding a sHASEGP. Another embodiment provides methods for identifying agents that modulate the expression of a nucleic acid encoding a sHASEGP. Such assays use any available means of monitoring for changes in the expression level of the nucleic acids encoding a sHASEGP.

Assay formats can be used to monitor the ability of the agent to modulate the expression of a nucleic acid encoding a sHASEGP. For instance, mRNA expression can be monitored directly by hybridization to the nucleic acids. Also enzyme assays as described can be used to detect agents that modulate the expression of sHASEGP.

Cell lines are exposed to the agent to be tested under appropriate conditions and time and total RNA or mRNA is isolated by standard procedures (see, e.g. Sambrook et al (1989) MOLECULAR CLONING: A LABORATORY MANUAL, 2nd Ed. Cold Spring Harbor Laboratory Press). Probes to detect differences in RNA expression levels between cells exposed to the agent and control cells can be prepared from the nucleic acids. It is typical, but not necessary, to design probes which hybridize only with target nucleic acids under conditions of high stringency. Only highly complementary nucleic acid hybrids form under conditions of high stringency. Accordingly, the stringency of the assay conditions determines the amount of complementarity that should exist between two nucleic acid strands in order to form a hybrid. Stringency should be chosen to maximize the difference in stability between the probe: target hybrid and potential probe: non-target hybrids.

For example, N- and C-terminal fragments of the sHASEGP can be expressed in bacteria and used to search for proteins that bind to these fragments. Fusion proteins, such as His-tag or GST fusion to the N- or C-terminal regions of the sHASEGP can be prepared for use as a substrate. These fusion proteins can be coupled to, for example, Glutathione-Sepharose beads and then probed with cell lysates or body fluids. Prior to lysis, the cells or body fluids can be treated with a candidate agent that can modulate a sHASEGP or proteins that interact with domains thereon. Lysate proteins binding to the fusion proteins can be resolved by SDS-PAGE, isolated and identified by protein sequencing or mass spectroscopy, as is known in the art.

Antibody probes are prepared by immunizing suitable mammalian hosts in appropriate immunization protocols using the peptides, polypeptides or proteins if they are of sufficient length (e.g., 4, 5, 6, 7, 8, 9, 10, 11, 12, 13, 14, 15, 20, 25, 30, 35, 40 or more consecutive amino acids the sHASEGP polypeptide or if required to enhance immunogenicity, conjugated to suitable carriers. Methods for preparing immunogenic conjugates with carriers, such as bovine serum albumin (BSA), keyhole limpet hemocyanin (KLH), or other carrier proteins are well known in the art. In some circumstances, direct conjugation using, for example, carbodiimide reagents can be effective; in other instances linking reagents such as those supplied by Pierce Chemical Co., Rockford, Ill., can be desirable to provide accessibility to the hapten. Hapten peptides can be extended at either the amino or carboxy terminus with a Cys residue or interspersed with cysteine residues, for example, to facilitate linking to a carrier.

Administration of the immunogens is conducted generally by injection over a suitable time period and with use of suitable adjuvants, as is generally understood in the art. During the immunization schedule, titers of antibodies are taken to determine adequacy of antibody formation.

Anti-peptide antibodies can be generated using synthetic peptides corresponding to, for example, the carboxy terminal amino acids of the sHASEGP.

Synthetic peptides can be as small as 1-3 amino acids in length, generally at least 4 or more amino acid residues long. The peptides can be coupled to KLH using standard methods and can be immunized into animals, such as rabbits or ungulates. Polyclonal antibodies can then be purified, for example using Actigel beads containing the covalently bound peptide.

While the polyclonal antisera produced in this way can be satisfactory for some applications, for pharmaceutical compositions, use of monoclonal preparations are generally used. Immortalized cell lines which secrete the desired monoclonal antibodies can be prepared using the standard method of Kohler et al., (Nature 256: 495-7 (1975)) or modifications which effect immortalization of lymphocytes or spleen cells, as is generally known. The immortalized cell lines secreting the desired antibodies are screened by immunoassay in which the antigen is the peptide hapten, polypeptide or protein.

When the appropriate immortalized cell culture secreting the desired antibody is identified, the cells can be cultured either in vitro or by production in vivo via ascites fluid. Of particular interest, are monoclonal antibodies that recognize the catalytic domain or activation cleavage site (region) of a sHASEGP.

The antibodies or fragments can also be produced. Regions that bind specifically to the desired regions of receptor also can be produced in the context of chimeras with multiple species origin.

Agents that are assayed in the above method can be randomly selected or rationally selected or designed.

The agents can be, as examples, peptides, small molecules, and carbohydrates. A skilled artisan can readily recognize that there is no limit as to the structural nature of the agents.

The peptide agents can be prepared using standard solid phase (or solution phase) peptide synthesis methods, as is known in the art. In addition, the DNA encoding these peptides can be synthesized using commercially available oligonucleotide synthesis instrumentation and produced recombinantly using standard recombinant production systems. The production using solid phase peptide synthesis is necessitated if non-gene-encoded amino acids are to be included.

I. Methods of Treatment sHASEGPs identified by the methods herein are used for treating or preventing abnormal accumulations of sHASEGP substrates in an animal, particularly a mammal, including a human. In one embodiment, the method includes administering to a mammal an effective amount of a sHASEGP glycoprotein, whereby the disease or disorder is treated or prevented.

In another embodiment, a sHASEGP inhibitor can be used in the treatment of an excess amount of neutral hyaluronidase activity. The mammal treated can be a human. The inhibitors provided herein are those identified by the screening assays.

In addition, antibodies and antisense nucleic acids or double-stranded RNA (dsRNA), such as RNAi, are contemplated.

1. Antisense treatment: In a specific embodiment, as described hereinabove, sHASEGP polypeptide function is reduced or inhibited by sHASEGP polypeptide antisense nucleic acids, to treat or prevent excessive chondroitinase activity. The therapeutic or prophylactic use of nucleic acids of at least six nucleotides, generally up to about 150 nucleotides, that are antisense to a gene or cDNA encoding sHASEGP polypeptide or a portion thereof is provided. A sHASEGP polypeptide "antisense" nucleic acid as used herein refers to a nucleic acid capable of hybridizing to a portion of a sHASEGP polypeptide RNA (generally mRNA) by virtue of some sequence complementarity, and generally under high stringency conditions. The antisense nucleic acid can be complementary to a coding and/or noncoding region of a sHASEGP polypeptide mRNA. Such antisense nucleic acids have utility as therapeutics that reduce or inhibit sHASEGP polypeptide function, and can be used in the treatment or prevention of disorders as described supra.

The sHASEGP polypeptide antisense nucleic acids are of at least six nucleotides and are generally oligonucleotides (ranging from 6 to about 150 nucleotides including 6 to 50 nucleotides). The antisense molecule can be complementary to all or a portion of the Hyaluronidase domain. For example, the oligonucleotide is at least 10 nucleotides, at least 15 nucleotides, preferably at least 20, 40, 80 to at least 100 nucleotides, or at least 125 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide can include other appending groups such as peptides, or agents facilitating transport across the cell membrane (see e.g., Letsinger et al., Proc. Natl. Acad. Sci. USA 86: 6553-6556 (1989); Lemaitre et al., Proc. Natl. Acad. Sci. USA 84: 648-652 (1987); PCT Publication No. WO 88/09810, published Dec. 15, 1988) or blood-brain barrier (see e.g., PCT Publication No. WO 89/10134, published Apr. 25, 1988), hybridization-triggered cleavage agents (see e.g., Krol et al., BioTechniques 6: 958-976 (1988)) or intercalating agents (see e.g., Zon. Pharm. Res. 5: 539-549 (1988)).

The sHASEGP polypeptide antisense nucleic acid generally is an oligo-nucleotide, typically single-stranded DNA or RNA or an analog thereof or mixtures thereof. For example, the oligonucleotide includes a sequence antisense to a portion of a nucleic acid that encodes a human sHASEGP polypeptide. The oligonucleotide can be modified at any position on its structure with substituents generally known in the art.

The sHASEGP polypeptide antisense oligonucleotide can include at least one modified base moiety which is selected from the group including, but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-apos-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-n-2-carboxypropyl)uracil, (ACP3) w, and 2,6-diaminopurine.

In another embodiment, the oligonucleotide includes at least one modified sugar moiety selected from the group including but not limited to arabinose, 2-fluoroarabinose, xylulose, and hexose. The oligonucleotide can include at least one modified phosphate backbone selected from a phosphorothioate, a phosphorodithioate, a phosphoramidothioate, a phosphoramidate, a phosphordiamidate, a methylphosphonate, an alkyl phosphotriester, and a formacetal or analog thereof.

The oligonucleotide can be an a-anomeric oligonucleotide. An a-anomeric oligonucleotide forms specific double-stranded hybrids with complementary RNA in which the strands run parallel to each other (Gautier et al., Nucl. Acids Res. 15: 6625-6641 (1987)).

The oligonucleotide can be conjugated to another molecule, such as, but are not limited to, a peptide; hybridization triggered cross-linking agent, transport agent or a hybridization-triggered cleavage agent. The oligonucleotides can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al., Nucl. Acids Res. 16: 3209 (1988)), methylphosphonate oligonucleotides can be prepared by use of controlled pore glass polymer supports (Sarin et al., Proc. Natl. Acad. Sci. USA 85: 7448-7451 (1988)), etc. In a specific embodiment, the sHASEGP polypeptide antisense oligonucleotide includes catalytic RNA or a ribozyme (see, e.g., PCT International Publication WO 90/11364, published Oct. 4, 1990; Sarver et al., Science 247: 1222-1225 (1990)). In another embodiment, the oligonucleotide is a 2'-O-methylribonucleotide (Inoue et al., Nucl. Acids Res. 15: 6131-6148 (1987)), or a chimeric RNA-DNA analogue Inoue et al., FEBS Lett. 215: 327-330 (1987)).

Alternatively, the oligonucleotide can be double-stranded RNA (dsRNA) such as RNAi.

In an alternative embodiment, the sHASEGP polypeptide antisense nucleic acid is produced intracellularly by transcription from an exogenous sequence.

For example, a vector can be introduced in vivo such that it is taken up by a cell, within which cell the vector or a portion thereof is transcribed, producing an antisense nucleic acid (RNA). Such a vector would contain a sequence encoding the sHASEGP polypeptide antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the sHASEGP polypeptide antisense RNA can be by any promoter known in the art to act in mammalian, including human, cells. Such promoters can be inducible or constitutive. Such promoters include but are not limited to: the SV40 early promoter region (Bernoist and Chambon, Nature 290: 304-310 (1981), the promoter contained in the 3' long terminal repeat of Rous sarcoma virus (Yamamoto et al., Ce//22: 787-797 (1980), the herpes thymidine kinase promoter (Wagner et al., Proc. Natl. Acad. Sci. USA 78: 1441-1445 (1981), the regulatory sequences of the metallothionein gene (Brinster et al., Nature 296: 39-42 (1982), etc.

The antisense nucleic acids include sequence complementary to at least a portion of an RNA transcript of a sHASEGP polypeptide gene, including a human sHASEGP polypeptide gene. Absolute complementarity is not required. The amount of sHASEGP polypeptide antisense nucleic acid that is effective in the treatment or prevention of neoplastic disease depends on the nature of the disease, and can be determined empirically by standard clinical techniques.

Where possible, it is desirable to determine the antisense cytotoxicity in cells in vitro, and then in useful animal model systems prior to testing and use in humans.

2. RNA interference RNA interference (RNAi) (see, e.g. Chuang et al. (2000) Proc. Natl. Acad. Sci. USA 97: 4985) can be employed to inhibit the expression of a gene encoding a sHASEGP. Interfering RNA (RNAi) fragments, particularly double-stranded (ds) RNAi, can be used to generate loss-of-sHASEGP function. Methods relating to the use of RNAi to silence genes in organisms including, mammals, C. elegans, Drosophila and plants, and humans are known (see, e.g., Fire et al. (1998) Nature 391: 806-811; Fire (1999) Trends Genet. 15: 358-363; Sharp (2001) Genes Dev. 15: 485-490; Hammond et al. (2001) Nature Rev, Genet. 2: 110-119; Tuschl (2001) Chem. Biochem. 2: 239-245; Hamilton et al. (1999) Science 286: 950-952; Hammond et al. (2000) Nature 404: 293-296; Zamore et al. (2000) Cell 101: 25-33; Bernstein et al. (2001) Nature 409: 363-366; Elbashir et al. (2001) Genes Dev. 15: 188-200; Elbashir et al. (2001) Nature 411: 494-498; International PCT application No. WO 01/29058; International PCT application No. WO 99/32619).

Double-stranded RNA (dsRNA)-expressing constructs are introduced into a host, such as an animal or plant using, a replicable vector that remains episomal or integrates into the genome. By selecting appropriate sequences, expression of dsRNA can interfere with accumulation of endogenous mRNA encoding a sHASEGP. RNAi also can be used to inhibit expression in vitro.

Regions include at least about 21 (or 21) nucleotides that are selective (i.e. unique) for sHASEGP are used to prepare the RNAi. Smaller fragments of about 21 nucleotides can be transformed directly (i.e., in vitro or in vivo) into cells; larger RNAi dsRNA molecules are generally introduced using vectors that encode them. dsRNA molecules are at least about 21 bp long or longer, such as 50, 100, 150, 200 and longer. Methods, reagents and protocols for introducing nucleic acid molecules into cells in vitro and in vivo are known to those of skill in the art.

3. Gene Therapy in an exemplary embodiment, nucleic acids that include a sequence of nucleotides encoding a sHASEGP polypeptide or functional domains or derivative thereof, are administered to promote sHASEGP polypeptide function, by way of gene therapy. Gene therapy refers to therapy performed by the administration of a nucleic acid to a subject. In this embodiment, the nucleic acid produces its encoded protein that mediates a therapeutic effect by promoting sHASEGP polypeptide function. Any of the methods for gene therapy available in the art can be used (see, Goldspiel et al., Clinical Pharmacy 12: 488-505 (1993); Wu and Wu, Biotherapy 3: 87-95 (1991); Tolstoshev, An. Rev. Pharmacol. Toxicol. 32: 573-596 (1993); Mulligan, Science 260: 926-932 (1993); and Morgan and Anderson, An. Rev. Biochem. 62: 191-217 (1993); TIBTECH 11 5: 155-215 (1993). For example, one therapeutic composition for gene therapy includes a sHASEGP polypeptide-encoding nucleic acid that is part of an expression vector that expresses a sHASEGP polypeptide or domain, fragment or chimeric protein thereof in a suitable host. In particular, such a nucleic acid has a promoter operably linked to the sHASEGP polypeptide coding region, the promoter being inducible or constitutive, and, optionally, tissue-specific. In another particular embodiment, a nucleic acid molecule is used in which the sHASEGP polypeptide coding sequences and any other desired sequences are flanked by regions that promote homologous recombination at a desired site in the genome, thus providing for intrachromosomal expression of the sHASEGP protein nucleic acid (Koller and Smithies, Proc. Natl. Acad. Sci. USA 86: 8932-8935 (1989); Zijlstra et al., Nature 342: 435-438 (1989)).

Delivery of the nucleic acid into a patient can be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, J. Biol. Chem., 262: 4429-4432 (1987)) (which can be used to target cell types specifically expressing the receptors), etc. In another embodiment, a nucleic acid-ligand complex can be formed in which the ligand is a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO 92/20316 dated Nov. 26, 1992 (Findeis et al.); WO 93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, Proc. Natl. Acad. Sci. USA 86: 8932-8935 (1989); Zijistra et al., Nature 342: 435-438 (1989)).

In a specific embodiment, a viral vector that contains the sHASEGP polypeptide nucleic acid is used. For example, a retroviral vector can be used (see Miller et al., Meth. Enzymol. 217: 581-599 (1993)). These retroviral vectors have been modified to delete retroviral sequences that are not necessary for packaging of the viral genome and integration into host cell DNA. The sHASEGP polypeptide nucleic acid to be used in gene therapy is cloned into the vector, which facilitates delivery of the gene into a patient. More detail about retroviral vectors can be found in Boesen et al., Biotherapy 6: 291-302 (1994), which describes the use of a retroviral vector to deliver the mdr1 gene to hematopoietic stem cells in order to make the stem cells more resistant to chemotherapy.

Other references illustrating the use of retroviral vectors in gene therapy are: Clowes et al., J. Clin. Invest. 93: 644-651 (1994); Kiem et al., Blood 83: 1467-1473 (1994); Salmons and Gunzberg, Human Gene Therapy 4: 129-141 (1993); and Grossman and Wilson, Curr. Opin. In Genetics And Devel. 3: 110-114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3: 499-503 (1993) present a review of adenovirus-based gene therapy. Bout et al., Human Gene Therapy 5: 3-10 (1994) demonstrated the use of adenovirus vectors to transfer genes to the respiratory epithelia of rhesus monkeys. Other instances of the use of adenoviruses in gene therapy can be found in Rosenfeld et al., Science 252: 431-434 (1991); Rosenfeld et al., Cell 68: 143-155 (1992); and Mastrangeli et al., J. Clin. Invest. 91: 225-234 (1993).

Adeno-associated virus (AAV) has also been proposed for use in gene therapy (Walsh et al., Proc. Soc. Exp. Biol. Med. 204: 289-300 (1993).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, Meth. Enzymol. 217: 599-618 (1993); Cohen et al., Meth. Enzymol. 217: 618-644 (1993); Cline, Pharmac. Ther. 29: 69-92 (1985)) and can be used, provided that the necessary developmental and physiological functions of the recipient cells are not disrupted. The technique should provide for the stable transfer of the nucleic acid to the cell, so that the nucleic acid is expressible by the cell and generally heritable and expressible by its cell progeny.

The resulting recombinant cells can be delivered to a patient by various methods known in the art. In an embodiment, epithelial cells are injected, e.g., subcutaneously. In another embodiment, recombinant skin cells can be applied as a skin graft onto the patient. Recombinant blood cells (e.g., hematopoietic stem or progenitor cells) can be administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., such as stem cells obtained from bone marrow, umbilical cord blood, peripheral blood, fetal liver, and other sources thereof.

For example, a cell used for gene therapy is autologous to the patient. In an embodiment in which recombinant cells are used in gene therapy, a sHASEGP polypeptide nucleic acid is introduced into the cells such that it is expressible by the cells or their progeny, and the recombinant cells are then administered in vivo for therapeutic effect. In a specific embodiment, stem or progenitor cells are used. Any stem and/or progenitor cells that can be isolated and maintained in vitro can potentially be used in accordance with this embodiment.

Such stem cells include but are not limited to hematopoietic stem cells (HSC), stem cells of epithelial tissues such as the skin and the lining of the gut, embryonic heart muscle cells, liver stem cells (PCT Publication WO 94/08598, dated Apr. 28, 1994), and neural stem cells (Stemple and Anderson, Cell 71: 973-985 (1992)).

Epithelial stem cells (ESC) or keratinocytes can be obtained from tissues such as the skin and the lining of the gut by known procedures (Rheinwald, Meth. Cell Bio. 21A: 229 (1980)). In stratified epithelial tissue such as the skin, renewal occurs by mitosis of stem cells within the germinal layer, the layer closest to the basal lamina. Stem cells within the lining of the gut provide for a rapid renewal rate of this tissue. ESC or keratinocytes obtained from the skin or lining of the gut of a patient or donor can be grown in tissue culture (Rheinwald, Meth. Cell Bio. 21A: 229 (1980); Pittelkow and Scott, Cano. Clinic Proc. 61: 771 (1986)). If the ESC are provided by a donor, a method for suppression of host versus graft reactivity (e.g., irradiation, drug or antibody administration to promote moderate immunosuppression) also can be used.

With respect to hematopoietic stem cells (HSC), any technique which provides for the isolation, propagation, and maintenance in vitro of HSC can be used in this embodiment. Techniques by which this can be accomplished include (a) the isolation and establishment of HSC cultures from bone marrow cells isolated from the future host, or a donor, or (b) the use of previously established long-term HSC cultures, which can be allergenic or xenogenic.

Non-autologous HSC generally are used with a method of suppressing transplantation immune reactions of the future host/patient. In a particular embodiment, human bone marrow cells can be obtained from the posterior iliac crest by needle aspiration (see, e.g., Kodo et al., J. Clin. Invest. 73: 1377-1384 (1984)). For example, the HSC can be made highly enriched or in substantially pure form. This enrichment can be accomplished before, during, or after long-term culturing, and can be done by any techniques known in the art. Long-term cultures of bone marrow cells can be established and maintained by using, for example, modified Dexter cell culture techniques (Dexter et al., J. Cell Physiol. 91: 335 (1977)) or Witlock-Witte culture techniques (Witlock and Witte, Proc. Natl. Acad. Sci. USA 79: 3608-3612 (1982)).

In a specific embodiment, the nucleic acid to be introduced for purposes of gene therapy includes an inducible promoter operably linked to the coding region, such that expression of the nucleic acid is controllable by controlling the presence or absence of the appropriate inducer of transcription.

4. Prodrugs—A method for treating tumors is provided. The method is practiced by administering a prodrug that is cleaved at a specific site by a HASEGP to release an active drug or precursor that can be converted to active drug in vivo. Upon contact with a cell that expresses sHASEGP activity, the prodrug is converted into an active drug. The prodrug can be a conjugate that contains the active agent, such as an anti-tumor drug, such as a cytotoxic agent, or other therapeutic agent (TA), linked to a substrate for the targeted sHASEGP, such that the drug or agent is inactive or unable to enter a cell, in the conjugate, but is activated upon cleavage. The prodrug, for example, can contain an chondroitin sulfate molecule, typically a relatively short, less than about 20 disaccharide units, that is catalytically cleaved by the targeted sHASEGP. Cytotoxic agents, include, but are not limited to, alkylating agents, antiproliferative agents and tubulin binding agents. Others include, vinca drugs, mitomycins, bleomycins and taxanes.

J. Pharmaceutical Compositions and Modes of Administration

1. Components of the Compositions

Pharmaceutical compositions containing an active sHASEGP are provided herein. Also provided are combinations of compounds that modulate the activity of a sHASEGP polypeptide and another treatment or compound for treatment of a hyaluronidase disorder, such as an antibody compound.

The sHASEGP polypeptide and a second agent can be packaged as separate compositions for administration together or sequentially or intermittently. Alternatively, they can be provided as a single composition for administration or as two compositions for administration as a single composition. The combinations can be packaged as kits.

2. Formulations and Route of Administration

The sHASEGP polypeptides and soluble human hyaluronidase domain thereof provided herein can be formulated as pharmaceutical compositions, typically for single dosage administration. The concentrations of the polypeptides in the formulations are effective for delivery of an amount, upon administration, that is effective for the intended treatment. Typically, the compositions are formulated for single dosage administration. To formulate a composition, the weight fraction of a sHASEGP polypeptide, soluble human hyaluronidase domains thereof or mixture thereof is dissolved, suspended, dispersed or otherwise mixed in a selected vehicle at an effective concentration such that the treated condition is relieved or ameliorated.

Pharmaceutical carriers or vehicles suitable for administration of the sHASEGP or soluble human hyaluronidase domains thereof provided herein include any such carriers known to those skilled in the art to be suitable for the particular mode of administration.

In addition, the polypeptides can be formulated as the sole pharmaceutically active ingredient in the composition or can be combined with other active ingredients. Liposomal suspensions, including tissue-targeted liposomes, can also be suitable as pharmaceutically acceptable carriers. These can be prepared according to methods known to those skilled in the art. For example, liposome formulations can be prepared as described in U.S. Pat. No. 4,522,811.

The active sHASEGP or soluble human hyaluronidase domain thereof is included in the pharmaceutically acceptable carrier in an amount sufficient to exert a therapeutically useful effect in the absence of undesirable side effects on the patient treated. The therapeutically effective concentration can be determined empirically by testing the polypeptides in known in vitro and in vivo systems such as by using the assays provided herein or see, e.g., Taliani et al. (1996) *Anal. Biochem.* 240: 60-67, Filocamo et al. (1997) *J. Virology* 71: 1417-1427, Sudo et al. (1996) *Antiviral Res.* 32: 9-18, Buffard et al. (1995) *Virology* 209: 52-59, Bianchi et al. (1996) *Anal. Biochem.* 237: 239-244, Hamatake et al. (1996) *Intervirology* 39:249-258, Steinkühler et al. (1998) *Biochem.* 37:8899-8905, D'Souza et al. (1995) *J. Gen. Virol.* 76:1729-1736, Takeshita et al. (1997) *Anal. Biochem.* 247: 242-246; see also, e.g., Shimizu et al. (1994) *J. Virol.* 68: 8406-8408; Mizutani et al. (1996) *J. Virol.* 70: 7219-7223, Mizutani et al. (1996) *Biochem. Biophys. Res. Commun.* 227: 822-826, Lu et al. (1996) *Proc. Natl. Acad. Sci.* (*USA*) 93: 1412-1417, Hahm et al. (1996) *Virology* 226: 318-326, Ito et al. (1996) *J. Gen. Virol.* 77: 1043-1054, Mizutani et al. (1995) *Biochem. Bio-* phys. Res. Commun. 212: 906-911, Cho et al. (1997) *J. Virol. Meth.* 65:201-207 and then extrapolated therefrom for dosages for humans.

Typically a therapeutically effective dosage is contemplated. The amounts administered can be on the order of 0.001 to 1 mg/ml, including about 0.005-0.05 mg/ml and about 0.01 mg/ml, of blood volume. Pharmaceutical dosage unit forms are prepared to provide from about 1 mg to about 1000 mg, including from about 10 to about 500 mg, and including about 25-75 mg of the essential active ingredient or a combination of essential ingredients per dosage unit form. The precise dosage can be empirically determined.

In some instances, a high Unit dose of human sHASEGP is preferable. For example, with intravenous administration of sHASEGP concentrations of sHASEGP from 500-100,000 Units per ml are preferable. Lyophilized formulations of sHASEGP are also ideal for storage of large Unit doses of sHASEGP. 200,000 Unit lyophilized vials of sHASEGP are contemplated for intravenous delivery.

High concentration doses are also contemplated for the delivery of small volumes of sHASEGP. Administration of 10-100 ul of 5000 Units/ml sHASEGP is contemplated for injection in the anterior chamber to dissolve pre administered viscoelastic substances during cataract and phakic intraocular lens implantation surgeries. Small volume injections of 50-200 U/ml doses are also contemplated for intravitreal procedures such as the treatment of vitreous hemorrhage or vitro-retinal detachment in diabetic retinopathy.

Somewhat larger volume injections (e.g. between about one to several ml, or more) are contemplated for somewhat larger and/or more readily drained spaces within the body. For example, as illustrated herein, periorbital injections of one to several ml or more can be made into one or more spaces surrounding the eye, e.g. by injection into the sub-Tenon's or episcleral space, in order to promote the transcleral delivery of pharmacologic agents to tissues at the back of the eye such as the choroid plexus and/or retina. As will be appreciated by those of skill in the art, some spaces within the body can readily accommodate larger volumes. By way of illustration, the episcleral or sub-Tenon's space around the eye can readily accommodate one to several ml or even larger volumes (e.g. up to or greater than 5 to 10 ml, depending for example on the characteristics of the particular tissue and the rate at which the volume is delivered).

In addition, as described and illustrated herein, it appears that the introduction of a sHASEGP (potentially in combination with one or more additional pharmacologic or other agents) in a larger volume can be used to further drive delivery of agents to desired target sites within the body. Without being restricted to a particular mechanism of action, it is believed that such larger volume injections can further drive permeation or spreading of both sHASEGP as well as other agent(s) present in the treated tissue by a process of convective transport that is promoted by an increased pressure differential. Again, without wishing to be restricted to a particular mechanism of action, it is believed that such an increased pressure differential can be brought about in the context of the present invention by, inter alia, one or both of the following: (i) an elevated driving pressure or elevated "pressure head" (e.g. caused by increased hydrostatic pressure associated with an injection that largely fills or somewhat overfills or distends a space or site of injection); and (ii) a reduced downstream pressure or reduced "impedance" (e.g. caused by the opening of channels in the interstitial matrix associated with localized hyaluronidase activity and consequent degradation of relatively hydrated hyaluronan). Preferred hyaluronidases for use in this and other applications of the present invention (such as facilitating the delivery pharmacologic and other agents) are sHASEGPs, particularly human sHASEGPs in the context of delivery of agents to one or more tissues in the human body. However, these and other approaches to the use and application of hyaluronidases can also be applied using non-human sHASEGPs, such as mammalian sHASEGPs, as well other human or mammalian hyaluronidases, preferably soluble forms of such hyaluronidases.

The active ingredient can be administered at once, or can be divided into a number of smaller doses to be administered at intervals of time. It is understood that the precise dosage and duration of treatment is a function of the disease being treated and can be determined empirically using known testing protocols or by extrapolation from in vivo or in vitro test data. It is to be noted that concentrations and dosage values can also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or use of the claimed compositions and combinations containing them.

Pharmaceutically acceptable derivatives include acids, salts, esters, hydrates, solvates and prodrug forms. The derivative is typically selected such that its pharmacokinetic properties are superior to the corresponding neutral sHASEGP or soluble human hyaluronidase domain thereof.

Thus, effective concentrations or amounts of one or more of the polypeptides herein or pharmaceutically acceptable derivatives thereof are mixed with a suitable pharmaceutical carrier or vehicle for systemic, topical or local administration to form pharmaceutical compositions. sHASEGP polypeptides or soluble human hyaluronidase domains thereof are included in an amount effective for ameliorating or treating the disorder for which treatment is contemplated. The concentration of active polypeptide in the composition depends on absorption, inactivation, excretion rates of the active polypeptide, the dosage schedule, amount administered, particular formulation as well as other factors known to those of skill in the art.

The therapeutic agents for use in the methods can be administered by any route known to those of skill in the art, such as, but are not limited to, topically, intraarticularly, intracisternally, intraocularly, peri-orbitally, intraventricularly, intrathecally, intravenously, intraarterially, intramuscularly, intraperitoneally, intradermally, subcutaneously, intratracheally, as well as by any combination of any two or more thereof. Dry powder pulmonary formulations can be envisioned as well.

The most suitable route for administration will vary depending upon the proposed use, such as, for example, use as a delivery agent to facilitate subcutaneous delivery of fluids, use to reduce intraocular pressure in the eyes of glaucoma patients receiving viscoelastics or use as a "spreading agent" to enhance the activity of chemotherapeutics, and the location of interest, such as a particular internal organ, a tumor growth, intraocular cavity and the epidermis. Modes of administration include, but are not limited to, topically, locally, intraarticularly, intracisternally, intraocularly, peri-orbitally, intraventricularly, intrathecally, intravenously, intramuscularly, intratracheally, intraperitoneally, intradermally, subcutaneously, and by a combination of any two or more thereof. For example, for treatment of various cancers, such as squamous cell carcinoma, breast cancer, urinary bladder cancer and gastrointestinal cancer, local administration, including administration to the site of the tumor growth (e.g., intrathecally, intraventricularly, or intracisternally) provides the advantage that the therapeutic agent can be administered in a high concentration without risk of the complications that can accompany systemic administration of a therapeutic agent.

As an exemplary class of pharmacologic agents that can be combined with sHASEGPs (or other glycosaminoglycanases) (e.g. combined by co-formulation with one or more sHASEGPs or by co-administration with one or more sHASEGPs (which may be administered prior to, coincident with or following administration of the agent)), a number of agents having effectiveness or potential effectiveness in the treatment of various cancers have been described in the art, and novel anti-cancer agents are regularly being developed which may likewise be combined with one or more sHASEGPs (e.g. provided by co-formulation or by co-administration before, coincident with and/or following administration of the agent) to improve the pharmacokinetics, pharacodynamics or other useful properties of the agent.

By way of illustration (and without limitation) a number of anti-cancer or chemotherapeutic agents have now been approved for the treatment of various cancers which can be combined with sHASEGPs (or other glycosaminoglycanases) by co-formulation or co-administration (before, coincident with or after administration of the anti-cancer agent). Such agents include, for example, Aldesleukins (e.g. PROLEUKIN™); Alemtuzumabs (e.g. CAMPATH™); Aliteretinoins (e.g. PANRETIN™); Allopurinols (e.g. ZYLOPRIM™); Altretamines (e.g. HEXALEN™); Amifostines (e.g. ETHYOL™); Anastrozoles (e.g. ARIMIDEX™); Arsenic Trioxides (e.g. TRISENOX™); Asparaginases (e.g. ELSPAR™); BCG Live (e.g. TICE™ BCG); Bexarotenes (e.g. TARGRETIN™); Bleomycins (e.g. BLENOXANE™); Busulfan intravenous (e.g. BUSULFEX™); Busulfan orals (e.g. MYLERAN™); Calusterones (e.g. METHOSARB™); Capecitabines (e.g. XELODA™); Carboplatins (e.g. PARAPLATINT™); Carmustines (e.g. BCNU™, BiCNU™); Carmustines with Polifeprosans (e.g. GLIADEL™ Wafer); Celecoxibs (e.g. CELEBREX™); Chlorambucils (e.g. LEUKERAN™); Cisplatins (e.g. PLATINOL™); Cladribines (e.g. LEUSTATIN™, 2-CdA™); Cyclophosphamides (e.g. CYTOXAN™, NEOSAR™); Cytarabines (e.g. CYTOSAR-U™); Cytarabine liposomals (e.g. DepoCyt™); Dacarbazines (e.g. DTIC-Dome™); Dactinomycins (e.g. COSMEGEN™); Darbepoetin Alphas (e.g. ARANESP™); Daunorubicin liposomals (e.g. DANUOXOME™); Daunorubicins/Daunomycins (e.g. CERUBIDINE™); Denileukin Diftitoxes (e.g. ONTAK™); Dexrazoxanes (e.g. ZINECARD™); Docetaxels (e.g. TAXOTERE™); Doxorubicins (e.g. ADRIAMYCIN,™ RUBEX™); Doxorubicin liposomals (e.g. DOXIL™); Dromostanolone propionates (e.g. DROMOSTANOLONE™ and MASTERONE™ Injection); Elliott's B Solutions (e.g. Elliott's B Solution™); Epirubicins (e.g. ELLENCE™); Epoetin alphas (e.g. EPOGEN™); Estramustines (e.g. EMCYT™); Etoposide phosphates (e.g. ETOPOPHOS™); Etoposide VP-16s (e.g. VEPESID™); Exemestanes (e.g. AROMASIN™); Filgrastims (e.g. NEUPOGEN™); Floxuridines (e.g. FUDR™); Fludarabines (e.g. FLUDARA™); Fluorouracils incl. 5-FUs (e.g. ADRUCIL)™; Fulvestrants (e.g. FASLODEX™); Gemcitabines (e.g. GEMZAR™); Gemtuzumabs/Ozogamicins (e.g. MYLOTARG™); Goserelin acetates (e.g. ZOLADEX™); Hydroxyureas (e.g. HYDREA™); Ibritumomabs/Tiuxetans (e.g. ZEVALIN™); Idarubicins (e.g. IDAMYCIN™); Ifosfamides (e.g. IFEX™); Imatinib mesylates (e.g. GLEEVEC™); Interferon alpha-2 as (e.g. ROFERON-A™); Interferon alpha-2bs (e.g. INTRON A™; Irinotecans (e.g. CAMPTOSAR™); Letrozoles (e.g. FEMARA™); Leucovorins (e.g. WELLCOVORIN™, LEUCOVORIN™); Levamisoles (e.g. ERGAMISOL™); Lomustines/CCNUs (e.g. CeeBU™); Meclorethamines/Nitrogen mustards (e.g. MUSTARGEN™); Megestrol acetates (e.g. MEGACE™); Melphalans/L-PAMs (e.g. ALKERAN™); Mercaptopurine incl. 6-MPs (e.g. PURINETHOL™); Mesnas (e.g. MESNEX™); Methotrexates; Methoxsalens (e.g. UVADEX™); Mitomycin Cs (e.g. MUTAMYCIN™, MITOZYTREX™); Mitotanes (e.g. LYSODREN)™; Mitoxantrones (e.g. NOVANTRONE™); Nandrolone Phenpropionates (e.g. DURABOLIN-50™); Nofetumomabs (e.g. VERLUMA™); Oprelvekins (e.g. NEUMEGA™); Oxaliplatins (e.g. ELOXATIN™); Paclitaxels (e.g. PAXENE™, TAXOL™); Pamidronates (e.g. AREDIA™); Pegademases (e.g. ADAGEN™); Pegaspargases (e.g. ONCASPAR™); Pegfilgrastims (e.g. NEULASTA™); Pentostatins (e.g. NIPENT™); Pipobromans (e.g. VERCYTE)™; Plicamycin/Mithramycins (e.g. MITHRACIN™); Porfimer sodiums (e.g. PHOTOFRIN™); Procarbazines (e.g. MATULANE™); Quinacrines (e.g. ATABRINE™); Rasburicases (e.g. ELITEKT™); Rituximabs (e.g. RITUXANT™); Sargramostims (e.g. PROKINE™); Streptozocins (e.g. ZANOSAR™); Talcs (e.g. SCLEROSOL™); Tamoxifens (e.g. NOLVADEX)™; Temozolomides (e.g. TEMODAR™); Teniposides/VM-26s (e.g. VUMON™); Testolactones (e.g. TESLAC™); Thioguanines incl. 6-TG; Thiotepas (e.g. THIOPLEX™); Topotecans (e.g. HYCAMTIN™); Toremifenes (e.g. FARESTON™); Tositumomabs (e.g. BEXXAR™); Trastuzumabs (e.g. HERCEPTIN)™; Tretinoins/ATRA (e.g. VESANOID™); Uracil Mustards; Valrubicins (e.g. VAILSTAR™); Vinblastines (e.g. VELBAN)™; Vincristines (e.g. ONCOVIN™); Vinorelbines (e.g. NAVELBINE™); Zoledronates (e.g. ZOMETA™); as well as other agents described herein and in the art.

As with other classes of pharmacologic agents described herein, a sHASEGP (or other glycosaminoglycanase) may be used in conjunction with the administration of (or co-formulated with) an individual pharmacologic agent (such as an antineoplastic for purposes of illustration, or with a member of another class of agents as described herein and/or known in the art). Alternatively, a sHASEGP (or other glycosaminoglycanase) may be used in conjunction with the administration of (or co-formulated with) more than one pharmacologic agent of a given class (such as multiple antineoplastic agents for purposes of illustration, or multiple members of other classes of agents as described herein and/or known in the art). In the case of combinations with two or more agents of a given class, it is often preferred that the two or more agents act by two or more different mechanisms of action. A sHASEGP (or other glycosaminoglycanase) may also be used in conjunction with the administration of (or co-formulated with) one pharmacologic agent of a first given class (such as an antineoplastic for purposes of illustration, or a member of one of the other classes of agents as described herein and/or known in the art), and one or more additional pharmacologic agents of one or more different classes that are useful for treating any of a variety of conditions. While certain principles are thus referred to here in the case of anticancer agents for purposes of illustration, these principles are also applicable to, for example, anti-infectives and the numerous members of other classes of agents that are described and illustrated herein, as well as additional agents that are already known in the art or are newly developed.

In the case of any of the combinations and/or co-formulations described herein (comprising at least one sHASEGP (or other glycosaminoglycanase) and at least one other agent (such as a pharmacologic agent, e.g., a member of one of the classes of agents illustrated herein)), it is also contemplated that such combination and/or co-formulation can further comprise one or more agents (such as various stabilizers, excipients and the like) which do not themselves exert substantial pharmacodynamic effects but which promote the usefulness of the combination and/or co-formulation (e.g. by stabilizing one or more of the components or an entire formulation, by helping to promote or target the activity of one or more of the agents or of the sHASEGP, and/or by reducing toxicity or otherwise improving the safety profile of the combination or co-formulation.

As will be appreciated by those of skill in the art, new versions and formulations of these and other anti-cancer agents (as well as members of other classes of agents as described herein) are regularly being developed that can likewise be combined with sHASEGPs (or other glycosaminoglycanases). Furthermore, since such enzymes can be used to improve pharmacokinetic and/or pharmacodynamic profiles of a large variety of agents, and allow agents to be delivered by different (and potentially more targeted) routes, for example, sHASEGPs (or other glycosaminoglycanases) can be used to enhance the PK and/or PD profiles of a number of agents previously considered to have sub-optimal profiles. Testing of agents in appropriate animal models with and without concomitant sHASEGP can be used to assess the relative effectiveness and toxicity of particular agents.

As illustrated and exemplified herein, a number of large molecule agents (such as antibodies and other proteins, particularly those administered by non-IV parenteral injection), exhibit relatively poor pharmacokinetic profiles and can be particularly enhanced by co-formulation or co-administration with sHASEGPs (or other glycosaminoglycanases). Without being restricted to a particular mechanism of action, it is generally considered that small molecule agents exhibiting relatively low hydrophobicity are more effectively dispersable by, e.g., convective transport within interstitial fluids as can be promoted by sHASEGPs (or other glycosaminoglycanases). A commonly used method for predicting such attributes is to assess the calculated and/or estimate octanol: water partition coefficients ($K_{ow}$) which have been reported for a number of compounds. In that regard, agents exhibiting log $K_{ow}$ of <3, more preferably <2 or <1, more preferably <0, still more preferably <(−1). As will be appreciated by those of skill in the art, many agents can also be modified covalently and/or non-covalently to increase their hydrophilicity, and/or to encompass such agents within vessicles or macromolecular complexes to facilitate their permeation and/or delivery.

For purposes of further illustration (and without limitation), exemplary anti-cancer or chemotherapeutic pharmacologic agents that can be combined with sHASEGPs (or other glycosaminoglycanases) are included in the following list (and others are known in the art): Acivicins; Aclarubicins; Acodazoles; Acronines; Adozelesins; Aldesleukins; Aliterninoins (9-Cis-Retinoic Acids); Altretamines; Alvocidibs; Ambazones; Ambomycins; Ametantrones; Aminoglutethimides; Amsacrines; Anastrozoles; Anaxirones; Ancitabines; Anthramycins; Apaziquones; Argimesnas; Asparaginases; Asperlins; Atrimustines; Azacitidines; Azetepas; Azotomycins; Banoxantrones; Batabulins; Batimastats; Benaxibines; Bendamustines; Benzodepas; Bexarotenes; Bicalutamides; Bietaserpines; Biricodars; Bisantrenes; Bisantrenes; Bisnafide Dimesylates; Bizelesins; Bleomycins; Bortezomibs; Brequinars; Bropirimines; Budotitanes; Busulfans; Cactinomycins; Calusterones; Canertinibs; Capecitabines; Caracemides; Carbetimers; Carboplatins; Carboquones; Carmofurs; Carmustines; Carubicins; Carzelesins; Cedefingols; Cemadotins; Chlorambucils; Cioteronels; Cirolemycins; Cisplatins; Cladribines; Clanfenurs; Clofarabines; Crisnatols; Cyclophosphamides; Cytarabines; Dacarbazines; Dactinomycins; Daunorubicins; Decitabines; Dexniguldipines; Dexormaplatins; Dezaguanines; Diaziquones; Dibrospidiums; Dienogests; Dinalins; Disermolides; Docetaxels; Dofequidars; Doxifluridines; Doxorubicins; Droloxifenes; Dromostanolone Propionates; Duazomycins; Ecomustines; Edatrexates; Edotecarins; Eflornithines; Elacridars; Elinafides; Elsamitrucins; Emitefurs; Enloplatins; Enpromates; Enzastaurins; Epipropidines; Epirubicins; Eptaloprosts; Erbulozoles; Esorubicins; Estramustines; Etanidazoles; Etoglucids; Etoposides; Etoprines; Exisulinds; Fadrozoles; Fazarabines; Fenretinides; Floxuridines; Fludarabines; Fluorouracils; Fluoxymesterones; Fluorocitabines; Fosquidones; Fostriecins; Fostriecins; Fotretamines; Galarubicins; Galocitabines; Gemcitabines; Geroquinols; Gimatecans; Gimeracils; Gloxazones; Glufosfamides; Hydroxyureas; Idarubicins; Ifosfamides; Ilmofosines; Ilomastats; Imexons; Improsulfans; Indisulams; Inproquones; Interferons; Interferon Alphas; Interferon Betas; Interferon Gammas; Interleukin-2s and other Interleukins (including recombinant Interleukins); Intoplicines; Iobenguanes [113-I]; Iproplatins; Irinotecans; Irsogladines; Ixabepilones; Ketotrexates; L-Alanosines; Lanreotides; Lapatinibs; Ledoxantrones; Letrozoles; Leuprolides; Leuprorelins (Leuprorelides); Lexacalcitols; Liarozoles; Lobaplatins; Lometerxols; Lomustines; Lonafamibs; Losoxantrones; Lurtotecans; Mafosfamides; Mannosulfans; Marimastats; Masoprocols; Maytansines; Mechlorethamines; Megestrols; Melengestrols; Melphalans; Menogarils; Mepitiostanes; Mercaptopurines; Metesinds; Methotrexates; Metomidates; Metoprines; Meturedepas; Miboplatins; Miproxifenes; Misonidazoles; Mitindomides; Mitocarcins; Mitocromins; Mitoflaxones; Mitogillins; Mitoguazones; Mitomalcins; Mitomycins; Mitonafides; Mitoquidones; Mitospers; Mitotanes; Mitoxantrones; Mitozolom ides; Mivobulins; Mizoribines; Mofarotenes; Mopidamols; Mubritinibs; Mycophenolic Acids; Nedaplatins; Nelzarabines; Nemorubicins; Nitracrines; Nocodazoles; Nogalamycins; Nolatrexeds; Nortopixantrones; Octreotides; Ormaplatins; Ortataxels; Oteracils; Oxisurans; Oxophenarsines; Paclitaxels; Pamidronates; Patubilones; Pegaspargases; Peldesines; Peliomycins; Peliterxols; Pemeterxeds; Pentamustines; Peplomycins; Perfosfamides; Perifosines; Picoplatins; Pinafides; Pipobromans; Piposulfans; Pirfenidones; Piroxantrones; Pixantrones; Plevitrexeds; Plicamycins; Plomestanes; Plomestanes; Porfimers; Porfiromycins; Prednimustines; Procarbazines; Propamidines; Prospidiums; Pumitepas; Puromycins; Pyrazofurins; Ranimustines; Riboprines; Ritrosulfans; Rogletimides; Roquinimexs; Rufocromomycins; Sabarubicins; Safingols; Satraplatins; Sebriplatins; Semustines; Simtrazenes; Sizofurans; Sobuzoxanes; Sorafenibs; Sparfosates; Sparfosic Acids; Sparsomycins; Spirogermaniums; Spiromustines; Spiroplatins; Spiroplatins; Squalamines; Streptonigrins; Streptovarycins; Streptozocins; Sufosfamides; Sulofenurs; Tacedinalines; Talisomycins; Tallimustines; Tariquidars; Tauromustines; Tecogalans; Tegafurs; Teloxantrones; Temoporfins; Teniposides; Teroxirones; Testolactones; Thiamiprines; Thioguanines; Thiotepas; Tiamiprines; Tiazofurins; Tilomisoles; Tilorones; Timcodars; Timonacics; Tirapazamines; Topixantrones; Toremifenes; Trabectedins (Ecteinascidin 743); Trastuzumabs; Trestolones; Triciribines; Triciribines; Trilostanes; Trimeterxates; Triplatin Tetranitrates; Triptorelins; Trofosfamides; Tubulozoles; Ubenimexs; Uracil Mustards; Uredepas; Valspodars; Vapreotides; Verteporfins; Vinblastines; Vincristines; Vindesines; Vinepidines; Vinflunines; Vinformides;

Vinglycinates; Vinleucinols; Vinleurosines; Vinorelbines; Vinrosidines; Vintriptols; Vinzolidines; Vorozoles; Xanthomycin A's (Guamecyclines); Zeniplatins; Zilascorbs [2-H]; Zinostatins; Zorubicins; Zosuquidars; and the like.

Pharmaceutical and cosmetic carriers or vehicles suitable for administration of the sHASEGP polypeptides or soluble human hyaluronidase domain thereof provided herein include any such carriers known to those skilled in the art to be suitable for the particular mode of administration. In addition, the polypeptides can be formulated as the sole pharmaceutically active ingredient in the composition or can be combined with other active ingredients that do not impair the desired action, or with materials that supplement the desired action known to those of skill in the art. For example, the sHASEGP polypeptides provided herein can be used as a delivery or "spreading" agent in combination with a second active compound, such as a therapeutically effective agent, including, but not limited to a drug or a prodrug, to facilitate delivery of or to enhance the activity of the second active ingredient. In a particular embodiment, a sHASEGP polypeptide or a soluble human hyaluronidase domain thereof can be co-formulated or co-administered with an anesthetic agent, such as Lignocaine, Bupivicaine or a mixture of the two, and, optionally, a hormonal agent, such as epinephrine, to decrease or stop blood uptake during ophthalmic surgery. In another particular embodiment, a sHASEGP polypeptide or a soluble human hyaluronidase domain thereof can be co-formulated or co-administered with a pharmacologic agent such as an anti-inflammatory agent to enhance the delivery of the pharmacologic to mammalian tissues in vivo (e.g. to portions of the eye) where such agent is desired for treating a particular condition. By co-administration is intended the administration of sHASEGP (or other glycosaminoglycanase) together with or in close temporal proximity to the administration of a pharmacologic agent. Typically it is preferred that the sHASEGP (or other glycosaminoglycanase) be administered shortly before (e.g. 5 to 60 minutes before) or, for maximal convenience, together with the pharmacologic agent. As will be appreciated by those of skill in the art, the desired proximity of co-administration depends in significant part on the effective half lives of the agents in the particular tissue setting, and the particular disease being treated, and can be readily optimized by testing the effects of administering the agents at varying times in suitable models, such as in suitable animal models. In some situations, the optimal timing of administration of the sHASEGP (or other glycosaminoglycanase) will exceed 60 minutes. By way of illustration and without wishing to be bound by theory, in some tumor situations for example the maximal entry of chemotherapeutic agent into the tumor may occur after the degradation of hyaluronan in the tumor is substantially complete so as to reduce tumor interstitial volume, which is followed by a hyaluronan-regenerative phase during which fluid is drawn back into the tumor resulting in increased adsorption of a chemotherapeutic agent from plasma. In the latter case, optimal administration of sHASEGP (or other glycosaminoglycanase) may be obtained between about one to twenty hours prior to administration of the pharmacologic agent. In order to optimize the timing of pre-administration relative to pharmacologic agent for a particular combination of disease condition and pharmacologic agent, one of skill can conduct a routine time course of pre-administration, typically comparing one or several time points of an hour or less with one or several timepoints of greater than hour (but typically not exceeding a day) in order to optimize the timing of administration. A sHASEGP polypeptide or a soluble human hyaluronidase domain thereof can also be co-formulated or co-administered with various chemotherapeutics, such as a toxin and a tumor necrosis factor, to enhance the activity of the chemotherapeutic and/or the accessibility of the target tumors to the chemotherapeutic. The active compound is included in the carrier in an amount sufficient to exert a therapeutically useful effect in the absence of serious toxic effects on the treated individual. The effective concentration can be determined empirically by testing the compounds using in vitro and in vivo systems, including the animal models described herein.

In the case of pharmacologic agents that are delivered by parenteral administration (i.e. by routes other than through the digestive tract, such as by subcutaneous, intradermal, intramuscular or intravenous routes for example), sHASEGPs (or other glycosaminoglycanases) can be readily co-formulated with or co-administered with any of a variety of such pharmacologic agents to enhance their delivery to desired sites within the body. For example, depending on the particular combination of pharmacologic agent and route of administration, delivery can be enhanced by increasing the extent (and/or rate) at which the agent diffuses through a tissue at or near the site of delivery (e.g. following its injection) and/or the extent (and/or rate) at which the agent diffuses and/or is carried by convective transport through a target tissue (e.g. following its release from the bloodstream, lymph, cerebrospinal fluid or other fluid system). The extent by which delivery is enhanced can be readily evaluated, for example, in animal model systems in which the addition of a sHASEGP results in a measurable increase in the bioavailability of the agent in tissues of interest within the body.

Without wishing to be bound by theory, it is believed that in the case of non-intravenous parenterals (such as subcutaneous, intradermal and intramuscular injectables), the presence of sHASEGP (or other glycosaminoglycanase) in the vicinity of an injection site and in "downstream" sites such as those between an injection site and a distal vascular bed, can enhance the diffusion and/or convective transport of the agent into a delivery system such as the vasculature. Enhanced delivery in such a situation can be associated with an increase in the amount of the agent that effectively passes through and out of the initial delivery site (potentially by both increasing the volume and rate of bulk fluid flow).

In the case of many pharmacologic agents, which are subject to degradation, removal or other forms of inactivation in tissues, increasing the rate of its passage through a tissue can in turn substantially increase the amount of effective agent that transits through the tissue, further increasing its bioavailability. For both non-intravenously-administered parenterals that subsequently enter the bloodstream or other conduit, as well agents delivered directly into the conduit vessels (such as by intravenous administration, IV), the ability of the agent to diffuse through a tissue supplied by the conduit can also be enhanced by the presence of sHASEGP in the tissue. Whether sHASEGP is present in the "delivery tissue" such as in the former case, and/or in the "target tissue" as in the latter case, the presence of sHASEGP can thus enhance the effective extent and/or rate of delivery of the pharmacologic to target tissues within the body. In either case, the sHASEGP can be used to increase the effective bioavailability of a pharmacologic agent with which it has been co-formulated or co-administered. As a result, the sHASEGP can be used to achieve elevated and/or more rapidly achieved concentrations of the agent to provide, for example, a more potent and/or more rapid response for a given dose. Alternatively, the sHASEGP can be used to allow a given response to be achieved with a lower dose of administered agent, for example. The ability of a sHASEGP (or other glycosaminoglycanase) to enhance bulk fluid flow at and near a site of injection can also improve other aspects of associated pharmacologic delivery. For example, the increase in bulk fluid flow can help to allow the volume of fluid injected to be more readily dispersed from the site of injection (reducing potentially painful or other adverse consequences of injection). Indeed, it has long been recognized that such adverse sensations associated with non-IV parenteral injections are a key reason that patients may resist or avoid non-IV parenteral administration (which may effectively require a product to be administered intravenously when it might otherwise be given more conveniently and/or safely through a non-IV route).

In using a sHASEGP (or other glycosaminoglycanase) of the present invention to enhance delivery of one or more pharmacologic or other agents in the body (a use that is sometimes referred to as "spreading"), the sHASEGP (or other glycosaminoglycanase) itself may be administered by the same route as is the pharmacologic agent (in which case it may be co-formulated or otherwise co-administered together with the pharmacologic agent or it may be administered separately, preferably in advance of the pharmacologic agent as discussed above. Alternatively, or in addition, the sHASEGP (or other glycosaminoglycanase) may be administered by a different route of administration. For example, the pharmacologic agent may be introduced locally by non-IV parenteral injection and the sHASEGP may be introduced intravenously. As another illustrative and non-limiting example, the sHASEGP may be introduced locally by non-IV parenteral injection (in a tissue that is desired to be targeted by the pharmacologic agent) and the pharmacologic agent itself may be introduced by another route, such as intravenous, non-parenteral (e.g. oral) or other route. As will thus be appreciated by those of skill in the art, sHASEGPs of the present invention can be used to enhance the delivery and bioavailability of a variety of pharmacologic and other agents including agents that are typically delivered by parenteral as well as non-parental routes.

For example, sHASEGPs (or other glycosaminoglycanases) can be co-formulated or co-administered with a variety of pharmacologic agents that are typically administered by parenteral delivery, e.g. to enhance their effectiveness and/or to improve their risk/benefit profile in treating disease.

By way of illustration of the variety of pharmacologic agents that can be parenterally-administered and their delivery and/or bioavailability enhanced through co-formulation and/or co-administration with sHASEGPs (or other glycosaminoglycanases) of the present invention, the following list is not exhaustive (and is thus not intended to be limiting) but simply to provide exemplary agents: Adalimumabs (e.g. HUMIRA™), Agalsidase Betas (e.g. FABRAZYME™), Aldesleukins (PROLEUKIN™ IL-2), Alefacepts (e.g. AMEVIVE™), Ampicillins (e.g. UNASYN™ Injection), Anakinras (e.g. KINERE™), Antipoliomyelitic Vaccines (e.g. PEDIARIX™), Anti-Thymocytes (e.g. THYMOGLOBULIN™), Azithromycins (e.g. ZITHROMAX™ IV), Becaplermins (e.g. REGRANEX™), Caspofungins (e.g. CANCIDAS™), Cefazolins (e.g. ANCEF™ and CEFAZOLIN™), Cefepimes (e.g. MAXIPIME™), Cefotetans (e.g. CEFOTAN™), Ceftazidimes (e.g. FORTAZ™), Ceftriaxones (e.g. ROCEFIN™), Cetuximabs (e.g. ERBITUX™), Cilastatins (e.g. PRIMAXIN™ IV), Clavulanic Acids (e.g. in conjunction with Amoxicillins such as in AUGMENTIN™), Clindamycins (e.g. CLEOCIN™), Darbepoetin Alphas (e.g. ARANESP™), Deaclizumabs (e.g. ZENAPAX™), Diphtheria Toxoids (typically in combinations e.g. DAPTACEL™, INFANRIX™ and PEDIARIX™), Efalizumabs (e.g. RAPTIVA™), Epinephrines (e.g. EPIPEN™), Erythropoietin Alphas (e.g. EPOGEN™ And PROCRIT™), Etanercepts (e.g. ENBREL™), Filgrastims (e.g. NEUPOGEN™), Fluconazoles (e.g. DIFLUCAN™ Injection), Follicle-Stimulating Hormones such as Follitropin Alphas (e.g. GONAL-F™) and Follitropin Betas (e.g. FOLLISTIM™), Fosphenyloins (e.g. CEREBYX™), Fluconazoles (e.g. DIFLUCAN™), Gadodiamides (e.g. OMNISCAN™), Gadopentetates (e.g. MAGNEVIST™), Gatifloxacins (e.g. TEQUIN™), Glatiramers (e.g. COPAXONE™), GM-CSF's (e.g. LEUKINE™), Goserelins (e.g. ZOLADEX™), Granisetrons (e.g. KYTRIL™), *Haemophilus Influenza* B's (e.g. COMVAX™ and HibTITERT™), Haloperidols (e.g. HALDOL™), Hepatitis A Vaccines (e.g. HAVRIX™, TWINRIX™ and VAQTA™), Hepatitis B Vaccines (e.g. recombinants COMVAX™, ENGERIX™-B, RECOMBIVAX™-HB, TWINRIX™, and non-recombinants BAYHEP™-B and NABI™-HB), Ibritumomab Tiuxetans (e.g. ZEVALIN™), Immunoglobulins, Influenza Virus Vaccines (e.g. FLUMIST™), Infliximabs (e.g. REMICADE™), Insulins (e.g. HUMALOG™, HUMALOG™ MIX 75/25™, HUMULIN™ products (incl. 50/50, 70/30, Regular, NPH, Ultra and Ultralente), and NOVOLIN™), Insulin Glargines (e.g. LANTUS™), Interferon Alpha-2a's (ROFERAN™-A), Interferon Alpha-2b's (e.g. INTRON-A™), Interferon Alphacon-1's (e.g. INFERGEN™), Interferon Alpha-n3s (e.g. ALFERON N™), Interferon Betas (e.g. BETASERON™ And BETAFERON™), Interferon Beta-1a's (e.g. AVONEX™ And REBIFT™), Interferon Gammas (e.g. ACTIMMUNET™), Iodixanols (e.g. VISIPAQUE™), Iohexyls (OMNIPAQUE™), Iopamidols, Ioversols (e.g. OPTIRAY™), Ketorolacs (e.g. TORADOL™), Laronidases (e.g. ALDURAZYMET™), Levofloxacins (e.g. LEVAQUIN™), Lidocaines, Linezolids (e.g. ZYVOX™), Lorazepams (e.g. ATIVAN™), Measles Vaccines (e.g. ATTENUVAX™), Measles-Mumps-Rubella Virus Vaccines (e.g. M-M-R™ II), Medroxyprogesterones (e.g. DEPO-PROVERA™), Meropenems (e.g. MERREM™ IV), Methylprednisolones (e.g. SOLU-MEDROL™), Midazolams (e.g. VERSED™), Morphines (e.g. ASTRAMORPH/PF™), Octreotides (e.g. SANDOSTATIN™), Omalizumabs (e.g. XOLAIR™), Ondansetrons (e.g. ZOFRAN™), Palivizumabs (e.g. SYNAGIS™), Pantoprazoles (e.g. PROTONIX™), Pegaspargases (e.g. ONCASPAR™), Pegfilgrastims (e.g. NEULASTA™), Peg-Interferon Alpha-2a's (e.g. PEGASYS™), Peg-Interferon Alpha-2b's (e.g. PEG-INTRON™), Pegvisomants (e.g. SOMAVER™), Pertussis vaccines, Piperacillins (e.g. ZOSYN™), Pneumococcal Vaccines (e.g. PNEUMOVAX™ 23) and Pneumococcal Conjugate Vaccines (e.g. PREVNAR™), Promethazines (e.g. PHENERGAN™), Reteplases (e.g. RETAVASE™), Somatropins (e.g. GENOTROPIN™, HUMATROPE™, NORDITROPIN™, NUTROPIN™, SAIZEN™, SEROSTIM™, ZORBTIVE™), Sulbactams, Sumatriptans (e.g. IMITREX™), Tazobactams, Tenecteplases (e.g. TNKASE™), Tetanus Purified Toxoids, Ticarcillins (e.g. TIMENTIN™), Tositumomabs (e.g. BEXXAR™), Triamcinolone Acetonides, Vancomycins (e.g. VANCOCIN™), Varicella vaccines (e.g. VARIVAX™) as well as other vaccines; and the like.

As described and illustrated herein, pharmacologic agents of a number of different classes and routes of administration can be benefited by co-administration and/or co-formulation with sHASEGPs (or other glycosaminoglycanases) to improve one or more of their aspects of use. Such improvements can comprise, for example, one or any combination of the following: (i) improving the extent and/or the rate of absorption and thus bioavailability of an agent (for example by causing more of it to reach the bloodstream after non-IV parenteral administration, and/or less of it to be degraded after such local administration by more rapid permeation), which can be brought about for example by accelerating interstitial flow and potentially convective transport following non-IV parenteral administration (e.g. by applying hydrostatic pressure associated with the volume of injection combined with a reduction in impedance to flow associated with degradation of hyaluronan); (ii) providing for a safer or more convenient route of administration (for example allowing for non-IV parenteral administration in place of IV, or for improved or more convenient non-IV parenteral administrations such as intradermal or subcutaneous in place of intramuscular); (iii) more favorable dosing regimens (for example less frequent dosing, or a more frequent but lower dose non-IV route as opposed to a less frequent but higher dose IV); (iv) reducing a side effect or otherwise decreasing toxicity (for example an effect associated with the initially high concentration (high Cmax) generated by IV dosing, or from a high local dose generated by slow and/or incomplete absorption following non-IV parenteral administration); (v) otherwise improving the pharmacokinetics and/or pharmacodynamics (for example by allowing more of an agent to reach a target site (e.g. by increased interstitial fluid flow and convective transport due to the presence of sHASEGP at or near a delivery site such as an injection site), and/or by enhancing the permeation within a target site (e.g. by increased interstitial fluid flow and convective transport due to the presence of sHASEGP within the target site), or by delivering an agent preferentially to a target site (e.g. by local administration to a target site in connection with local or systemic administration of a sHASEGP to promote permeation of the target, or by using vehicles or macromolecular complexes to preferentially target an agent to a particular site combined with local or systemic administration of sHASEGP to promote permeation of the target site); Agents that have been delivered orally can also be benefited by reformulations for parenteral delivery to, e.g., avoid loss of agent to the gastrointestinal tract or subsequent degradation or toxicity, allow for more effective targeting to a desired site of action and therefore potentially greater effectiveness and/or less toxicity, or otherwise provide for more favorable pharmacokinetic and/or pharmacodynamic profiles. In addition, sHASEGPs can be used to improve the pharmacodynamics of agents that are administered orally (for example, by enhancing the permeation of an orally administered agent within its desired target site (e.g. by increased interstitial fluid flow and convective transport due to the presence of sHASEGP within the target site following systemic administration of sHASEGP and/or following local administration of sHASEGP to the target site).

Even in situations in which the desired target site for an agent such as pharmacologic is the bloodstream itself, such agents can be enhanced by co-administration and/or co-formulation with sHASEGPs (or other glycosaminoglycanases). For example, there are a number of agents that act as blood modifiers, which may be administered by one of several routes including oral dosing as well as parenteral administration (such as IV injection). A number of agents that are or could be administered orally nevertheless exhibit relatively limited or slow uptake and/or are subject to undesirable degradation (and there are other agents that are generally safe and effective once introduced into the bloodstream but are not administered orally for that reason). Parenteral administration of such agents (e.g. by intramuscular, subcutaneous, intradermal or transdermal routes in combination with administration of sHASEGP, preferably at or near the site of parenteral administration) can thus be employed to provide for introduction into the bloodstream. In addition, there are a number of urgent medical situations in which rapid delivery of an agent to the bloodstream is essential but oral dosing is too slow and intravenous dosing is either inconvenient, unsafe or unavailable. These urgent situations include those in which the blood is the target as well as those in which the bloodstream is simply the route of delivery to another target tissue. In such situations, the ability to combine administration with a sHASEGP (or apply a ready-prepared co-formulation with a sHASEGP) can allow for rapid delivery of the agent via non-IV parenteral administration. As will also be appreciated by those of skill in the art, there are a number of formulations and devices designed for non-IV parenteral administrations that can provide for, e.g., timed or other triggered release of agents, as well as variably controlled dosing and the like. A large number of such pharmacologic agents (that can be co-formulated with or used in combination with a sHASEGP) are regularly applied in medical practice and aspects of their use well described (see, e.g., the Physicians' Desk Reference, Thomson 2003, 2004, 2005), and many other such agents are known in the art. In the latter regard, as will be appreciated by those of skill in the art, sHASEGPs can be employed in combination with agents currently used (to e.g. improve their applicability as described herein), with agents that are not currently used (to e.g. improve their pharacokinetics and/or pharmacodynamics and thus make them useful), or with agents that are newly developed.

Thus for pharmacologic agents (such as anticancer agents, blood modifiers or members of other classes of agents as described herein) that are typically introduced parenterally (e.g. by IV injection), sHASEGPs (or other glycosaminoglycanases) can be used for example to allow such agents to be administered by other potentially more convenient and/or safe routes such as by non-IV parenteral administration (e.g. by intramuscular, subcutaneous, intradermal or transdermal routes). For agents that are already deliverable by a non-IV parenteral route, sHASEGPs may be used to enhance its extent and/or rate of uptake and delivery (e.g. by promoting its dispersion and subsequent entry into the bloodstream, which can likely be aided by convective transport as described herein). Advantages of such effects include having a greater portion of the agent reach the bloodstream, having reduced local exposure to agent (in terms of concentration and/or time) (e.g. at or near the injection site, which often limits dosing or results in local toxicity issues), increasing the speed at which an agent can be delivered into the bloodstream, other improved pharmacokinetic and/or pharmadynamic properties, and convenience of administration. In the last regard, non-IV parenteral administrations can allow many agents to be administered out-of-hospital that would otherwise require hospitalization or other medical attention typically required for intravenous administrations.

Illustrative examples of blood modifiers include agents such as antihemophilic agents and blood factor deficiency agents (including, for example, antihemophilic factors (e.g. ADVATE™, HEMOFIL™, KOATE™-DVI, KOGENATE™-FS, RECOMBINATE™ and REFACTO™), anti-inhibitor coagulent complexes (e.g. FEIBA™ VH), antithrombin IIIs (e.g. THROMBATE™ III), coagulations Factor VIIs (e.g. NOVOSEVEN™), coagulation Factor VIIs (e.g. ADVATE™, KOGENATET™-FS and RECOMBINATE™), coagulation Factor IXs (e.g. BEBULIN™, BENEFIX™ and PROPLEXT™ T), plasma protein fractions (e.g. PLASMANATE™), von Willebrand factors)); antiplatelet agents (including, for example, abciximabs (e.g. REOPRO™), anagrelides (e.g. AGRYLIN™), cilostazols (e.g. PLETAL™), clopidogrel bisulfates (e.g. PLAVIX™), dipyridamoles (e.g. AGGRENOX™ and PERSANTINE™), epoprostenols (e.g. FLOLAN™), eptifibatides (e.g.

INTEGRILIN™), tirofibans (e.g. AGGRASTAT™)); colony stimulating factors (CSFs) (including, for example, Granulocyte CSFs (e.g. NEULASTA™ and NEUPOGEN™) and Granulocyte Macrophage CSFs (e.g. LEUKINE™)); erythropoiesis stimulators (including, for example, erythropoietins such as darbepoetin alphas (e.g. ARANESP™) and epoetin alphas (e.g. EPOGEN™ and PROCRIT™); hemostatics and albumins (including, for example, aprotinins (e.g. TRASYLOL™), combinations of antihemophilic factors and plasma (e.g. ADVATE™), Desmopressin Acetates (e.g. DDAVP™), and albumins (e.g. BUMINATE™ and PLASBUMIN™)); immune globulins (e.g. BAYGAM™, CARIMUNE™ NF IV, FLEBOGAMMA™, GAMIMUNE™, GAMMAGARD S/D™, GAMUNEX™, IVEEGAM™, IVEEGAM™ EN IGIV, MICRHOGAM™, RHOGAM™, PANGLOBULIN™ and THYMOGLOBULIN™, as well as hepatitis B immune globulins (e.g. BAYHEP™ B, NABI-HB™, and NOVAPLUS™ NABI-HB); thrombin inhibitors (including for example direct thrombin inhibitors (e.g. ARGATROBAN™) and lepirudin (e.g. REFLUDAN™), and drotecogin alphas (e.g. XIGRIS™); anticoagulants (including, for example, dalteparins, enoxaperins and other heparins (e.g. FRAGMIN™ and LOVENOX™), warfarins (e.g. COUMADIN™ and JANTOVEN™)); and the like.

By way of further illustration, examples of various types of agents that have been administered parameterally and which can be co-administered and/or co-formulated with sHA-SEGPs (or other glycosaminoglycanases) are included in the following list: Acetazolamides; Acyclovirs; Adipiodones; Alatrofloxacins; Aldesleukins; Alemtuzumabs; Alfentanils; Allergenic extracts; Allopurinols; Alpha 1-proteinase inhibitors; Alprostadils; Amifostines; Amikacins; Aminoacids; Aminocaproic acids; Aminophyllines; Amitriptylines; Amobarbitals; Amrinones; Anakinras; Analgesics; Anti-poliomyelitic vaccines; Anti-rabic serums; Anti-tetanus immunoglobulins; Antithrombin IIIs; Antivenom serums; Argatrobans; Arginines; Arsenics; Ascorbic acids; Asparaginases; Atenolols; Atracuriums; Atropines; Aurothioglucoses; Azathioprines; Azithromycins; Aztreonams; *Bacillus* Calmette-Guerin (BCG) vaccines; Bacitracins; Baclofens; Basiliximabs; Benzoic acids; Benztropines; Betamethasones; Biotins; Bivalirudins; Bleomycins; Botulism antitoxins; Bretyliums; Bumetanides; Bupivacaines; Buprenorphines; Busulfans; Butorphanols; Calcitonins; Calcitriols; Calciums; Capreomycins; Carboprosts; Carmustines; Carnitines; Caspofungins; Cefamandoles; Cefazolins; Cefoperazones; Cefotaximes; Cefotetans; Cefoxitins; Ceftazidimes; Ceftizoximes; Cefuroximes; Chloramphenicols; Chloroprocaines; Chloroquines; Chlorothiazides; Chlorpromazines; Chondroitinsulfuric acids; Choriogonadotropin alphas; Chromiums; Cidofovirs; Cimetidines; Ciprofloxacins; Cisatracuriums; Cisplatins; Cladribines; Clavulanic acids; Clindamycins; Clonidines; Codeines; Colchicines; Colistins; Collagens; Corticorelin ovine triflutates; Corticotrophins; Cosyntropins; Cyanocobalamins; Cyclophosphamides; Cyclosporines; Cysteines; Cytarabines; Dacarbazines; Dacliximabs; Dactinomycins; Dalfopristins; Dalteparins; Danaparoids; Dantrolenes; Daunorubicins; Deferoxamines; Denileukin diftitoxs; Desmopressins; Dexamethasones; Dexmedetomidines; Dexpanthenols; Dexrazoxanes; Dextrans; Diatrizoic acids; Diazepams; Diazoxides; Dicyclomines; Digibinds; Digoxins; Dihydroergotamines; Diltiazems; Diphenhydramines; Diphteria, tetanus and pertussis vaccines; Diptheria antitoxins; Dipyridamoles; Dobutamines; Dopamines; Doxacuriums; Doxaprams; Doxercalciferols; Doxycyclines; Droperidols; Drotrecogin alphas; Dyphyllines; Edetic acids; Edrophoniums; Enalaprilats; Ephedrines; Epoprostenols; Ergocalciferols; Ergonovines; Ertapenems; Erythromycins; Esmolols; Estradiols; Estrogenics; Ethacrynic acids; Ethanolamines; Ethanols; Ethiodized oils; Etidronic acids; Etomidates; Etoposides; Factor VIIs; Famotidines; Fenoldopams; Fentanyls; Floxuridines; Fludarabines; Flumazenils; Fluoresceins; Fluorouracils; Fluphenazines; Folic acids; Follicle-stimulating hormones; Fomepizoles; Fomivirsens; Fondaparinuxs; Foscamets; Fosphenyloins; Fulvestrants; Furosemides; Gadoteridols; Gadoversetamides; Gancliclovirs; Gatifloxacins; Gemtuzumab ozogamicins; Gentamicins; Glucagons; Glucoses; Glycines; Glycopyrrolates; Gonadorelins; Gonadotropin chorionics; *Haemophilus* B polysaccharides; Haloperidols; Hemins; *Hemophilus influenza* vaccines; Hepatitis vaccines; Herbals; Histamines; Hydralazines; Hydrocortisones; Hydromorphones; Hydroxocobalam ins; Hydroxyzines; Hyoscyamines; Ibutilides; Idarubicins; Ifosfamides; Imiglucerases; Immunoglobulins; Indigo carmines; Indomethacins; Interferon alpha-conls; Interferon alpha-2As; Interferon alpha-N3s; Interferon beta-1 As; Iodides; Iopromides; Iothalamic acids; Ioxaglic acids; Ioxilans; Iron dextran injections; Isoniazids; Isoproterenols; Japanese encephalitis vaccines; Kanamycins; Ketamines; Ketorolacs; Labetalols; Lepirudins; Leucovorins; Leuprolides; Levobupivacaines; Levothyroxines; Lidocaines; Lincomycins; Linezolids; Liothyronines; Lorazepams; Luteinising hormones; Lyme disease vaccines; Mangafodipirs; Mannitols; Measles virus; Mechlorethamines; Melphalans; Meningococcal polysaccharide vaccines; Meperidines; Mepivacaines; Meropenems; Mesnas; Mesoridazines; Metaraminols; Methadones; Methocarbamols; Methohexitals; Methotrexates; Methyldopates; Methylergonovines; Metoclopramides; Metoprolols; Metronidazoles; Midazolams; Minocyclines; Mithramycins; Mitomycins; Mitoxantrones; Mivacuriums; Morrhuic acids; Moxifloxacins; Mumps viruses; Muromonab-CD3s; Mycophenolate mofetils; Nafcillins; Nalbuphines; Nalmefenes; Naloxones; Nandrolones; Neostigmines; Niacinamides; Nicardipines; Nitroglycerins; Nitroprussides; Norepinephrines; Oprelvekins; Orphenadrines; Oxacillins; Oxaliplatins; Oxymorphones; Oxytetracyclines; Oxytocins; Pancuroniums; Panthenols; Pantothenic acids; Papaverines; Pegaspargases; Peginterferon alpha 2As; Penicillin Gs; Pentamidines; Pentazocines; Pentobarbitals; Pentostatins; Perflutrens; Perphenazines; Pertussis vaccines; Phenobarbitals; Phentolamines; Phenylephrines; Phenyloins; Physostigmines; Phytonadiones; Pneumococcal vaccines; Polymyxin bs; Porfimers; Pralidoximes; Prilocalnes; Procainamides; Procaines; Prochlorperazines; Progesterones; Promethazines; Propranolols; Pyridostigmine hydroxides; Pyridoxines; Quinidines; Quinupristins; Rabies immunoglobulins; Rabies vaccines; Ranitidines; Rasburicases; Remifentanils; Riboflavins; Rifampins; Ropivacaines; Rubella vaccines; Samariums; Scopolamines; Seleniums; Sermorelins; Sincalides; Somatrems; Spectinomycins; Streptokinases; Streptomycins; Streptozocins; Succinylcholines; Sufentanils; Sulbactams; Sulfamethoxazoles; Sumatriptans; Tacrolimuss; Teniposides; Terbutalines; Teriparatides; Testosterones; Tetanus antitoxins; Tetracaines; Tetradecyl sulfates; Theophyllines; Thiamines; Thiethylperazines; Thiopentals; Thyroid stimulating hormones; Ticarcillins; Tinzaparins; Tirofibans; Tobramycins; Tolazolines; Tolbutamides; Topotecans; Torsemides; Tranexamic acids; Treprostinils; Triamcinolone acetonides; Triamcinolone hexacetonides; Triamcinolones; Triethylenethiophosphoramides (Thiotepa); Trifluoperazines; Trimethobenzamides; Trimethoprims; Trimeterxates; Triptorelins; Tromethamines; Tuberculins; Typhoid vaccines; Urofollitropins; Urokinases; Valproic acids; Valrubicins;

Varicella Zoster immunoglobulins; Vasopressins; Vecuroniums; Verapamils; Vinblastines; Vincristines; Voriconazoles; Warfarins; Yellow fever vaccines; Zidovudines; Zincs; Ziprasidone hydrochlorides; and agents related to the foregoing or in the same or similar classes as the foregoing.

Solutions or suspensions used for parenteral administration (including by intramuscular, intradermal, subcutaneous, topical application and other non-oral routes) can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; cheating agents, such as ethylenediaminetetraacetic acid (EDTA); buffers, such as acetates, citrates and phosphates; and agents for the adjustment of tonicity, including, but not limited to sodium chloride, calcium chloride, magnesium chloride, dextrose, glycerol or boric acid. Parenteral preparations can be enclosed in ampoules, disposable syringes or single or multiple dose vials made of glass, plastic or other suitable material.

The sHASEGP polypeptides or soluble human hyaluronidase domains thereof can be suspended in micronized or other suitable form or can be derivatized to produce a more soluble active product or to produce a prodrug. The form of the resulting mixture depends upon a number of factors, including the intended mode of administration and the solubility of the polypeptide in the selected carrier or vehicle. The effective concentration is sufficient for ameliorating the targeted condition and can be empirically determined using methods known to those of skill in the art. To formulate a composition, the weight fraction of polypeptide is dissolved, suspended, dispersed, or otherwise mixed in a selected vehicle at an effective concentration such that the targeted condition is relieved or ameliorated.

In instances in which the sHASEGP polypeptides or soluble human hyaluronidase domain thereof exhibit insufficient solubility, methods for solubilizing polypeptides can be used. Such methods are known to those of skill in this art, and include, but are not limited to, using cosolvents, such as dimethylsulfoxide (DMSO), using surfactants, such as TWEEN™ and Pluronic' F68; or dissolution in aqueous sodium bicarbonate. Derivatives of the polypeptides, such as prodrugs of the polypeptides can also be used in formulating effective pharmaceutical compositions. For ophthalmic indications, the compositions are formulated in an ophthalmically acceptable carrier. For the ophthalmic uses herein, local administration, either by topical administration or by injection is contemplated. Time-release formulations are also desirable. Typically, the compositions are formulated for single dosage administration, so that a single dose administers an effective amount.

Upon mixing or addition of the polypeptide with the vehicle, the resulting mixture can be a solution, suspension, emulsion or other composition and can be formulated as an aqueous mixtures, a creams, gels, ointments, emulsions, solutions, elixirs, lotions, suspensions, tinctures, pastes, foams, aerosols, irrigations, sprays, suppositories, bandages, or any other formulation suitable for systemic, topical or local administration.

The form of the resulting mixture depends upon a number of factors, including the intended mode of administration and the solubility of the compound in the selected carrier or vehicle. If necessary, pharmaceutically acceptable salts or other derivatives of the compounds are prepared. For local internal administration, such as, intramuscular, parenteral or intra-articular administration, the compounds are preferably formulated as a solution suspension in an aqueous-based medium, such as isotonically buffered saline or are combined with a biocompatible support or bioadhesive intended for internal administration.

The sHASEGP polypeptide or soluble human hyaluronidase domain thereof is included in the pharmaceutically acceptable carrier in an amount sufficient to exert a therapeutically useful effect in the absence of undesirable side effects on the patient treated. It is understood that number and degree of side effects depends upon the condition for which the compounds are administered. For example, certain toxic and undesirable side effects are tolerated when treating life-threatening illnesses that would not be tolerated when treating disorders of lesser consequence. Amounts effective for therapeutic use will, of course, depend on the severity of the disease and the weight and general state of the subject as well as the route of administration. Local administration of the therapeutic agent will typically require a smaller dosage than any mode of systemic administration, although the local concentration of the therapeutic agent can, in some cases, be higher following local administration than can be achieved with safety upon systemic administration.

Since individual subjects can present a wide variation in severity of symptoms and each therapeutic agent has its unique therapeutic characteristics, it is up to the practitioner to determine the response of a subject to treatment and vary the dosages accordingly. Dosages used in vitro can provide useful guidance in the amounts useful for in situ administration of the pharmaceutical composition, and animal models can in some cases be used to determine effective dosages for treatment of particular disorders. In general, however, for local administration, it is contemplated that an effective amount of the therapeutic agent will be an amount within the range from about 0.1 picograms (pg) up to about 1 ng per kg body weight. Various considerations in arriving at an effective amount are known to those of skill in the art and are described (see, e.g., Goodman And Gilman's: The Pharmacological Bases of Therapeutics, 8th ed., Pergamon Press, 1990; Remington's Pharmaceutical Sciences, 17th ed., Mack Publishing Co., Easton, Pa., 1990; and Mantyh et al., (Science, 278: 275-79, 1997) involving the intrathecal injection of a neuronal specific ligand-toxin, each of which is herein incorporated by reference in its entirety).

The formulations of the sHASEGP polypeptides or soluble human hyaluronidase domains thereof for use herein include those suitable for oral, rectal, topical, inhalational, buccal, sublingual, other parenteral (e.g., subcutaneous, intramuscular, intradermal, transdermal or intravenous), administration or any route. The most suitable route in any given case depends on the nature and severity of the condition being treated and on the nature of the particular active compound that is being used. The formulations are provided for administration to humans and animals in unit dosage forms, such as tablets, capsules, pills, powders, granules, sterile parenteral solutions or suspensions, and oral solutions or suspensions, and oil-water emulsions containing suitable quantities of the polypeptides and/or other agents or pharmaceutically acceptable derivatives thereof. The pharmaceutical therapeutically active polypeptides and/or other agents and derivatives thereof are typically formulated and administered in unit-dosage forms or multiple-dosage forms. A unit-dose form as used herein refers to physically discrete units suitable for human and animal subjects and packaged individually as is known in the art.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the sHASEGP polypeptide or soluble human hyaluronidase domain thereof and, optionally, another agent or pharmaceutically acceptable derivatives thereof. The pharmaceutically therapeutically active compounds and derivatives thereof are typically formulated and administered in unit-dosage forms or multiple-dosage forms. A unit-dose form as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include, but are not limited to, ampoules, syringes and individually packaged tablets or capsules. For example, a small volume formulation containing a stabilized solution with 1 to 5000 Units of sHASEGP in a small volume, such as 5 to 50 µl, can be prepackaged in a syringe for use, such as after viscoelastic injection. Unit-dose forms can be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses that are not segregated in packaging.

The composition can contain along with the active ingredient, such as a sHASEGP polypeptide: a diluent, such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polyvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered can also contain minor amounts of nontoxic auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Methods of preparing such dosage forms are known, or will be apparent, to those skilled in this art (see e.g., Remington's Pharmaceutical Sciences, Mack Publishing Company, Easton, Pa., 15th Edition, 1975). The composition or formulation to be administered contains a quantity of the active compound in an amount sufficient to alleviate the symptoms of the treated subject. For example, a standard stabilized formulation of sHASEGP or a soluble human hyaluronidase domain thereof as provided herein includes 150 Units/ml of the soluble glycoprotein formulated in EDTA, NaCl and $CaCl_2$. Additionally, an antibacterial or anti-fungal agent, including, but not limited to thiomersal, can be present in the formulation. Another formulation provided herein is a stabilized solution or lyophilized form of sHASEGP or a soluble human hyaluronidase domain thereof in EDTA, NaCl and $CaCl_2$, containing an effective active amount of the soluble glycoprotein, such as 150 Unit/ml, with the addition of lactose, such as 13 mg/ml. Also provided herein is a formulation containing a stabilized solution or lyophilized form of sHASEGP or a soluble human hyaluronidase domain thereof in EDTA, NaCl and $CaCl_2$ containing an effective active amount of the soluble glycoprotein, such as 150 Unit/ml, with the addition of lactose, such as 13 mg/ml, and Albumin, Pluronic™ F68, TWEEN™ and/or other detergent. Another formulation provided herein, either lyophilized or as a stabilized solution, contains an effect amount of sHASEGP or a soluble human hyaluronidase domain thereof, such as 1 to 300 Units/ml, in EDTA, NaCl and $CaCl_2$.

Dosage forms or compositions containing active ingredient in the range of 0.005% to 100% with the balance made up from non-toxic carrier can be prepared. For oral administration, the pharmaceutical compositions can take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art.

The sHASEGPs or a soluble human hyaluronidase domain thereof or pharmaceutically acceptable derivatives can be prepared with carriers that protect the soluble glycoprotein against rapid elimination from the body, such as time release formulations or coatings. The compositions can include other pharmaceutically effective agents known in the general art to be of value in treating one or more of the diseases or medical conditions, including, but not limited to, a chemotherapeutic agent, an analgesic agent, an anti-inflammatory agent, an antimicrobial agent, an amoebicidal agent, a trichomonocidal agent, an anti-parkinson agent, an anti-malarial agent, an anticonvulsant agent, an anti-depressant agent, and antiarthritics agent, an anti-fungal agent, an antihypertensive agent, antipyretic agent, an anti-parasite agent, an antihistamine agent, an alpha-adrenargic agonist agent, an alpha blocker agent, an anesthetic agent, a bronchi dilator agent, a biocide agent, a bactericide agent, a bacteriostat agent, a betadrenergic blocker agent, a calcium channel blocker agent, a cardiovascular drug agent, a contraceptive agent, a decongestant agent, a diuretic agent, a depressant agent, a diagnostic agent, a electrolyte agent, a hypnotic agent, a hormone agent, a hyperglycemic agent, a muscle relaxant agent, a muscle contractant agent, an ophthalmic agent, a parasympathomimetic agent, a psychic energizer agent, ophthalmic agent, a parasympathomimetic agent, a psychic energizer agent, a sedative agent, a sympathomimetic agent, a tranquilizer agent, an urinary agent, a vaginal agent, a viricide agent, a vitamin agent, a non-steroidal anti-inflammatory agent, an angiotensin converting enzyme inhibitor agent, a polypeptide, a protein, a nucleic acid, a drug, a prodrug, a organic molecule and a sleep inducer, to obtain desired combinations of properties. It is to be understood that such combination therapy constitutes a further aspect of the compositions and methods of treatment provided herein.

1. Compositions for Oral Administration

Oral pharmaceutical dosage forms are solid, gel or liquid. The solid dosage forms are tablets, capsules, granules, and bulk powders. Types of oral tablets include compressed, chewable lozenges and tablets, which can be enteric-coated, sugarcoated or film-coated. Capsules can be hard or soft gelatin capsules, while granules and powders can be provided in non-effervescent or effervescent form with the combination of other ingredients known to those skilled in the art.

The pharmaceutical compositions containing a sHASEGP or a soluble human hyaluronidase domain thereof can be in liquid form, for example, solutions, syrups or suspensions, or can be presented as a drug product for reconstitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid).

In certain embodiments, the formulations are solid dosage forms, preferably capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, *lycopodium* and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the sHASEGP or a soluble human hyaluronidase domain thereof could be provided in a composition that protects it from the acidic environment of the stomach. For example, the composition can be formulated in an enteric coating that maintains its integrity in the stomach and releases the active compound in the intestine. The composition can also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup can contain, in addition to the active compounds, sucrose as a sweetening agent and certain preservatives, dyes and colorings and flavors.

The sHASEGP or a soluble human hyaluronidase domain thereof can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient can be included.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents can also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and can contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic additives include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds that produce a pleasant taste sensation.

For a solid dosage form, the solution or suspension, in for example propylene carbonate, vegetable oils or triglycerides, is encapsulated in a gelatin capsule. Such solutions, and the preparation and encapsulation thereof, are disclosed in U.S.

Pat. Nos. 4,328,245; 4,409,239; and 4,410,545. For a liquid dosage form, the solution, e.g., for example, in a polyethylene glycol, can be diluted with a sufficient quantity of a pharmaceutically acceptable liquid carrier, e.g., water, to be easily measured for administration.

Alternatively, liquid or semi-solid oral formulations can be prepared by dissolving or dispersing the sHASEGP or a soluble human hyaluronidase domain thereof in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603.

Formulations suitable for buccal (sublingual) administration include, for example, lozenges containing the sHASEGP or a soluble human hyaluronidase domain thereof in a flavored base, usually sucrose and acacia or tragacanth; and pastilles containing the compound in an inert base such as gelatin and glycerin or sucrose and acacia.

In all embodiments, tablets and capsules formulations can be coated as known by those of skill in the art in order to modify or sustain dissolution of the active ingredient. Thus, for example, they can be coated with a conventional enterically digestible coating, such as phenylsalicylate, waxes and cellulose acetate phthalate.

2. Injectables, Solutions and Emulsions

Parenteral administration of the sHASEGP or a soluble human hyaluronidase domain thereof, generally characterized by injection, either subcutaneously, intramuscularly or intravenously is also contemplated herein. Injectables can be prepared in conventional forms, either as liquid solutions or suspensions; solid forms suitable for solution or suspension in liquid prior to injection, or as emulsions. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as, for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. The percentage of the sHASEGP or a soluble human hyaluronidase domain thereof contained in such parenteral compositions is dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent or sterile solution just prior to use, including hypodermic tablets, sterile suspensions ready for injection, sterile dry insoluble products ready to be combined with a vehicle just prior to use and sterile emulsions. The solutions can be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thiomersal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, preferably more than 1% w/w of the active compound to the treated tissue(s). The active ingredient, such as a sHASEGP or a soluble human hyaluronidase domain thereof, can be administered at once, or can be divided into a number of smaller doses to be administered at intervals of time. It is understood that the precise dosage and duration of treatment is a function of the tissue being treated and can be determined empirically using known testing protocols or by extrapolation from in vivo or in vitro test data. It is to be noted that concentrations and dosage values can also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compounds provided herein can be formulated for parenteral administration by injection, e.g., by bolus injection or continuous infusion. Formulations for injection can be presented in unit dosage form, e.g., in ampoules or in multi-dose containers, with an added preservative. The compositions can be suspensions, solutions or emulsions in oily or aqueous vehicles, and can contain formulatory agents such as suspending, stabilizing and/or dispersing agents. Alternatively, the active ingredient can be in powder form for reconstitution with a suitable vehicle, e.g., sterile pyrogen-free water or other solvents, before use. For example, provided herein are parenteral formulations containing an effective amount of sHASEGP or a soluble human hyaluronidase domain thereof, such as 500 to 500,000 Units, in a stabilized solution or a lyophilized from.

The compound can be suspended in micronized or other suitable form or can be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and can be empirically determined.

3. Lyophilized Powders

Also provided herein are lyophilized powders containing sHASEGP or a soluble human hyaluronidase domain thereof, which can be reconstituted for administration as solutions, emulsions and other mixtures. These formulations can also be reconstituted and formulated as solids or gels.

The sterile, lyophilized powder is prepared by dissolving a solid portion of or mixing an aliquot of a solution containing a sHASEGP or a soluble human hyaluronidase domain thereof in a suitable solvent. The solvent can contain an excipient that improves the stability or other pharmacological component of the powder or reconstituted solution, prepared from the powder. Excipients that can be used include, but are not limited to, dextrose, sorbitol, fructose, corn syrup, xylitol, glycerin, glucose, sucrose, lactose or other suitable agent. The solvent can also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the lyophilized formulation. Generally, the solution resulting from the sterile filtration is apportioned into vials for lyophilization. Each vial can contain a single dosage, such as 10-1000 mg or 100-500 mg, or multiple dosages of the compound.

Briefly, the lyophilized powder is prepared by dissolving dextrose, sorbitol, fructose, corn syrup, xylitol, glycerin, glucose, sucrose, lactose or other suitable agent, about 1-20%, in a suitable buffer, such as citrate, sodium or potassium phosphate or other such buffer known to those of skill in the art at about neutral pH. Then, a selected salt, such as, for example, the sodium salt of the sHASEGP (about 1 gm of the salt per 10-100 gms of the buffer solution, typically about 1 gm/30 gms), is added to the resulting mixture above room temperature, such as at about 30-35° C., and stirred until it dissolves. The resulting mixture is diluted by adding more buffer, to decrease the resulting concentration of the salt by about 10-50%, typically about 15-25%). The resulting mixture is sterile filtered or treated to remove particulates and to insure sterility, and apportioned into vials for lyophilization. The lyophilized powder can be stored under appropriate conditions, such as at about 4 C to room temperature.

Reconstitution of this lyophilized powder with water for injection provides a formulation for use in parenteral administration. For reconstitution, a therapeutically effective amount of the lyophilized powder containing a sHASEGP or a soluble human hyaluronidase domain thereof is added per milliliter of sterile water or other suitable carrier. The precise amount depends upon the selected compound and can be empirically determined by methods known to those of skill in the art.

4. Topical Administration

Topical mixtures are prepared as described for the local and systemic administration. Topical administration, which is sometimes referred to in the art as percutaneous administration, typically involves applications designed for absorption across skin, mucous membranes or other surfaces of the body (e.g., applications applied directly onto the skin, under the tongue (sublingual), against the cheek (buccal), to the eyes, nose or ears, or to the lungs (inhalation)). The resulting mixture can be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compositions of sHASEGP or a soluble human hyaluronidase domain thereof or pharmaceutically acceptable derivatives thereof can be formulated as aerosols for topical application, such as by inhalation (see, e.g., U.S. Pat. Nos. 4,044,126, 4,414,209, and 4,364,923, which describe aerosols for delivery of a steroid useful for treatment inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, such as less than 10 microns.

For administration by inhalation, the compositions for use herein can be delivered in the form of an aerosol spray presentation from pressurized packs or a nebulizer, with the use of a suitable propellant, including, but not limited to, dichlorodifluoromethane, trichlorofluoromethane, dichlorotetrafluoroethane, carbon dioxide and other suitable gases. In the case of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

The compositions can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

For example, formulations suitable for topical application to the skin or to the eye generally are formulated as an ointment, cream, lotion, paste, gel, spray, aerosol and oil. Carriers that can be used include vaseline, lanoline, polyethylene glycols, alcohols, and combinations of two or more thereof. The topical formulations can further advantageously contain 0.05 to 15 percent by weight of thickeners, including, but not limited to, hydroxypropylmethylcellulose, methylcellulose, polyvinylpyrrolidone, polyvinyl alcohol, poly(alkylene glycols), poly/hydroxyalkyl, (meth)acrylates or poly(meth) acrylamides. A topical formulation is often applied by instillation or as an ointment into the conjunctival sac. It also can be used for irrigation or lubrication of the eye, facial sinuses, and external auditory meatus. The topical formulations in the liquid state can be also present in a hydrophilic three-dimensional polymer matrix in the form of a strip, contact lens, and the like from which the active components are released. It can also be injected into the anterior eye chamber, into the episcleral space, and other places. For example, provided herein is a formulation for intraocular use after viscoelastic injecting containing a stabilized solution of an effective amount of a sHASEGP or a soluble human hyaluronidase domain thereof, such as 1 to 5000 Units of the soluble glycoprotein with 30 to 150,000 Units/mg of specific activity, in a small volume, such as 5 to 50 µl. As another example, provided herein is a formulation for intraocular use to enhance delivery of one or more pharmacologic agents to tissues within the eye following injection by routes of administration such as a Sub-Tenon's injection into the episcleral space surrounding the sclera, comprising a stabilized solution of an effective amount of a sHASEGP or a soluble human hyaluronidase domain thereof, such as 50 to 5,000 Units of the soluble glycoprotein with 30 to 150,000 Units/mg of specific activity, in a volume such as 0.05 to 10 ml.

These solutions, particularly those intended for ophthalmic use, can be formulated as 0.01%-10% isotonic solutions, pH about 5-7, with appropriate salts.

Co-Applications with Iontophoresis

In the case of topical administrations and other applications to tissues that are susceptible to iontophoresis, the use of one or more sHASEGPs (potentially co-formulated or co-administered with another pharmacologic or other agent) can be combined with iontophoretic techniques in order to further drive permeation of a tissue. In these regards, iontophoresis and sHASEGPs can function cooperatively in that iontophoresis can promote delivery of sHASEGPs into a tissue or other location within the body, and the sHASEGP so delivered can further drive permeation of the enzyme, as well as co-formulated or co-administered or other molecules present in the tissue, i.e. by enzymatically opening channels that facilitate diffusion as well as promoting bulk fluid flow and thus convective transport of solutes such as pharmacologics.

5. Compositions for Other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum that melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases can be used. Agents to raise the melting point of suppositories include spermaceti and wax. Rectal suppositories can be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

Formulations suitable for transdermal administration can be presented as discrete patches adapted to remain in intimate contact with the epidermis of the recipient for a prolonged period of time. Such patches suitably contain the active compound as an optionally buffered aqueous solution of, for example, 0.1 to 0.2 M concentration with respect to the active compound. Formulations suitable for transdermal administration can also be delivered by iontophoresis (see e.g., *Pharmaceutical Research* 3 (6): 318 (1986)) and typically take the form of an optionally buffered aqueous solution of the active compound.

The pharmaceutical compositions can also be administered by controlled release means and/or delivery devices (see e.g., in U.S. Pat. Nos. 3,536,809; 3,598,123; 3,630,200; 3,845,770; 3,847,770; 3,916,899; 4,008,719; 4,687,610; 4,769,027; 5,059,595; 5,073,543; 5,120,548; 5,354,566; 5,591,767; 5,639,476; 5,674,533 and 5,733,566). The active compounds or pharmaceutically acceptable derivatives can be prepared with carriers that protect the compound against rapid elimination from the body, such as time-release formulations or coatings.

In one embodiment of the compositions and methods provided herein, the therapeutic agent is administered locally in a slow release delivery vehicle, for example, encapsulated in a colloidal dispersion system or in polymer stabilized crystals. Useful colloidal dispersion systems include nanocapsules, microspheres, beads, and lipid-based systems, including oil-in-water emulsions, micelles, mixed micelles, and liposomes. For example, the colloidal dispersion system can be a liposome or microsphere. Liposomes are artificial membrane vesicles that are useful as slow release delivery vehicles when injected or implanted. Some examples of lipid-polymer conjugates and liposomes are disclosed in U.S. Pat. No., 5,631,018, which are incorporated herein by reference in its entirety. Other examples of slow release delivery vehicles are biodegradable hydrogel matrices (U.S. Pat. No. 5,041,292), dendritic polymer conjugates (U.S. Pat. No. 5,714,166), and multivesicular liposomes (Depofoam™ Depotech, San Diego, Calif.) (U.S. Pat. Nos. 5,723,147 and 5,766,627). One type of microspheres suitable for encapsulating therapeutic agents for local injection (e.g., into subdermal tissue) is poly (D,L)lactide microspheres, as described in D. Fletcher, *Anesth. Analg.* 84:90-94, (1997). For example, a slow release formulation containing an effective amount of sHASEGP or a soluble human hyaluronidase domain thereof, such as 1 to 5000 Units/ml, can be employed for various uses or to treat various conditions, including, but not limited to, cosmetic formulations, treatment of spinal cord injuries and other nervous system disorders, certain opthalmic disorders, inflammatory or autoimmune conditions, cancers, and other chronic disease conditions, in which prolonged delivery of the sHASEGP is beneficial.

Desirable blood levels can be maintained by a continuous infusion of the active agent as ascertained by plasma levels. It should be noted that the attending physician would know how to and when to terminate, interrupt or adjust therapy to lower dosage due to toxicity, or bone marrow, liver or kidney dysfunctions. Conversely, the attending physician would also know how to and when to adjust treatment to higher levels if the clinical response is not adequate (precluding toxic side effects).

The efficacy and/or toxicity of the sHASEGP polypeptide and/or its inhibitor (s), alone or in combination with other agents, such as therapeutically effective agents, also can be assessed by the methods known in the art (see, e.g., O &Apos; Reilly, *Investigational New Drugs* 15: 5-13 (1997)).

6. Articles of Manufacture

The sHASEGP polypeptides or soluble human hyaluronidase domains thereof or compositions containing any of the preceding agents can be packaged as articles of manufacture containing packaging material, a compound or suitable derivative thereof provided herein, which is effective for treatment of a diseases or disorders contemplated herein, within the packaging material, and a label that indicates that the compound or a suitable derivative thereof is for treating the diseases or disorders contemplated herein. The label can optionally include the disorders for which the therapy is warranted.

The articles of manufacture provided herein contain packaging materials. Packaging materials for use in packaging pharmaceutical products are well known to those of skill in the art (see, e.g., U.S. Pat. Nos. 5,323,907, 5,052,558 and 5,033,352). Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated, as are variety treatments for any disorder in which HCV infection is implicated as a mediator or contributor to the symptoms or cause.

Kits containing the compositions and/or the combinations with instructions for administration thereof are also provided herein. The kit can further include a needle or syringe, typically packaged in sterile form, for injecting the complex, and/or a packaged alcohol pad. Instructions are optionally included for administration of the active agent by a clinician or by the patient. For example, provided herein is a kit containing a small volume syringe with an effective amount of sHASEGP or a soluble human hyaluronidase domain thereof, such as 1 to 5000 Units of the soluble glycoprotein, in a 5 to 50 µl volume, optionally containing a second syringe containing a viscoelastic. Also provided herein is a kit containing a small volume syringe containing an effective amount of sHASEGP or a soluble human hyaluronidase domain thereof, such as 1 to 500 Units of the soluble glycoprotein, and a therapeutic amount of a second active ingredient, such as a drug, a small molecule, a protein or a nucleic acid.

K. Animal Models

Transgenic animal models and animals, such as rodents, including mice and rats, cows, chickens, pigs, goats, sheep, monkeys, including gorillas, and other primates, are provided herein. In particular, transgenic non-human animals that contain heterologous nucleic acid encoding a sHASEGP polypeptide or a transgenic animal in which expression of the polypeptide has been altered, such as by replacing or modifying the promoter region or other regulatory region of the endogenous gene are provided. Such an animal can by produced by promoting recombination between endogenous nucleic acid and an exogenous sHASEGP gene that could be over-expressed or mis-expressed, such as by expression under a strong promoter, via homologous or other recombination event.

Transgenic animals can be produced by introducing the nucleic acid using any know method of delivery, including, but not limited to, microinjection, lipofection and other modes of gene delivery into a germline cell or somatic cells, such as an embryonic stem cell. Typically the nucleic acid is introduced into a cell, such as an embryonic stem cell (ES), followed by injecting the ES cells into a blastocyst, and implanting the blastocyst into a foster mother, which is followed by the birth of a transgenic animal. Generally introduction of a heterologous nucleic acid molecule into a chromosome of the animal occurs by a recombination between the heterologous sHASEGP-encoding nucleic acid and endogenous nucleic acid. The heterologous nucleic acid can be targeted to a specific chromosome. In some instances, knockout animals can be produced. Such an animal can be initially produced by promoting homologous recombination between a sHASEGP polypeptide gene in its chromosome and an exogenous sHASEGP polypeptide gene that has been rendered biologically inactive (typically by insertion of a heterologous sequence, e.g., an antibiotic resistance gene). In one embodiment, this homologous recombination is performed by transforming embryo-derived stem (ES) cells with a vector containing the insertionally inactivated sHASEGP polypeptide gene, such that homologous recombination occurs, followed by injecting the ES cells into a blastocyst, and implanting the blastocyst into a foster mother, followed by the birth of the chimeric animal ("knockout animal") in which a sHASEGP polypeptide gene has been inactivated (see Capecchi, Science 244: 1288-1292 (1989)). The chimeric animal can be bred to produce homozygous knockout animals, which can then be used to produce additional knockout animals. Knockout animals include, but are not limited to, mice, hamsters, sheep, pigs, cattle, and other non-human mammals. For example, a knockout mouse is produced. The resulting animals can serve as models of specific diseases, such as cancers, that exhibit under-expression of a sHASEGP polypeptide. Such knockout animals can be used as animal models of such diseases e.g., to screen for or test molecules for the ability to treat or prevent such diseases or disorders.

Other types of transgenic animals also can be produced, including those that over-express the sHASEGP polypeptide. Such animals include "knock-in" animals that are animals in which the normal gene is replaced by a variant, such as a mutant, an over-expressed form, or other form. For example, one species', such as a rodent's endogenous gene can be replaced by the gene from another species, such as from a human. Animals also can be produced by non-homologous recombination into other sites in a chromosome; including animals that have a plurality of integration events.

After production of the first generation transgenic animal, a chimeric animal can be bred to produce additional animals with over-expressed or mis-expressed sHASEGP polypeptides. Such animals include, but are not limited to, mice, hamsters, sheep, pigs, cattle and other non-human mammals. The resulting animals can serve as models of specific diseases, such as cancers, that are exhibit over-expression or mis-expression of a sHASEGP polypeptide. Such animals can be used as animal models of such diseases e.g., to screen for or test molecules for the ability to treat or prevent such diseases or disorders. In a specific. embodiment, a mouse with over-expressed or mis-expressed sHASEGP polypeptide is produced.

The following examples are included for illustrative purposes only and are not intended to limit the scope of the invention.

L. Therapeutic Uses of sHASEGP

Naturally occurring hyaluronidase enzymes from slaughterhouses have been the principle source of clinical enzyme preparations for over forty years. Bovine and Ovine testicles are the principle source of this material. These clinical enzyme preparations however are very crude, sold in preparations ranging from 0.5-5% purity based upon known specific activities between 30-100,000 Units/mg. Thus their lack of purity combined with their slaughterhouse origin, leave them as both immunogenic to humans and as potential source of Jacob Creutzfeld disease and other bovine and ovine pathogens. Anaphylactic reactions to bovine and ovine hyaluronidase preparations are known to occur.

Cattle or bacterially derived hyaluronidase have been used in the treatment of diseases associated with excess hyaluronic acid and to enhance the circulation of physiological fluids and/or therapeutic agents. For example, bovine hyaluronidase can be co injected with anesthesia in peribulbar, retrobulbar and sub-Tenon's blocks for ophthalmic surgical procedures. Moreover, increased surgical complications occur in its absence (Brown S M et al. *J Cataract Refract*

*Surg.* 1999 September; 25(9): 1245-9.). Bovine hyaluronidase is also used as an antidote to local necrosis from paravenous injection of necrotic substances such as vinka alkaloids (Few, B. J. (1987) *Amer. J. Matern. Child Nurs.* 12, 23-26). Bovine testes hyaluronidase is also useful for the treatment of ganglion cysts (Paul et al. *J Hand Surg* 1997 April; 22 (2): 219-21). Hyaluronidase can also be used to facilitate subcutaneous delivery of fluids in hypodermoclysis (Berger E Y, *Am Geriatr Soc* 1984 March; 32(3):199-203). Hyaluronidase has also been utilized to reduce intraocular pressure in the eyes of glaucoma patients and cataract patients receiving viscoelastics (U.S. Pat. No. 4,820,516 issued Apr. 11, 1989).

Cattle or bacterially derived hyaluronidases have also been used as a "spreading agent" to enhance the activity of chemotherapeutics and/or the accessibility of tumors to chemotherapeutics (Schuller et al., 1991, Proc. Amer. Assoc. Cancer Res. 32:173, abstract no. 1034; Czejka et al., 1990, Pharmazie 45:H.9). Combination chemotherapy with hyaluronidase is effective in the treatment of a variety of cancers including urinary bladder cancer (Horn et al., 1985, J. Surg. Oncol. 28:304-307), squamous cell carcinoma (Kohno et al., 94, J. Cancer Res. Oncol. 120:293-297), breast cancer (Beckenlehner et al., 1992, J. Cancer Res. Oncol. 118:591-596), and gastrointestinal cancer (Scheithauer et al., 1988, Anticancer Res. 8:391-396). Hyaluronidase is effective as the sole therapeutic agent in the treatment of brain cancer (gliomas) (PCT published application no. WO88/02261, published Apr. 7, 1988). Administration of hyaluronidase also induces responsiveness of previously chemotherapy-resistant tumors of the pancreas, stomach, colon, ovaries, and breast (Baumgartner et al., 1988, Reg. Cancer Treat. 1:55-58; Zanker et al., 1986, Proc. Amer. Assoc. Cancer Res. 27:390). Unfortunately, the contaminants and non human nature of such hyaluronidases result in anaphylactic reactions.

In addition to its indirect anticancer effects, cattle derived hyaluronidase has direct anticarcinogenic effects. Hyaluronidase prevents growth of tumors transplanted into mice (De Maeyer et al., 1992, Int. J. Cancer 51:657-660) and inhibits tumor formation upon exposure to carcinogens (Pawlowski et al., 1979, Int. J. Cancer 23:105-109; Haberman et al., 1981, Proceedings of the 17th Annual Meeting of the American Society of Clinical Oncology, Washington, D.C., 22:105, abstract no. 415).

Given the value of cattle-derived hyaluronidases as a therapeutic, particularly in chemotherapy in conjunction with conventional chemotherapeutics or as a chemotherapeutic in and of itself, there is a need in the field for substantially pure preparations of hyaluronidase of human origin. There is also a need for efficient, cost-effective methods of making hyaluronidase to provide commercially significant quantities of the enzyme. The present invention addresses these problems.

Hyaluronic acid is an essential component of the extracellular matrix. Hyaluronic acid is found in the connective tissue of mammals and is the main constituent of the vitreous of the eye. In connective tissue, the water of hydration associated with hyaluronic acid creates spaces between tissues, thus creating an environment conducive to cell movement and proliferation. Hyaluronic acid plays a key role in biological phenomena associated with cell motility including rapid development, regeneration, repair, embryogenesis, embryological development, wound healing, angiogenesis, and tumorigenesis (Toole, 1991, Cell Biol. Extracell. Matrix, Hay (ed), Plenum Press, New York, 305-341; Bertrand et al., 1992, Int. J. Cancer 52:1-6; Knudson et al., 1993, FASEB J. 7:1233-1241). In addition, hyaluronic acid levels correlate with tumor aggressiveness (Ozello et al., 1960, Cancer Res. 20:600-604; Takeuchi et al., 1976, Cancer Res. 36:2133-2139; Kimata et al., 1983, Cancer Res. 43:1347-1354).

Following spinal cord injury, glial scars are produced by astrocytes and contain chondroitin sulfate proteoglycans (CSPGs). CSPGs play a crucial role in the inhibition of axon growth (Levine, 1994; Powell et al., 1997). For example, during fetal development, CSPGs repel axons and inhibit neural cell adhesion. CSPG's also play an important role in boundary formation (Snow et al., 1990, 1992; Powell and Geller, 1999). In addition the expression of CSPG increases following injury of CNS (Mckeon et al., 1991; Davies et al., 1997).

Studies indicate that the inhibitory effects of CSPGs are principally due to the chondroitin sulfate (CS) glycosaminoglycan (GAG) sugar chain (Snow et al., 1990; Cole and McCable, 1991; Geisert and Bidanset, 1993). This is supported by the finding that administration of bacterial chondroitinase in fact promote axon regeneration when administered intrathecally. Moreover, electrophysiological experiments determined that regenerated CST axons established functional connections (Bradbury, et al 2002). In addition to their direct inhibitory effects, CSPGs could also interact with cell adhesion molecules or neurotrophic factors to influence neurite outgrowth (Roberts et al., 1988; Ruoslahti and Yamaguchi, 1991; Miley et al., 1994). Recombinant mammalian Hyaluronidases are thus useful to reverse the inhibition of CSPG's in the glial scar and to promote axon regeneration following injury.

The amount of sHASEGP required to sufficiently degrade CSPG's in the glial scar will vary. In some cases repeated administration of 10-5000 Units of sHASEGP by intrathecal delivery will be required to remove the CSPG's in the scar. In other cases, sustained release of sHASEGP through use of a slow release formulation may be preferred. Alternatively, administration of gene therapy vectors encoding sHASEGP may be effective to enhance clearance of CSPG's.

sHASEGPs can also be utilized for the treatment of herniated disks in a process known as chemonucleolysis. Chondroitinase ABC, and enzyme cleaving similar substrates as sHASEGP can induce the reduction of intradiscal pressure in the lumbar spine. (Sasaki et al., 2001, Ishikawa et al., 1999). There are three types of disk injuries. A protruded disk is one that is intact but bulging. In an extruded disk, the fibrous wrapper has torn and the NP has oozed out, but is still connected to the disk. In a sequestered disk, a fragment of the NP has broken loose from the disk and is free in the spinal canal. Chemonucleolysis is effective on protruded and extruded disks, but not on sequestered disk injuries. In the United States, chemonucleolysis is approved only for use in the lumbar (lower) spine. In other countries, it has also been used successfully to treat cervical (upper spine) hernias. Chemonucleolysis is thus a conservative alternative to disk surgery when it is preferable to reduce disk pressure.

The precise composition and structure of the carbohydrate chain(s) on a glycoprotein can directly influence its serum lifetime, since cells in the liver and reticulo-endothelial system can bind and internalize circulating glycoproteins with specific carbohydrates. Hepatocytes have receptors on their surfaces that recognize oligosaccharide chains with terminal (i.e., at the outermost end(s) of glycans relative to the polypeptide) Gal residues, macrophages contain receptors for terminal Man or GlcNAc residues, and hepatocytes and lymphocytes have receptors for exposed fucose residues. No sialic acid-specific receptors have been found, however. Although somewhat dependent on the spatial arrangement of the oligosaccharides, as a general rule, the greater the number of exposed sugar residues recognized by cell surface receptors in the liver and reticulo-endothelial system, the more rapidly a glycoprotein will be cleared from the serum. Because of the absence of sialic acid-specific receptors, however, oligosaccharides with all branches terminated, or "capped," with sialic acid will not promote the clearance of the protein to which they are attached.

The presence and nature of the oligosaccharide chain(s) on a glycoprotein can also affect important biochemical properties in addition to its recognition by sugar-specific receptors on liver and reticulo-endothelial cells. Removal of the carbohydrate from a glycoprotein will usually decrease its solubility, and it may also increase its susceptibility to proteolytic degradation by destabilizing the correct polypeptide folding pattern and/or unmasking protease-sensitive sites. For similar reasons, the glycosylation status of a protein can affect its recognition by the immune system.

sHASEGPs can be used to remove the cumulus cells surrounding an egg prior to cryopreservation and other In Vitro fertilization techniques such an intracytoplasmic sperm injection (ICSI). Hyaluronidase can be added to harvested oocytes between 10-200 U/ml in buffered salt solutions. Oocytes are separated from the released cumulus cells through aspiration and washed through several washes with media lacking hyaluronidase. The eggs can then be processed for cryopreservation or IVF techniques.

sHASEGPs are also useful for the more effective penetration of chemotherapeutic agents into solid tumors. sHASEGPs can be injected intratumorally with anti-cancer agents or intravenously for disseminated cancers or hard to reach tumors. The anticancer agent can be a chemotherapeutic, an antibody, a peptide, or a gene therapy vector, virus or DNA. Additionally, sHASEGPs can be used to recruit tumor cells into the cycling pool for sensitization in previously chemorefractory tumors that have acquired multicultural drug resistance St Croix et al Cancer Lett 1998 Sep. 11; 131(1): 35-44). sHASEGPs are also useful to enhance delivery of biologics such as monoclonal antibodies, cytokines and other drugs to tumors that accumulate glycosaminoglycans. Many tumors delete genes involved with the catabolism of glycosaminoglycans such that localized accumulation can prevent anti-neoplastic agents and the immune system from reaching the tumor mass.

sHASEGP can also be used to increase the sensitivity of tumors that are resistant to conventional chemotherapy. In one embodiment, sHASEGP is administered to a patient having a tumor associated with a LuCa-1 defect in an amount effective to increase diffusion around the tumor site (e.g., to increase circulation of chemotherapeutic factors (e.g., to facilitate circulation and/or concentrations of chemotherapeutic agents in and around the tumor site), inhibit tumor cell motility (e.g., by HA degradation) and/or to lower the tumor cell(s) threshold of apoptosis (i.e., bring the tumor cell(s) to a state of anoikis), a state that renders the tumor cell(s) more susceptible to the action of chemotherapeutic agents or other agents that may facilitate cell death, preferably preferentially facilitate programmed cell death of cells in anoikis. Chemotherapeutic agents as used herein is meant to encompass all molecules, synthetic (e.g., cisplatin) as well as naturally occurring (e.g., tumor necrosis factor IF)), that facilitate inhibition of tumor cell growth, and preferably facilitate, more preferably preferentially facilitate tumor cell death.

Of particular interest is the use of sHASEGP for the treatment of metastatic and non-metastatic cancers, particularly metastatic cancers, having decreased to undetectable hyaluronidase activity relative to non-cancerous (normal) cells. sHASEGP can be used as a chemotherapeutic agent (alone or in combination with other chemotherapeutics) in the treatment of any of a variety of cancers, particularly invasive tumors. For example, sHASEGP can be used in the treatment of small lung cell carcinoma, squamous lung cell carcinoma, as well as cancers of the breast, ovaries, head and neck, or any other cancer associated with depressed levels of hyaluronidase or with a defective LuCa-1 (hpHAse) gene (e.g., a LuCa-1 gene that does not provide for expression of adequate hpHAse levels or encodes a defective hpHAse that does not provide for an adequate level of hyaluronidase activity) or other defect associated with decreased hyaluronan catabolism. sHASEGP is preferable for the treatment of malignancies associated with deficient HA catabolism as it does not require cellular participation for degradation to occur.

The specific dosage appropriate for administration can be readily determined by one of ordinary skill in the art according to the factors discussed above (see, for example, Harrison's Principles of Internal Medicine, 11th Ed., 1987). In addition, the estimates for appropriate dosages in humans may be extrapolated from determinations of the level of enzymatic activity of sHASEGP in vitro and/or dosages effective in animal studies. For example, 70-300 TRU hyaluronidase is effective in reducing the tumor load in a scid mouse. Given this information, the corresponding dosages in the average 70 kg human would range from about 250,000-1,200,000 TRU hyaluronidase. The amount of sHASEGP administered to a human patient is generally in the range of 1 TRU to 5,000,000 TRU of enzymatic activity, preferably between about 1,000 TRU to 2,500,000 TRU, more preferably between about 100,000 TRU to 1,500,000 TRU, normally between about 250,000 TRU and 1,200,000 TRU, with about 725,000 TRU representing average prescribed doses.

In one embodiment, a sHASEGP is formulated in a 0.15 M saline solution containing sHASEGP at a concentration of about 150,000 TRU/cc. The formulation is then injected intravenously at 15,000 TRU/kg body weight of the patient. Alternatively, the enzyme formulation may also be injected subcutaneously to allow the hyaluronidase to perfuse around the tumor site. In a preferred embodiment, sHASEGP is injected peritumorally or into the tumor mass. In another preferred embodiment, sHASEGP is formulated as a liposome and is delivered by injection either intravenously or at or near the site of cancerous cells associated with a defect in the LuCa-1 (hpHAse) gene. Injection of sHASEGP intravenously results in sHASEGP in the tumor site. Moreover, Super Sialated sHASEGP is preferably for parenteral administration in that the terminal sialic acids on sHASEGP prevent the clearance of the enzyme from circulation by the reticuloendothelial system. Comparisons of super sialated sHASEGP to non-sialated bovine and ovine hyaluronidases reveal that substantially more favorable pharmacokinetics is achieved.

Facilitation of Gene Therapy

The efficacy of most gene delivery vehicles in vivo does not correspond to the efficacy found in vitro. Glycosaminoglycans can hinder the transfer and diffusion of DNA and viral vectors into many cell types. The levels such extracellular matrix material can hinder the process considerably. Dubensky et al., (Proc Natl Acad Sci USA 1984 December; 81(23): 7529-33) demonstrated that hyaluronidase when combined with collagenase could facilitate transduction of DNA in vivo. It has been demonstrated that adeno associated virus is also amenable to hyaluronidase mediated gene therapy Favre et al., (*Gene Ther* 2000 August; 7(16):1417-20).

We have determined herein that channels of defined size in the extracellular matrix are opened with sHASEGP. These pores generally do not enhance the diffusion of substances greater than about 200-500 nm in diameter. However, smaller molecules such as retroviruses, adenoviruses, adeno-associated viruses and DNA complexes are amenable to sHASEGP mediated diffusion. The fact that sHASEGPs generally act to open channels that are substantially large enough to permit the movement of most therapeutic and other pharmacological agents of interest (including macromolecules such as proteins and nucleic acids as well as macromolecular complexes such as gene therapy vectors) and yet are generally not so large as to promote the dislocation and movement of cells, provides particularly advantageous applications in treating, preventing and/or diagnosing a variety of diseases for example.

Alternatively, viruses can be armed with the sHASEGP gene to facilitate their replication and spread within a target tissue for example. The target tissue can be a cancerous tissue whereby the virus is capable of selective replication within the tumor. The virus can also be a non-lytic virus wherein the virus selectively replicates under a tissue specific promoter. As the viruses replicate, the coexpression of sHASEGP with viral genes will facilitate the spread of the virus in vivo.

Alternatively the nucleic acid of interest and a sHASEGP, can be used simultaneously or consecutively or so as to be staggered over time. Simultaneously refers to a coadministration. In this case, these two essential components can be mixed to form a composition prior to being administered, or can be administered at the same time to the cell or the host organism. It is also possible to administer them consecutively, that is to say one after the other, irrespective of which component of the combination product according to the invention is administered first. Finally, it is possible to use a mode of administration which is staggered over time or is intermittent and which stops and restarts at intervals which may or may not be regular. It is pointed out that the routes and sites of administration of the two components can be different. According to one particularly preferred embodiment, the sHASEGP is administered before the nucleic acid, with the route of administration of the two components preferably being similar. The time interval between the injections is not critical and can be defined by the skilled person. It is possible to recommend an interval of from 10 min to 72 h, advantageously of from 30 min to 48 h, preferably of from 1 to 24 h and, very preferably, of from 1 to 6 h.

In addition, the combination product according to the invention can also be combined with one or more molecule(s) which is/are intended to improve the nucleic acid administration. The molecules can be molecules which have a protective effect on the nucleic acid (protection with regard to degradation in the cell), which improve its penetration or its expression in the host cell (fusogenic peptide, nuclear localization signal, etc.), which enable one particular cell type to be targeted (ligand or antibody which recognizes a cell surface protein, etc.), or which prolong the therapeutic effect (immunosuppressive agent, etc.). The combination product can also be combined with agents that facilitate transfection (proteins, etc.).

The combination product according to the invention can be prepared with a view to local or parenteral administration or to administration by the digestive route. Routes which may in particular be mentioned are the intragastric, subcutaneous, intracardiac, intravenous, intraperitoneal, intrasynovial, intratumor, intrapulmonary, intranasal and intratracheal routes, and, very particularly, the intramuscular route. The administration can be effected by means of any technique of the art (injection, oral route, aerosol, instillation, etc.), as a single dose or as a dose that is repeated once or several times after a particular time interval. The route of administration can be adjusted to suit the gene of interest to be transferred and the disease to be treated. The formulation can include pharmaceutically acceptable vehicles (excipients, adjuvants, etc.). The substance leading to disorganization of the extracellular matrix and the nucleic acid of interest are preferably dissolved in a buffer which is suitable for pharmaceutical use and which can be hypertonic, hypotonic or isotonic. Various buffers can be envisaged. Those which may be mentioned by way of illustration are a physiological saline solution (0.9% NaCl), a nonphysiological saline solution (1.8% NaCl), a Hepes-Ringer solution, a Lactate-Ringer solution, a buffer which is based on Tris-HCl (10 mM Tris-HCl, pH 7.5 to 8, 1 mM EDTA; 10 mM Tris-HCl, pH 7.5 to 8, 1 mM $MgCl_2$), a phosphate buffer (Krebs phosphate $H_2O$ buffer), a sugar (glucose, sucrose, trehalose, etc.) solution, or simply water.

Hypodermoclysis

Hypodermoclysis, the subcutaneous infusion of fluids, is a useful and easy hydration technique suitable for mildly to moderately dehydrated adult patients, especially the elderly. The method is considered safe and does not pose any serious complications. The most frequent adverse effect is mild subcutaneous edema that can be treated by local massage or systemic diuretics. Approximately 3 L can be given in a 24-hour period at two separate sites. Common infusion sites are the chest, abdomen, thighs and upper arms. The preferred solution is normal saline, but other solutions, such as half-normal saline, glucose with saline or 5 percent glucose, can also be used. Potassium chloride can be added to the solution bag if needed. Additionally, other drugs can be delivered through similar routes. Human sHASEGP can be added to enhance fluid absorption and increase the overall rate of administration. Human sHASEGP is preferable for repeated Hypodermoclysis over slaughter house-derived enzymes in that it not likely to be immunogenic as the bovine enzyme is known to be. It may be administered at home by family members or a nurse; the technique should be familiar to every family physician.

In ambulatory patients, hypodermoclysis sites include the abdomen, upper chest, above the breast, over an intercostal space and the scapular area. In bedridden patients, preferred sites are the thighs, the abdomen and the outer aspect of the upper arm. After one to four days, the needle and tubing should be changed, although infusion sets have been left in place for much longer periods without complications. Administration of 500-mL boluses over one or two hours three times a day can also be given, with 150 U of sHASEGP given at the subcutaneous site before the first morning infusion Facilitation of Therapeutic Injections.

Many molecules injected percutaneously (e.g. by using a needle or other device that penetrates the skin and is used to deposit the molecules into a sub-dermal layer) reach circulation slowly or with very low efficiency. Several factors regulate the pharmacokinetics and pharmacodynamics of molecules injected subcutaneously (SC) or intramuscularly (IM). Generally, larger molecules reach circulation more slowly and less efficiently without active transport into circulation. Subcutaneous bioavailability is determined by calculating the ratio of area under the curves for SC verses intravenous administration ($AUC_{SC}/AUC_{intravenous}$). A second factor is charge and affinity for matrix molecules that may play a role in sequestration of molecules subcutaneously. If these materials are degraded locally they may never reach their desired targets and thus demonstrate a decreased overall systemic bioavailability to the target organs.

Large proteins are normally given intravenously so the medicament directly available in the blood stream. It would however be advantageous if a medicament could be given subcutaneously, intramuscularly or intradermally (ID) as these administration forms are much easier to handle for the patient. Especially, if the medicament must be taken regularly during the whole life and treatment is to start early, already when the patient is a child. However, a medicament with a very large and labile molecule, such as coagulation factor VIII of 170 to 300 kDa, have normally a very low bioavailability if given subcutaneously, intramuscularly or intradermally, since the uptake is not enough and degradation is severe.

In addition to the need to increase bioavailability of many subcutaneously administered biologics, more rapid pharmacokinetics is also critically important in instances of emergency medicine. The time required to reach intravenous access in many patients can prevent an otherwise rapid acting drug when administered systemically from being utilized. In some cases failure to reach intravenous access is then followed by subcutaneous injection, which leads to additional delay in reaching the target organs. Thus, the more rapid availability of subcutaneous drugs would be of benefit as a first line of treatment rather than to risk the time required to achieve intravenous access. Examples of molecules that can be delivered subcutaneously as well as intravenously include epinephrine, atropine, narcan, lignocaine, and dextrose.

An additional benefit of the invention lies in the ability to deliver equivalent or larger volumes of solutions ID, SC or IM without the pain and morbidity associated with the pressure and volume of the solution at the site of injection.

By way of illustration (and without limitation), there are a number of biologics that can be enhanced by combination with one or more sHASEGPs (e.g. by co-formulation or co-administration of sHASEGP before, coincident with or after administration of the biologic), including for example: Abciximabs (e.g. REOPRO™), Adalimumabs (e.g. HUMIRA™), Agalsidase betas (e.g. FABRAZYME™), Aldesleukins (e.g. PROLEUKIN™), Alefacepts (e.g. AMEVIVE™), Alemtuzumabs (e.g. CAMPATH™), Alteplases (e.g. ACTIVASE™), Alteplases (e.g. CATHFLO ACTIVASE™), Anakinras (e.g. KINERET™), Arcitumomabs (e.g. CEA-Scan'), Asparaginases (e.g. ELSPAR™), Basiliximabs (e.g. SIMULECT™), Becaplermins (e.g. REGRANEX™), bevacizumabs (e.g. AVASTIN™), Botulinum Toxin Type A's (e.g. BOTOX™), Botulinum Toxin Type B's (e.g. MYOBLOC™), Capromab Pendetides (e.g. PROSTASCINT™), Cetuximabs (e.g. ERBITUX™), Daclizumabs (e.g. ZENAPAX™), Darbepoetin alphas (e.g. ARANESP™), Denileukin diftitoxs (e.g. ONTAK™), Dornase alphas (e.g. PULMOZYME™), Drotrecogin alphas (e.g. XIGRIS™), Efalizumabs (e.g. RAPTIVA™), Epoetin alphas (e.g. EPOGEN™), Etanercepts (e.g. ENBREL™), Filgrastims (e.g. NEUPOGEN™), Ibritumomabs/Tiuxetans (e.g. ZEVALIN™), Imciromab Pentetates (e.g. MYOSCINT™), Infliximabs (e.g. REMICADE™), Interferon alpha-2 as (e.g. ROFERON-A™), Interferon alphacon-1s (e.g. INFERGEN™), Interferon alpha-n3s (e.g. ALFERON N™), Interferon beta-1 as (e.g. AVONEX™, BETASERON™), Interferon beta-1as (e.g. REBIF™), Interferon gamma-1bs (e.g. ACTIMMUNE™), Laronidases (e.g. ALDURAZYME™), Nofetumomabs (e.g. VERLUMA™), Omalizumabs (e.g. XOLAIR™), Oprelvekins (e.g. NEUMEGA™), Palivizumabs (e.g. SYNAGIS™), Pegfilgrastims (e.g. NEULASTA™), Peg-interferon alpha-2 as (e.g. PEGASYS™), Peginterferon alpha-2bs (e.g. PEG-INTRON™), Rasburicases (e.g. ELITEK™), Reteplases (e.g. RETAVASE™), Rituximabs (e.g. RITUXAN™), Tenecteplases (e.g. TNKase™), Tositumomab and Iodine 1-131s (e.g. BEXXAR™), Trastuzumabs (e.g. HERCEPTIN™), Urokinases (e.g. ABBOKINASE™).

Vitreous Hemorrhage

In an effort to minimize the potential for causing further detachment or tearing of the retina during performance of vitrectomy, it has previously been proposed in U.S. Pat. No. 5,292,509 (Hageman), to inject certain protease-free glycosaminoglycanase enzymes into the vitreous body, to cause the vitreous body to become uncoupled or "disinserted" from the retina, prior to removal of the vitreous body. Such disinsertion or uncoupling of the vitreous body is purported to minimize the likelihood that further tearing or detachment of the retina will occur as the vitreous body is removed. Examples of specific protease-free glycosaminoglycanase enzymes which may be used to bring about this vitreal disinsertion purportedly include; chondroitinase ABC, chondroitinase AC, chondroitinase B, chondroitin 4-sulfatase, chondroitin 6-sulfatase, hyaluronidase and beta-glucuronidase.

Although hyaluronidase enzyme has been known to be usable for various ophthalmic applications, including the vitrectomy adjunct application described in U.S. Pat. No. 5,292, 509 (Hageman), published studies have indicated that the hyaluronidase enzyme may itself be toxic to the retina and/or other anatomical structures of the eye. See, The Safety of Intravitreal Hyaluronidase; Gottleib, J. L.; Antoszyk, A. N., Hatchell, D. L. and Soloupis, P., Invest Ophthalmol V is Sci 31:11, 2345-52 (1990). Moreover, the used of impure slaughterhouse preparations of hyaluronidase can cause uveitis or inflammation of the eye. The use of human sHASEGP is thus preferable in both its increased potency, purity and lack of animal origin that can give rise to immunogenic reactions and antibody mediated neutralization following repeated administration. In another embodiment, a pegylated form of a sHASEGP can be injected into the eye. Such a pegylated sHASEGP is not cleared from the vitreous in such a rapid fashion and maintains its activity in the vitreous for a longer period of time.

The ophthalmic toxicity of some hyaluronidase preparations has been confirmed by other investigators, who have proposed that such hyaluronidase preparations be used as a toxic irritant for causing experimentally induced neovascularization of the eye, in animal toxicity models, (see An Experimental Model of Preretinal Neovascularization in the Rabbit; Antoszyk, A. N., Gottleib, J. L., Casey, R. C., Hatchell, D. L. and Machemer, R., Invest Ophthalmol V is Sci 32:1, 46-51 (1991). The use of a highly purified sHASEGP devoid of mercury-based and cattle or bacterially derived contaminants is preferable for intraocular procedures. Moreover, a recombinant human sHASEGP is preferable over slaughterhouse derived preparations in both purity lack of bovine pathogens and reduced risk of immunogenicity. Most preferably a pegylated sHASEGP is envisioned.

An enzymatic method using a human sHASEGP is thus provided for treating ophthalmic disorders of the mammalian eye. In one embodiment of the invention, said sHASEGP is PEGylated to prolong its residence within the vitreous and prevent localized uptake. Prevention of neovascularization, and the increased rate of clearance from the vitreous of materials toxic to retina, are accomplished by administering an amount of hyaluronidase effective to liquefy the vitreous humor of the treated eye without causing toxic damage to the eye. Liquefaction of the vitreous humor increases the rate of liquid exchange from the vitreal chamber. This increase in exchange removes those materials and conditions whose presence causes ophthalmologic and retinal damage.

Cosmetic Uses of sHASEGP

It is known that hyaluronidase has the effect of depolymerizing the long mucopolysaccharide chains of the fundamental substance, responsible for the retention of bound water and of the slowing, by capillary compression, of the diffusion of organic liquids, which eliminate metabolic wastes. Such retention of water and wastes associated with fat overloading of the lipocytes, constitutes classical "pigskin" edema or "orange peel" edema. This depolymerization will therefore cut the long chains of mucopolysaccharides into shorter chains, whence the elimination of the bound water, of wastes, restoration of the venous and lymphatic circulation and disappearance of local edema.

Use of sHASEGP by way of subcutaneous administration is thus preferred for the removal of glycosaminoglycans involved in the accumulation of so-called cellulite and to promote lymphatic flow. Human sHASEGP is preferred for the treatment of cellulite in that it is capable of removal of said glycosaminoglycans without the inflammatory components of slaughter house derived proteins and is of high purity and is not likely to be immunogenic. The sHASEGP can be administered through repeated subcutaneous injections, through transdermal delivery in the form of ointments or creams or through the use of injectable slow release formulations to promote the continual degradation of glycosaminoglycans and prevent their return.

Organ Transplantation

Hyaluronan has several biological effects, that are in part related to its molecular size (West, D. C., Kumar, S. Exp. Cell. Res. 183, 179-196, 1989). The content of hyaluronan in an organ increases in different conditions of inflammation of that organ. Thus, an increased concentration of hyaluronan has been shown in tissue from different organs characterized by inflammatory-immunological injury such as alveolitis (Nettelbladt et al., Am Rev Resp Dis 1989; 139: 759-762) and myocardial infarction (Waldenstrom et al., J Clin Invest 1991; 88(5): 1622-1628). Other examples are allograft rejection after a renal (Hallgren et al., J Exp Med 1990a; 171: 2063-2076; Wells et al., Transplantation 1990; 50: 240-243), small bowel (Wallander et al., Transplant Int 1993; 6: 133-137) or cardiac (Hallgren et al., J Clin Invest 1990b; 85:668-673) transplantation; or a myocardial inflammation of viral origin (Waldenstrom et al., Eur J Clin Invest 1993; 23: 277-282).

The occurrence of interstitial edemas in connection with the grafting of an organ constitutes a severe problem in the field of transplantation surgery. As much as 25% of the grafts, will swell to such a degree that the function will temporarily be lost. Moreover, in 2-3% of the cases, the swelling causes disruption of the kidney, resulting in a massive haemorrhage.

sHASEGP may be used to degrade accumulated glycosaminoglycans in an organ transplant. Removal of such glycosaminoglycans promotes removal of water from the graft and thus organ function. Dose ranging from 500-10,000 Units/kg may be administered to reduce interstitial pressure as such.

Pathologic Accumulations of Glyxosamionoglycans in the Brain

Hyaluronan levels are elevated in a number of cerebrospinal pathologic conditions. Levels of cerebrospinal hyaluronan are normally less than 200 µg/L in adults (Laurent et al., Acta Neurol Scand 1996 September; 94(3):194-206). These levels can elevate to over 8,000 µg/L in diseases such as meningitis, spinal stenosis, head injury and cerebral infarction. Thus administration of sHASEGP (for example by intrathecal delivery or systemic injection of a sHASEGP, PEGylated sHASEGP or super-sialated sHASEGP) can be utilized to degrade critically elevated levels of substrate.

The lack of effective lymphatics in the brain can also lead to life threatening edema following head trauma. Hyaluronan accumulation is a result of increased synthesis by HA synthases, and decreased degradation. Accumulation of hyaluronan can initially serve the beneficial purpose of increasing water content in the damaged tissue, to facilitate leukocyte extravasation, but continued accumulation can be lethal. Administration of human sHASEGP to a patient suffering from head trauma can thus removal tissue hyaluronan accumulation and the water associated with it. Human sHASEGP can be administered intrathecally through a shunt or alternatively, sHASEGP, PEGylated sHASEGP or Super-Sialated sHASEGP (preferably human versions thereof) can be administered intravenously to reach the brain tissue.

Following ischemia and reperfusion of the brain as occurs in stroke, the hyaluronan content typically increases dramatically due to increased expression of HA synthases and decreased catabolism. Failure of ion pumps and leakage of plasma into the interstitium results in fluid retention that if not properly cleared by the lymphatics, results in tissue necrosis. Some groups have attempted to prevent interstitial fluid accumulation following ischemia reperfusion by blocking vascular permeability. However, once the fluid has extravasated, preventing vascular permeability can prevent resolution of edema and exacerbate conditions. As noted above, human sHASEGP can be administered intrathecally (e.g. through a shunt), or sHASEGP, PEGylated sHASEGP or Super-Sialated sHASEGP (preferably human versions thereof) can be administered intravenously to reach the brain tissue.

Human sHASEGP can also be used in the treatment of edema associated with brain tumors, particularly that associated with glioblastoma multiform. The edema associated with brain tumors results from the accumulation of hyaluronan in the non-cancerous portions of the brain adjacent the tumor. Administration of hyaluronidase to the sites of hyaluronan accumulation (e.g., by intravenous injection or via a shunt) can relieve the edema associated with such malignancies by degrading the excess hyaluronan at these sites. Thus, hyaluronidase is successful in the treatment of brain tumors not only in the reduction of the tumor mass and inhibition of tumor growth and/or metastasis, but it also is useful in relieving edema associated with the malignancy. Human sHASEGP can be administered for treatment of edema in a manner similar to that for administration of bovine testicular hyaluronidase to treat edema (see, e.g., Sa Earp Arq. Braz. Med. 44:217-20).

Without being bound to a particular application or mechanism of action, sHASEGPs can potentially ameliorate ischemic or hemorrhagic stroke and/or other CNS damaging conditions by one or more of the following: (i) increasing oxygenation of damaged tissue by reducing intracranial pressure; (ii) facilitating the dissolution of clots and resorption of toxic metabolites; (iii) suppressing leukocyte extravasation into infarcted or hemorrhaged regions (e.g. by removal of hyaluronan which is a receptor for CD44); (iv) promotion of neural regeneration of damaged tissue; or (v) increasing cerebral vasculogenesis.

Treatment of Glycosaminoglycan Accumulation in Cardiovascular Disease

It has been shown that the administration of hyaluronidase in animal models following experimental myocardial infarct can reduce infarct size (Maclean et al., Science 1976 Oct. 8; 194(4261):199-200). The proposed mechanism by which bovine hyaluronidase reduces infarct size in animals is by reducing hyaluronan accumulation that occurs following ischemia reperfusion. Reduction of infarct size is believed to occur from increased lymph drainage and increased tissue oxygenation and reduction of myocardial water content. While reduced infarct size could be obtained in animal models, the benefits were not realized in larger clinical studies in humans. Bovine testes hyaluronidase possesses a remarkably short serum half life of approximately 3 minutes in animals and man (Wolf et al., J Pharmacol Exp Ther 1982 August; 222(2):331-7). This short half-life is due to the terminal mannose residues that are readily recognized by the scavenger receptors of the reticuloendothelial system. While small animals may benefit from hyaluronidase due to a smaller vascular bed, an enzyme with increased half-life is needed. Super sialated sHASEGP possesses more favorable pharmacokinetics due to sialyation for which there is no scavenger receptor. Super sialated sHASEGP in doses ranging from 100-200,000 Units/kg may be utilized to facilitate resolution of excess hyaluronan following ischemia reperfusion and to reduce infarct size.

Super sialated sHASEGP may also be used to limit coronary plaques from arteriosclerosis. Such plaques accumulate glycosaminoglycans and mediate macrophage and foam cell adhesion (Kolodgie et al., Arterioscler Thromb Vasc Biol. 2002 Oct. 1; 22(10):1642-8). Administration of Super Sialated sHASEGP can be used to reduce plaque formation. As repeated administration of hyaluronidase is contemplated at doses from 100-100,000 U/kg, the need to utilize a human recombinant protein with low risk of immunogenicity and increased half-life will result in superior reduction of plaques.

Treatment of Peripheral Tissue Necrosis

Tissue necrosis occurs in many diseases due to venous insufficiency. The lack of sufficient oxygenation is one of the main obstacles for regrowth of the tissue. It has been demonstrated that intra-arterial hyaluronidase treatment significantly improves the clinical picture in patients with peripheral arterial occlusive disease (Elder et al., Lancet (1980) 648-649). sHASEGP can be injected intra-arterially 3-5 times a week at doses from 10-200,000 Units.

Enhanced Delivery of Anesthetics and Other Pharmacologic Agents to Mammalian Tissues Slaughterhouse-derived hyaluronidase is commonly used for peribulbar block in local anesthesia prior ophthalmic surgery. The presence of the enzyme prevents the need for additional blocks and speeds the time to the onset of akinesias (loss of eye movement). Peribulbar and sub-Tenon's block are the most common applications of hyaluronidase for ophthalmic procedures. Since the discontinuation of Wydase™, reports of increased diplopia and ptosis have been reported with peribulbar block (Brown et al *J Cataract Refract Surg* 1999; 25:1245-9).

With Wyeth's discontinuance of Wydase®, bovine testes-derived hyaluronidase material is now supplied by compounding pharmacies. However, there are several concerns with using an extemporaneously compounded sterile product (www.ashp.org/shortage/hyaluronidase.cfm?cfid=11944667&CFToken=9426953-ref#ref). Compounded preparations are not FDA-approved products. As such, the FDA has no control over the quality or consistency of the manufacturing process.

sHASEGP from 10-500 Units can be mixed directly with 5 ml 2% lidocaine (Xylocalne), 5 ml 0.5% bupivacaine (Marcaine) and optionally with epinephrine 1:200,000. sHASEGP can be used to increase the onset of akinesias and to remove the need for additional blocks. sHASEGP is also ideal for akinesias for cosmetic surgery in blepharoplasties and face lifts. sHASEGP can also be utilized following such surgical procedures to diffuse anti inflammatories and to reduce tissue swelling.

sHASEGP may also be mixed with a buffering solution such as bicarbonate to prevent discomfort during the injection procedure. sHASEGP can also be mixed with anesthesia for lacerations to both reduce the total volume of material required for injection and to reduce pain from swelling of tissue.

Use of sHASEGPs to Promote Dispersion of Pharmacologic and Other Agents

As described herein, the compositions and methods of the present invention can be used to promote or enhance the delivery of anesthetics and other pharmacologic agents (such as members of the various classes of pharmaceutically effective agents referred to herein) to any of a variety of mammalian tissues in vivo. In that regard, sHASEGP or a soluble human hyaluronidase domain thereof can be used to facilitate the diffusion and therefore promote the delivery of small molecule pharmacologic agents, such as anesthetics, anti-infectives and anti-inflammatories for example, as well as larger molecule pharmacologic agents, such as proteins (including, e.g., enzymes, monoclonal antibodies, and the like), nucleic acids (including deoxyribonucleic acids (e.g. genes and antisense molecules) and ribonucleic acids (including molecules for RNA interference (RNAi) and the like), and macromolecular compositions which may comprise a combination of such components (including combinations of nucleic acids, proteins, carbohydrates, lipids and lipid-based molecules, and the like). By way of illustration and without limitation, molecules and macromolecular complexes ranging from less than about 10 nm to around 500 nm in diameter, particularly from about 20 to 200 nm, are likely to exhibit dramatic improvements in delivery through interstitial spaces when the interstitial space has been previously, or is coincidentally, exposed to a sHASEGP as described and illustrated herein.

Without being restricted to a particular theory of mechanism of action, it is believed that sHASEGP of the present invention functions principally by hydrolyzing glycosaminoglycans within the extracellular matrix surrounding mammalian cells to create pore-like passages or channels that facilitate diffusion or other movement of molecules within the exposed extracellular matrix; and, furthermore, that permeabilizing such portions of the extracellular matrix has the greatest effect on the diffusion or "spreading" of molecules that are not so large as to be also hindered by other macromolecular components of the extracellular matrix, such as an overarching network of collagen. The extent of the spreading effect obtainable with a given sHASEGP or a soluble human hyaluronidase domain thereof in a particular tissue setting can be readily ascertained as illustrated herein by assessing the effect of the sHASEGP or domain thereof on the diffusion of detectable test molecules of various sizes (such as fluoresceinated or otherwise labeled beads) within the test tissue, either with or without pretreatment or concomitant treatment with sHASEGP or domain thereof at a range of times and concentrations. By way of illustration, in the case of recombinant rHuPH20 injected subcutaneously into the lateral skin of mice, fluoresceinated bead diffusion tests (as exemplified herein) indicated that the effects on diffusion were greatest with particles of less than about 500 nm in diameter.

It is further believed that larger macromolecules (exemplified by beads of 500 nm or larger) may be hindered in diffusion not only by their larger size but by their potential interaction with other relatively more open networks within the extracellular matrix, such as a network formed from strands of interstitial collagen. In addition, and unlike described animal-derived hyaluronidases, presently preferred sHASEGPs of the present invention do not contain agents that promote extravasation or contaminating agents such as collagenases (that may open larger channels) or other contaminants that may provoke immune reactions. In particular applications in which larger pores or channels are desired, sHASEGP or a soluble human hyaluronidase domain thereof can be combined with preferably relativelty pure forms of other matrix-degrading enzymes such as collagenases to facilitate further spreading of larger size macromolecular complexes or cells. For most applications, the use of an agent that promotes the permeability of macromolecules having a size of less than about 500 nm, and more preferably less than about 200 nm, is very advantageous in that the agent does not substantially promote the movement of cells within a treated tissue but promotes the passage of smaller complexes and agents.

As described and illustrated herein, sHASEGPs can be used to enhance the delivery of a variety of other pharmacologic and/or other agents to tissues within the human body (including tissues such as those at the back of the eye that are typically relatively difficult to reach). Without wishing to be bound by theory, it is believed that sHASEGPs can enhance the pharmacokinetic and/or pharmacodynamic profiles of a number of such agents by potentially enhancing their diffusion or permeation within a tissue, and/or by enhancing their convective transport by increasing bulk fluid flow within the interstitial space of a tissue. For purposes of illustration (and without limitation), examples of pharmacologic agents that can be combined with sHASEGPs of the present invention (e.g. combined by co-formulation with one or more sHASEGPs or by co-administration with one or more sHASEGPs (which may be administered prior to, coincident with or following administration of the agent) for treatment of various conditions affecting the eye include, for example, Angiogenesis inhibitors (such as angiostatins, anecortave acetates (e.g. RETAANE™), endostatins, thrombospondins (e.g. thrombospondin-1 and thrombospondin-2), anti-angiogenic antibodies and other anti-angiogenic agents or vascular targeting agents (VTAs) (e.g. anti-VEGF antibodies such as bevacizumabs (e.g. AVASTIN™), carboxyamido triazole (CAI), Interleukin-12 (IL-12), OLTIPRAZ™ (5-[2-pyrazinyl]-4-methyl-1,2,3-thio-ne), SU-5416, TNP-470, thalidomide), and the like); Anti-cataract and anti-diabetic retinopathy substances (such as aldose reductase inhibitors (AR15) for example tolrestats (e.g. ALREDASE™ and zopolrestats (e.g. ALOND™), lisinoprils, enalaprils, statils, and thiol crosslinking substances and the like); Anti-inflammatory agents (including steroidal and non-steroidal anti-inflammatory agents as described herein and in the art); Anti-infectives (including compounds as described below, as well as a number of opthalmic preparations thereof such as BLEPHAMIDE™, CLLOXAN™, POLYTRIM™, QUIXIN™, TOBRADEX™, VIGAMOX™., ZYMAR™); Beta-adrenergic blocking agents (such as betaxolols (e.g. BETOPTIC S™), timolols (e.g. BETIMOL™ and TIMOPTIC™) and combinations thereof (e.g. timolols and a carbonic anhydrase inhibitor such as a dorzolamide (e.g. COSOP™); Carbonic anhydrase inhibitors (such as acetazolamides, brinzolamides (e.g. AZOP™), dichlorophenamides, dorzolamides (e.g. TRUSOPT™, and in combinations with other agents as in e.g. COSOP™), methazolamides and the like); Mydriatics (such as atropine sulfates, cyclopentolates, homatropines, scopolamines, tropicamides, eucatropines, and hydroxyamphetamines and the like); Photodynamic therapy agents (such as verteporfin (e.g. VISUDYNE™); Prostaglandin analogs (such as bimatoprosts (e.g. LUMIGAN™), latanoprosts (e.g. XALATAN™), and travoprosts (e.g. TRAVATAN™); Sympathomimetics (such as brimonidines (e.g. ALPHAGAN™ P); as well as combinations thereof (such as combinations of a beta-adrenergic blocking agent and a carbonic anhydrase inhibitor as in COSOPT™); and numerous other classes of agents such as anti-infectives and various other physiological modulators as described below or elsewhere herein, and/or as known in the art or newly developed.

A number of other pharmacologic agents that can be combined with sHASEGPs of the present invention (e.g. combined by co-formulation with one or more sHASEGPs or by co-administration with one or more sHASEGPs (which may be administered prior to, coincident with or following administration of the agent) can be used for treatment of various conditions affecting the eye or affecting various other tissues of the body. For purposes of illustration (and without limitation), such agents include, for example: Anesthetics; Antimetholites, anti-neoplastics and other anti-cancer agents; Anti-virals; Anti-infectives, including Anti-bacterials and other antibiotics, Anti-fungals and other anti-infectives; Immunomodulatory agents; Steroidal and non-steroidal anti-inflammatories; Beta blockers; Sympathomimetics; Ducosanoids, prostaglandins and prostaglandin analogs; Miotics, cholinergics and anti-cholinesterases; Anti-allergenics and Decongestants; Hormonal agents; Growth factors; other synthetic and biologically derived agents; and combinations thereof. Some illustrative examples of agents having such properties that can be combined with sHASEGPs in the formulation of novel pharmacologics and/or reformulations of existing pharmacologics include the various categories of agents described above and below (as well as other known and novel agents that are regularly being identified for the diagnosis, prevention or treatment of various disease):

Anesthetics, particularly non-inhalation local anesthetics (such as ambucaines; amoxecaines; amylocalnes; aptocaines; articaines; benoxinates; benzyl alcohols; benzocaines; betoxycaines; biphenamines; bucricaines; bumecaines; bupivacaines; butacaines; butambens; butanilicaines; carbizocaines; chloroprocaine; clibucaines; clodacaines; cocaines; dexivacaines; diamocaines; dibucaines; dyclonines; elucaines; etidocaines; euprocins; fexicaines; fomocaines; heptacaines; hexylcaines; hydroxyprocaines; hydroxytetracaines; isobutambens; ketocaines; leucinocaines; lidocaines; mepivacaines; meprylcaines; octocaines; orthocaines; oxethacaines; oxybuprocaines; phenacaines; pinolcaines; piperocaines; piridocaines; polidocanols; pramocaines; prilocalnes; procaines; propanocaines; propipocaines; propoxycaines; proxymetacaines; pyrrocaines; quatacaines; quinisocaines; risocaines; rodocaines; ropivacaines; salicyl alcohols; suicaines; tetracaines; trapencaines; trimecaines) and the like; as well as various other non-inhalation anesthetics (such as alfaxalones; amolanones; etoxadrols; fentanyls; ketamines; levoxadrols; methiturals; methohexitals; midazolams; minaxolones; propanidids; propoxates; pramoxines; propofols; remifentanyls; sufentanyls; tiletamines; zolamine and the like);

Anti-metabolites (such as folic acid analogs (e.g., denopterins, edatrexates, methotrexates, piritrexims, pteropterins, Tomudex, trimeterxates), purine analogs (e.g., cladribines, fludarabines, 6-mercaptopurines, thiamiprines, thiaguanines), and pyrimidine analogs (e.g., ancitabines, azacitidines, 6-azauridines, carmofurs, cytarabines, doxifluridines, emitefurs, enocitabines, floxuridines, fluorouracils, gemcitabines, tegafurs) and the like;

Anti-neoplastics (such as aclacinomycins, actinomycins, adriamycins, ancitabilles, anthramycins, azacitidines, azaserines, 6-azauridines, bisantrenes, bleomycins, cactinomycins, carmofurs, carmustines, carubicins, carzinophilins, chromomycins, cisplatins, cladribines, cytarabines, dactinomycins, daunorubicins, denopterins, 6-diazo-5-oxo-L-norleucines, doxifluridines, doxorubicins, edatrexates, emitefurs, enocitabines, fepirubicins, fludarabines, fluorouracils, gemcitabines, idarubicins, loxuridines, menogarils, 6-mercaptopurines, methotrexates, mithramycins, mitomycins, mycophenolic acids, nogalamycins, olivomycines, peplomycins, pirarubicins, piritrexims, plicamycins, porfironiycins, pteropterins, puromycins, retinoic acids, streptonigrins, streptozocins, tagafurs, tamoxifens, thiamiprines, thioguanines, triamcinolones, trimeterxates, tubercidins, vinblastines, vincristines, zinostatins, zorubicins and the like) (see also the illustrative anticancer agents described herein);

Anti-virals (such as abacavirs (e.g. ZIAGEN™), acyclovirs (e.g. ZOVIRAX™), amantadines and rimantadines (e.g. SYMMETREL™), amprenavirs (e.g. AGENERASE™), cidofovirs (e.g. VISTIDE™), delavirdines (e.g. RESCRIPTOR™), didanosines (e.g. VIDEX™), efavirenz (e.g. SUSTIVA™), famciclovirs (e.g. FAMVIR™), fomivirsens (e.g. VITRAVENE™), foscarnets (e.g. FOSCAVIR™), ganciclovirs (e.g. CYTOVENE™) and valganciclovirs (e.g. VALCYTE™), idoxuridines (e.g. HERPLEX™), indinavirs (e.g. CRIXIVAN™), interferons (e.g. ALFERON N™, INTRON™ A, PEGASYS™, PEG-INTRON™, ROFERON-AT™, and combinations of interferons and other antivirals such as ROBETRON™ and PEGASYS/COPEGUS™), lamivudines (e.g. 3TC™ and EPIVIR™.) and combinations of lamivudines and zidovudines (e.g. COMBIVIR™), monoclonal antibodies such as palivizumabs (e.g. SYNAGIS™), nelfinavirs (e.g. VIRACEP™), nevirapines (e.g. VIRAMUNE™), oseltamivirs (TAMIFLU™), penciclovirs (e.g. DENAVIR™), pleconarils, ribavirins (e.g. COPEGUS™ and REBETOL™), rimantadines (e.g. FLUMADINE™), ritonavirs (NORVIR™), saquinavirs (e.g. INVERASE™), stavudines (d4T, e.g., ZERIT™), valacyclovirs (e.g. VALTREX™), vidarabines (e.g. VIRA-A™), zalcitabines (e.g. HIVID™), zanamivirs (RELENZA™), zidovudines (e.g. AZT, RETROVIR™), and the like);

Anti-bacterials and other antibiotics, including, for example, Aminoglycosides; Amphenicols; Ansamycins; Carbacephems; Carbapenems; Cephalosporins or Cephems; Cephamycins; Clavams; Cyclic lipopeptides; Diaminopyrimidines; Ketolides; Lincosamides; Macrolides; Monobactams; Nitrofurans; Oxacephems; Oxazolidinones; Penems, thienamycins and miscellaneous beta-lactams; Penicillins; Polypeptides antibiotics; Quinolones; Sulfonamides; Sulfones; Tetracyclines; and other antibiotics, illustrative members of which are provided below (and others known in the art or newly developed):

Aminoglycosides (e.g., amikacins, apramycins, arbekacins, bambermycins, butirosins, dibekacins, dihydrostreptomycins, fortimicins, gentamicins, isepamicins, kanamycins, micronomicins, neomycins, neomycin undecylenates, netilmicins, paromomycins, ribostamycins, sisomicins, spectinomycins, streptomycins, tobramycins, trospectomycins and the like);

Amphenicols (e.g., azidamfenicols, chloramphenicols, florfenicols, thiamphenicols and the like);

Ansamycins (e.g., rifamides, rifampins or rifampicins (e.g. RIFADIN™, RIFADIN IV™, as well as combinations comprising rifampins such as rifampin/isoniazid (e.g. RIFAMATE™) and rifampin/isoniazid/pyrazinamide (e.g. RIFATER™), rifamycins, rifapentines, rifaximins (e.g. XIFAXAM™), and the like);

Carbacephems (e.g. loracarbefs, 3-chloro-1-carbacephems, 3-thio substituted carbacephems, carbacephems described in U.S. Published Patent Application No. 20050004095, and the like);

Carbapenems (e.g., biapenems, imipenems, meropenems, panipenems and the like);

Cephalosporins or cephems (e.g., cefaclors (e.g. CECLOR™), cefadroxils, cefamandoles, cefatrizines, cefazedones, cefazolins (e.g. ANCEF)™, cefcapene pivoxils, cefclidins, cefdinirs, cefditorens, cefepimes (e.g. MAXIPIME™), cefetamets, cefiximes, cefinenoximes, cefinetazoles, cefodizimes, cefonicids, cefoperazones, cefloranides, cefotaximes, cefotiams, cefotetans, cefoxitins, cefozoprans, cefpimizoles, cefpiramides, cefpiromes, cefpodoxime proxetils, cefprozils, cefroxadines, cefsulodins, ceftazidimes (e.g. FORTAZ™), cefterams, ceftezoles, ceftibutens, ceftizoximes, ceftriaxones (e.g. ROCEPHIN™), cefuroximes (e.g. ZINACEF™), cefuzonams, cephacetriles, cephalexins, cephaloglycins, cephaloridines, cephalosporins, cephalothins, cephapirins, cephradines, pivcefalexins and the like);

Cephamycins (e.g., cefbuperazones, cefinetazoles, cefininoxes, cefotetans, cefoxitins (e.g. MEFOXIN™), and the like);

Clavams (e.g., clavulinic acid or clavulanates, 2- and 3-phenyl clavams, and combinations comprising such agents such as amoxicillin/clavulanates (e.g. AUGMENTIN™) and ticarcillin/clavulanate-s (e.g. TIMENTIN™), and the like);

Cyclic lipopeptides (e.g. daptomycins (e.g. CUBICIN™);

Diaminopyrimidines such as 2,4-diaminopyrimidines (e.g., brodimoprims, tetroxoprims, trimethoprims and the like);

Ketolides (e.g. telithromycins (e.g. KETEK™), and bridged bicyclic ketolides (e.g. Enanta EP-013420 and 6-11 bycyclic ketolides as described in U.S. Published patent application 20040157787), and the like);

Lincosamides (e.g., clindamycins, lincomycins and the like);

Macrolides (e.g., azithromycins (e.g. ZITHROMAX™), carbomycins, clarithromycins, dirithromycins, erythromycins, erythromycin acistrates, erythromycin estolates, erythromycin glucoheptonates, erythromycin lactobionates, erythromycin propionates, erythromycin stearates, josamycins, leucomycins, midecamycins, miokamycins, oleandomycins, primycins, rokitamycins, rosaramicins, roxithromycins, spiramycins, troleandomycins and the like);

Monobactams (e.g., aztreonams (e.g. AZACTAM™), carumonams, tigemonams and the like);

Nitrofurans (e.g., furaltadones, furazolium chlorides, nifuradenes, nifuratels, nifurfolines, nifurpirinols, nifurprazines, nifurtoinols, nitrofurantoins and the like);

Oxacephems (e.g. flomoxefs, latamoxefs or moxalactams (e.g. MOXAM™), and the like);

Oxazolidinones (e.g. linezolids (e.g. ZYVOX™), eperezolids, and the like);

Penems, thienamycins and miscellaneous beta-lactams (e.g. ertapenems (e.g. INVANZ™), imipenems (e.g. with Cilastatin as in PRIMAXIN™), meropenems (e.g. MERREM™), and the like);

Penicillins (e.g., amdinocillins, amdinocillin pivoxils, amoxicillins, ampicillins (including combinations thereof (e.g. with sublactams as in UNASYN™)), apalcillins, aspoxicillins, azidocillins, azlocillins, bacampicillins, benzylpenicillinic acids, benzylpenicillin sodiums, carbenicillins, carindacillins, clometocillins, cloxacillins, coamoxiclays, cyclacillins, dicloxacillins, epicillins, fenbenicillins, floxacillins, hetacillins, lenampicillins, metampicillins, methicillin sodiums, mezlocillins, nafcillins, oxacillins, penamecillins, penethamate hydriodides, penicillin G benethamines, penicillin G benzathines (e.g. L-A), penicillin G benzhydrylamines, penicillin G calciums, penicillin G hydrabamines, penicillin G potassiums, penicillin G procaines, penicillin N, penicillin O, penicillin V, penicillin V benzathines, penicillin V hydrabamines, penimepicyclines, phenethicillin potassiums, piperacillins (including combinations thereof (e.g. with beta-lactamase inhibitors such as tazobactam, as in ZOSYN™)), pivampicillins, propicillins, quinacillins, sulbenicillins, sultamicillins, talampicillins, tazocillins, temocillins, ticarcillins (e.g. with clavulanates as in TIMENTIN™), and the like);

Polypeptides antibiotics (e.g., amphomycins, bacitracins, capreomycins, colistimethates (e.g. COLI-MYCIN™ M), colistins, enduracidins, enviomycins, fusafungines, gramicidins, mikamycins, polymyxins, pristinamycins (and pristinamycin derivatives such as quinupristins and dalfopristins (e.g. SYNERCID™)), ristocetins, teicoplanins, thiostreptons, tuberactinomycins, tyrocidines, tyrothricins, vancomycins, viomycins, virginiamycins, zinc bacitracins and the like);

Quinolones (incl. fluoroquinolones and analogs) (e.g., alatrofloxacin mesylates, cinoxacins, ciprofloxacins (e.g. CIPRO™), clinafloxacins, difloxacins, enoxacins, fleroxacins, flumequines, gatifloxacins (e.g. TEQUIN™), grepafloxacins, levofloxacins (e.g. LEVAQUIN™), lomefloxacins, miloxacins, moxyfloxacins (e.g. AVELOX™), nadifloxacins, nalidixic acids, norfloxacins, ofloxacins, oxolinic acids, pazufloxacins, pefloxacins, pipemidic acids, piromidic acids, rosoxacins, rufloxacins, sparfloxacins, temafloxacins, tosufloxacins, trovafloxacin mesylates and the like);

Sulfonamides (e.g., acetyl sulfamethoxypyrazines, benzylsulfamides, chloramine-B, chloramine-T, dichloramine T, formylsulfisomidines, beta-glucosylsulfanilamides, mafenides, 4'-(methylsulfamoyl)sulfanilanili-des, noprylsulfamides, phthalylsulfacetamides, phthalylsulfathiazoles, salazosulfadimidines, succinylsulfathiazoles, sulfabenzamides, sulfacetamides, sulfachlorpyridazines, sulfachrysoidines, sulfacytines, sulfadiazines, sulfadicramides, sulfadimethoxines, sulfadoxines, sulfaethidoles, sulfaguanidines, sulfaguanols, sulfalenes, sulfaloxic acids, sulfamerazines, sulfameters, sulfamethazines, sulfamethizoles, sulfamethomidines, sulfamethoxazoles, sulfamethoxypyridazines, sulfametroles, sulfamidochrysoidines, sulfamoxoles, sulfanilamides, 4-sulfanilamidosalicylic acids, sulfanilylsulfanilamides, sulfanilylureas, n-sulfanilyl-3,4-xylamides, sulfanitrans, sulfaperines, sulfaphenazoles, sulfaproxylines, sulfapyrazines, sulfapyridines, sulfasomizoles, sulfasymazines, sulfathiazoles, sulfathioureas, sulfatolamides, sulfisomidines, sulfisoxazoles and the like);

Sulfones (e.g., acedapsones, acediasulfones, acetosulfone sodiums, dapsones, diathymosulfones, glucosulfone sodiums, solasulfones, sublactams, succisulfones, sulfanilic acids, p-sulfanilylbenzylamines, sulfoxone sodiums, thiazolsulfones and the like);

Tetracyclines (e.g., apicyclines, chlortetracyclines, clomocyclines, demeclocyclines, doxycyclines, guamecyclines, lymecyclines, meclocyclines, methacyclines, minocyclines, oxytetracyclines, penimepicyclines, pipacyclines, rolitetracyclines, sancyclines, tetracycline), and others (e.g., cycloserines, mupirocins, tuberins and the like);

and other antibiotics (such as clofoctols, fusidic acids, hexedines, methenamines (including e.g., methenamine, methenamine anhydromethylene-citrates, methenamine hippurates, methenamine mandelates, methenamine sulfosalicylates), nitrofurantoins (e.g. FURADANTIN™), nitroxolines, ritipenems, taurolidines, xibomols and the like);

Anti-fungals, including polyenes such as amphotericin Bs (e.g. ABELCET™ and AMBISOME™), candicidins, dermostatins, filipins, fungichromins, hachimycins, hamycins, lucensomycins, mepartricins, natamycins (e.g. Natacyn), nystatins, pecilocins, perimycins, and others (e.g., azaserines, griseofulvins, oligomycins, neomycin undecylenates, pyrroInitrins, siccanins, tubercidins, viridins); as well as synthetic anti-fungals such as allylamines (e.g., butenafines, naftifines, terbinafines); imidazoles (e.g., bifonazoles, butoconazoles, chlordantoins, chlormidazoles, cloconazoles, clotrimazoles, econazoles, enilconazoles, fenticonazoles, flutrimazoles, isoconazoles, itraconazole, ketoconazoles, lanoconazoles, miconazoles, omoconazoles, oxiconazole nitrates, sertaconazoles, sulconazoles, tioconazoles, voriconazoles (e.g. VFEND™)); thiocarbamates (e.g., tolciclates, tolindates, tolnaftates); triazoles (e.g., fluconazoles (e.g. DIFLUCAN™), itraconazoles (e.g. SPORANOX™), saperconazoles, terconazoles); and other synthetics (e.g., acrisorcins, amorolfines, biphenamines, bromosalicylchloranilides, buclosamides, calcium propionates, chlorphenesins, ciclopiroxes, cloxyquins, coparaffinates, diamthazole dihydrochlorides, exalamides, flucytosines, halethazoles, hexetidines, lipopeptides such as echinocandin (as in caspofingin CANCIDAS™), loflucarbans, nifuratels, potassium iodides, propionic acids, pyrithiones, salicylanilides, sodium propionates, sulbentines, tenonitrozoles, triacetins, ujothions, undecylenic acids, zinc propionate) and the like;

Amebicides and anti-protozoals (including, e.g., atovaquone, chloroquine hydrochloride, chloroquine phosphate, metronidazole, metronidazole hydrochloride, pentamidine isethionate and the like); Anti-helmenthics and anti-parasitics (including, e.g., mebendazole, pyrantel pamoate, thiabendazole and the like); Anti-malarials (including, e.g., chloroquine hydrochloride, chloroquine phosphate, doxycycline, hydroxychloroquine sulfate, mefloquine hydrochloride, primaquine phosphate, pyrimethamine, pyrimethamine with sulfadoxine; Anti-tuberculotics and anti-leprotics (including, e.g., clofazimine, cycloserine, dapsone, ethambutol hydrochloride, isoniazid, pyrazinamide, rifabutin, rifampin, rifapentine, streptomycin sulfate and the like, as well as combinations thereof such as rifampin/isoniazid (e.g. RIFAMATE™) and rifampin/isoniazid/pyrazinamide (e.g. RIFATER™).

For purposes of further illustration (and without limitation), examples of immuno-modulatory agents that can be combined with sHASEGPs of the present invention (e.g. combined by co-formulation with one or more sHASEGPs or by co-administration with one or more sHASEGPs (which may be administered prior to, coincident with or following administration of the agent) include, for example, members of the following classes of agents:

Immunosuppressants (including, e.g., azathioprine, basiliximab, cyclosporine, daclizumab, lymphocyte immune globulin, muromonab-CD3, mycophenolate mofetil, mycophenolate mofetil hydrochloride, sirolimus, tacrolimus and the like);

Vaccines and toxoids (including, e.g., BCG vaccine, cholera vaccine, diphtheria and tetanus toxoids (adsorbed), diphtheria and tetanus toxoids and acellular pertussis vaccine adsorbed, diphtheria and tetanus toxoids and whole-cell pertussis vaccine, *Haemophilus* b conjugate vaccines, hepatitis A vaccine (inactivated), hepatisis B vaccine (recombinant), influenza virus vaccines (based on purified surface antigens), influenza virus vaccines (based on subvirions or purified subvirions), influenza virus vaccines (based on whole virions), Japanese encephalitis virus vaccine (inactivated), Lyme disease vaccine (recombinant OspA), measles and mumps and rubella virus vaccine (live), measles and mumps and rubella virus vaccine (live attenuated), measles virus vaccine (live attenuated), meningococcal polysaccharide vaccine, mumps virus vaccine (live), plague vaccine, pneumococcal vaccine (polyvalent), poliovirus vaccine (inactivated), poliovirus vaccine (live, oral, trivalent), rabies vaccine (adsorbed), rabies vaccine (human diploid cell), rubella and mumps virus vaccine (live), rubella virus vaccine (live, attenuated), tetanus toxoid (adsorbed), tetanus toxoid (fluid), typhoid vaccine (oral), typhoid vaccine (parenteral), typhoid VI polysaccharide vaccine, varicella virus vaccine, yellow fever vaccine and the like);

Altitoxins and antivenins (including, e.g., black widow and other spider antivenins; Crotalidae antivenom (polyvalent), diphtheria antitoxin (equine), Micrurus fulvius antivenin and the like);

Immune sera (including, e.g., cytomegalovirus immune globulin (intraveneous), hepatitis B immune globulin (human), immune globulin intramuscular, immune globulin intravenous, rabies immune globulin (human), respiratory syncytial virus immune globulin intravenous (human), immune globulins (human), tetanus immune globulin (human), varicella-zoster immune globulin and the like);

and other immunomodulators (including, e.g., aldesleukin, epoetin alpha, filgrastim, glatiramer acetate for injection, interferon alphacon-1, interferon alpha-2a (recombinant), interferon alpha-2b (recombinant), interferon alpha-n3, interferon beta-1a, interferon beta-1b (recombinant), interferon gamma-1b, levamisole hydrochloride, oprelvekin, sargramostim and the like).

Other agents that can be combined with sHASEGPs of the present invention (e.g. combined by co-formulation with one or more sHASEGPs or by co-administration with one or more sHASEGPs (which may be administered prior to, coincident with or following administration of the agent) include, e.g., the following:

Steroidal anti-inflammatories (such as alclomethasones, algestones, beclomethasones, betamethasones, budesonides, clobetasols, clobetasones, clocortolones, cloprednols, corticosterones, cortisones and hydrocortisones (e.g. hydrocortisone acetate), cortivazols, deflazacorts, desonides, desoximetasones, dexamethasones (e.g. dexamethasone 21-phosphate), difluorosones, diflucortolones, difluprednates, enoxolones, fluazacorts, flucloronides, flumethasones, flunisolides, fluocinolones, fluocinonides, fluocortins, fluocortolones, fluorometholones, fluperolones, fluprednidenes, fluprednisolones, flurandrenolides, fluticasones, formocortals, halcinonides, halobetasols, halometasones, halopredones, hydrocortamates, hydrocortisones, loteprednol etabonate, mazipredones, medrysones, meprednisones, methylprednisolones, mometasone furoate, paramethasones, prednicarbates, prednisolones (e.g. prednisolone 25-diethylamino-acetate, prednisolone sodium phosphate), prednisones, prednivals, prednylidenes, rimexolones, tixocortols, triamcinolones (e.g. triamcinolone acetonide, triamcinolone benetonide, and triamcinolone hexacetonide) and the like);

Non-steroidal anti-inflammatories (such as cromoglicates, diclofenacs, flurbiprofens, indomethacins, ibuprofens, ketorolacs (e.g. ketorolac tromethamine), lodoxamides, nedocromils, piroxicams, salicylates, and the like);

Beta blockers (such as betaxolols (e.g. betaxolol hydrochloride), carteolols, esmolols, levobunolols, metipranalols, timolols (e.g. timolol hemihydrate and various forms of timolol maleate) and the like);

Sympathomimetics (such as adrenaline, brimonidines, dipivefrins, epinephrines and the like);

Ducosanoids, prostaglandins and prostaglandin analogs (such as bimatoprosts, latanoprosts, travoprosts, unoprostones, and the like) as well as antiprostaglandins and prostaglandin precursors;

Miotics, cholinergics and anti-cholinesterases (such as acetylcholine chlorides, carbachols, demecarium bromides, diisopropyl fluorophosphates, eserines, physostigmines, pilocarpines, phospholine iodines, salicylates, and the like);

Anti-allergenics (such as sodium antazolines, cetirizines, chlorpheniramines, cromoglycates, cromolyn sodium (Crolom), emedastine difumarate, ketotifins (e.g. ketotifen fumarate), levocabastines, methapyrilines, nedocromil sodium, olopatadines, pyrilamines, prophenpyridamines, and the like);

Decongestants (such as phenylephrines, naphazolines, tetrahydrozolines and the like);

Hormonal agents (such as estrogens, estradiols, progestationals, progesterones, insulins, calcitonins, parathyroid hormone and peptide and vasopressin hypothalamus releasing factor and the like);

Growth factors (such as epidermal growth factor, fibroblast growth factor, platelet derived growth factor, transforming growth factor beta, somatotropin and fibronectin and the like);

Analgesics (such as acetaminophen; alfentanil; aminobenzoate; aminobenzoate; anidoxime; anileridine; anileridine; anilopam; anirolac; antipyrine; aspirin; benoxaprofen; benzydamine; bicifadine hydrochloride; brifentanil; brom adoline; bromfenac; buprenorphine; butacetn; butixirate; butorphanol; butorphanol; carbamazepine; carbaspirin calcium; carbiphene; carfentanil; ciprefadol succinate; ciramadol; ciramadol; clonixeril; clonixin; codeine; codeine phosphate; codeine sulfate; conorphone; cyclazocine; dexoxadrol; dexpemedolac; dezocine; diflunisal; dihydrocodeine; dimefadane; dipyrone; doxpicomine; drinidene; enadoline; epirizole; ergo tamine tartrate; ethoxazene; etofenamate; eugenol; fenoprofen; fenoprofen calcium; fentanyl citrate; floctafenine; flufenisal; flunixin; flunixin meglumine; flupirtine; fluproquazone; fluradoline; flurbiprofen; hydromorphone; ibufenac; indoprofen; ketazocine; ketorfanol; ketorolac; letimide; levomethadyl acetate; levomethadyl acetate hydrochloride; levonantradol; levorphanol; lofemizole; lofentanil oxalate; lorcinadol; lomoxicarn; magnesium salicylate; mefenamic add; menabitan; meperidine; meptazinol; methadone; methadyl acetate; methopholine; methotrimeprazine; metkephamid acetate; mimbane; mirfentanil; molinazone; morphine sulfate; moxazocine; nabitan; nalbuphine; nalmexone; namoxyrate; nantradol; naproxen; naproxen; naproxol; nefopam; nexeridine; noracymethadol; ocfentanil; octazamide; olvanil; oxetorone; oxycodone; oxycodone; oxycodone terephthalate; oxymorphone; pemedolac; pentamorphone; pentazocine; pentazocine; phenazopyridine; phenyramidol; picenadol; pinadoline; pirfenidone; piroxicam olamine; pravadoline; prodilidine; profadol; propiram; propoxyphene; propoxyphene napsilate; proxazole; proxorphan; pyrroliphene; remifentanil; salcolex; salethamide maleate; salicylamide; salicylate meglumine; salsalate; salicylate; spiradoline; sufentanil; sufentanil; sucapsaicin; talmetacin; talniflumate; talosalate; tazadolene; tebufelone; tetrydamine; tifurac; tilidine; tiopinac; tonazocine; tramadol; trefentanil; trolamine; veradoline; verilopam; volazocine; xorphanol; xylazine; zenazocine mesilate; zomepirac; and the like);

Other macromolecular pharmacologic agents such as other proteins, nucleic acids, and the like; as well as complexes of macromolecules such as various drug delivery, protein delivery and/or gene delivery vehicles (including synthetically-prepared vehicles such as liposomes and the like, as well as biologically-generated vehicles such as viral vectors and the like); and Other agents used for a variety of conditions (and additional information regarding usage, dosages, contraindications etc. of various agents including those identified herein), as known in the art, including for example those additional agents identified in references such as the Physicians' Desk Reference (PDR) (Thomson 2003, 2004, 2005); the American College of Physicians Complete Home Medical Guide (DK Publishing 2003); and additional agents indentified in patent references including, for example, U.S. Published applications 20040224023, 20040224012 and 20050002865 (which lists of agents are hereby incorporated by reference herein).

Combinations of agents (e.g. two or more agents selected from one or more of the preceding groups of agents and/or from other groups or classes of pharmacologic and other agents specified herein or known in the art).

Use of sHASEGPs for Reduction of Intraocular Pressure and Other Opthalmic Indications A common side effect occurring in postoperative cataract patients is a significant early, and occasionally prolonged, rise in intraocular pressure. Such a condition is sometimes serious, especially in patients with glaucomatous optic disc changes. Although the pressure increase tends to be more severe when visco-elastic agents such as hyaluronic acid are injected into the eye during surgery, the intraocular pressure can become elevated postoperatively even when such agents are not utilized. Furthermore, such a pressure increase can occur even when no additional medications are used during the surgical procedure. In some cases, it is advantageous to leave a viscoelastic agent in the eye, which often necessitates giving patients large doses of carbonic anhydrase inhibitors. These inhibitors lower the intraocular pressure by decreasing the formation of aqueous humor, a fluid that is normally secreted in the eye, by the ciliary body. Current methods for relieving postoperative pressure increases in the eye include various types of eye drops such as beta-adrenergic blocking agents, sympathomimetic agents, miotics, alpha II selective agents, carbonic anhydrase inhibitors and prostaglandin agents.

A preferred method of removing the viscoelastic such as hyaluronic acid is by injection of sHASEGP during or immediately following anterior segment or posterior segment surgical procedures, although other methods of administration known in the art are possible as well. It is preferred if the hyaluronic acid and the sHASEGP are administered by injection into the anterior chamber during anterior segment ocular surgical procedures to allow the hyaluronic acid to act as a spacer during the start of the surgical procedure. In some cases of corneal transplantation, the hyaluronic acid and sHASEGP combination may be placed on the surface of the intraocular structures prior to suturing the corneal transplant in place. This combination may also be used in posterior segment surgery, such as retina or vitreous surgery.

In some cases, it may be advisable to leave a visco-elastic agent such as Healon™, Viscoat™, or other space-occupying substances in the anterior chamber of the eye at the conclusion of surgery. This is especially true in positive pressure rise when the intraocular contents tend to come forward and press against the posterior surface of the cornea. If this occurs in an eye with a synthetic intraocular lens in place, pressure on the corneal endothelium can cause significant damage to the cells and subsequent corneal swelling and opacification can occur, which are associated with decreased vision. Typically, if a patient's intraocular pressure is significantly elevated at the conclusion of the operative procedure, it is necessary to give such a patient large doses of carbonic anhydrase inhibitors, as well as topical eye drops such as beta-blockers and alpha II agonists in order to decrease aqueous formation and/or to increase aqueous outflow. These agents all have significant side effects and, in some instances, are contraindicated in patients with various types of medical conditions such as breathing problems, heart disease or high blood pressure. However, the use of sHASEGP in these situations will eliminate the necessity of giving these patients large doses of such drugs.

Furthermore, there is a significant amount of hyaluronic acid in the trabecular meshwork. The sHASEGP will break this down and therefore improve the outflow of the aqueous through the trabecular meshwork. The patient's intraocular pressure will therefore decrease. The combination of sHASEGP with other anterior chamber agents, such as a methylcellulose (Ocucoat™ for example, commercially available from Storz Instrument Co.), used as spacers and/or protective agents in cataract surgery, will also be efficacious in preventing significant pressure rises because it will in effect open the trabecular meshwork and allow more aqueous humor drainage by breaking down a significant amount of the hyaluronic acid present in the trabecular meshwork.

Removal of glycosaminoglycans from the trabecular meshwork is also useful for the reduction of intraocular pressure in individuals suffering form open angle glaucoma. Human sHASEGP can be administered by subconjunctuval injection or injection directly in the anterior chamber. Since the sHASEGP acts enzymatically, even relatively limited amounts of sHASEGP can effectively function as a viscoelastic antidote or for other situations that are aided or improved by application of a glycosaminoglycanase. As with other uses, the units of hyaluronidase activity provided by the sHASEGP for optimum application will depend in part on the particular situation being treated—especially the amount of glycosaminoglycan degradation that is desired—but can be readily assessed using appropriate models and then optimized as appropriate for particular uses. By way of illustration, the units of sHASEGP to be applied as an antidote will be influenced, inter alia, by the particular procedure employed and the amount of viscoelastic applied, and also on whether any of the applied viscoelastic is to be removed using other procedures such as irrigation and aspiration. Where sHASEGP is used following irrigation and aspiration, generally amounts providing in the range of 10 to 12,000 units, typically 100 to 5,000 units, more typically 500 to 2,000 units may be applied, although this will again depend on the particular application. Where sHASEGP is used to obviate the need for irrigation and aspiration, larger amounts will be applied in order to effectively digest a larger volume of applied viscoelastic, with amounts generally providing in the range of 50 to 20,000 units, typically 400 to 10,000, more typically 1,500 to 5,000 units may be applied, although this will again depend on the particular application.

In the case of sHASEGPs being used to reduce intraocular pressure associated with glaucoma, application of sHASEGPs can also be used as a primary treatment to reduce IOP associated with glaucoma and thereby potentially avoid the need for surgical procedures such as glaucomal filtration, glaucomal drainage implants (tube shunts), laser trabeculoplasty, cyclophotocoagulation or iridotomy. Thus sHASEGPs of the present invention can be introduced, for example, by injection into the anterior chamber of the eye to provide a minimally invasive means for reducing intraocular pressure associated with glaucoma. Without wishing to be bound by theory, it is believed that the administration of sHASEGPs in such settings can enhance fluid outflow via the trabecular meshwork and thus lower IOP by reducing hydrostatic and/or oncotic pressures within the anterior chamber.

In the case of sHASEGPs being used to used to dissolve vitreous aggregates or "floaters", which are generally macroscopic opaque aggregates of vitreous fibers, the administration of sHASEGP to the vitreous body can be used to promote disaggregation.

Similarly, sHASEGPs as described herein can be applied to the vitreous to promote the resolution of vitreous hemorrhages (i.e. extravasation of blood into the vitreous) which can occur in connection with conditions such as diabetic retinopathy, retinal neovascularization, retinal vein occlusion, posterior vitreous detachment, retinal tears, ocular traumas and the like. The presence of vitreous hemorrhages, which are typically slow to resolve, can delay, complicate or prevent procedures that require the retina to be visualized through the vitreous for diagnosis and/or for treatment procedures such as laser photocoagulation and the like which are often primary treatments for conditions such as proliferative diabetic retinopathy. Use of sHASEGPs to promote resolution of such vitreous hemorrhages can thus be used to facilitate diagnosis of retinal conditions and/or to obviate the need for more radical procedures such as vitrectomy.

In the case of sHASEGPs being used to promote vitreoretinal detachment in treating conditions such as diabetic retinopathy, the administration of sHASEGP into the vitreous can be used to promote detachment or uncoupling of the vitreous body from the retina. In this context, sHASEGP may not only promote the detachment but help it to occur in a manner that reduces the potential for retinal distortion or tearing.

sHASEGPs of the present invention can also be used for treating corneal opacities. In that regard, a variety of distortions or deformities can affect the normally organized structure of the cornea and lead to disruptions in the passage of light through the cornea and concomitant impairments in vision. Thus, a number of conditions and causes lead to corneal distortions that may appear as scars, hazing or opacification. In applying sHASEGPs to the improvement or treatment of such corneal conditions, the sHASEGP (in a pharmaceutically acceptable solution which may comprise one or more additional pharmacologic agents) can be introduced to the cornea by any of several routes of administration, depending in part on the extent and location of the corneal injury. By way of illustration, sHASEGPs can be introduced onto the outer surface of the eye (using drops or other topical application for example), potentially encapsulated within carriers such as liposomes and the like that can be used to facilitate transfer across the corneal epithelium, by injection or microinjection onto or into the cornea itself, or by other approaches to the corneal tissue. In addition to biochemical or mechanical aids for promoting delivery, other means for promoting permeation such as iontophoresis can likewise be applied.

sHASEGPs of the present invention can also be used, for example, to enhance the permeability of agents employed in photodynamic therapy (PDT). PDT is a treatment for choroidal neovascular membranes (CNVM), which are generally leaky vascular structures under the retina in the "wet" form of age-related macular degeneration (AMD). In PDT, a photosensitive dye such as VISUDYNE™ (verteporfin) is typically administered intravenously (IV) and allowed to perfuse the CNVM, as well as the remainder of the body. An ophthalmologist then generally treats the CNVM with a red laser of a specific wavelength (e.g. 689 nm) for about 90 seconds. The non-thermal laser light activates the dye (such as VISUDYNE™) producing an active form of oxygen that both coagulates and reduces the growth of abnormal blood vessels, which in turn inhibits the leakage of fluid from the CNVM. sHASEGPs of the present invention can be used, for example, to promote more localized administration of a dye (such as VISUDYNE™) directly to the eye; and/or to facilitate the delivery of other agents that are usefully administered to the eye in connection with procedures such as PDT.

Ganglion Cysts

The ganglion cyst (also known as a wrist cyst, Bible cyst, or dorsal tendon cyst) is the most common soft tissue mass of the hand. It is a fluid filled sac that can be felt below the skin. It is usually attached to a tendon sheath (lining which lubricates the tendon) in the hand or wrist or connected with an underlying joint; however, some have no obvious connection to any structures. These may also occur in the foot. It often occurs when there is a tear in the ligaments overlying the lining of tendons or joints and the lining herniates out of the ligamentous defect causing a bump under the skin. Because there is often inflammation associated, the inflamed tissue produces a jelly-like fluid that fills the protruding sac. They may be rock hard due to a high pressure of the mucous like fluid contained within the cyst, and are often mistaken for a bony prominence.

sHASEGP can be used to ameliorate ganglion cysts. Intralesional injection of sHASEGP from 5-1000 Units followed by fine needle aspiration will remove the cyst without the need for surgery. Corticosteroids may be optionally injected as well with the sHASEGP. Additional injection may be required for some patients.

Myxedema

Glycosaminoglycan (GAG) infiltration of the skin is a feature of hyperthyroidism, hypothyroidism, pretibial myxedema, scleromyxedema, and scleredema. Hyaluronic acid is the main GAG in all the conditions and in normal skin. There is minimal histologic variability of GAG dermal distribution. The acquired cutaneous mucinoses exhibit similar skin GAG distribution and biochemical composition. The morphologic differences in fibroblastic activity suggest that the mucinoses of scleredema and scleromyxedema represent a local process, whereas the GAG infiltration of thyroid diseases may have a systemic origin. These disorders may be ameliorated with a sHASEGP from both a local and systemic route of administration. For chronic therapy, a PEGylated sHASEGP may be envisioned.

Pulmonary Uses of sHASEGP

Levels of Hyaluronan in broncheoalveolar lavages (BAL) from normal individuals are generally below 15 ng/ml. However, BAL levels rise dramatically in conditions of respiratory distress (Bjermer Br Med J (Clin Res Ed) 1987 Oct. 3; 295 (6602):803-6). In ARDS for example, hyaluronan levels can increase to 500 ng/ml whereas in farmers lung, BAL levels can surpass 1000 ng/ml (Hallgren et al Am Rev Respir Dis. 1989 March; 139(3):682-7), (Larrson et al Chest. 1992 January; 101(1):109-14). The increased hyaluronan in the lung can prevent oxygen diffusion and gas exchange as well as activating neutrophil and macrophage responses.

Bovine preparations of hyaluronidase are no preferable for the treatment of such conditions for a number of reasons. First, slaughterhouse testes-derived preparations of hyaluronidase are known to be contaminated with serine proteases such as acrosin. Secondly, the foreign nature of the bovine enzymes increase the probability of an anaphylactic reaction, which could result in death of the patient. Thus a highly purified preparation of recombinant human sHASEGP can be delivered by either pulmonary or intravenous delivery. Human sHASEGP can also be administered to patients suffering from other pulmonary complications that are associated with elevated glycosaminoglycans or to enhance the delivery of other co delivered molecules to the lung.

The invention will now be described in greater detail by reference to the following non-limiting examples

EXAMPLE 1

Microtiter Based Hyaluronidase Assays

The following example provides for a rapid assay for measurement of the hyaluronidase activity of sHASEGP. This assay can be related to the TRU, the IU or NFU through use of a W.H.O. standard preparation of hyaluronidase.

Biotinylated Hyaluronan Microtiter Assay

The free carboxyl groups on glucuronic acid residues of Hyaluronan are biotinylated in a one step reaction using biotin-hydrazide (Pierce), Sulfo NHS (Pierce) and 1-Ethyl dimethylaminopropyl-carbodiimide (Sigma). This biotinylated HA substrate is covalently coupled to a 96 well microtiter plate in a second reaction. At the completion of the enzyme reaction, residual substrate is detected with an avidin-peroxidase reaction that can be read in a standard ELISA plate reader. As the substrate is covalently bound to the microtiter plate, artifacts such as pH-dependent displacement of the biotinylated substrate does not occur. The sensitivity permits rapid measurement of Hyaluronidase activity from cultured cells and biological samples with an inter-assay variation of less than 10%.

a. Protocol

Preparation of Biotinylated HA Substrate

One hundred mg of HA (Sigma Chemicals) was dissolved in 0.1 M MES, pH 5.0, to a final concentration of 1 mg/ml and allowed to dissolve for at least 24 hr at 4° C. prior to coupling of biotin. Sulfo-NHS (Pierce; Rockford Ill.) was added to the $CSO_4$ MES solution to a final concentration of 0.184 mg/ml. Biotin hydrazide (Pierce) was dissolved in DMSO as a stock solution of 100 mM and added to the $CSO_4$ solution to a final concentration of 1 mM. A stock solution of 1-ethyl-3-(3-dimethylaminopropyl) carbodiimide (EDAC) was prepared as a 100 mM stock solution in distilled water and added to the HA biotin solution at a final concentration of 30 mM. This solution was left stirring overnight at 4° C. Unlinked biotin and EDAC were removed by dialysis against water with 3 changes of 1000× volume of water. The dialyzed, biotinylated HA (bHA) was aliquoted and stored at −20° C. for up to several months.

Sulfo-NHS was diluted to 0.184 mg/ml in water with the bHA at a concentration of 0.2 mg/ml and pipetted into 96 well COVALINK-NH plates (NUNC; Placerville N.J.) at 50 μl per well. EDAC was diluted to 0.123 mg/ml in water and pipetted into the COVALINK-NH plates with the bHA solution resulting in a final concentration of 10 μg/well bHA and 6.15 μg/well EDAC. The plates were incubated overnight at 4° C. or for 2 hr at 23° C., which gave comparable results. After covalent immobilization of $bCSO_4$ on the microtiter plates, the coupling solution was removed by shaking and the plates were washed 3 times in PBS containing 2M NaCl and 50 mM $MgSO_4$ (Buffer A). The plates could be stored at 4° C. for up to one week.

The COVALINK-NH plates with immobilized bHA were equilibrated with 100 μl/well assay buffer—either 0.1 M formate, pH 3.7, 0.1 M NaCl, 1% TRITON X-100 detergent, 5 mM saccharolactone for lysosomal Hyaluronidase; or 10 mM Hepes PH 7.4 with 1 mM $CaCl_2$ and 1 mg/ml Human Serum Albumin (ICN) for neutral-active enzymes. A set of standards for the calibration of enzyme activity against "relative Turbidity Reducing Units" (rTRU's) was generated by diluting bovine testicular hyaluronidase (Sigma Type VI-S) in neutral enzyme buffer from 1.0 to $1 \times 10^{-6}$ rTRU/well and assaying 100 μl/well in triplicate. Samples of acid-active Hyaluronidase were diluted in lysosomal assay buffer from 1:10 to 1:130,000 were pipetted in triplicate at 100 μl/well. For most assays of tissue extracts and human plasma, a 30 min incubation at 37° C. was sufficient. Positive and negative control wells (no enzyme or no ABC (see below), respectively) were included in triplicate.

The reaction was terminated by the addition of 200 μl/well of 6M Guanidine HCl followed by three washes of 300 μl/well with PBS, 2 M NaCl, 50 mM $MgSO_4$, 0.05% TWEEN 20 detergent (Buffer B). An avidin biotin complex (ABC) kit (Vector Labs; Burlingame Calif.) was prepared in 10 ml of PBS containing 0.1% TWEEN 20 detergent, which was pre-incubated for 30 min at room temperature during the incubation. The ABC solution was added (100 μl/well) and incubated for 30 min at room temperature. The plate was washed five times with Buffer B, then an o-phenylenediamine (OPD) substrate was added at 100 μl/well by dissolving one 10 mg tablet of OPD in 10 ml of 0.1 M citrate-$PO_4$ buffer, pH 5.3 and adding 7.5 μl of 30% $H_2O_2$. The plate was incubated in the dark for 10-15 min, then read using a 492 nm filter in an ELISA plate reader (Titertek Multiskan PLUS; ICN) monitored by computer using the Delta Soft II plate reader software from Biometallics (Princeton N.J.). A standard curve using the bovine testicular hyaluronidase was generated by a four parameter curve fit of the commercial hyaluronidase preparation and unknown samples were interpolated through their absorbance at 492 nm.

To analyze pH dependence of Hyaluronidases, purified recombinant sHASEGP and bovine testicular hyaluronidase are used. The pH dependence of enzyme activity is measured by diluting purified sHASEGP or partially purified bovine testicular hyaluronidase to 0.1 rTRU in the following buffers: 50 mM formate, pH 3-4.5; 50 mM acetate, pH 5-6; 50 mM MES, pH 6-7; or 50 mM HEPES, pH 7-8. Samples are assayed for 30 min at 37° C. and activity was expressed as a percent of maximal activity. NaCl was not used in buffers, as it can alter the pH optima of testicular hyaluronidase preparations (Gold, *Biochem. J.* 205:69-74, 1982; Gacesa et al. *Biochem. Soc. Trans.* 7:1287-1289, 1979); physiological salt concentrations (0.15 M) decreased the apparent pH optimum, an effect that was more pronounced in purified preparations of the testicular enzyme than in the original crude sample.

b. Results

Hyaluronan was biotinylated in a one step reaction using biotin-hydrazide and EDAC. By limiting the EDAC, which couples the free carboxyl groups on HA with biotin hydrazide, only a small fraction of the total glucuronic acid residues on HA were labeled. This amount of EDAC ($3 \times 10^{-5}$ M) added to HA ($2.8 \times 10^{-3}$ M) results in a maximum of one molecule of biotin hydrazide coupled per 93 disaccharide units of HA.

A four-parameter curve fit of bovine testicular hyaluronidase standard reactions measured at pH 3.7, and diluted from 1.0 to $1 \times 10$ TRU/well, was prepared. Four parameter curve fits were established from the equation $y=((A-D)/(1+(conc/C)^B))+D$ where $\log_{it} y = \ln(y'/1-y')$, $y'=(y-D)/(A-D)$, $B=-b/\ln 10$ and $C=EXP(a/B)$. The four parameters (A, B, C, D) were calculated with a software program that utilized the 2+2 algorithm with linear regression (Rodbard et al., *Clin. Chem.* 22:350, 1976). This curve fit incorporates the sigmoidal aspects the standard curve. Optimal accuracy for measurement of a sample typically occurs from 0.001 to 0.01 TRU/well for a 30 min incubation. During a 60 min incubation, 1/1000th of a TRU is detectable. A standard logarithmic curve also can be utilized over a shorter range of values to establish a standard curve fit.

EXAMPLE 2

Cloning of sHASEGP cDNA

Nucleic acid encoding Human sHASEGP may be obtained by one skilled in the art through a number of procedures including, but not limited to, artificial gene synthesis, RT-PCR, and cDNA library hybridization (for example see, Gmachl et al *FEBS* 336(3):545-548 (1993), Lin et al., *Proc. Natl. Acad. Sci. USA* 90:10071-10075 (1993)). Alternatively, clones encoding human sHASEGP may be obtained from IMAGE, or other suppliers of human gene sequences (Invitrogen Clone ID IOH10647).

The full length human PH20 cDNA was calculated to be 2009 nucleotides in length and contained an open reading frame of 1530 nucleotides. The 5' UTR is unusually large, which can indicate a retained intron and can inhibit translation by preventing the ribosome from binding to the correct initiating methionine codon due to 9 non coding start codons in the 5'UTR. The protein (Genbank Accession number NP 003108) is predicted to comprise 509 amino acids SEQ ID No. 1 with a calculated molecular mass of 58 kDa.

For sequencing of clones, PCR amplified bands were excised, and eluted with the Gel Extraction Kit (Qiagen) and cloned into the appropriate vectors with compatible ends after restriction digestion. All sequencing reactions were performed on double stranded DNA with the Taq dye deoxy terminator cycle sequencing kit (Applied Biosystems) according to the manufacturer's instructions, and run on an ABI Prism™ automated sequencer (Applied Biosystems).

The human PH-20 open reading frame was obtained by amplifying a human testis cDNA library (Clontech, Palo Alto Calif.) by Polymerase Chain Reaction using primers SEQ ID NO: 14 and SEQ ID NO: 47. PCR products were digested with NheI and BamHI and cloned into the NheI and BamHI sites of the vector IRESpuro2 (Clontech).

EXAMPLE 4

Isolation of sHASEGP from Human pH20 cDNA

A catalytically active secreted recombinant human sHA-SEGP expression vector capable of effective glycosylation in mammalian cells was generated as described below. Other expression constructs with promoters and selection genes for different species such as yeast and insect cells that are also capable of generating sHASEGP are contemplated. Positive selection genes such as Glutamine Synthase or Dihydrofolate Reductase (DHFR) may also be used. The examples given below is not intended to restrict but is rather provided as an example of several plasmid expression systems that may be used.

In order to construct secreted forms of sHASEGP, truncation mutants that lack the hydrophobic C terminal end were constructed. Using a GPI cleavage prediction program the GPI anchor cleavage site was located around amino acid position N 483 in the full-length GPI-anchored protein. A set of seven nested 3' primers were used to construct a set of seven truncated deletion mutants lacking predicted GPI anchor starting at position Y 482 and deleted progressively by one amino acid. These primers were designed to have compatible NheI (5') and BamHI (3') sites to clone the truncation mutants in vector Irespuro2 either untagged with a stop codon in the 3' primer, or as a C terminus His tagged protein for ease of purification and detection. For example reverse primers SEQ ID NO. 8, SEQ ID NO. 9, and SEQ ID NO. 10 were used to generate deletion mutants ending at position Y 482, F 481 and I 480 without a 6 His tag. Other mutant primers were generated with the same base design with the appropriate modifications to include and exclude the particular amino acids. For generating His-tagged variants the same set of primers are used as for non tagged variants except that primers lack the stop codon in the respective reverse primers, the forward primer remaining the same (for His tagged construction refer to primers with SEQ ID No 19, 20, 21, 22, 23, 24 and 25 which are the reverse primers without stop codon corresponding to non tagged reverse primers for their respective constructs). Overlapping primers were used to construct a six amino acid spacer followed by hexahistidine within BamHI and NotI sites in Irespuro2 vector such that His-tagged mutants were generated by ligation of the PCR amplified and restriction digested products within the NheI and BamHI sites in the his tag containing Irespuro2 vector.

To identify whether human sHASEGP could be modified at its carboxy terminus to generate a secreted and neutral active enzyme, a series of truncations were made from the GPI anchor attachment site to the predicted "catalytic domain" based upon homology with the bee venom enzyme.

DNA encoding the human sHASEGP full length GPI anchored clone in IRESPuro2 was used as a template to generate the various truncated deletion mutants. Software modeling programs gave several predicted cleavage sites for the full length polypeptide. One of such predicted sites was at amino acid position N 483 (SEQ ID No. 1). PCR primers were designed to successively truncate the protein from N483 to generate six deletion mutants starting at Y 482 (lacking N) and ending at E 477 (lacking P).

a. Protocol

Generating Truncation Mutant Lacking N483:

The full length GPI anchored sHASEGP clone between NheI and BanHI site in pIRESPuro2 was used as a template. This template was amplified with 5' primer containing NheI site that starts at starting Methionine of the native signal peptide at M 1(SEQ ID No. 14), and a 3' primer containing BamHI site that ends at Y 482 (SEQ ID No. 8). The PCR product was ran on a 1% agarose gel to resolve and confirm the correct sized amplified band, gel purified, restriction digested with NheI and BamHI and cloned into vector pIRESPuro2 (Clontech) between NheI and BamHI sites generating an expression vector for expressing this truncation mutant of sHASEGP ending at amino acid position N482 and lacking the GPI anchor with amino acid sequence (SEQ ID No. 5 for the sequence of the resulting polypeptide of sHASEGP up to Y 482) and nucleotide sequence (SEQ ID No. 48—coding nucleotides for polypeptide in SEQ ID No. 5) as indicated.

Generation of the other truncation mutants lacking Y 482, F 481, I480, Q 479, and P 478 respectively.

The same strategy was used with the only difference being using the appropriate 3' primer for each mutant. The respective 3' primers are as follows:

3' primer for sHASEGP mutant that lacks the Y 482-SEQ ID No. 9

3' primer for mutant that lacks the F 481—SEQ ID No. 10

3' primer for mutant that lacks the I480—SEQ ID No. 11

3' primer for mutant that lacks the Q 479—SEQ ID No. 12

3' primer for mutant that lacks the P 478—SEQ ID No. 13

Generating further deletion mutants to determine the minimally active domain of sHASEGP:

Further deletions, in blocks of ten to twenty amino acids were made from the 3' end of innermost neutral pH active truncation mutant of sHASEGP, which is sHASEGP up to E 477. The NheI forward primer SEQ ID No. 14) was used with an appropriately positioned 3' primer to PCR amplify a deletion mutant of sHASEGP of the desired length from the carboxy terminal end. For example PCR with primers described in SEQ ID No. 14 and SEQ ID No. 26 as the 5' and 3' primers respectively was used to generate the polypeptide in SEQ ID No. 49 when expressed from an expression construct in IresPuro2 vector. Similarly, PCR with reverse 3' primers described in SEQ ID No 27,28,29,30,31 and 32 were used to generate deletion mutants ending at amino acid positions A 447, S 430, G 413, S 394, A 372, and S 347 respectively of the mature sHASEGP. The PCR products in each case were digested with NheI and BamHI enzymes and the digested product cloned into pIresPuro2 vector between NheI and BamHI sites. A few independent clones in the final expression construct from each group were tested for secreted neutral active sHASEGP activity by transient transfection in CHO cells in CD-CHO serum free media (Invitrogen, CA) and samples drawn at indicated time points for assay. Miniprep DNA prepared from overnight cultures was transfected with Genejuice (Novagen, CA) transfection reagent following manufacturer recommended protocols. Hyaluronidase activity was measured by microtiter assay as described above.

b. Results

Hyaluronidase activity was measured in sHASEGP truncation mutants to identify the minimally active domain for secreted neutral active hyaluronidase activity.

| AMINO ACID 1 TO: | U/ML/24 HRS PH 7.4 |
|---|---|
| 347 | 0.000 |
| 372 | 0.000 |
| 394 | 0.000 |
| 413 | 0.000 |
| 430 | 0.000 |
| 447 | 0.000 |
| 467 | 0.089 |
| 477 | 0.567 |
| 478 | 0.692 |
| 479 | 0.750 |
| 480 | 0.575 |
| 481 | 0.740 |
| 482 | 0.329 |
| 483 | 0.800 |
| 509 | 0.044 |

The results showed that all six one amino acid deletion mutants ending at indicated amino acids from Y 482 to E 477 gave higher secreted activity than GPI anchored sHASEGP. The results also showed that deletions beyond A 467 eliminated any secreted activity. Secreted neutral activity from the A 467 clones decreased to approximately 10% of that found P478 or N 483 clones. It was therefore concluded that more of the carboxy terminal domain of human sHASEGP was required to create the neutral active hyaluronidase domain than previously assumed from the bee venom enzyme. The cysteines in the carboxy terminal domain are thus necessary for neutral activity. A very narrow range spanning approximately 10 amino acids before the GPI cleavage site at N 483 thus defined the minimally active domain.

EXAMPLE 5

Effects of Signal Peptide Modification on sHASEGP Secretory Activity

Human sHASEGP possesses an unusually long predicted native leader peptide. Additionally, the existence of two adjacent cysteine residues in the leader peptide may lead to aggregation of polypeptide multimers within the endoplasmic reticulum during high level expression and therefore prevent high level expression of a sHASEGP. A series of more efficient secretory leader peptides were therefore tested to examine for their ability to enhance the targeting of sHASEGP for secretion.

a. Protocol

The Kappa leader peptide was constructed by overlapping primer annealing and extension PCR with primers corresponding to sequences in SEQ ID No 37, 38, 39 and 40. The resulting PCR amplified kappa sequence was amplified with flanking primers containing NheI site in the 5' end (as described in SEQ ID No. 41) and EcoRI site at the 3' end (as described in SEQ ID No. 42). This allowed cloning the Kappa leader peptide (the polypeptide sequence is as described in SEQ ID No. 43) in the Litmus 39 (NEB) vector between NheI and EcoRI sites. sHASEGP has an internal EcoRI site; therefore this kappa construct between NheI site and EcoRI site was further amplified with a 5' SpeI primer (as described in SEQ ID No. 44) and a 3' MluI primer (as described in SEQ ID No. 45). sHASEGP without GPI anchor ending at P 478 was cut out from pIresPuro2 with NheI and BamHI and cloned into a Litmus 39(NEB) vector within the NheI and BamHI sites of the Litmus39 vector. This resulting sHASEGP-containing Litmus vector was digested with SpeI and MluI restriction enzymes and the kappa leader construct amplified with SpeI and MluI was cloned into it. Site directed mutagenesis was performed on this Litmus 39 vector containing both Kappa and sHASEGP sequences to generate the in frame fusion of Kappa leader sequence to the mature polypeptide of sHASEGP. Primer pairs corresponding to SEQ ID No. 34 and 35 were used to generate the kappa leader with the native Asp as the terminal amino acid fused to the F 38 of sHASEGP (up to P 478) (as described in SEQ ID No. 46 for the polypeptide sequence of the fusion protein). Other primer pair combinations such as embodied by SEQ ID No. 33 with SEQ ID No. 35 were used to generate Kappa leader ending at the terminal Asp (D) fused to L 36 of sHASEGP, SEQ ID No. 33 with SEQ ID No. 36 were used to generate Kappa leader ending at the Gly (G) (before the terminal Asp (D)) fused to L 36 of sHASEGP, and SEQ ID No. 34 with SEQ ID No. 36 were used to generate Kappa ending at the Gly (G) (before the terminal Asp (D)) fused to F 38 of sHASEGP. The Kappa-sHASEGP fusions obtained by site directed mutagenesis were gel purified, digested with enzyme DpnI to digest any carryover parental DNA, and then digested with NheI and BamHI and cloned in to the NheI/BamHI digested HisIresPuro2 backbone which has the his tag (six amino acid spacer followed by six histidines) cloned in between BamHI and NoII sites in pIresPuro2 vector. Therefore upon ligation we obtain a construct that is NheI-kappa-sHASEGP-BamHI-His in pIresPuro2. Four sets of such construct were obtained that would correspond to the combinations of G or D at the Kappa leader end and L 36 or F 38 at the beginning of mature sHASEGP. A few independent clones from each type of construct were transfected into CHO cells in CD-CHO medium (Invitrogen, CA) to test whether the presence of kappa secretion leader would promote increased levels of secreted protein as compared to native secretion leader. Miniprep DNA prepared from overnight cultures were transfected with Genejuice (Novagen, CA) transfection reagent following manufacturer recommended protocols and samples were drawn for testing by microtiter assay at indicated time points. Hyaluronidase activity was measured by microtiter assay as described above.

Mouse IgG Kappa chain leader peptide sHASEGP fusion constructs were tested to test for higher levels of secreted neutral active sHASEGP activity.

b. Results

| HUMAN sHASEGP GENE CONSTRUCT | U/mL/24 HOURS pH 7.4 |
|---|---|
| IgG Kappa Leader sHASEGP AA 38-478 HIS6 | 3.0257 |
| Native Leader sHASEGP AA 1-478 HIS6 | 0.4857 |

The enzyme assay results indicated that the IgG Kappa leader was capable of enhancing secretion of sHASEGP approximately 7 to 8 fold higher than the native secretion leader when compared with clones P478, Y 482 or N 483 that lacked such a leader. Other kappa leader constructs with variations of the leader fusion site from the Asp or the Gly of the Kappa leader to L36 or F38 of sHASEGP yielded increased levels of secreted neutral active hyaluronidase activity as well. These examples are intended to expand rather than limit the scope of the invention, as other efficient secretory leader sequences may be utilized with the same technology.

EXAMPLE 6

Generation of a Human sHASEGP Expression Vector

A sHASEGP without an eptiope tag was generated by cloning into a bicistronic expression cassette, HZ24 (SEQ ID NO: 51). The HZ24 plasmid vector for expression of sHASEGP comprises a pCI vector backbone (Promega), DNA sequence encoding amino acids 1-482 of human PH20 hyaluronidase, an internal ribosomal entry site (IRES) from the ECMV virus (Clontech), and the mouse dihydrofolate reductase (DHFR) gene. The pCI vector backbone also includes DNA encoding the Beta-lactamase resistance gene (AmpR), an f1 origin of replication, a Cytomegalovirus immediate-early enhancer/promoter region (CMV), a chimeric intron, and an SV40 late polyadenylation signal (SV40). The DNA encoding the sHASEGP construct contained a Kozak consensus sequence in the Methionine of the native signal leader and a stop codon at Tyrosine 482. The resultant construct pCI-PH20-IRES-DHFR-SV40pa (HZ-24) results in a single mRNA species driven by the CMV promoter that encodes amino acids 1-482 of PH20 and amino acids 1-187 of the dihydrofolate reductase separated by the internal ribosomal entry site.

The human PH20 open reading frame was amplified from an Invitrogen ORF clone (IOH10647, Invitrogen, Carlsbad Calif.) with a 5' primer that introduced an NheI site and Kozack consensus sequence before the Methionine of PH20 and a reverse primer that introduced a stop codon following Tyrosine 482 and introduced a BamHI restriction site. The resultant PCR product was ligated into the plasmid pIre-sPuro2 (Clontech, Palo Alto, Calif.) following digest of the PH20 PCR fragment with NheI and BamHI.

EXAMPLE 7

Generation of a sHASEGP Expressing Cell Line

Non-transfected DG44 CHO cells growing in GIBCO Modified CD-CHO media for DHFR(−) cells, supplemented with 4 mM Glutamine and 18 ml Plurionic F68/L (Gibco), were seeded at $0.5 \times 10^6$ cells/ml in a shaker flask in preparation for transfection. Cells were grown at 37° C. in 5% CO, humidified incubator with 120 rpm for shaking. Exponentially growing non-transfected DG44 CHO cells were tested for viability prior to transfection.

60,000,000 viable cells of the non-transfected DG44 CHO cell culture was pelleted and resuspended to a density of 20,000,000 cells in 0.7 mL of 2×transfection buffer (2×HeBS=40 mM Hepes, pH 7.0, 274 mM NaCl, 10 mM KCl, 1.4 mM $Na_2HPO_4$, 12 mM dextrose). To each aliquot of resuspended cells, 0.09 mL of the linear HZ24 plasmid (250 μg) was added, and the cell/DNA solutions were transferred into 0.4 cm gap BTX (Gentronics) electroporation cuvettes at room temperature. A negative control electroporation was performed with no plasmid DNA mixed with the cells. The cell/plasmid mixes were electroporated with a capacitor discharge of 330 V and 960 μF or at 350 V and 960 μF.

The cells were removed from the cuvettes after electroporation and transferred into 5 mL of Modified CD-CHO media for DHFR(−) cells, supplemented with 4 mM Glutamine and 18 ml Plurionic F68/L (Gibco), and allowed to grow in a well of a 6-well tissue culture plate without selection for 2 days at 37° C. in 5% $CO_2$ humidified incubator.

Two days post electroporation, 0.5 mL of tissue culture media was removed from each well and tested for presence of hyaluronidase activity.

Initial Hyaluronidase Activity of HZ24 Transfected DG44 CHO Cells at 40 Hours Post Transfection

|  | Dilution | Activity Units/ml |
|---|---|---|
| Transfection 1 330 V | 1 to 10 | 0.25 |
| Transfection 2 350 V | 1 to 10 | 0.52 |
| Negative Control | 1 to 10 | 0.015 |

Cells from transfection 2 (350V), were collected from the tissue culture well, counted and diluted to 10,000 to 20,000 viable cells per mL. A 0.1 mL aliquot of the cell suspension was transferred to each well of five, 96 well round bottom tissue culture plates. 0.1 mL of CD-CHO media (GIBCO) containing 4 mM Glutamax-1, and without hypoxanthine and thymidine supplements were added to the wells containing cells (final volume 0.2 mL).

Ten clones were identified from the 5 plates grown without methotrexate.

| Plate/Well ID | Relative Hyaluronidase Activity |
|---|---|
| 1C3 | 261 |
| 2C2 | 261 |
| 3D3 | 261 |
| 3E5 | 243 |
| 3C6 | 174 |
| 2G8 | 103 |
| 1B9 | 304 |
| 2D9 | 273 |
| 4D10 | 302 |
| 1E11 | 242 |
| A1 (+) control | 333 |
| H12 (−) control | 0 |

Six HZ24 clones were expanded in culture and transferred into shaker flasks as single cell suspensions. Clones 3D3, 3E5, 2G8, 2D9, 1E11, and 4D10 were plated into 96-well round bottom tissue culture plates using a two-dimensional infinite dilution strategy. Diluted clones were grown in a background of 500 non-transfected DG44 CHO cells per well, to provide necessary growth factors for the initial days in culture. Ten plates were made per subclone.

Clone 3D3 produced 24 visual subclones. Significant hyaluronidase activity was measured in the supernatants from 8 of the 24 subclones (>50 Units/mL), and these 8 subclones were expanded into T-25 tissue culture flasks in the presence of 50 nM methotrexate. Clone 3D3 50 nM was further expanded in 500 nM methotrexate giving rise to clones producing in excess of 1,000 Units/ml in shaker flasks (clone 3D3 5M).

EXAMPLE 8

Production of sHASEGP

A vial of 3D3 5M was thawed and expanded from T flasks through 1 L spinner flasks in CHO CDM (Invitrogen, Carlsbad Calif.) supplemented with 100 nM Methotrexate and Glutamax (Invitrogen). Cells were transferred from spinner flasks to a 5 L bioreactor (Braun) at an inoculation density of 4.0×10E5 viable cells per ml. Parameters were temperature setpoint, 37C, pH 7.2 (starting Setpoint), with Dissolved Oxygen Setpoint 25% and an air overlay of 0-100 cc/min. At 168 hrs, 250 ml of Feed #1 Medium (CD CHO+50 g/L Glucose) was added. At 216 hours, 250 ml of Feed #2 Medium (CD CHO+50 g/L Glucose +10 mM Sodium Butyrate) was added, and at 264 hours 250 ml of Feed #2 Medium was added. This process resulted in a final productivity of 1600 Units per ml with a maximal cell density of 6 million cells/ml. The addition of sodium butyrate was found to dramatically enhance the production of sHASEGP in the final stages of production.

3D3-5M Growth & sHASEGP Production, 5 L Bioreactor

| Run Hours | Viable Cells ×10$^5$ | % Viable | Units/ml | Vol (mL) | [Glucose] | Feed |
|---|---|---|---|---|---|---|
| 0 | 4.4 | 100 | 0 | 4500 | 547 | |
| 24 | 5.7 | 100 | 0 | 4500 | 536 | |
| 48 | 10.1 | 100 | 37 | 4500 | 501 | |
| 72 | 17.1 | 99 | 62 | 4500 | 421 | |
| 96 | 28.6 | 99 | 118 | 4500 | 325 | |
| 120 | 28.8 | 99 | 240 | 4500 | 274 | |
| 144 | 60.2 | 100 | 423 | 4500 | 161 | |
| 168 | 55 | 100 | 478 | 4500 | 92 | 250 ml Feed #1 |
| 192 | 66.6 | 98 | 512 | 4750 | 370 | |
| 216 | 55.2 | 92 | 610 | 4750 | 573 | 250 ml Feed #2 |
| 240 | 53 | 88 | 710 | 5000 | 573 | |
| 264 | 49.8 | 84 | 852 | 5000 | 474 | 250 ml Feed #2 |
| 288 | 40 | 70 | 985 | 5250 | 770 | |
| 312 | 31 | 61 | 1467 | 5250 | 773 | |
| 336 | 25.4 | 52 | 1676 | 5250 | 690 | |

EXAMPLE 9

Purification of sHASEGP

Conditioned media from the 3D3 clone was clarified by depth filtration and tangential flow diafiltration into 10 mM Hepes pH 7.0. Soluble HASEGP was then purified by sequential chromatography on Q Sepharose (Pharmacia) ion exchange, Phenyl Sepharose (Pharmacia) hydrophobic interaction chromatography, phenyl boronate (Prometics) and Hydroxapatite Chromatography (Biorad, Richmond, Calif.).

sHASEGP bound to Q Sepharose and eluted at 400 mM NaCl in the same buffer. The eluate was diluted with 2M Ammonium sulfate to a final concentration of 500 mM ASO4 and passed through a Phenyl Sepharose (low sub) column, followed by binding under the same conditions to a phenyl boronate resin. The sHASEGP was eluted from the phenyl sepharose resin in Hepes pH 6.9 after washing at pH 9.0 in 50 mM bicine without ASO$_4$. The eluate was loaded onto a ceramic hydroxyapatite resin at pH 6.9 in 5 mM PO$_4$ 1 mM CaCl$_2$ and eluted with 80 mM PO$_4$ pH 7.4 with 0.1 mM CaCl$_2$.

The resultant purified sHASEGP possessed a specific activity in excess of 65,000 USP Units/mg protein by way of the microturbidity assay using the USP reference standard. Purified sHASEGP eluted as a single peak from 24 to 26 minutes from a Pharmacia 5RPC styrene divinylbenzene column with a gradient between 0.1% TFA/H$_2$O and 0.1% TFA/90% acetonitrile/10% H$_2$O and resolved as a single broad 61 kDa band by SDS electrophoresis that reduced to a sharp 51 kDa band upon treatment with PNGASE-F. N-terminal amino acid sequencing revealed that the leader peptide had been efficiently removed.

N-terminal Amino Acid Sequence biochemically purified sHASEGP.

| | Position | | | | | | | | | | |
|---|---|---|---|---|---|---|---|---|---|---|---|
| | 1 | 2 | 3 | 4 | 5 | 6 | 7 | 8 | 9 | 10 | 11 |
| Theoretical | Leu | Asn | Phe | Arg | Ala | Pro | Pro | Val | Ile | Pro | Asn |
| Observed | — | Asn | Phe | Arg | Ala | Pro | Pro | Val | Ile | Pro | Asn |

EXAMPLE 10

Analysis of DG44 CHO-Derived sHASEGP Glycosylation

Conflicting data exists as to whether sHASEGPs from different species require glycosylation for their catalytic activity. For example, it is reported that enzymatically active bee venom hyaluronidase can be synthesized in cells that lack glycosylation machinery, i.e. such as E. coli. Moreover, treatment of purified bovine testes hyaluronidase with PNGase did not inactivate enzyme activity (Yamagata et al 1997). Other studies report loss of activity following deglycosylation and that disulfide bonds are additionally required.

As all such previous tests were made using either crude or partially purified preparations however, it was not apparent whether the loss of activity was a result of exposure of deglycosylated enzyme to contaminating proteases in the crude preparations or a direct functional relationship between glycosylation and catalytic activity.

a. Protocol

To determine if functional N-linked glycosylation could be introduced into human sHASEGP using a CHO based expression system under protein free conditions, a cDNA encoding human sHASEGP-HIS6 was expressed in CHO cells using an IRESpuro bicistronic cassette in chemically defined media. Cells were grown for 72 hours in CHO CDM (Invitrogen/Gibco) followed by concentration and tangential flow diafiltration on a Pellicon TFF unit (Millipore) with 30 kDa cutoff membranes. The concentrate was exchanged with 10 mM Hepes pH 7.4 50 mM NaCl. The diafiltrate was then loaded on a DEAE streamline sepharose resin and eluted with a NaCl gradient from 0-1 M NaCl on a Pharmacia FPLC resin. Human sHASEGP eluted between 10-30% NaCl. Levels of sHASEGP in column fractions determined that the majority of enzyme was recovered in the 10-30% NaCl gradient. The enzyme from the 10-30% NaCl gradient was then further purified through affinity chromatography on an IMAC resin charged with Ni. Human sHASEGP was eluted from the IMAC resin after washing with 10 mM Imidizole with 50 mM Acetate pH 5.0. The protein was concentrated and dialyzed against 10 mM Hepes pH 7.4. The highly purified enzyme was determined to possess a specific activity of 97,000 Units/mg protein in the presence of 1 mM Calcium and 1 mg/ml HSA in the ELISA-based biotinylated substrate microtiter assay.

To detect changes in protein relative molecular mass, purified human sHASEGP was treated with PNGASE or Neuraminidase overnight followed by gel electrophoresis, electotransfer and western blot analysis with an HRP linked anti His6 monoclonal antibody (Qiagen) and ECL detection.

b. Results

Western blot analysis determined that the human sHASEGP produced in CHO cells was sensitive to PNGASE treatment. The relative molecule mass of human sHASEGP revealed that the protein was highly glycosylated. Upon complete overnight digestion with PNGASE, human sHASEGP reduced to a single species confirming that mild heterogeneity of the undigested band could be attributed to N-linked sugar residues. PNGaseF partial digestion showed a series of intermediates shifting from untreated and progressive shift with longer treatment. Although bands were somewhat diffuse on a 7% Gel, at least 6 different intermediate isoforms could be visualized.

Treatment of sHASEGP with Neuraminidase revealed that CHO cells were in fact capable of synthesizing sialated human sHASEGP. Upon treatment with neuraminidase and Western Blot analysis of sHASEGP on 7% Gels, CHO derived Human recombinant sHASEGP revealed an approximately 1-3 kDa shift in mobility compared to untreated sHASEGP. This is thus the first report of the generation of a substantially sialated human sHASEGP. This is very valuable for both stability and to enhance serum half-life of a human sHASEGP as native sperm sHASEGP from many species lacks sialation and does not react with sialic acid specific lectins.

FACE Analysis of sHASEGP

Analysis of active sHASEGP oligosaccharides by FACE analysis permits rapid determination of profiles of catalytically active sHASEGPs.

Protocol

Purified Hyaluronidase from the 3D3 5M clone was evaluated using FACE® N-Linked Oligosaccharide Profiling (Prozyme). Oligosaccharides were cleaved from 128.7 µg of glycoproteins by enzymatic digestion with N-Glycanase (a.k.a PNGase), labeled using the fluorophore ANTS, and separated by electrophoresis. The relative positions of the oligosaccharide bands were determined by running the sample and dilutions of the sample alongside an oligosaccharide standard ladder which designated the migration distance in Degree of Polymerization (DP) units.

Results

The N-Profile for the Hyaluronidase sample consists of ten bands of which six (running concomitant with the oligosaccharide standard bands G5-G12) had intensities greater than 9%. Furthermore, the band running alongside the G9 standard was the most intense with intensities of 35%-46%.

sHASEGP Oligosaccharide Analysis

| sHASEGP Oligosacharide | Degree of Polymerization | Percent of Total |
|---|---|---|
| 1 | 15.64 | 1.2 |
| 2 | 13.68 | 3.4 |
| 3 | 11.61 | 10.0 |
| 4 | 10.04 | 10.4 |
| 5 | 8.37 | 35.4 |
| 6 | 7.32 | 9.7 |
| 7 | 6.14 | 9.0 |
| 8 | 5.57 | 12.4 |
| 9 | 3.84 | 2.3 |
| 10 | 3.26 | 0.5 |

EXAMPLE 11

Dependence of sHASEGP N-Linked Glycosylation for Enzyme Activity a. Protocol

Samples of purified HIS6 sHASEGP were mixed with buffer containing Neuraminidase and PNGASE with and without 50 mM Octylglucoside overnight at 37° C. Oligosaccharides were verified to have been removed by gel shift from Western Blot analysis.

b. Results

| SAMPLE | U/mL |
|---|---|
| No Rx | 22.01 |
| Neuraminidase O/N 50 mM OG | 23.57 |
| PNGaseF w/ 50 mM OG | 0.0 |
| PNGaseF without 50 mM OG o/n | 10.74 |

EXAMPLE 12

Activity of sHASEGP Towards Sulfated and Non-Sulfated Glycosaminoglycans

In addition to the microtiter-based assay using HA, the substrate specificity of sHASEGP towards other glycosaminoglycans or proteoglycans can be tested using a gel shift assay with purified substrates to determine the activity of sHASEGP towards other glycosaminoglycans. Many Hyaluronidase assays have been based upon the measurement of the generation of new reducing N-acetylamino groups (Bonner and Cantey, Clin. Chim. Acta 13:746-752, 1966), or loss of viscosity (De Salegui et al., Arch. Biochem. Biophys. 121: 548-554, 1967) or turbidity (Dorfman and Ott, J. Biol. Chem. 172:367, 1948). With purified substrates all of these methods suffice for determination of the presence or absence of endoglucosamidic activity.

a. Protocol

GEL SHIFT ASSAY—Purified substrates are mixed with recombinant sHASEGP to test for endoglucosidase activity that give rise to increased mobility in substrate within the gel. Chondroitin Sulfate A, Aggrecan and D were from Calbiochem. Hyaluronan (Human Umbilical Cord) Chondroitin Sulfate C, Dermatan sulfate, and Heparan-sulfate are obtained from Calbiochem. Human umbilical cord Hyaluronan was obtained from ICN. Each test substrate is diluted to 0.1 mg/ml. 10 µl samples of purified sHASEGP or conditioned media from sHASEGP expressing cells as well as are mixed with 90 µl of test substrate in desired buffer and incubated for 3 hours at 37° C. Following incubation samples are neutralized with sample buffer (Tris EDTA PH 8.0, Bromophenol Blue and glycerol) followed by electrophoresis on 15% polyacrylamide gels. Glycosaminoglycans are detected by staining the gels in 0.5% Alcian Blue in 3% Glacial Acetic Acid overnight followed by destaining in 7% Glacial Acetic Acid. Degradation is determined by comparison substrate mobility in the presence and absence of enzyme.

b. Results

100 Units of sHASEGP$_{HIS6}$ in 10 µA was incubated with 90 µl 10 mM Hepes Buffer with 50 ug/ml Human Serum Albumin for 2 hours at 37° C. containing 10 µg of various glycosaminoglycans and proteoglycans. Electrophoretic analysis followed by Alcian blue staining revealed increased mobility shifts to a single species in Chondroitin Sulfate A, C and D, Aggrecan and Hyaluronan but not Heparan Sulfate nor Chondroitin Sulfate B. Whereas the undigested glycosaminoglycans ran as a smear in the middle of the gel, the digested products showed the majority of alcian blue stain running at the dye front with a small amount of material running as an incremental ladder.

EXAMPLE 13

Effects of Metal Ions on sHASEGP Activation

In addition to the requirement of glycosylation for optimal enzyme activity, human sHASEGP was found to be activated with cations for optimal enzyme activity. In the process of purification, sHASEGP was found to have a low specific activity following successive chromatography steps. The HIS6 tagged sHASEGP was found to have a very low specific activity when purified to homogeneity from DEAE followed by successive Ni-IMAC purifications. As IMAC resins can chelate metal ions, various metals were added back to sHASEGP to determine the relative enzyme activity.

a. Protocol

Purified sHASEGP was tested following incubation with 0.1 mM nickel (Ni), Cobalt (Co) Zinc (Zn) Calcium (Ca) and Magnesium (Mg) for 2 hours at room temperature followed by determination of hyaluronidase activity in microtiter based assay.

b. Results

| Metal Salt Additive | Neutral Activity U/ml |
|---|---|
| NO ADDITIVES | 11.909 |
| 100 µM Ni | 6.0306 |
| 100 µM Co | 8.972 |
| 100 µM Zn | 3.7476 |
| 100 µM Ca | 101.9892 |

A significant increase in hyaluronidase activity was found following incubation of sHASEGP with 0.1 mM Calcium or 0.1 mM Magnesium. No such activation was found following incubation with other metals. The addition of Calcium to sHASEGP increased the specific activity of the enzyme to approximately 97,000 units per mg protein based upon A280 measurement. A dose response curve of Calcium and Magnesium metals was then tested to determine the optimal concentration of metal ions to enzyme.

| mM Divalent Metal | [Ca$^{++}$] | [Mg$^{++}$] |
|---|---|---|
| 100 | 1 | 1.3 |
| 10 | 108 | 104 |
| 1 | 169 | 164 |
| 0.1 | 123 | 78 |
| 0.01 | 59 | 18 |
| 0.001 | 47 | 13 |
| 0.0001 | 39 | 13 |
| 0.00001 | 55 | 15 |

Activation of sHASEGP was found to occur in the micromolar range. Concentrations above 10mM were inhibitory for both Calcium and Magnesium. To rule out nonspecific activation of substrate rather than enzyme, Calcium Chloride in 10mM Hepes buffer was incubated with the immobilized biotinylated substrate on the microtiter plate followed by washing. No activation was found when the enzyme was added to the Calcium preincubated plate that had been washed. The activation was also tested on phospholipase C released native sHASEGP which revealed a similar activation with Calcium ruling out an artifact of the carboxy terminus HIS6 epitope tag.

EXAMPLE 14

Effects of Albumin on the Activity of sHASEGP

It was found that the dilution of recombinant rHUPH20 and other preparations of slaughterhouse testes-derived hyaluronidases required albumin in addition to Calcium for optimal activity.

a. Protocol

Human Serum Albumin (ICN) was diluted into 10mM Hepes buffer with Calcium to determine the effects of albumin protein on enzyme activity. Enzyme assays with sHASEGP and commercial preparations were examined using both 1mM CaCl$_2$ and 1mg/ml Human Serum Albumin.

b. Results

Activation of hyaluronidase activity was found at high dilutions in the presence of albumin. It was not clear whether this activation was a result of preventing denaturation or if the albumin affected the availability of the substrate. A preferable formulation of human sHASEGP could therefore include Albumin and a metal salt consisting of either Calcium or Magnesium.

EXAMPLE 15

Spreading Activity of Purified sHASEGP In Vivo a. Protocol

Purified sHASEGP in 10mM Hepes PH 7.4, 150mM NaCl 0.1% Pluronic was diluted to 0.5U/μl in pyrogen free water with 0.15M NaCl. A series of dilutions in 20 μl final of Saline were made to give a total of 0.01, 0.05, 0.1 Units per injection. 20 μl of Trypan Blue solution was added to a final volume of 40 μl and injected subcutaneously into the lateral skin on each side of balb$^{Nu/Nu}$ mice that had been previously anesthetized i.p. by ketamine/xylazine administration. Dye areas were measured in 2 dimensions with a microcaliper from t=0 to t=45 min. Area was represented as mm$^2$. As a control recombinant Human HYAL1 that lacks neutral activity but is secreted was included.

b. Results

| TEST ARTICLE | DYE AREA @ 45 MIN |
|---|---|
| A. Saline Control | 51.5 mm2 |
| B. sHASEGP 0.01U | 76.8 mm2 |
| C. sHASEGP 0.05U | 98.22 mm2 |
| D. sHASEGP 0.10U | 180.4 mm2 |
| E. HYAL1 100U | 67.48 mm2 |

EXAMPLE 16

Kinetics of sHASEGP Diffusion Activity a. Protocol

Recombinant purified sHASEGP$_{His6}$ was separated into 2 aliquots. One was heated to 95° C. for 15 minutes in a thermocycler with a heated lid. The other remained at room temperature. Thermal inactivation of enzyme activity was verified in the microtiter based enzyme assay. For kinetic analysis heat inactivated verses native material was tested. 4 Units of purified sHASEGP or equivalent heat inactivated material was injected subcutaneously with trypan blue dye. Areas were tested at various time points up to 15 minutes.

b. Results

| 4 UNITS<br>t$_{minute\ post\ injection}$ | 4 UNITS HEAT INACTIVATED<br>t$_{minute\ post\ injection}$ |
|---|---|
| t$_0$ = 52.38 | t$_0$ = 50.58 |
| t$_3$ = 116.51 | t$_3$ = 65.48 |
| t$_{6.5}$ = 181.93 | T$_{6.5}$ = 63.87 |
| t$_{10}$ = 216.96 | T$_{10}$ = 65.80 |
| t$_{16}$ = 279.99 | T$_{16}$ = 74.3 |

EXAMPLE 17

Restoration of the Dermal Barrier Broken Down by sHASEGP a. Protocol

To establish the regeneration time of the pores opened with sHASEGP following subcutaneous administration, 2 Units of purified sHASEGP or saline control was injected into two opposing lateral sites subcutaneously in animals at t=0 followed by injection with trypan blue at the same site at 30 min 60 min and 24 hours. Area of the dye diffusion at t=15 minutes post injection was recorded for each time point compared to the control.

b. Results

| 2 UNITS<br>T$_{hour\ post\ injection\ sHASEGP}$ | SALINE CONTROL<br>t$_{hour\ post\ injection\ sHASEGP}$ |
|---|---|
| t$_{0.5h}$ = 183 | t$_{0.5h}$ = 54 |
| t$_{1hr}$ = 167 | t$_{1hr}$ = 50 |
| t$_{22h}$r = 61 | t$_{22h}$r = 48 |

The results demonstrate that the dermal barrier reconstitutes within 24 hours of administration of 2 Units of enzyme.

EXAMPLE 18

Determination of the Size of Channels Opened by sHASEGP

It was shown that human sHASEGP opened channels in the interstitial space sufficient to permit the diffusion of a small molecule, i.e. trypan blue dye. However, it was unknown what the upper limits were on the size of particles that could diffuse in the presence of sHASEGP.

a. Protocol

Fluorescent molecules of varying sizes were used to determine the size of the channels opened by human sHASEGP, Fluoresceinated Dextrans of 4,400 and 2 million Da Average Molecular Weight (Sigma) as well as fluorescein labeled beads of defined diameters from 20 nanometers to 500 nanometers (Molecular Probes), were administered subcutaneously in a volume of 40 μl with following injection of sHASEGP or saline control in the same sites. Area of the dye front was then measured in two dimensions at 15 minutes post injection.

b. Results

| Diffusion Agent | Diffusion Test Particle Size | | Area at 15 min | Stand Dev |
|---|---|---|---|---|
| sHASEGP | 4400 | Da | 84.2 | 25.7 |
| Control | 4400 | Da | 38.0 | 5.8 |
| sHASEGP | 2 × 10E6 | Da | 141.2 | 4.5 |
| Control | 2 × 10E6 | Da | 51.7 | 8.1 |
| sHASEGP | 20 | nm Diameter | 92.3 | 20.6 |
| Control | 20 | nm Diameter | 51.6 | 3.0 |
| sHASEGP | 100 | nm Diameter | 61.0 | 5.7 |
| Control | 100 | nm Diameter | 40.0 | 7.0 |
| sHASEGP | 200 | nm Diameter | 35.5 | 1.6 |
| Control | 200 | nm Diameter | 27.9 | 8.2 |
| sHASEGP | 500 | nm Diameter | 44.8 | 13.6 |
| Control | 500 | nm Diameter | 41.2 | 9.8 |

The results demonstrated that molecules from approximately 1kDa (Trypan Blue) to 50nm in diameter (Latex Beads) showed enhanced diffusion following administration of sHASEGP. While bovine serum albumin (66kDA) showed similar kinetics of diffusion to trypan blue, the 50nm latex beads required significantly more time to diffuse. 500nm beads showed no diffusion up to 480 minutes.

EXAMPLE 19

Serum Pharmacokinetics Profiles of Biotinylated Antibodies Following Subcutaneous Co-Injection of Human sHASEGP a. Protocol Female Balb/c mice were anesthetized with a mixture of ketamine/xylazine. The mice were then injected subcutaneously with 20μl of 0.5mg/ml solution of biotinylated mouse IgG mixed with 20μl of either saline or 20μl sHASEGP containing 4Units of activity.

b. Results

| TIME POST INJECTION | CONTROL | sHASEGP (4U) |
| --- | --- | --- |
| Serum IgG t = 0 hrs | 0 ng/ml | 0 ng/ml |
| Serum IgG t = 2 hrs | 0 ng/ml | 360 ng/ml |
| Serum IgG t = 51 hrs | 4152 ng/ml | 4176 ng/ml |

The results demonstrate that sHASEGP increases the kinetics of serum distribution of large molecules in circulation. Where no biotinylated IgG could be detected in the control group at 2 hours, 360ng/ml was apparent by 2 hours in the sHASEGP group.

EXAMPLE 20

Spreading Activity of Subcutaneously Injected Molecules Following Intravenous Injection of Human sHASEGP a. Protocol Four sites for dye injection were utilized per dose of each Test Article and carrier control. Dye injection was 45 minutes after i.v. injection. Each dose of test or control article was injected i.v. into 2 animals. Measurement of the dye front area post 45 minute enzyme administration was calculated at 2.5, 5, 10 and 15 minutes for each dose or carrier control.

b. Results

Results demonstrated that highly purified sHASEGP was systemically available to distal tissues upon intravenous administration. The spreading activity of systemically administered sHASEGP was dose dependent, with a 10 unit injection being indistinguishable from carrier control.

| Type | Dose IV | Time Minutes | Mean Area (mm$^2$) | SD |
| --- | --- | --- | --- | --- |
| PH20 | 1000 | 2.5 | 86.417 | 2.834193 |
| PH20 | 1000 | 5 | 102.17 | 2.221146 |
| PH20 | 1000 | 10 | 124.53 | 6.304944 |
| PH20 | 1000 | 15 | 129.81 | 1.434319 |
| PH20 | 300 | 2.5 | 59.137 | 7.218615 |
| PH20 | 300 | 5 | 73.638 | 7.51197 |
| PH20 | 300 | 10 | 87.092 | 8.686008 |
| PH20 | 300 | 15 | 92.337 | 10.66466 |
| PH20 | 100 | 2.5 | 56.308 | 7.741934 |
| PH20 | 100 | 5 | 63.156 | 11.42052 |
| PH20 | 100 | 10 | 76.519 | 16.18449 |
| PH20 | 100 | 15 | 77.432 | 17.32264 |
| PH20 | 30 | 2.5 | 50.534 | 10.64287 |
| PH20 | 30 | 5 | 59.493 | 5.163971 |
| PH20 | 30 | 10 | 68.102 | 11.00071 |
| PH20 | 30 | 15 | 71.118 | 9.934212 |
| PH20 | 10 | 2.5 | 36.4 | 3.807072 |
| PH20 | 10 | 5 | 39.859 | 6.680932 |
| PH20 | 10 | 10 | 45.649 | 4.44936 |
| PH20 | 10 | 15 | 48.41 | 6.546835 |
| Control | 0 | 2.5 | 34.652 | 5.935037 |
| Control | 0 | 5 | 36.279 | 3.614544 |
| Control | 0 | 10 | 44.687 | 5.821216 |
| Control | 0 | 15 | 53.002 | 2.812439 |

EXAMPLE 21

Illustrative Use of PEGylation to Generate Modified sHASEGPs Exhibiting Improved Pharmocokinetics As an illustrative example of the use of pegylation to generate modified forms of sHASEGPs having improved pharmacokinetics, such as increased serum half life, we attached either linear or branched polyethylene glycol (PEG) moieties to an exemplary sHASEGP, recombinant human PH20 (rHuPH20) as described above.

A number of different functionally activated groups can be used for attaching PEG moieties to sHASEGPs such as rHuPH20 (including, by way of illustration, aldehydes, succinimides, maleimides and others). A number of different pegylation reagents are commercially available from various sources including Nektar Therapeutics (nektar.com) as well as a number of other suppliers. For purposes of illustration, the sHASEGPs in rHuPH20 have been PEGylated.

In addition to varying the functional group, PEGs of a variety of different lengths and structures are available which can be incorporated using a particular functional group. For purposes of illustration, PEG lengths ranging from 5 to 40 KDa have been conjugated to rHuPH20. Again a variety of different PEGs having different lengths and structures are readily available from sources including Nektar, Sunbio, Celares and others.

As an exemplary illustration of the PEGylation of an illustrative sHASEGP, PEG aldehydes, succinimides and maleimides have each been applied to conjugate PEG moieties to rHuPH20. Of these three chemistries, succinimidyl PEGs have typically been the most convenient to use in the case of rHuPH20. For example, rHuPH20 has been conjugated with exemplary succinimidyl monoPEG (MPEG) reagents including mPEG-Succinimidyl Propionates (mPEG-SPA), mPEG-Succinimidyl Butanoates (mPEG-SBA), and mPEG2-N-Hydroxylsuccinimide. These pegylated succinimidyl esters contain different length carbon backbones between the PEG group and the activated cross-linker, and either a single or branched PEG group. These differences can be used, for example, to provide for different reaction kinetics and to potentially restrict sites available for PEG attachment to rHuPH20 during the conjugation process.

Succinimidyl PEGs (as above) comprising either linear or branched PEGs have been conjugated to rHuPH20. Using compositions and techniques as described in the art, succinimidyl PEGs have been used to generate rHuPH20s reproducibly comprising a combination of molecules having between about three to six PEG molecules per sHASEGP. Such pegylated rHuPH20 compositions were readily purified to yield compositions having specific activities of approximately 25,000 Unit/mg protein hyaluronidase activity, and being substantially free of non-PEGylated rHuPH20 (less than 5% non-PEGylated). As is known in the art, and described for example in PEGylation references including those cited above, a variety of reagents and techniques are also available for achieving mono-disperse as opposed to poly-disperse PEG products (see, e.g., the reviews and references cited above related to site-specific monoPEGylation and site-directed PEGylation).

Improvements in both pharmacokinetics and pharmacodynamics have been observed in animal models following administration of a PEGylated sHASEGP as compared to the unmodified version of the sHASEGP. For example, following intravenous administration to mice of either 1,000 Units of an unmodified rHuPH20 or 1,000 Units of rHuPH20 conjugated to PEGs having a molecular weight of approximately 40 kDa (rHuPH20-PEG40), it was observed that the serum half-life of neutral active hyaluronidase activity (PH20) in serum of mice treated with rHuPH20-PEG40 was significantly longer (16-20 fold) than that of mice treated with unmodified rHuPH20. In addition, the effectiveness of rHuPH20-PEG40 has been compared to non-PEGylated rHuPH20 in a rat stroke model. Initial results from these studies demonstrate greater effectiveness of rHuPH20-PEG40 (greater than 75% survival, versus less than 50% in controls) in rat survival 7 days post stroke-inducement.

EXAMPLE 22

Illustrative Use of a sHASEGP to Promote Spreading of a Small Molecule Pharmacologic Agent In Vivo As an illustrative example of the use of sHASEGP compositions of the present invention to promote spreading or diffusion of pharmacologic agents into and within organs and tissues in a mammal, we assessed the use of rHUPH20 to promote penetration of dexamethasone ("dex", an anti-inflammatory agent used as an exemplary small molecule pharmacologic) into tissues of the mammalian eye in vivo For injection of agents such as anesthetics to the mammalian eye, commonly used periorbital routes for achieving anesthetic blocks include peribulbar, retrobulbar and sub-Tenon's injections. For this illustrative example, we compared sub-Tenon's injections of dex, with or without concomitant administration of sHASEGP, into the episcleral space, and then examined the concentrations of dex within tissues of the posterior of the eye, particularly the choroid and retinal layers, which are important drug targets but are often difficult to efficiently reach with pharmacologic agents.

New Zealand red male rabbits (approximately 2.1 to 3.2 kg) were employed and were placed under general anesthesia using intramuscular injections of ketamine hydrochloride (21 mg/kg) and xylazine hydrochloride (5.25 mg/kg). Topical 0.5% proparacaine was used for anesthetizing the ocular surface. Pupils were dilated with 1% tropicamide and 2.5% phenylephrine. After opening the conjunctiva of the right eye of each rabbit using Vannas scissors, the tip of a Medez tri-port anesthetic cannula (Eagle Laboratories, Rancho Cucamonga, Calif.) was inserted into the episcleral space and 1.5 ml of either dex alone (American Pharmaceutical Partners, n=18) or dex plus sHASEGP (3000 units of rHUPH20, n=18) was injected adjacent to the posterior pole of the eye. A cotton-tipped applicator was placed at the site of conjunctival entry to prevent egress of fluid.

At 1, 2, 3 or 6 hours after the injection, rabbits were anesthetized as described above and sacrificed by intracardiac injection of pentobarbital sodium (120 mg/kg). Following euthanasia, 1 ml of blood sample was taken and both eyes were enucleated from each animal. Immediately after the enucleation, a 2-ml sample of aqueous humor was collected via anterior chamber paracentesis with tuberculin syringe from each eye. After removal of anterior segment from enucleated eyes, 1 ml of vitreous sample was withdrawn and placed into labeled Eppendorf tubes. The remainder of the eye was dissected and 6-mm trephine (Fine Science Tools, Foster City, Calif.) was used to punch the tissue sample inferior to the optic nerve where drug was injected on the extrascleral side. From the punched tissue the retina was scraped off with a blunt blade and placed into labeled tube as was the choroid.

Mass spectrometry was used to assess dex levels in tissues with the minimum quantifiable limits being on the order of 5 ng/ml. For the choroid and retinal samples, a buffer containing 50 mM Tris base, 1 mM $MgCl_2$, pH 9.0, was added to the tissue so the final concentration was 20 mg/mL. The tissue was disrupted using an ultrasonic homogenizer (BioLogics, Inc., model 150 V/T) for 5-15 seconds. The samples of tissue homogenate, the vitreous fluid, aqueous fluid, and plasma were all analyzed by the following procedure. Samples containing dexamethasone and prednisolone as the internal standard (I.S.) were extracted with methyl t-butyl ether by vortex mixing for five minutes. The organic and aqueous layers were separated by centrifugation at 1,300 g for five minutes, the aqueous layer was frozen at −70° C. for fifteen minutes, and the organic layer was poured into new tubes and evaporated under a stream of nitrogen at 40° C. The residue was reconstituted with water:acetonitrile (50:50 v/v). The processed samples were analyzed by high-performance liquid chromatography using a Phenomenex Synery Polar RP column maintained at 45° C. The mobile phase was nebulized using heated nitrogen in a Z-spray source/interface and the ionized compounds were detected using a tandem quadrupole mass spectrometer. Peak heights of dexamethasone and prednisolone were acquired and integrated using MassLynx™ software, Micromass, Beverly, Mass. The calibration curves were obtained by fitting the peak height ratios of the standards to the internal standard a power equation in MassLynx™. The equation of the calibration curve was then used to interpolate the concentration of dexamethasone in the samples using their peak height ratios.

The mass spec results revealed that the choroidal, retinal and vitreous dexamethasone levels of rabbits treated with dex alone reached peak concentrations at the first time point (i.e. 1 hour after injection); whereas the choroidal and retinal dex concentrations of rabbits that received concomitant sHASEGP were higher and continued to increase to the second time point (i.e. 2 hours after injection). Peak choroidal, retinal and vitreous concentrations were approximately 10-fold, 5-fold and 8-fold higher, respectively, in tissues that had been treated with sHASEGP, and the areas under the curve (AUC) were also at least 50% higher.

These results indicate that the administration of sHASEGP can be used to substantially enhance the delivery of pharmacologic agents such as dex, even to relatively difficult to reach tissues in vivo such as segments at the posterior of the mammalian eye. Furthermore, since the relatively thick scleral layer forms a tissue barrier between the sub-Tenon's injection space and the targeted choroid and retinal layers, the high levels of pharmacologic agent delivered to the latter layers indicate that sHASEGP can be used to effectively promote delivery of pharmacologics across tissue layers within the body.

In the case of promoting transcleral delivery, sHASEGP can thus be applied in a minimally-invasive procedure to promote the delivery of agents used to treat conditions affecting the back of the eye which are of particular interest in a number of ocular disease situations. This can provide, for example, a less invasive delivery route for the treatment of choroidal neovascularization (e.g. by administering steroids), macular degeneration and other diseases affecting these tissues which are typically treated via intravitreal injection. There are a wide variety of agents currently used for these conditions, such as, but not limited to, dexamethasone, triamcinolone, Macugen™ and VEGF antagonists.

In addition to the enzymatic activities of sHASEGP that contribute to spreading in the context of delivery routes such as via sub-Tenon's injection, it is also believed that the introduction of the sHASEGP in a volume of fluid that effectively fills or distends the tissue space into which it is injected generates positive hydrostatic pressures that serve to further drive delivery of fluids, and the agents comprised therein, into the surrounding tissues (e.g. by promoting convective transport).

EXAMPLE 23

Illustrative Use of a sHASEGP to Reduce Tumor Interstitial Fluid Pressure Thereby Promoting the Susceptibility of a Tumor to Anti-Tumor Pharmacologic Agents As described and illustrated herein, sHASEGPs can be used to generate interstitial channels that can increase fluid flow and facilitate the delivery of pharmacologic and other agents to desired tissue sites in vivo. Tumors present a particularly important target issue for a number of known and regularly developed pharmacologic agents, especially antineoplastics, antimetabolites, antiangiogenics and various cytotoxic and cytostatic agents. The challenges associated with targeting such pharmacologics to tumor sites in vivo are exacerbated by the fact that many tumors exhibit elevated interstitial pressures that tend to impede infusion of administered pharmacologics, particularly to sites deep within a tumor mass. It is believed that sHASEGPs can reduce this impedance, and therefore faciliate delivery of any of a variety of known and newly developed pharmacologic agents into tumors, thereby rendering them more sensitive to and more treatable by a given dose of a pharmacologic. In these regards, sHASEGPs of the present invention have been shown to be capable of promoting the formation of interstitial channels and to enhance the dispersion of markers of various sizes as described above. In addition, we have observed that sHASEGPs can be used to increase hydraulic conductivity of interstitial tissues over ten fold.

As confirmation of these principles in the context of tumor cells, application of an exemplary sHASEGP (rHuPH20, 50 Units) to tumor cells in vitro resulted in substantial removal of pericellular matrices, which are believed to be a major contributor to elevated tumor interstitial fluid pressure.

In addition, administration of rHuPH20 in vivo, in a xenograft human tumor model, resulted in a significant reduction in tumor interstitial fluid pressure within one hour of administration.

As described in the detailed description of the invention above, sHASEGPs of the present invention can be applied in combination with any of a number of known or newly developed antitumor agents for use in the treatment of various cancers.

EXAMPLE 24

Illustrative Use of a sHASEGP to Enhance the Pharmacokinetics of a Macromolecule Delivered by Non-IV Parenteral Injection As discussed above, sHASEGPs can be used to modulate the pharmacokinetics of known or newly developed pharmacologic and other agents by, example, facilitating their absorption and/or distribution with the body. Such improved pharmacokinetic parameters can in turn be used to improve the pharmacodynamics of a particular agent (e.g. reducing local toxicity by lowering the amount of an agent left near a site of injection and/or raising effectiveness by increasing the amount of an agent delivered to (and/or through) a desired target). Alternatively, since sHASEGPs can be used to effectively drive dispersion of a locally-administered pharmacologic agent (e.g., through a site of injection and into the bloodstream), it is also possible to use the sHASEGP to essentially improve the pharmacokinetics of absorption and achieve similar pharmacodynamics with a reduced amount of applied agent.

As an illustrative example of the use of sHASEGPs to enhance the pharmacokinetics of a macromolecular drug that is normally administered by non-intravenous parenteral injection, we combined recombinant human PH20 (rHuPH20) with a pegylated version of interferon alpha 2b (PEG-INTRON™ available from Schering-Plough). PEG-INTRON is a macromolecule of approximately 31 kD that is typically administered by subcutaneous injection for the treatment of Hepatitis C virus (HCV) (generally in combination with the small molecule drug ribavirin). Like many macromolecules administered subcutaneously, PEG-INTRON is relatively slowly absorbed and a substantial portion of the agent never makes it to the bloodstream, with bioavailability on the order of 50-60%. In addition, a substantial fraction of patients (typically more than half) develop various injection-site reactions, presumably as a result of or exacerbated by the retained local concentrations of the pharmacologic. As appreciated by those of skill in the art, the consequences of such pharmacokinetics are several-fold; and include not only the "wasting" of agent trapped near the injection site but also reactions to the locally metabolized compound.

We administered Iodine-125 labeled PEG-INTRON by different routes of administration, with or without concomitant administration of rHuPH20, to examine the effects of rHuPH20 on the pharmacokinetic parameters of the PEG-INTRON. To determine the absolute bioavailability of rHuPH20, we also measured the pharmacokinetic parameters of PEG-INTRON administered by intravenous administration.

Briefly, eighteen Sprague-Dawley rats (each weighing approximately 225-250 grams) were divided into three groups of six animals each. A first group was administered test article (i.e. 1-125 labeled PEG-INTRON) by intravenous administration (1.5 micrograms/kg in a volume of 100 microliters via tail vein injection). Specific activity of the I-125 labeled interferon was 55 µCi/microgram. Blood samples (100 microliters) were collected pre-dose and at 0.5, 1, 2, 4, 8, 24, 48, 72, 96 and 120 hours after dosing and processed for quantification of labeled drug by gamma counting (expressed as Counts Per Minute (CPM) per gram plasma). A second group of six animals was administered an equivalent dose and volume of test article by intradermal injection into a shaved and prepared spot over the back of the neck, and blood samples were processed as for the first group. A third group of six animals was administered an equivalent dose of test article mixed with rHuPH20 (100 I.U.) in a combined volume of 100 microliters by intradermal injection as in the preceding group, and blood samples were then processed as for groups one and two. The results of this study are shown below in Table 24-1.

TABLE 24-1

Effects of sHASEGP on the Pharmacokinetic Profile of Interferon

| Time (Hours) | PEG-INTRON (1.5 µg/kg) Intradermal | SD | PEG-INTRON (1.5 µg/kg) + sHASEGP 100U Intradermal | SD | PEG-INTRON (1.5 µg/kg) Intravenous |
|---|---|---|---|---|---|
| 0.5 | 30,289 | 9,989 | 54,808 | 12,995 | 281,781 |
| 1 | 43,137 | 9,434 | 76,672 | 17,570 | 185,630 |
| 2 | 54,655 | 11,128 | 102,159 | 17,626 | 155,591 |
| 3 | 55,261 | 11,055 | 115,329 | 24,910 | 128,656 |
| 6 | 61,214 | 15,528 | 118,364 | 23,817 | 93,065 |
| 8 | 59,277 | 14,704 | 110,443 | 21,735 | 79,275 |
| 12 | 46,696 | 12,752 | 85,710 | 28,078 | 58,457 |
| 24 | 16,233 | 6,595 | 26,047 | 9,006 | 16,966 |
| 36 | 7,954 | 1,777 | 12,498 | 1,762 | 9,277 |
| 48 | 3,862 | 499 | 5,517 | 1,030 | 5,847 |
| AUC | 1,222,952 | | 2,212,583 | | 1,910,723 |
| $C_{max}$ | 61,214 | | 118,364 | | — |
| $T_{max}$ | 6 | | 6 | | — |
| Absolute Bioavailability | 64% | | 116% | | 100% |

As can be seen in Table 24-1, the bioavailability of the exemplary pharmacologic PEG-INTRON (as assessed by AUC) was dramatically improved when the intradermal dosing was combined with a dose of sHASEGP. In fact, the absolute bioavailability achieved with an intradermal dosing in combination with sHASEGP were statistically indistinguishable from the direct intravenous administration, where all of the material is delivered directly into the bloodstreams. Thus, the use of sHASEGP in combination with a pharmacologic that is introduced by non-IV parenteral administration can provide levels of delivery comparable to administration directly into the bloodstream. Although the Tmax is necessarily longer following ID administration (since some amount of time is necessary for the agent to reach the bloodstream), within several hours after ID dosing with sHASEGP, the concentrations of agent in the bloodstream essentially reached those achieved by IV dosing, and thereafter apparently exceeded them.

EXAMPLE 25

Illustrative Use of a sHASEGP to Facilitate Intradermal Delivery of a Macromolecule Normally Delivered by Intravenous Injection As discussed above, sHASEGPs can be used to facilitate the delivery of known or newly developed pharmacologic and other agents by different routes of administration that may provide for greater convenience, safety, reduced costs and/or other benefits. As an illustrative example of such a reformulation, we used a sHASEGP to facilitate intradermal delivery of a macromolecular drug that is normally administered by intravenous injection. For this particular example, we combined recombinant human PH20 (rHuPH20) with a chimeric human-murine anti-TNFalpha monoclonal antibody (Infliximab, available as REMICADE™ from Centocor). REMICADE is a macromolecule of approximately 150 kD that is typically administered by intravenous injection for the treatment of arthritis or Crohn's disease. Administration of REMICADE thus generally requires the involvement if intravenous access and concomitant professional care and risks, and also requires on the order of two hours for each dosing.

REMICADE (20 mg/ml) was labeled with .sup.125I to a specific activity of 10 μCi/mg. Eighteen rats were divided into three groups of six animals each and were administered a mixture of radioactive and cold REMICADE (combined 10 mg/kg) in a final volume of 100 μl (i) by intravenous administration, (ii) by intradermal administration or (iii) or by intradermal administration in combination with 100 Unit sHASEGP (from a 100,000 U/ml stock); and then blood and tissues processed by gamma counting at various points after dosing, essentially as described for the preceding example. The results are summarized in Table:

TABLE 25-1

Effects of sHASEGP on the Pharmacokinetic Parameters of REMICADE

| Time (Hours) | CPM REMICADE (10 mg/kg) Intradermal | SD | CPM REMICADE (10 mg/kg) + sHASEGP100 U Intradermal | SD | CPM REMICADE (10 mg/kg) Intravenous |
|---|---|---|---|---|---|
| 0.5 | 27,451 | 2,221 | 94,888 | 31,318 | 1,657,849 |
| 1 | 37,213 | 10,775 | 146,793 | 42,014 | 1,645,571 |
| 2 | 66,001 | 6,078 | 412,047 | 61,240 | 1,576,145 |
| 4 | 120,704 | 21,744 | 691,626 | 89,002 | 1,260,646 |
| 8 | 256,987 | 32,459 | 833,826 | 133,887 | 1,157,268 |
| 24 | 493,004 | 75,694 | 853,423 | 65,777 | 790,357 |
| 48 | 515,439 | 53,431 | 728,302 | 74,848 | 684,599 |
| 72 | 454,717 | 54,388 | 640,303 | 81,492 | 558,307 |
| 96 | 375,993 | 39,744 | 598,413 | 59,533 | 496,658 |
| 120 | 336,067 | 66,964 | 518,861 | 53,643 | 434,008 |
| AUC | 53,350,555 | | 118,424,609 | | 82,718,550 |
| $C_{max}$ | 515,439 | | 853,423 | | 1,657,849 |
| $T_{max}$ | 48 | | 24 | | 0 |
| Absolute Bioavailability | 62% | | 121% | | 100% |

As can be seen in Table 25-1, the bioavailability of the exemplary pharmacologic REMICADE (as assessed by AUC) was dramatically improved when the intradermal dosing was combined with a dose of sHASEGP. As was observed with enhanced delivery of PEG-INTRON, the overall levels of REMICADE bioavailability achieved with an intradermal dosing in combination with sHASEGP were statistically similar to those of the intravenous administration when all material was delivered directly into the bloodstream. Although the REMICADE $T_{max}$ is necessarily longer following ID versus IV administration, within twenty four hours after ID dosing with sHASEGP, the concentrations of agent in the bloodstream exceeded that observed with IV dosing, and thereafter approached or exceeded the IV concentrations. Compared with ID dosing without sHASEGP, the observed $T_{max}$ was reached about twice as quickly with sHASEGP (24 hours versus 48 hours); and the $C_{max}$ and bioavailability (AUC) both substantially increased (by about 65% and 95%, respectively).

EXAMPLE 26

Illustrative Use of a sHASEGP to Facilitate Intradermal Delivery of a Larger Macromolecular Complex Normally Delivered by Non-IV Parenteral Injection As another illustrative example of the use of sHASEGPs to enhance the pharmacokinetics of a macromolecular drug that is normally administered by non-intravenous parenteral injection, we combined recombinant human PH20 (rHuPH20) with recombinant human Factor VIII (RECOMBINATE™ available from Baxter). Factor VIII is a large glycoprotein complex comprising multiple polypeptides, and has a combined molecular of approximately 280 kD. Factor VIII is typically only administered by intravenous injection for the treatment of hemophilia. Like many macromolecules administered subcutaneously, Factor VIII is relatively slowly absorbed and a substantial portion of the agent never makes it to the bloodstream, with bioavailability on the order of 0.5-1%.

Eighteen rats were divided into three groups of six animals each and were administered 125-I labeled Factor VIII (i) by intravenous administration, (ii) by intradermal administration or (iii) by intradermal administration in combination with sHASEGP; and then blood and tissues processed at various points after dosing to measure counts per minute (CPM) per gram plasma, essentially as described for the preceding example.

TABLE 26-1

| Effects of rHuPH20 on the Pharmacokinetics of Factor VIII | | | | | |
|---|---|---|---|---|---|
| Time (Hours) | CPM FACTOR VIII (50 IU/kg) Intradermal | SD | CPM FACTOR VIII (50 IU/kg) + sHASEGP100 U Intradermal | SD | CPM FACTOR VIII (50 IU/kg) Intravenous |
| 0.5 | 29,748 | 12,002 | 46,376 | 5,503 | 670,743 |
| 1 | 43,767 | 9,415 | 70,249 | 14,614 | 379,558 |
| 2 | 49,507 | 14,592 | 72,736 | 14,985 | 247,397 |
| 3 | 56,087 | 17,621 | 76,631 | 14,454 | 200,602 |
| 4 | 55,494 | 12,721 | 84,066 | 8,646 | 177,846 |
| 5 | 55,277 | 14,181 | 79,735 | 9,363 | 165,914 |
| 6 | 50,195 | 13,970 | 72,176 | 6,848 | 121,198 |
| 8 | 52,290 | 13,707 | 66,419 | 10,495 | 114,579 |
| 12 | 48,336 | 10,765 | 58,817 | 11,760 | 75,912 |
| 24 | 23,173 | 4,700 | 24,596 | 4,426 | 29,610 |

TABLE 26-1-continued Effects of rHuPH20 on the Pharmacokinetics of Factor VIII

| Time (Hours) | CPM FACTOR VIII (50 IU/kg) Intradermal | SD | CPM FACTOR VIII (50 IU/kg) + sHASEGP100 U Intradermal | SD | CPM FACTOR VIII (50 IU/kg) Intravenous |
|---|---|---|---|---|---|
| AUC | 1,014,521 | | 1,303,078 | | 2,554,607 |
| $C_{max}$ | 56,087 | | 84,066 | | — |
| $T_{max}$ | 4 | | 4 | | — |
| Absolute Bioavailability | 39.7% | | 51% | | 100% |

As shown in Table 26-1, co-administration of Factor VIII with rHuPH20 significantly increased the systemic bioavailability relative to Factor VIII alone (P<0.01). The use of TCA precipitation was necessary to eliminate the contribution of completely degraded 1-125 labeled Factor VIII protein entering the blood stream.

EXAMPLE 27

Illustrative Use of a sHASEGP to Improve Survival and/or Behavioral Outcomes Following Stroke In a first set of studies, sHASEGPs were evaluated in a rat model of stroke. Briefly, stroke was surgically induced in Sprague-Dawley rats by middle cerebral artery occlusion, followed at various times by intravenous administration of either a control solution (saline) or a test solution (saline comprising a sHASEGP). Animals were allowed to recover and were followed over a period of time to assess rates of survival in control versus test groups. In addition, survivors were assessed over a range of timepoints using multiple analyses of behavioral conditions typically associated with stroke. Only rats that performed normally in an initial qualifying forelimb flexion test were included in the study, and were then randomly assigned to a control or test group of animals.

Aseptic surgical procedures were performed by Zivic Laboratories essentially as follows. Rats were anesthetized in a chamber supplied with 2.5% halothane. A ventral midline incision was made and the musculature was separated to expose the right external carotid artery, which was then isolated and double ligated. An untied but constrictive 5/0 polyamide ligature was then placed around the external carotid stump. A small hole was cut into the lumen of the stump and an 18-20 mm length of 4/0 microfilament suture material was inserted into the lumen and advanced into the internal carotid artery. When completely advanced, the internalized tip of the monofilament should block flow into the middle cerebral artery. The constrictive polyamide ligature was then tied to secure the monofilament. Retraction was removed and the skin incision closed with a wound clip.

Intravenous injection procedures were performed essentially as follows. Rats were anesthetized in a chamber supplied with 2.5% halothane. A ventral skin incision was made to expose the jugular vein. A sterile 1 ml disposable syringe was fitted with a 30-gauge needle and loaded with injection material. Using the clavicle for support, the syringe was inserted into the jugular vein (using slight negative pressure on the syringe to draw bloodflow into the syringe and thereby confirm proper placement for IV injection) and then the injection material was slowly injected into the jugular vein. After injection, the needle was slowly withdrawn (and any bleeding controlled with a sterile cotton applicator), and then the skin incision was closed with a wound clip.

Survival of animals in the various groups (approximately 40 animals in each group) was monitored following induction of stroke, and the number of survivors at each day were then plotted against days following stroke to generate a Kaplan-Meier stroke curve. Substantial differences between the groups were apparent by the 3$^{rd}$ day following stroke. By one week following the induction of stroke, more than half of the control animals had died, whereas nearly three quarters of the sHASEGP-treated animals had survived, which was a statistically significant difference (p=0.03).

In addition to measuring rates of survival following stroke, survivors were also tested (at 1, 2, 3 and 4 weeks following stoke) using other analyses designed to assess the incidence of certain behavioral problems associated with stroke. Behavioral conditions assessed included forelimb flexion, torso twist, hind limb, gait disturbances and wall walk, which were used to generate a PNEGS behavioral score (higher scores reflecting an increase in behavioral problems associated with the stroke). By the second week following induction of stroke, the sHASEGP-treated animals exhibited significantly higher behavioral scores (p=0.02), and the relative differences between the treated group and the control were even greater over subsequent weeks (p=0.007 and p=0.003 for weeks three and four respectively).

What is claimed:

1. A pharmaceutical composition, comprising:
  a) a soluble neutral active human hyaluronidase glycoprotein (sHASEGP), wherein:
  the hyaluronidase glycoprotein is active at neutral pH and contains at least one sugar moiety that is covalently attached to an asparagine (N) residue of the hyaluronidase polypeptide;
  the hyaluronidase polypeptide does not comprise the complete sequence of amino acids set forth in SEQ ID NO:1; and
  the hyaluronidase polypeptide consists of:
    (i) a sequence of amino acid residues contained within SEQ ID NO:1 that includes at least amino acids 36-464 of SEQ ID NO:1, wherein the polypeptide is truncated within the C-terminus of SEQ ID NO:1 at a C-terminal amino acid residue selected from among 467, 477, 478, 479, 480, 481, 482, 483 and 494 of SEQ ID NO:1; or
    (ii) a sequence of amino acid residues that has at least 95% amino acid sequence identity with a sequence of amino acids set forth in (i); and
  b) an anti-cancer agent selected from among Alemtuzumab, Bevacizumab, Docetaxel, Gemcitabine, Ibritumomab tiuxetan, Ortataxel, Paclitaxel, Rituximab, Tositumomab and Trastuzumab.

2. The pharmaceutical composition of claim 1, wherein the hyaluronidase glycoprotein is selected from among:
  (i) a hyaluronidase polypeptide that has a C-terminal amino acid residue selected from among 477, 478, 479, 480, 481, 482 and 483 of SEQ ID NO:1; and
  (ii) a hyaluronidase protein that has at least 97% amino acid sequence identity with a sequence of amino acids of (i) that has a C-terminal amino acid residue selected from among 477, 478, 479, 480, 481, 482 and 483 of SEQ ID NO:1.

3. The pharmaceutical composition of claim 1, wherein:
  (i) the hyaluronidase glycoprotein consists of the sequence of amino acids set forth as amino acids 36-477, 36-478, 36-479, 36-480, 36-481, 36-482, or 36-483 of SEQ ID NO:1; or
  (ii) the hyaluronidase glycoprotein contains amino acid substitutions in the sequence of amino acids set forth as amino acids 36-477, 36-478, 36-479, 36-480, 36-481, 36-482, or 36-483 of SEQ ID NO:1, whereby the amino acid-substituted hyaluronidase glycoprotein consists of a sequence of amino acids that has at least 95% amino acid sequence identity with the sequence of amino acids set forth as amino acids 36-477, 36-478, 36-479, 36-480, 36-481, 36-482, or 36-483 of SEQ ID NO:1.

4. The pharmaceutical composition of claim 1, wherein the hyaluronidase glycoprotein is expressed and secreted from mammalian cells.

5. The pharmaceutical composition of claim 4, wherein the mammalian cells are Chinese Hamster Ovary (CHO) cells.

6. The pharmaceutical composition of claim 1, wherein the hyaluronidase glycoprotein is modified with a polymer.

7. The pharmaceutical composition of claim 6, wherein the polymer is PEG or dextran.

8. The pharmaceutical composition of claim 7 that is formulated for intravenous administration.

9. The pharmaceutical composition of claim 1 that is formulated for subcutaneous administration.

10. The pharmaceutical composition of claim 1, wherein the hyaluronidase glycoprotein has a C-terminal amino acid residue selected from among 477, 478, 479, 480, 481, 482 and 483 of SEQ ID NO:1.

11. The pharmaceutical composition of claim 1, wherein in (ii) the hyaluronidase polypeptide has at least 97% sequence identity.

12. The pharmaceutical composition of claim 1, wherein the hyaluronidase polypeptide consists of a sequence of amino acids that has at least 98% sequence identity with residues 36-483 of SEQ ID NO:1.

13. The pharmaceutical composition of claim 1, wherein in b) the anti-cancer agent is paclitaxel, docetaxel, or ortataxel.

14. The pharmaceutical composition of claim 1, wherein in b) the anti-cancer agent is paclitaxel.

15. The pharmaceutical composition of claim 1, wherein in b) the anticancer agent is Alemtuzumab, Bevacizumab, Ibritumomab tiuxetan, Rituximab, Tositumomab, or Trastuzumab.

16. The pharmaceutical composition of claim 1, wherein in b) the anti-cancer agent is Trastuzumab.

17. A combination, comprising:
  a) a first composition comprising a soluble neutral active human hyaluronidase glycoprotein (sHASEGP), wherein:
  the hyaluronidase glycoprotein is active at neutral pH and contains at least one sugar moiety that is covalently attached to an asparagine (N) residue of the hyaluronidase polypeptide;
  the hyaluronidase polypeptide does not comprise the complete sequence of amino acids set forth in SEQ ID NO:1; and the hyaluronidase polypeptide consists of:
    (i) a sequence of amino acid residues contained within SEQ ID NO:1 that includes at least amino acids 36-464 of SEQ ID NO:1, wherein the polypeptide is truncated within the C-terminus of SEQ ID NO:1 at a C-terminal amino acid residue selected from among 467, 477, 478, 479, 480, 481, 482, 483 and 494 of SEQ ID NO:1; or (ii) a sequence of amino acid residues that has at least 95% amino acid sequence identity with a sequence of amino acids set forth in (i); and b) a second composition, comprising an anti-cancer agent selected from among Alemtuzumab, Bevacizumab, Docetaxel, Gemcitabine, Ibritumomab tiuxetan, Ortataxel, Paclitaxel, Rituximab, Tositumomab and Trastuzumab.

18. The combination of claim 17, wherein the hyaluronidase glycoprotein is selected from among:
   (i) a hyaluronidase polypeptide that has a C-terminal amino acid residue selected from among 477, 478, 479, 480, 481, 482 and 483 of SEQ ID NO:1; and
   (ii) a hyaluronidase protein that has at least 97% amino acid sequence identity with a sequence of amino acids of (i) that has a C-terminal amino acid residue selected from among 477, 478, 479, 480, 481, 482 and 483 of SEQ ID NO:1.

19. The combination of claim 17, wherein the hyaluronidase glycoprotein is expressed and secreted from mammalian cells.

20. The combination of claim 19, wherein the mammalian cells are Chinese Hamster Ovary (CHO) cells.

21. The combination of claim 17, wherein the hyaluronidase glycoprotein is modified with a polymer.

22. The combination of claim 12, wherein the polymer is PEG or dextran.

23. The combination of claim 22, wherein one of the first and second compositions is formulated for intravenous administration.

24. The combination of claim 22, wherein each of the pharmaceutical compositions is formulated for intravenous administration.

25. The combination of claim 17, wherein one of the first and second compositions is formulated for subcutaneous administration.

26. The combination of claim 17, wherein each of the pharmaceutical compositions is formulated for subcutaneous administration.

27. The combination of claim 17, wherein the hyaluronidase glycoprotein has a C-terminal amino acid residue selected from among 477, 478, 479, 480, 481, 482 and 483 of SEQ ID NO:1.

28. The combination of claim 17, wherein in (ii) the hyaluronidase polypeptide has at least 97% sequence identity.

29. The combination of claim 17, wherein the hyaluronidase polypeptide consists of a sequence of amino acids that has at least 98% sequence identity with residues 36-483 of SEQ ID NO:1.

30. The combination of claim 17, wherein in b) the anti-cancer agent is paclitaxel, docetaxel or ortataxel.

31. The combination of claim 17, wherein in b) the anti-cancer agent is paclitaxel.

32. The combination of claim 17, wherein in b) the anti-cancer agent is Alemtuzumab, Bevacizumab, Ibritumomab tiuxetan, Rituximab, Tositumomab, or Trastuzumab.

33. The combination of claim 17, wherein in b) the anti-cancer agent is Trastuzumab.

34. The combination of claim 17, wherein:
   (i) the hyaluronidase glycoprotein consists of the sequence of amino acids set forth as amino acids 36-477, 36-478, 36-479, 36-480, 36-481, 36-482, or 36-483 of SEQ ID NO:1; or
   (ii) the hyaluronidase glycoprotein contains amino acid substitutions in the sequence of amino acids set forth as amino acids 36-477, 36-478, 36-479, 36-480, 36-481, 36-482, or 36-483 of SEQ ID NO:1, whereby the amino acid-substituted hyaluronidase glycoprotein consists of a sequence of amino acids that has at least 95% amino acid sequence identity with the sequence of amino acids set forth as amino acids 36-477, 36-478, 36-479, 36-480, 36-481, 36-482, or 36-483 of SEQ ID NO:1.

* * * * *

UNITED STATES PATENT AND TRADEMARK OFFICE
CERTIFICATE OF CORRECTION

PATENT NO. : 8,580,252 B2
APPLICATION NO. : 13/507540
DATED : November 12, 2013
INVENTOR(S) : Bookbinder et al.

It is certified that error appears in the above-identified patent and that said Letters Patent is hereby corrected as shown below:

IN THE CLAIMS:

Claim 22, Column 205, lines 26 to line 27 should read as follows:

22. The combination of claim 21, wherein the polymer is PEG or dextran.

Signed and Sealed this
Twenty-seventh Day of May, 2014

Michelle K. Lee
*Deputy Director of the United States Patent and Trademark Office*

SEQUENCE LISTING

```
<160> NUMBER OF SEQ ID NOS: 53

<210> SEQ ID NO 1
<211> LENGTH: 509
<212> TYPE: PRT
<213> ORGANISM: Homo sapiens
<220> FEATURE:
<221> NAME/KEY: CARBOHYD
<222> LOCATION: 82, 166, 235, 254, 368, 393, 490
```

<400> SEQUENCE: 1

```
Met Gly Val Leu Lys Phe Lys His Ile Phe Arg Ser Phe Val Lys
 1               5                  10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Pro
                35                  40                  45

Phe Leu Trp Ala Trp Asn Ala Pro Ser Glu Phe Cys Leu Gly Lys Phe
         50                  55                  60

Asp Glu Pro Leu Asp Met Ser Leu Phe Ser Phe Ile Gly Ser Pro Arg
 65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
                100                 105                 110

Gly Ile Pro Gln Lys Ile Ser Leu Gln Asp His Leu Asp Lys Ala Lys
            115                 120                 125

Lys Asp Ile Thr Phe Tyr Met Pro Val Asp Asn Leu Gly Met Ala Val
130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
            195                 200                 205

Leu Leu Arg Pro Asn His Leu Trp Gly Tyr Tyr Leu Phe Pro Asp Cys
210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
            275                 280                 285

Ser Lys Ile Pro Asp Ala Lys Ser Pro Leu Pro Val Phe Ala Tyr Thr
            290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
            355                 360                 365

Val Thr Leu Ala Ala Lys Met Cys Ser Gln Val Leu Cys Gln Glu Gln
370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415
```

-continued

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
        435                 440                 445

Val Lys Asp Thr Asp Ala Val Asp Val Cys Ile Ala Asp Gly Val Cys
450                 455                 460

Ile Asp Ala Phe Leu Lys Pro Pro Met Glu Thr Glu Glu Pro Gln Ile
465                 470                 475                 480

Phe Tyr Asn Ala Ser Pro Ser Thr Leu Ser Ala Thr Met Phe Ile Val
                485                 490                 495

Ser Ile Leu Phe Leu Ile Ile Ser Ser Val Ala Ser Leu
                500                 505

<210> SEQ ID NO 2
<211> LENGTH: 35
<212> TYPE: PRT
<213> ORGANISM: Homo sapiens

<400> SEQUENCE: 2

Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
                20                  25                  30

Cys Leu Thr
        35

<210> SEQ ID NO 3
<211> LENGTH: 474
<212> TYPE: PRT
<213> ORGANISM: Homo sapiens

<400> SEQUENCE: 3

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
                20                  25                  30

Leu Asp Met Ser Leu Phe Ser Phe Ile Gly Ser Pro Arg Ile Asn Ala
            35                  40                  45

Thr Gly Gln Gly Val Thr Ile Phe Tyr Val Asp Arg Leu Gly Tyr Tyr
        50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Asn Val Gln Leu
130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

```
His Tyr Lys Lys Pro Gly Tyr Asn Gly Ser Cys Phe Asn Val Glu Ile
            195                 200                 205

Lys Arg Asn Asp Asp Leu Ser Trp Leu Trp Asn Glu Ser Thr Ala Leu
210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
            245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
        290                 295                 300

Gly Thr Leu Ser Ile Met Arg Ser Met Lys Ser Cys Leu Leu Leu Asp
305                 310                 315                 320

Asn Tyr Met Glu Thr Ile Leu Asn Pro Tyr Ile Ile Asn Val Thr Leu
            325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
        370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
            405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr Asn
        435                 440                 445

Ala Ser Pro Ser Thr Leu Ser Ala Thr Met Phe Ile Val Ser Ile Leu
        450                 455                 460

Phe Leu Ile Ile Ser Ser Val Ala Ser Leu
465                 470

<210> SEQ ID NO 4
<211> LENGTH: 448
<212> TYPE: PRT
<213> ORGANISM: Homo sapiens

<400> SEQUENCE: 4

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95
```

```
Thr Phe Tyr Met Pro Val Asp Asn Leu Gly Met Ala Val Ile Asp Trp
            100                 105                 110
Glu Glu Trp Arg Pro Thr Trp Ala Arg Asn Trp Lys Pro Lys Asp Val
        115                 120                 125
Tyr Lys Asn Arg Ser Ile Glu Leu Val Gln Gln Asn Val Gln Leu
    130                 135                 140
Ser Leu Thr Glu Ala Thr Glu Lys Ala Lys Gln Glu Phe Glu Lys Ala
145                 150                 155                 160
Gly Lys Asp Phe Leu Val Glu Thr Ile Lys Leu Gly Lys Leu Leu Arg
                165                 170                 175
Pro Asn His Leu Trp Gly Tyr Tyr Leu Phe Pro Asp Cys Tyr Asn His
            180                 185                 190
His Tyr Lys Lys Pro Gly Tyr Asn Gly Ser Cys Phe Asn Val Glu Ile
        195                 200                 205
Lys Arg Asn Asp Asp Leu Ser Trp Leu Trp Asn Glu Ser Thr Ala Leu
    210                 215                 220
Tyr Pro Ser Ile Tyr Leu Asn Thr Gln Gln Ser Pro Val Ala Ala Thr
225                 230                 235                 240
Leu Tyr Val Arg Asn Arg Val Arg Glu Ala Ile Arg Val Ser Lys Ile
                245                 250                 255
Pro Asp Ala Lys Ser Pro Leu Pro Val Phe Ala Tyr Thr Arg Ile Val
            260                 265                 270
Phe Thr Asp Gln Val Leu Lys Phe Leu Ser Gln Asp Glu Leu Val Tyr
        275                 280                 285
Thr Phe Gly Glu Thr Val Ala Leu Gly Ala Ser Gly Ile Val Ile Trp
    290                 295                 300
Gly Thr Leu Ser Ile Met Arg Ser Met Lys Ser Cys Leu Leu Leu Asp
305                 310                 315                 320
Asn Tyr Met Glu Thr Ile Leu Asn Pro Tyr Ile Ile Asn Val Thr Leu
                325                 330                 335
Ala Ala Lys Met Cys Ser Gln Val Leu Cys Gln Glu Gln Gly Val Cys
            340                 345                 350
Ile Arg Lys Asn Trp Asn Ser Ser Asp Tyr Leu His Leu Asn Pro Asp
        355                 360                 365
Asn Phe Ala Ile Gln Leu Glu Lys Gly Gly Lys Phe Thr Val Arg Gly
    370                 375                 380
Lys Pro Thr Leu Glu Asp Leu Glu Gln Phe Ser Glu Lys Phe Tyr Cys
385                 390                 395                 400
Ser Cys Tyr Ser Thr Leu Ser Cys Lys Glu Lys Ala Asp Val Lys Asp
                405                 410                 415
Thr Asp Ala Val Asp Val Cys Ile Ala Asp Gly Val Cys Ile Asp Ala
            420                 425                 430
Phe Leu Lys Pro Pro Met Glu Thr Glu Glu Pro Gln Ile Phe Tyr Asn
        435                 440                 445

<210> SEQ ID NO 5
<211> LENGTH: 482
<212> TYPE: PRT
<213> ORGANISM: Homo sapiens

<400> SEQUENCE: 5

Met Gly Val Leu Lys Phe Lys His Ile Phe Phe Arg Ser Phe Val Lys
1               5                   10                  15
Ser Ser Gly Val Ser Gln Ile Val Phe Thr Phe Leu Leu Ile Pro Cys
            20                  25                  30
```

-continued

```
Cys Leu Thr Leu Asn Phe Arg Ala Pro Pro Val Ile Pro Asn Val Pro
     35                  40                  45

Phe Leu Trp Ala Trp Asn Ala Pro Ser Glu Phe Cys Leu Gly Lys Phe
 50                  55                  60

Asp Glu Pro Leu Asp Met Ser Leu Phe Ser Phe Ile Gly Ser Pro Arg
 65                  70                  75                  80

Ile Asn Ala Thr Gly Gln Gly Val Thr Ile Phe Tyr Val Asp Arg Leu
                 85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
            115                 120                 125

Lys Asp Ile Thr Phe Tyr Met Pro Val Asp Asn Leu Gly Met Ala Val
130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
            195                 200                 205

Leu Leu Arg Pro Asn His Leu Trp Gly Tyr Tyr Leu Phe Pro Asp Cys
210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
            275                 280                 285

Ser Lys Ile Pro Asp Ala Lys Ser Pro Leu Pro Val Phe Ala Tyr Thr
290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
            355                 360                 365

Val Thr Leu Ala Ala Lys Met Cys Ser Gln Val Leu Cys Gln Glu Gln
370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
            435                 440                 445

Val Lys Asp Thr Asp Ala Val Asp Val Cys Ile Ala Asp Gly Val Cys
450                 455                 460
```

```
Ile Asp Ala Phe Leu Lys Pro Pro Met Glu Thr Glu Pro Gln Ile
465                 470                 475                 480

Phe Tyr

<210> SEQ ID NO 6
<211> LENGTH: 1530
<212> TYPE: DNA
<213> ORGANISM: Homo sapiens
<220> FEATURE:
<221> NAME/KEY: CDS
<222> LOCATION: (1)...(1530)
<223> OTHER INFORMATION: PH-20 GPI Anchored Hyaluronidase Glycoprotein

<400> SEQUENCE: 6 atg gga gtg cta aaa ttc aag cac atc ttt ttc aga agc ttt gtt aaa       48
Met Gly Val Leu Lys Phe Lys His Ile Phe Phe Arg Ser Phe Val Lys
1               5                   10                  15 tca agt gga gta tcc cag ata gtt ttc acc ttc ctt ctg att cca tgt       96
Ser Ser Gly Val Ser Gln Ile Val Phe Thr Phe Leu Leu Ile Pro Cys
            20                  25                  30 tgc ttg act ctg aat ttc aga gca cct cct gtt att cca aat gtg cct      144
Cys Leu Thr Leu Asn Phe Arg Ala Pro Pro Val Ile Pro Asn Val Pro
        35                  40                  45 ttc ctc tgg gcc tgg aat gcc cca agt gaa ttt tgt ctt gga aaa ttt      192
Phe Leu Trp Ala Trp Asn Ala Pro Ser Glu Phe Cys Leu Gly Lys Phe
50                  55                  60 gat gag cca cta gat atg agc ctc ttc tct ttc ata gga agc ccc cga      240
Asp Glu Pro Leu Asp Met Ser Leu Phe Ser Phe Ile Gly Ser Pro Arg
65                  70                  75                  80 ata aac gcc acc ggg caa ggt gtt aca ata ttt tat gtt gat aga ctt      288
Ile Asn Ala Thr Gly Gln Gly Val Thr Ile Phe Tyr Val Asp Arg Leu
                85                  90                  95 ggc tac tat cct tac ata gat tca atc aca gga gta act gtg aat gga      336
Gly Tyr Tyr Pro Tyr Ile Asp Ser Ile Thr Gly Val Thr Val Asn Gly
            100                 105                 110 gga atc ccc cag aag att tcc tta caa gac cat ctg gac aaa gct aag      384
Gly Ile Pro Gln Lys Ile Ser Leu Gln Asp His Leu Asp Lys Ala Lys
        115                 120                 125 aaa gac att aca ttt tat atg cca gta gac aat ttg gga atg gct gtt      432
Lys Asp Ile Thr Phe Tyr Met Pro Val Asp Asn Leu Gly Met Ala Val
130                 135                 140 att gac tgg gaa gaa tgg aga ccc act tgg gca aga aac tgg aaa cct      480
Ile Asp Trp Glu Glu Trp Arg Pro Thr Trp Ala Arg Asn Trp Lys Pro
145                 150                 155                 160 aaa gat gtt tac aag aat agg tct att gaa ttg gtt cag caa caa aat      528
Lys Asp Val Tyr Lys Asn Arg Ser Ile Glu Leu Val Gln Gln Gln Asn
                165                 170                 175 gta caa ctt agt ctc aca gag gcc act gag aaa gca aaa caa gaa ttt      576
Val Gln Leu Ser Leu Thr Glu Ala Thr Glu Lys Ala Lys Gln Glu Phe
            180                 185                 190 gaa aag gca ggg aag gat ttc ctg gta gag act ata aaa ttg gga aaa      624
Glu Lys Ala Gly Lys Asp Phe Leu Val Glu Thr Ile Lys Leu Gly Lys
        195                 200                 205 tta ctt cgg cca aat cac ttg tgg ggt tat tat ctt ttt ccg gat tgt      672
Leu Leu Arg Pro Asn His Leu Trp Gly Tyr Tyr Leu Phe Pro Asp Cys
210                 215                 220 tac aac cat cac tat aag aaa ccc ggt tac aat gga agt tgc ttc aat      720
Tyr Asn His His Tyr Lys Lys Pro Gly Tyr Asn Gly Ser Cys Phe Asn
225                 230                 235                 240 gta gaa ata aaa aga aat gat gat ctc agc tgg ttg tgg aat gaa agc      768
Val Glu Ile Lys Arg Asn Asp Asp Leu Ser Trp Leu Trp Asn Glu Ser
```

```
                     245                 250                 255
act gct ctt tac cca tcc att tat ttg aac act cag cag tct cct gta       816
Thr Ala Leu Tyr Pro Ser Ile Tyr Leu Asn Thr Gln Gln Ser Pro Val
            260                 265                 270 gct gct aca ctc tat gtg cgc aat cga gtt cgg gaa gcc atc aga gtt       864
Ala Ala Thr Leu Tyr Val Arg Asn Arg Val Arg Glu Ala Ile Arg Val
            275                 280                 285 tcc aaa ata cct gat gca aaa agt cca ctt ccg gtt ttt gca tat acc       912
Ser Lys Ile Pro Asp Ala Lys Ser Pro Leu Pro Val Phe Ala Tyr Thr
            290                 295                 300 cgc ata gtt ttt act gat caa gtt ttg aaa ttc ctt tct caa gat gaa       960
Arg Ile Val Phe Thr Asp Gln Val Leu Lys Phe Leu Ser Gln Asp Glu
305                 310                 315                 320 ctt gtg tat aca ttt ggc gaa act gtt gct ctg ggt gct tct gga att      1008
Leu Val Tyr Thr Phe Gly Glu Thr Val Ala Leu Gly Ala Ser Gly Ile
            325                 330                 335 gta ata tgg gga acc ctc agt ata atg cga agt atg aaa tct tgc ttg      1056
Val Ile Trp Gly Thr Leu Ser Ile Met Arg Ser Met Lys Ser Cys Leu
            340                 345                 350 ctc cta gac aat tac atg gag act ata ctg aat cct tac ata atc aac      1104
Leu Leu Asp Asn Tyr Met Glu Thr Ile Leu Asn Pro Tyr Ile Ile Asn
            355                 360                 365 gtc aca cta gca gcc aaa atg tgt agc caa gtg ctt tgc cag gag caa      1152
Val Thr Leu Ala Ala Lys Met Cys Ser Gln Val Leu Cys Gln Glu Gln
370                 375                 380 gga gtg tgt ata agg aaa aac tgg aat tca agt gac tat ctt cac ctc      1200
Gly Val Cys Ile Arg Lys Asn Trp Asn Ser Ser Asp Tyr Leu His Leu
385                 390                 395                 400 aac cca gat aat ttt gct att caa ctt gag aaa ggt gga aag ttc aca      1248
Asn Pro Asp Asn Phe Ala Ile Gln Leu Glu Lys Gly Gly Lys Phe Thr
            405                 410                 415 gta cgt gga aaa ccg aca ctt gaa gac ctg gag caa ttt tct gaa aaa      1296
Val Arg Gly Lys Pro Thr Leu Glu Asp Leu Glu Gln Phe Ser Glu Lys
            420                 425                 430 ttt tat tgc agc tgt tat agc acc ttg agt tgt aag gag aaa gct gat      1344
Phe Tyr Cys Ser Cys Tyr Ser Thr Leu Ser Cys Lys Glu Lys Ala Asp
            435                 440                 445 gta aaa gac act gat gct gtt gat gtg tgt att gct gat ggt gtc tgt      1392
Val Lys Asp Thr Asp Ala Val Asp Val Cys Ile Ala Asp Gly Val Cys
450                 455                 460 ata gat gct ttt cta aaa cct ccc atg gag aca gaa gaa cct caa att      1440
Ile Asp Ala Phe Leu Lys Pro Pro Met Glu Thr Glu Glu Pro Gln Ile
465                 470                 475                 480 ttc tac aat gct tca ccc tcc aca cta tct gcc aca atg ttc att gtt      1488
Phe Tyr Asn Ala Ser Pro Ser Thr Leu Ser Ala Thr Met Phe Ile Val
            485                 490                 495 agt att ttg ttt ctt atc att tct tct gta gcg agt ttg taa              1530
Ser Ile Leu Phe Leu Ile Ile Ser Ser Val Ala Ser Leu
            500                 505

<210> SEQ ID NO 7
<211> LENGTH: 509
<212> TYPE: PRT
<213> ORGANISM: Homo sapiens
<220> FEATURE:
<221> NAME/KEY: CARBOHYD
<222> LOCATION: 82, 166, 235, 254, 368, 393, 490

<400> SEQUENCE: 7

Met Gly Val Leu Lys Phe Lys His Ile Phe Phe Arg Ser Phe Val Lys
1               5                   10                  15
```

-continued

```
Ser Ser Gly Val Ser Gln Ile Val Phe Thr Phe Leu Leu Ile Pro Cys
         20              25               30

Cys Leu Thr Leu Asn Phe Arg Ala Pro Pro Val Ile Pro Asn Val Pro
         35              40               45

Phe Leu Trp Ala Trp Asn Ala Pro Ser Glu Phe Cys Leu Gly Lys Phe
 50              55              60

Asp Glu Pro Leu Asp Met Ser Leu Phe Ser Phe Ile Gly Ser Pro Arg
 65              70              75              80

Ile Asn Ala Thr Gly Gln Gly Val Thr Ile Phe Tyr Val Asp Arg Leu
             85              90              95

Gly Tyr Tyr Pro Tyr Ile Asp Ser Ile Thr Gly Val Thr Val Asn Gly
             100             105             110

Gly Ile Pro Gln Lys Ile Ser Leu Gln Asp His Leu Asp Lys Ala Lys
             115             120             125

Lys Asp Ile Thr Phe Tyr Met Pro Val Asp Asn Leu Gly Met Ala Val
 130             135             140

Ile Asp Trp Glu Glu Trp Arg Pro Thr Trp Ala Arg Asn Trp Lys Pro
 145             150             155             160

Lys Asp Val Tyr Lys Asn Arg Ser Ile Glu Leu Val Gln Gln Gln Asn
             165             170             175

Val Gln Leu Ser Leu Thr Glu Ala Thr Glu Lys Ala Lys Gln Glu Phe
             180             185             190

Glu Lys Ala Gly Lys Asp Phe Leu Val Glu Thr Ile Lys Leu Gly Lys
             195             200             205

Leu Leu Arg Pro Asn His Leu Trp Gly Tyr Tyr Leu Phe Pro Asp Cys
 210             215             220

Tyr Asn His His Tyr Lys Lys Pro Gly Tyr Asn Gly Ser Cys Phe Asn
225              230             235             240

Val Glu Ile Lys Arg Asn Asp Asp Leu Ser Trp Leu Trp Asn Glu Ser
             245             250             255

Thr Ala Leu Tyr Pro Ser Ile Tyr Leu Asn Thr Gln Gln Ser Pro Val
             260             265             270

Ala Ala Thr Leu Tyr Val Arg Asn Arg Val Arg Glu Ala Ile Arg Val
             275             280             285

Ser Lys Ile Pro Asp Ala Lys Ser Pro Leu Pro Val Phe Ala Tyr Thr
             290             295             300

Arg Ile Val Phe Thr Asp Gln Val Leu Lys Phe Leu Ser Gln Asp Glu
305             310             315             320

Leu Val Tyr Thr Phe Gly Glu Thr Val Ala Leu Gly Ala Ser Gly Ile
             325             330             335

Val Ile Trp Gly Thr Leu Ser Ile Met Arg Ser Met Lys Ser Cys Leu
             340             345             350

Leu Leu Asp Asn Tyr Met Glu Thr Ile Leu Asn Pro Tyr Ile Ile Asn
             355             360             365

Val Thr Leu Ala Ala Lys Met Cys Ser Gln Val Leu Cys Gln Glu Gln
             370             375             380

Gly Val Cys Ile Arg Lys Asn Trp Asn Ser Ser Asp Tyr Leu His Leu
385             390             395             400

Asn Pro Asp Asn Phe Ala Ile Gln Leu Glu Lys Gly Gly Lys Phe Thr
             405             410             415

Val Arg Gly Lys Pro Thr Leu Glu Asp Leu Glu Gln Phe Ser Glu Lys
             420             425             430

Phe Tyr Cys Ser Cys Tyr Ser Thr Leu Ser Cys Lys Glu Lys Ala Asp
             435             440             445
```

```
Val Lys Asp Thr Asp Ala Val Asp Val Cys Ile Ala Asp Gly Val Cys
    450                 455                 460

Ile Asp Ala Phe Leu Lys Pro Pro Met Glu Thr Glu Glu Pro Gln Ile
465                 470                 475                 480

Phe Tyr Asn Ala Ser Pro Ser Thr Leu Ser Ala Thr Met Phe Ile Val
                485                 490                 495

Ser Ile Leu Phe Leu Ile Ile Ser Ser Val Ala Ser Leu
                500                 505
```

```
<210> SEQ ID NO 8
<211> LENGTH: 34
<212> TYPE: DNA
<213> ORGANISM: Artificial Sequence
<220> FEATURE:
<223> OTHER INFORMATION: Reverse Primer to generate GPI anchor lacking
      N483 and terminating at Y482 with BamHI site in the 5' end

<400> SEQUENCE: 8
aattggatcc tcagtagaaa atttgaggtt cttc                              34

<210> SEQ ID NO 9
<211> LENGTH: 33
<212> TYPE: DNA
<213> ORGANISM: Artificial Sequence
<220> FEATURE:
<223> OTHER INFORMATION: Reverse Primer to generate GPI anchor lacking
      Y482 and terminating at F481 with BamHI site in the 5' end

<400> SEQUENCE: 9
aattggatcc tcagaaaatt tgaggttctt ctg                               33

<210> SEQ ID NO 10
<211> LENGTH: 34
<212> TYPE: DNA
<213> ORGANISM: Artificial Sequence
<220> FEATURE:
<223> OTHER INFORMATION: Reverse Primer to generate GPI anchor lacking
      F481 and terminating at I480 with BamHI site in the 5' end

<400> SEQUENCE: 10
aattggatcc tcaaatttga ggttcttctg tctc                              34

<210> SEQ ID NO 11
<211> LENGTH: 32
<212> TYPE: DNA
<213> ORGANISM: Artificial Sequence
<220> FEATURE:
<223> OTHER INFORMATION: Reverse Primer to generate GPI anchor lacking
      I480 and terminating at Q479 with BamHI site in the 5' end

<400> SEQUENCE: 11
aattggatcc tcattgaggt tcttctgtct cc                                32

<210> SEQ ID NO 12
<211> LENGTH: 32
<212> TYPE: DNA
<213> ORGANISM: Artificial Sequence
<220> FEATURE:
<223> OTHER INFORMATION: Reverse Primer to generate GPI anchor lacking
      Q479 and terminating at P478 with BamHI site in the 5' end

<400> SEQUENCE: 12
aattggatcc tcaaggttct tctgtctcca tg                                32

<210> SEQ ID NO 13
```

-continued

```
<211> LENGTH: 31
<212> TYPE: DNA
<213> ORGANISM: Artificial Sequence
<220> FEATURE:
<223> OTHER INFORMATION: Reverse Primer to generate GPI anchor lacking
      P478 and terminating at E477 with BamHI site in the 5' end

<400> SEQUENCE: 13
aattggatcc tcattcttct gtctccatgg g                               31

<210> SEQ ID NO 14
<211> LENGTH: 32
<212> TYPE: DNA
<213> ORGANISM: Artificial Sequence
<220> FEATURE:
<223> OTHER INFORMATION: Forward Primer with NheI restriction site at 5'
      end

<400> SEQUENCE: 14
aattgctagc atgggagtgc taaaattcaa gc                              32

<210> SEQ ID NO 15
<211> LENGTH: 1473
<212> TYPE: DNA
<213> ORGANISM: Homo sapiens
<220> FEATURE:
<221> NAME/KEY: CDS
<222> LOCATION: (1)...(1473)
<223> OTHER INFORMATION: sHASEGPup to P478 and His Tagged

<400> SEQUENCE: 15 atg gga gtg cta aaa ttc aag cac atc ttt ttc aga agc ttt gtt aaa    48
Met Gly Val Leu Lys Phe Lys His Ile Phe Phe Arg Ser Phe Val Lys
1               5                   10                  15 tca agt gga gta tcc cag ata gtt ttc acc ttc ctt ctg att cca tgt    96
Ser Ser Gly Val Ser Gln Ile Val Phe Thr Phe Leu Leu Ile Pro Cys
            20                  25                  30 tgc ttg act ctg aat ttc aga gca cct cct gtt att cca aat gtg cct   144
Cys Leu Thr Leu Asn Phe Arg Ala Pro Pro Val Ile Pro Asn Val Pro
        35                  40                  45 ttc ctc tgg gcc tgg aat gcc cca agt gaa ttt tgt ctt gga aaa ttt   192
Phe Leu Trp Ala Trp Asn Ala Pro Ser Glu Phe Cys Leu Gly Lys Phe
    50                  55                  60 gat gag cca cta gat atg agc ctc ttc tct ttc ata gga agc ccc cga   240
Asp Glu Pro Leu Asp Met Ser Leu Phe Ser Phe Ile Gly Ser Pro Arg
65                  70                  75                  80 ata aac gcc acc ggg caa ggt gtt aca ata ttt tat gtt gat aga ctt   288
Ile Asn Ala Thr Gly Gln Gly Val Thr Ile Phe Tyr Val Asp Arg Leu
                85                  90                  95 ggc tac tat cct tac ata gat tca atc aca gga gta act gtg aat gga   336
Gly Tyr Tyr Pro Tyr Ile Asp Ser Ile Thr Gly Val Thr Val Asn Gly
            100                 105                 110 gga atc ccc cag aag att tcc tta caa gac cat ctg gac aaa gct aag   384
Gly Ile Pro Gln Lys Ile Ser Leu Gln Asp His Leu Asp Lys Ala Lys
        115                 120                 125 aaa gac att aca ttt tat atg cca gta gac aat ttg gga atg gct gtt   432
Lys Asp Ile Thr Phe Tyr Met Pro Val Asp Asn Leu Gly Met Ala Val
    130                 135                 140 att gac tgg gaa gaa tgg aga ccc act tgg gca aga aac tgg aaa cct   480
Ile Asp Trp Glu Glu Trp Arg Pro Thr Trp Ala Arg Asn Trp Lys Pro
145                 150                 155                 160 aaa gat gtt tac aag aat agg tct att gaa ttg gtt cag caa caa aat   528
Lys Asp Val Tyr Lys Asn Arg Ser Ile Glu Leu Val Gln Gln Gln Asn
                165                 170                 175
```

```
gta caa ctt agt ctc aca gag gcc act gag aaa gca aaa caa gaa ttt      576
Val Gln Leu Ser Leu Thr Glu Ala Thr Glu Lys Ala Lys Gln Glu Phe
        180                 185                 190 gaa aag gca ggg aag gat ttc ctg gta gag act ata aaa ttg gga aaa      624
Glu Lys Ala Gly Lys Asp Phe Leu Val Glu Thr Ile Lys Leu Gly Lys
        195                 200                 205 tta ctt cgg cca aat cac ttg tgg ggt tat tat ctt ttc ccg gat tgt      672
Leu Leu Arg Pro Asn His Leu Trp Gly Tyr Tyr Leu Phe Pro Asp Cys
    210                 215                 220 tac aac cat cac tat aag aaa ccc ggt tac aat gga agt tgc ttc aat      720
Tyr Asn His His Tyr Lys Lys Pro Gly Tyr Asn Gly Ser Cys Phe Asn
225                 230                 235                 240 gta gaa ata aaa aga aat gat gat ctc agc tgg ttg tgg aat gaa agc      768
Val Glu Ile Lys Arg Asn Asp Asp Leu Ser Trp Leu Trp Asn Glu Ser
                245                 250                 255 act gct ctt tac cca tcc att tat ttg aac act cag cag tct cct gta      816
Thr Ala Leu Tyr Pro Ser Ile Tyr Leu Asn Thr Gln Gln Ser Pro Val
            260                 265                 270 gct gct aca ctc tat gtg cgc aat cga gtt cgg gaa gcc atc aga gtt      864
Ala Ala Thr Leu Tyr Val Arg Asn Arg Val Arg Glu Ala Ile Arg Val
        275                 280                 285 tcc aaa ata cct gat gca aaa agt cca ctt ccg gtt ttt gca tat acc      912
Ser Lys Ile Pro Asp Ala Lys Ser Pro Leu Pro Val Phe Ala Tyr Thr
    290                 295                 300 cgc ata gtt ttt act gat caa gtt ttg aaa ttc ctt tct caa gat gaa      960
Arg Ile Val Phe Thr Asp Gln Val Leu Lys Phe Leu Ser Gln Asp Glu
305                 310                 315                 320 ctt gtg tat aca ttt ggc gaa act gtt gct ctg ggt gct tct gga att     1008
Leu Val Tyr Thr Phe Gly Glu Thr Val Ala Leu Gly Ala Ser Gly Ile
                325                 330                 335 gta ata tgg gga acc ctc agt ata atg cga agt atg aaa tct tgc ttg     1056
Val Ile Trp Gly Thr Leu Ser Ile Met Arg Ser Met Lys Ser Cys Leu
            340                 345                 350 ctc cta gac aat tac atg gag act ata ctg aat cct tac ata atc aac     1104
Leu Leu Asp Asn Tyr Met Glu Thr Ile Leu Asn Pro Tyr Ile Ile Asn
        355                 360                 365 gtc aca cta gca gcc aaa atg tgt agc caa gtg ctt tgc cag gag caa     1152
Val Thr Leu Ala Ala Lys Met Cys Ser Gln Val Leu Cys Gln Glu Gln
    370                 375                 380 gga gtg tgt ata agg aaa aac tgg aat tca agt gac tat ctt cac ctc     1200
Gly Val Cys Ile Arg Lys Asn Trp Asn Ser Ser Asp Tyr Leu His Leu
385                 390                 395                 400 aac cca gat aat ttt gct att caa ctt gag aaa ggt gga aag ttc aca     1248
Asn Pro Asp Asn Phe Ala Ile Gln Leu Glu Lys Gly Gly Lys Phe Thr
                405                 410                 415 gta cgt gga aaa ccg aca ctt gaa gac ctg gag caa ttt tct gaa aaa     1296
Val Arg Gly Lys Pro Thr Leu Glu Asp Leu Glu Gln Phe Ser Glu Lys
            420                 425                 430 ttt tat tgc agc tgt tat agc acc ttg agt tgt aag gag aaa gct gat     1344
Phe Tyr Cys Ser Cys Tyr Ser Thr Leu Ser Cys Lys Glu Lys Ala Asp
        435                 440                 445 gta aaa gac act gat gct gtt gat gtg tgt att gct gat ggt gtc tgt     1392
Val Lys Asp Thr Asp Ala Val Asp Val Cys Ile Ala Asp Gly Val Cys
    450                 455                 460 ata gat gct ttt cta aaa cct ccc atg gag aca gaa gaa cct gga tcc     1440
Ile Asp Ala Phe Leu Lys Pro Pro Met Glu Thr Glu Glu Pro Gly Ser
465                 470                 475                 480 ggt tct ggt gct cac cat cac cat cac cat taa                         1473
Gly Ser Gly Ala His His His His His His
                485                 490
```

<210> SEQ ID NO 16
<211> LENGTH: 490
<212> TYPE: PRT
<213> ORGANISM: Homo sapiens

<400> SEQUENCE: 16

| Met | Gly | Val | Leu | Lys | Phe | Lys | His | Ile | Phe | Arg | Ser | Phe | Val | Lys |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Ser | Ser | Gly | Val | Ser | Gln | Ile | Val | Phe | Thr | Phe | Leu | Leu | Ile | Pro | Cys |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

Cys Leu Thr Leu Asn Phe Arg Ala Pro Pro Val Ile Pro Asn Val Pro
            35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
        115                 120                 125

Lys Asp Ile Thr Phe Tyr Met Pro Val Asp Asn Leu Gly Met Ala Val
130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
        275                 280                 285

Ser Lys Ile Pro Asp Ala Lys Ser Pro Leu Pro Val Phe Ala Tyr Thr
290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
            325                 330                 335

Val Ile Trp Gly Thr Leu Ser Ile Met Arg Ser Met Lys Ser Cys Leu
        340                 345                 350

Leu Leu Asp Asn Tyr Met Glu Thr Ile Leu Asn Pro Tyr Ile Ile Asn
355                 360                 365

Val Thr Leu Ala Ala Lys Met Cys Ser Gln Val Leu Cys Gln Glu Gln
370                 375                 380

```
Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
            405                 410                 415

Val Arg Gly Lys Pro Thr Leu Glu Asp Leu Glu Gln Phe Ser Glu Lys
        420                 425                 430

Phe Tyr Cys Ser Cys Tyr Ser Thr Leu Ser Cys Lys Glu Lys Ala Asp
    435                 440                 445

Val Lys Asp Thr Asp Ala Val Asp Val Cys Ile Ala Asp Gly Val Cys
    450                 455                 460

Ile Asp Ala Phe Leu Lys Pro Pro Met Glu Thr Glu Glu Pro Gly Ser
465                 470                 475                 480

Gly Ser Gly Ala His His His His His His
                485                 490

<210> SEQ ID NO 17
<211> LENGTH: 39
<212> TYPE: DNA
<213> ORGANISM: Artificial Sequence
<220> FEATURE:
<223> OTHER INFORMATION: SpacerHisFor Primer

<400> SEQUENCE: 17
ataattggat ccggttctgg tgctcaccat caccatcac                        39

<210> SEQ ID NO 18
<211> LENGTH: 38
<212> TYPE: DNA
<213> ORGANISM: Artificial Sequence
<220> FEATURE:
<223> OTHER INFORMATION: SpacerHisRev Primer

<400> SEQUENCE: 18
tataattgcg gccgcctaat ggtgatggtg atggtgag                         38

<210> SEQ ID NO 19
<211> LENGTH: 30
<212> TYPE: DNA
<213> ORGANISM: Artificial Sequence
<220> FEATURE:
<223> OTHER INFORMATION: 3' REVERSE PRIMER WITHOUT STOP CODON FOR
      GENERATING truncation product HIS-sHASEGP lacking GPI
      anchor and ending at N 483

<400> SEQUENCE: 19
aatggatcca ttgtagaaaa tttgaggttc                                  30

<210> SEQ ID NO 20
<211> LENGTH: 30
<212> TYPE: DNA
<213> ORGANISM: Artificial Sequence
<220> FEATURE:
<223> OTHER INFORMATION: 3' REVERSE PRIMER WITHOUT STOP CODON FOR
      GENERATING truncation product HIS-sHASEGP lacking GPI
      anchor and ending at Y 482

<400> SEQUENCE: 20
aatggatccg tagaaaattt gaggttcttc                                  30

<210> SEQ ID NO 21
<211> LENGTH: 30
<212> TYPE: DNA
<213> ORGANISM: Artificial Sequence
<220> FEATURE:
<223> OTHER INFORMATION: 3' REVERSE PRIMER WITHOUT STOP CODON FOR
```

GENERATING truncation product HIS-sHASEGP lacking GPI
anchor and ending at F 481

<400> SEQUENCE: 21
aattggatcc gaaaatttga ggttcttctg                                  30

<210> SEQ ID NO 22
<211> LENGTH: 30
<212> TYPE: DNA
<213> ORGANISM: Artificial Sequence
<220> FEATURE:
<223> OTHER INFORMATION: 3' REVERSE PRIMER WITHOUT STOP CODON FOR
      GENERATING truncation product HIS-sHASEGP lacking GPI
      anchor and ending at I 480

<400> SEQUENCE: 22
attggatcca atttgaggtt cttctgtctc                                  30

<210> SEQ ID NO 23
<211> LENGTH: 29
<212> TYPE: DNA
<213> ORGANISM: Artificial Sequence
<220> FEATURE:
<223> OTHER INFORMATION: 3' REVERSE PRIMER WITHOUT STOP CODON FOR
      GENERATING truncation product HIS-sHASEGP lacking GPI
      anchor and ending at Q 479

<400> SEQUENCE: 23
aattggatcc ttgaggttct tctgtctcc                                   29

<210> SEQ ID NO 24
<211> LENGTH: 29
<212> TYPE: DNA
<213> ORGANISM: Artificial Sequence
<220> FEATURE:
<223> OTHER INFORMATION: 3' REVERSE PRIMER WITHOUT STOP CODON FOR
      GENERATING truncation product HIS-sHASEGP lacking GPI
      anchor and ending at P 478

<400> SEQUENCE: 24
aattggatcc aggttcttct gtctccatg                                   29

<210> SEQ ID NO 25
<211> LENGTH: 28
<212> TYPE: DNA
<213> ORGANISM: Artificial Sequence
<220> FEATURE:
<223> OTHER INFORMATION: 3' REVERSE PRIMER WITHOUT STOP CODON FOR
      GENERATING truncation product HIS-sHASEGP lacking GPI
      anchor and ending at E 477

<400> SEQUENCE: 25
aattggatcc ttcttctgtc tccatggg                                    28

<210> SEQ ID NO 26
<211> LENGTH: 36
<212> TYPE: DNA
<213> ORGANISM: Artificial Sequence
<220> FEATURE:
<223> OTHER INFORMATION: Reverse primer to amplify sHASEGP deletion
      mutant ending at A 467

<400> SEQUENCE: 26
aattggatcc ctaagcatct atacagacac catcag                           36

<210> SEQ ID NO 27
<211> LENGTH: 35
<212> TYPE: DNA

```
<213> ORGANISM: Artificial Sequence
<220> FEATURE:
<223> OTHER INFORMATION: Reverse primer to amplify sHASEGP deletion
      mutant ending at A 447

<400> SEQUENCE: 27
aattggatcc ctaagctttc tccttacaac tcaag                              35

<210> SEQ ID NO 28
<211> LENGTH: 34
<212> TYPE: DNA
<213> ORGANISM: Artificial Sequence
<220> FEATURE:
<223> OTHER INFORMATION: Reverse primer to amplify sHASEGP deletion
      mutant ending at S 430

<400> SEQUENCE: 28
aattggatcc ctaagaaaat tgctccaggt cttc                               34

<210> SEQ ID NO 29
<211> LENGTH: 36
<212> TYPE: DNA
<213> ORGANISM: Artificial Sequence
<220> FEATURE:
<223> OTHER INFORMATION: Reverse primer to amplify sHASEGP deletion
      mutant ending at G 413

<400> SEQUENCE: 29
aattggatcc ctatccacct ttctcaagtt gaatag                             36

<210> SEQ ID NO 30
<211> LENGTH: 36
<212> TYPE: DNA
<213> ORGANISM: Artificial Sequence
<220> FEATURE:
<223> OTHER INFORMATION: Reverse primer to amplify sHASEGP deletion
      mutant ending at S 394

<400> SEQUENCE: 30
aattggatcc ctatgaattc cagttttttcc ttatac                            36

<210> SEQ ID NO 31
<211> LENGTH: 35
<212> TYPE: DNA
<213> ORGANISM: Artificial Sequence
<220> FEATURE:
<223> OTHER INFORMATION: Reverse primer to amplify sHASEGP deletion
      mutant ending at A 372

<400> SEQUENCE: 31
aattggatcc ctatgctagt gtgacgttga ttatg                              35

<210> SEQ ID NO 32
<211> LENGTH: 33
<212> TYPE: DNA
<213> ORGANISM: Artificial Sequence
<220> FEATURE:
<223> OTHER INFORMATION: Reverse primer to amplify sHASEGP deletion
      mutant ending at S 347

<400> SEQUENCE: 32
aattggatcc ctaacttcgc attatactga ggg                                33

<210> SEQ ID NO 33
<211> LENGTH: 29
<212> TYPE: DNA
<213> ORGANISM: Artificial Sequence
<220> FEATURE:
```

-continued

```
<223> OTHER INFORMATION: LN forward primer for site directed mutagenesis
      to generate sHASEGP fusion with kappa leader with L 36
      as the first sHASEGP amino acid after the kappa
      leader

<400> SEQUENCE: 33
ctgaatttca gagcacctcc tgttattcc                                    29

<210> SEQ ID NO 34
<211> LENGTH: 28
<212> TYPE: DNA
<213> ORGANISM: Artificial Sequence
<220> FEATURE:
<223> OTHER INFORMATION: FR forward primer for site directed mutagenesis
      to generate sHASEGP fusion with kappa leader with F 38
      as the first sHASEGP amino acid after the kappa
      leader

<400> SEQUENCE: 34
ttcagagcac ctcctgttat tccaaatg                                     28

<210> SEQ ID NO 35
<211> LENGTH: 23
<212> TYPE: DNA
<213> ORGANISM: Artificial Sequence
<220> FEATURE:
<223> OTHER INFORMATION: Asp reverse primer for site directed
      mutagenesis to generate sHASEGP fusion with kappa leader with
      Asp as the last Kappa leader amino acid before L
      36 or F 38 of PH-20

<400> SEQUENCE: 35
gtcaccagtg gaacctggaa ccc                                          23

<210> SEQ ID NO 36
<211> LENGTH: 24
<212> TYPE: DNA
<213> ORGANISM: Artificial Sequence
<220> FEATURE:
<223> OTHER INFORMATION: Gly reverse primer for site directed
      mutagenesis to generate sHASEGP fusion with kappa leader with
      Gly as the last Kappa leader amino acid before L
      36 or F 38 of PH-20

<400> SEQUENCE: 36
accagtggaa cctggaaccc agag                                         24

<210> SEQ ID NO 37
<211> LENGTH: 30
<212> TYPE: DNA
<213> ORGANISM: Artificial Sequence
<220> FEATURE:
<223> OTHER INFORMATION: Forward primer for first fragment of kappa
      leader

<400> SEQUENCE: 37
gagacagaca cactcctgct atgggtactg                                   30

<210> SEQ ID NO 38
<211> LENGTH: 30
<212> TYPE: DNA
<213> ORGANISM: Artificial Sequence
<220> FEATURE:
<223> OTHER INFORMATION: Reverse primer for first fragment of kappa
      leader

<400> SEQUENCE: 38
cccagagcag cagtacccat agcaggagtg                                   30
```

```
<210> SEQ ID NO 39
<211> LENGTH: 30
<212> TYPE: DNA
<213> ORGANISM: Artificial Sequence
<220> FEATURE:
<223> OTHER INFORMATION: Forward primer for second fragment of kappa
      leader

<400> SEQUENCE: 39
ggtactgctg ctctgggttc caggttccac                                      30

<210> SEQ ID NO 40
<211> LENGTH: 27
<212> TYPE: DNA
<213> ORGANISM: Artificial Sequence
<220> FEATURE:
<223> OTHER INFORMATION: Reverse primer for second fragment of kappa
      leader

<400> SEQUENCE: 40
gcgtcaccag tggaacctgg aacccag                                         27

<210> SEQ ID NO 41
<211> LENGTH: 30
<212> TYPE: DNA
<213> ORGANISM: Artificial Sequence
<220> FEATURE:
<223> OTHER INFORMATION: Nhe Forward primer for kappa leader

<400> SEQUENCE: 41
attgctagca tggagacaga cacactcctg                                      30

<210> SEQ ID NO 42
<211> LENGTH: 28
<212> TYPE: DNA
<213> ORGANISM: Artificial Sequence
<220> FEATURE:
<223> OTHER INFORMATION: EcoR1 reverse  primer for kappa leader

<400> SEQUENCE: 42
aattgaattc gtcaccagtg gaacctgg                                        28

<210> SEQ ID NO 43
<211> LENGTH: 21
<212> TYPE: PRT
<213> ORGANISM: Artificial Sequence
<220> FEATURE:
<223> OTHER INFORMATION: Mouse IgK-chain leader sequence

<400> SEQUENCE: 43

Met Glu Thr Asp Thr Leu Leu Leu Trp Val Leu Leu Leu Trp Val Pro
1               5                   10                  15

Gly Ser Thr Gly Asp
            20

<210> SEQ ID NO 44
<211> LENGTH: 30
<212> TYPE: DNA
<213> ORGANISM: Artificial Sequence
<220> FEATURE:
<223> OTHER INFORMATION: K-leader SPE 1 FORWARD Primer

<400> SEQUENCE: 44
actcactagt gctagcatgg agacagacac                                      30

<210> SEQ ID NO 45
```

```
<211> LENGTH: 30
<212> TYPE: DNA
<213> ORGANISM: Artificial Sequence
<220> FEATURE:
<223> OTHER INFORMATION: K-leader MLU1 REV primer

<400> SEQUENCE: 45
aattacgcgt gaattcgtca ccagtggaac                                        30

<210> SEQ ID NO 46
<211> LENGTH: 462
<212> TYPE: PRT
<213> ORGANISM: Artificial Sequence
<220> FEATURE:
<223> OTHER INFORMATION: Kappa leader fusion protein with sHASEGP with
      F 38 as the first amino acid of the putative mature
      secreted sHASEGP (up to P478)

<400> SEQUENCE: 46
```

Met Glu Thr Asp Thr Leu Leu Leu Trp Val Leu Leu Leu Trp Val Pro
 1               5                  10                  15

Gly Ser Thr Gly Asp Phe Arg Ala Pro Pro Val Ile Pro Asn Val Pro
            20                  25                  30

Phe Leu Trp Ala Trp Asn Ala Pro Ser Glu Phe Cys Leu Gly Lys Phe
        35                  40                  45

Asp Glu Pro Leu Asp Met Ser Leu Phe Ser Phe Ile Gly Ser Pro Arg
    50                  55                  60

Ile Asn Ala Thr Gly Gln Gly Val Thr Ile Phe Tyr Val Asp Arg Leu
65                  70                  75                  80

Gly Tyr Tyr Pro Tyr Ile Asp Ser Ile Thr Gly Val Thr Val Asn Gly
                85                  90                  95

Gly Ile Pro Gln Lys Ile Ser Leu Gln Asp His Leu Asp Lys Ala Lys
            100                 105                 110

Lys Asp Ile Thr Phe Tyr Met Pro Val Asp Asn Leu Gly Met Ala Val
        115                 120                 125

Ile Asp Trp Glu Glu Trp Arg Pro Thr Trp Ala Arg Asn Trp Lys Pro
    130                 135                 140

Lys Asp Val Tyr Lys Asn Arg Ser Ile Glu Leu Val Gln Gln Gln Asn
145                 150                 155                 160

Val Gln Leu Ser Leu Thr Glu Ala Thr Glu Lys Ala Lys Gln Glu Phe
                165                 170                 175

Glu Lys Ala Gly Lys Asp Phe Leu Val Glu Thr Ile Lys Leu Gly Lys
            180                 185                 190

Leu Leu Arg Pro Asn His Leu Trp Gly Tyr Tyr Leu Phe Pro Asp Cys
        195                 200                 205

Tyr Asn His His Tyr Lys Lys Pro Gly Tyr Asn Gly Ser Cys Phe Asn
    210                 215                 220

Val Glu Ile Lys Arg Asn Asp Asp Leu Ser Trp Leu Trp Asn Glu Ser
225                 230                 235                 240

Thr Ala Leu Tyr Pro Ser Ile Tyr Leu Asn Thr Gln Gln Ser Pro Val
                245                 250                 255

Ala Ala Thr Leu Tyr Val Arg Asn Arg Val Arg Glu Ala Ile Arg Val
            260                 265                 270

Ser Lys Ile Pro Asp Ala Lys Ser Pro Leu Pro Val Phe Ala Tyr Thr
        275                 280                 285

Arg Ile Val Phe Thr Asp Gln Val Leu Lys Phe Leu Ser Gln Asp Glu
    290                 295                 300

Leu Val Tyr Thr Phe Gly Glu Thr Val Ala Leu Gly Ala Ser Gly Ile

```
                305                 310                 315                 320
Val Ile Trp Gly Thr Leu Ser Ile Met Arg Ser Met Lys Ser Cys Leu
                    325                 330                 335

Leu Leu Asp Asn Tyr Met Glu Thr Ile Leu Asn Pro Tyr Ile Ile Asn
                340                 345                 350

Val Thr Leu Ala Ala Lys Met Cys Ser Gln Val Leu Cys Gln Glu Gln
            355                 360                 365

Gly Val Cys Ile Arg Lys Asn Trp Asn Ser Ser Asp Tyr Leu His Leu
        370                 375                 380

Asn Pro Asp Asn Phe Ala Ile Gln Leu Glu Lys Gly Gly Lys Phe Thr
385                 390                 395                 400

Val Arg Gly Lys Pro Thr Leu Glu Asp Leu Glu Gln Phe Ser Glu Lys
                405                 410                 415

Phe Tyr Cys Ser Cys Tyr Ser Thr Leu Ser Cys Lys Glu Lys Ala Asp
                    420                 425                 430

Val Lys Asp Thr Asp Ala Val Asp Val Cys Ile Ala Asp Gly Val Cys
                435                 440                 445

Ile Asp Ala Phe Leu Lys Pro Pro Met Glu Thr Glu Glu Pro
450                 455                 460

<210> SEQ ID NO 47
<211> LENGTH: 40
<212> TYPE: DNA
<213> ORGANISM: Artificial Sequence
<220> FEATURE:
<223> OTHER INFORMATION: 3' Primer BAM REV sHASEGP with GPI anchor up
      to L 509 including STOP

<400> SEQUENCE: 47
aattggatcc ctacagaaga aatgataaga aacaaaatac                              40

<210> SEQ ID NO 48
<211> LENGTH: 1449
<212> TYPE: DNA
<213> ORGANISM: Homo sapiens

<400> SEQUENCE: 48
atgggagtgc taaaattcaa gcacatcttt ttcagaagct tgttaaatc aagtggagta         60 tcccagatag ttttcacctt ccttctgatt ccatgttgct tgactctgaa tttcagagca       120
cctcctgtta ttccaaatgt gcctttcctc tgggcctgga atgccccaag tgaattttgt       180
cttggaaaat tgatgagcc actagatatg agcctcttct ctttcatagg aagcccccga       240
ataaacgcca ccgggcaagg tgttacaata ttttatgttg atagacttgg ctactatcct       300
tacatagatt caatcacagg agtaactgtg aatggaggaa tcccccagaa gatttcctta       360
caagaccatc tggacaaagc taagaaagac attacatttt atatgccagt agacaatttg       420
ggaatggctg ttattgactg gaagaatgg agacccactt gggcaagaaa ctggaaacct       480
aaagatgttt acaagaatag gtctattgaa ttggttcagc aacaaaatgt acaacttagt       540
ctcacagagg ccactgagaa agcaaaacaa gaatttgaaa aggcagggaa ggatttcctg       600
gtagagacta aaaattggg aaaattactt cggccaaatc acttgtgggg ttattatctt       660
tttccggatt gttacaacca tcactataag aaacccggtt acaatggaag ttgcttcaat       720
gtagaaataa aagaaatga tgatctcagc tggttgtgga atgaaagcac tgctctttac       780
ccatccattt atttgaacac tcagcagtct cctgtagctg ctacactcta tgtgcgcaat       840
cgagttcggg aagccatcag agtttccaaa atacctgatg caaaaagtcc acttccggtt       900
```

```
tttgcatata cccgcatagt ttttactgat caagttttga aattcctttc tcaagatgaa    960
cttgtgtata catttggcga aactgttgct ctgggtgctt ctggaattgt aatatgggga   1020
accctcagta taatgcgaag tatgaaatct tgcttgctcc tagacaatta catggagact   1080
atactgaatc cttacataat caacgtcaca ctagcagcca aaatgtgtag ccaagtgctt   1140
tgccaggagc aaggagtgtg tataaggaaa aactggaatt caagtgacta tcttcacctc   1200
aacccagata attttgctat tcaacttgag aaaggtggaa agttcacagt acgtggaaaa   1260
ccgacacttg aagacctgga gcaattttct gaaaaatttt attgcagctg ttatagcacc   1320
ttgagttgta aggagaaagc tgatgtaaaa gacactgatg ctgttgatgt gtgtattgct   1380
gatggtgtct gtatagatgc ttttctaaaa cctcccatgg agacagaaga acctcaaatt   1440
ttctactaa                                                           1449
```

<210> SEQ ID NO 49
<211> LENGTH: 467
<212> TYPE: PRT
<213> ORGANISM: Homo sapiens

<400> SEQUENCE: 49

```
Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Pro
        35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
        115                 120                 125

Lys Asp Ile Thr Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
    210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
```

|     |     |     |     |     |     |     |     |     |     |     |     |     |     |
|---|---|---|---|---|---|---|---|---|---|---|---|---|---|
|     |     | 275 |     |     |     | 280 |     |     |     | 285 |     |     |     |
| Ser | Lys | Ile | Pro | Asp | Ala | Lys | Ser | Pro | Leu | Pro | Val | Phe | Ala | Tyr | Thr |
| 290 |     |     |     |     | 295 |     |     |     |     | 300 |     |     |     |
| Arg | Ile | Val | Phe | Thr | Asp | Gln | Val | Leu | Lys | Phe | Leu | Ser | Gln | Asp | Glu |
| 305 |     |     |     |     | 310 |     |     |     |     | 315 |     |     |     |     | 320 |
| Leu | Val | Tyr | Thr | Phe | Gly | Glu | Thr | Val | Ala | Leu | Gly | Ala | Ser | Gly | Ile |
|     |     |     |     | 325 |     |     |     |     | 330 |     |     |     |     | 335 |
| Val | Ile | Trp | Gly | Thr | Leu | Ser | Ile | Met | Arg | Ser | Met | Lys | Ser | Cys | Leu |
|     |     |     | 340 |     |     |     |     | 345 |     |     |     |     | 350 |
| Leu | Leu | Asp | Asn | Tyr | Met | Glu | Thr | Ile | Leu | Asn | Pro | Tyr | Ile | Ile | Asn |
|     |     | 355 |     |     |     |     | 360 |     |     |     |     | 365 |
| Val | Thr | Leu | Ala | Ala | Lys | Met | Cys | Ser | Gln | Val | Leu | Cys | Gln | Glu | Gln |
| 370 |     |     |     |     | 375 |     |     |     |     | 380 |
| Gly | Val | Cys | Ile | Arg | Lys | Asn | Trp | Asn | Ser | Ser | Asp | Tyr | Leu | His | Leu |
| 385 |     |     |     | 390 |     |     |     |     | 395 |     |     |     |     | 400 |
| Asn | Pro | Asp | Asn | Phe | Ala | Ile | Gln | Leu | Glu | Lys | Gly | Gly | Lys | Phe | Thr |
|     |     |     |     | 405 |     |     |     |     | 410 |     |     |     |     | 415 |
| Val | Arg | Gly | Lys | Pro | Thr | Leu | Glu | Asp | Leu | Glu | Gln | Phe | Ser | Glu | Lys |
|     |     |     | 420 |     |     |     |     | 425 |     |     |     |     | 430 |
| Phe | Tyr | Cys | Ser | Cys | Tyr | Ser | Thr | Leu | Ser | Cys | Lys | Glu | Lys | Ala | Asp |
|     |     |     | 435 |     |     |     |     | 440 |     |     |     |     | 445 |
| Val | Lys | Asp | Thr | Asp | Ala | Val | Asp | Val | Cys | Ile | Ala | Asp | Gly | Val | Cys |
|     | 450 |     |     |     |     | 455 |     |     |     |     | 460 |
| Ile | Asp | Ala |
| 465 |

<210> SEQ ID NO 50
<211> LENGTH: 1536
<212> TYPE: DNA
<213> ORGANISM: Homo sapiens

<400> SEQUENCE: 50

| atgggagtgc | taaaattcaa | gcacatctttt | ttcagaagct | tgttaaaatc | aagtggagta | 60 |
| tcccagatag | ttttcacctt | ccttctgatt | ccatgttgct | tgactctgaa | ttcagagca | 120 |
| cctcctgtta | ttccaaatgt | gcctttcctc | tgggcctgga | atgccccaag | tgaattttgt | 180 |
| cttggaaaat | ttgatgagcc | actagatatg | agcctcttct | ctttcatagg | aagcccccga | 240 |
| ataaacgcca | ccgggcaagg | tgttacaata | tttatgttg | atagacttgg | ctactatcct | 300 |
| tacatagatt | caatcacagg | agtaactgtg | aatggaggaa | tcccccagaa | gatttcctta | 360 |
| caagaccatc | tggacaaagc | taagaaagac | attacatttt | atatgccagt | agacaatttg | 420 |
| ggaatggctg | ttattgactg | ggaagaatgg | agacccactt | gggcaagaaa | ctggaaacct | 480 |
| aaagatgttt | acaagaatag | gtctattgaa | ttggttcagc | aacaaaatgt | acaacttagt | 540 |
| ctcacagagg | ccactgagaa | agcaaaacaa | gaatttgaaa | aggcagggaa | ggatttcctg | 600 |
| gtagagacta | taaaattggg | aaaattactt | cggccaaatc | acttgtgggg | ttattatctt | 660 |
| tttccggatt | gttacaacca | tcactataag | aaacccggtt | acaatggaag | ttgcttcaat | 720 |
| gtagaaataa | aagaaatga | tgatctcagc | tggttgtgga | atgaaagcac | tgctcttttac | 780 |
| ccatccatttt | atttgaacac | tcagcagtct | cctgtagctg | ctacactcta | tgtgcgcaat | 840 |
| cgagttcggg | aagccatcag | agtttccaaa | atacctgatg | caaaaagtcc | acttccggtt | 900 |
| tttgcatata | cccgcatagt | ttttactgat | caagttttga | aattcctttc | tcaagatgaa | 960 |
| cttgtgtata | catttggcga | aactgttgct | ctgggtgctt | ctggaattgt | aatatgggga | 1020 |

| | |
|---|---|
| accctcagta taatgcgaag tatgaaatct tgcttgctcc tagacaatta catggagact | 1080 |
| atactgaatc cttacataat caacgtcaca ctagcagcca aaatgtgtag ccaagtgctt | 1140 |
| tgccaggagc aaggagtgtg tataaggaaa aactggaatt caagtgacta tcttcacctc | 1200 |
| aacccagata attttgctat tcaacttgag aaaggtggaa agttcacagt acgtggaaaa | 1260 |
| ccgacacttg aagacctgga gcaattttct gaaaaatttt attgcagctg ttatagcacc | 1320 |
| ttgagttgta aggagaaagc tgatgtaaaa gacactgatg ctgttgatgt gtgtattgct | 1380 |
| gatggtgtct gtatagatgc ttttctaaaa cctcccatgg agacagaaga acctcaaatt | 1440 |
| ttctacaatg cttcaccctc cacactatct gccacaatgt tcatttggag ctggaagtc | 1500 |
| tgggatcaag gtattagcag aattggtttc ttctga | 1536 |

<210> SEQ ID NO 51
<211> LENGTH: 6630
<212> TYPE: DNA
<213> ORGANISM: Artificial Sequence
<220> FEATURE:
<223> OTHER INFORMATION: HZ24 plasmid vector

<400> SEQUENCE: 51

| | |
|---|---|
| tcaatattgg ccattagcca tattattcat tggttatata gcataaatca atattggcta | 60 |
| ttggccattg catacgttgt atctatatca taatatgtac atttatattg gctcatgtcc | 120 |
| aatatgaccg ccatgttggc attgattatt gactagttat taatagtaat caattacggg | 180 |
| gtcattagtt catagcccat atatggagtt ccgcgttaca taacttacgg taaatggccc | 240 |
| gcctggctga ccgcccaacg accccgccc attgacgtca taatgacgt atgttcccat | 300 |
| agtaacgcca atagggactt tccattgacg tcaatgggtg gagtatttac ggtaaactgc | 360 |
| ccacttggca gtacatcaag tgtatcatat gccaagtccg cccccctattg acgtcaatga | 420 |
| cggtaaatgg cccgcctggc attatgccca gtacatgacc ttcgggact ttcctacttg | 480 |
| gcagtacatc tacgtattag tcatcgctat taccatggtg atgcggtttt ggcagtacac | 540 |
| caatgggcgt ggatagcggt ttgactcacg gggatttcca agtctccacc ccattgacgt | 600 |
| caatgggagt ttgttttggc accaaaatca acgggacttt ccaaaatgtc gtaataaccc | 660 |
| cgccccgttg acgcaaatgg gcggtaggcg tgtacggtgg gaggtctata taagcagagc | 720 |
| tcgtttagtg aaccgtcaga tcactagaag ctttattgcg gtagtttatc acagttaaat | 780 |
| tgctaacgca gtcagtgctt ctgacacaac agtctcgaac ttaagctgca gaagttggtc | 840 |
| gtgaggcact gggcaggtaa gatcaaggt tacaagacag gtttaaggag accaatagaa | 900 |
| actgggcttg tcgagacaga gaagactctt gcgtttctga taggcaccta ttggtcttac | 960 |
| tgacatccac tttgcctttc tctccacagg tgtccactcc cagttcaatt acagctctta | 1020 |
| aggctagagt acttaatacg actcactata ggctagcatg ggagtgctaa aattcaagca | 1080 |
| catctttttc agaagctttg ttaaatcaag tggagtatcc cagatagttt tcaccttcct | 1140 |
| tctgattcca tgttgcttga ctctgaattt cagagcacct cctgttattc caaatgtgcc | 1200 |
| tttcctctgg gcctggaatg ccccaagtga atttgtctt ggaaaatttg atgagccact | 1260 |
| agatatgagc ctcttctctt tcataggaag ccccgaata aacgccaccg gcaaggtgt | 1320 |
| tacaatattt tatgttgata gacttggcta ctatccttac atagattcaa tcacaggagt | 1380 |
| aactgtgaat ggaggaatcc cccagaagat ttccttacaa gaccatctgg acaaagctaa | 1440 |
| gaaagacatt acattttata tgccagtaga caatttggga atggctgtta ttgactggga | 1500 |
| agaatggaga cccacttggg caagaaactg gaaacctaaa gatgtttaca agaataggtc | 1560 |

```
tattgaattg gttcagcaac aaaatgtaca acttagtctc acagaggcca ctgagaaagc    1620
aaaacaagaa tttgaaaagg cagggaagga tttcctggta gagactataa aattgggaaa    1680
attacttcgg ccaaatcact tgtggggtta ttatcttttt ccggattgtt acaaccatca    1740
ctataagaaa cccggttaca atggaagttg cttcaatgta gaaataaaaa gaatgatga    1800 tctcagctgg ttgtggaatg aaagcactgc tctttaccca tccatttatt tgaacactca    1860
gcagtctcct gtagctgcta cactctatgt gcgcaatcga gttcgggaag ccatcagagt    1920
ttccaaaata cctgatgcaa aaagtccact ccggttttt gcatataccc gcatagtttt    1980
tactgatcaa gtttttgaaat tcctttctca agatgaactt gtgtatacat ttggcgaaac    2040
tgttgctctg ggtgcttctg gaattgtaat atggggaacc ctcagtataa tgcgaagtat    2100
gaaatcttgc ttgctcctag acaattacat ggagactata ctgaatcctt acataatcaa    2160
cgtcacacta gcagccaaaa tgtgtagcca agtgctttgc caggagcaag gagtgtgtat    2220
aaggaaaaac tggaattcaa gtgactatct tcacctcaac ccagataatt ttgctattca    2280
acttgagaaa ggtggaaagt tcacagtacg tggaaaaccg acacttgaag acctggagca    2340
attttctgaa aaattttatt gcagctgtta tagcaccttg agttgtaagg agaaagctga    2400
tgtaaaagac actgatgctg ttgatgtgtg tattgctgat ggtgtctgta tagatgcttt    2460
tctaaaacct cccatggaga cagaagaacc tcaaattttc tactgaggat ccatagctaa    2520
cgcccctctc cctccccccc ccctaacgtt actggccgaa gccgcttgga ataaggccgg    2580
tgtgcgtttg tctatatgtt attttccacc atattgccgt cttttggcaa tgtgagggcc    2640
cggaaacctg gccctgtctt cttgacgagc attcctaggg gtctttcccc tctcgccaaa    2700
ggaatgcaag gtctgttgaa tgtcgtgaag gaagcagttc ctctggaagc ttcttgaaga    2760
caaacaacgt ctgtagcgac cctttgcagg cagcggaacc ccccacctgg cgacaggtgc    2820
ctctgcggcc aaaagccacg tgtataagat acacctgcaa aggcggcaca accccagtgc    2880
cacgttgtga gttggatagt tgtggaaaga gtcaaatggc tctcctcaag cgtattcaac    2940
aaggggctga aggatgccca gaaggtaccc cattgtatgg gatctgatct ggggcctcgg    3000
tgcacatgct ttacatgtgt ttagtcgagg ttaaaaaaac gtctaggccc cccgaaccac    3060
ggggacgtgg ttttcctttg aaaaacacga tgataagctt gccacaaccc acagcggccg    3120
ctgccatcat ggttcgacca ttgaactgca tcgtcgccgt gtcccaaaat atggggattg    3180
gcaagaacgg agacctaccc tggcctccgc tcaggaacga gttcaagtac ttccaaagaa    3240
tgaccacaac ctcttcagtg gaaggtaaac agaatctggt gattatgggt aggaaaacct    3300
ggttctccat tcctgagaag aatcgacctt taaggacag aattaatata gttctcagta    3360
gagaactcaa agaaccacca cgaggagctc attttcttgc caaaagtttg gatgatgcct    3420
taagacttat tgaacaaccg gaattggcaa gtaaagtaga catggtttgg atagtcggag    3480
gcagttctgt ttaccaggaa gccatgaatc aaccaggcca cctcagactc tttgtgacaa    3540
ggatcatgca ggaatttgaa agtgacacgt ttttcccaga aattgatttg gggaaatata    3600
aacttctccc agaataccca ggcgtcctct ctgaggtcca ggaggaaaaa ggcatcaagt    3660
ataagtttga agtctacgag aagaaagact aaacgcgtgg tacctctaga gtcgacccgg    3720
gcggccgctt cgagcagaca tgataagata cattgatgag tttggacaaa ccacaactag    3780
aatgcagtga aaaaaatgct ttatttgtga aatttgtgat gctattgctt tatttgtaac    3840
cattataagc tgcaataaac aagttaacaa caacaattgc attcatttta tgtttcaggt    3900 tcaggggag atgtgggagg ttttttaaag caagtaaaac ctctacaaat gtggtaaaat    3960
```

```
cgataaggat ccgggctggc gtaatagcga agaggcccgc accgatcgcc cttcccaaca   4020
gttgcgcagc ctgaatggcg aatggacgcg ccctgtagcg gcgcattaag cgcggcgggt   4080
gtggtggtta cgcgcagcgt gaccgctaca cttgccagcg ccctagcgcc cgctcctttc   4140
gctttcttcc cttcctttct cgccacgttc gccggctttc cccgtcaagc tctaaatcgg   4200 gggctcccctt tagggttccg atttagtgct ttacggcacc tcgaccccaa aaacttgat   4260 tagggtgatg gttcacgtag tgggccatcg ccctgataga cggttttcg ccctttgacg    4320 ttggagtcca cgttctttaa tagtggactc ttgttccaaa ctggaacaac actcaaccct   4380
atctcggtct attcttttga tttataaggg attttgccga tttcggccta ttggttaaaa   4440
aatgagctga tttaacaaaa atttaacgcg aattttaaca aaatattaac gcttacaatt   4500
tcctgatgcg gtattttctc cttacgcatc tgtgcggtat ttcacaccgc atatggtgca   4560
ctctcagtac aatctgctct gatgccgcat agttaagcca gccccgacac ccgccaacac   4620
ccgctgacgc gccctgacgg gcttgtctgc tcccggcatc cgcttacaga caagctgtga   4680
ccgtctccgg gagctgcatg tgtcagaggt tttcaccgtc atcaccgaaa cgcgcgagac   4740
gaaagggcct cgtgatacgc ctatttttat aggttaatgt catgataata atggtttctt   4800
agacgtcagg tggcactttt cggggaaatg tgcgcggaac ccctatttgt ttatttttct   4860
aaatacattc aaatatgtat ccgctcatga caataaacc ctgataaatg cttcaataat    4920
attgaaaaag gaagagtatg agtattcaac atttccgtgt cgcccttatt ccctttttg    4980 cggcattttg ccttcctgtt tttgctcacc cagaaacgct ggtgaaagta aaagatgctg   5040
aagatcagtt gggtgcacga gtgggttaca tcgaactgga tctcaacagc ggtaagatcc   5100
ttgagagttt tcgccccgaa gaacgttttc caatgatgag cacttttaaa gttctgctat   5160
gtggcgcggt attatcccgt attgacgccg ggcaagagca actcggtcgc cgcatacact   5220
attctcagaa tgacttggtt gagtactcac cagtcacaga aaagcatctt acggatggca   5280
tgacagtaag agaattatgc agtgctgcca taaccatgag tgataacact gcggccaact   5340
tacttctgac aacgatcgga ggaccgaagg agctaaccgc ttttttgcac aacatggggg   5400
atcatgtaac tcgccttgat cgttgggaac cggagctgaa tgaagccata ccaaacgacg   5460
agcgtgacac cacgatgcct gtagcaatgg caacaacgtt gcgcaaacta ttaactggcg   5520
aactacttac tctagcttcc cggcaacaat taatagactg gatggaggcg gataaagttg   5580
caggaccact tctgcgctcg gcccttccgg ctggctggtt tattgctgat aaatctggag   5640
ccggtgagcg tgggtctcgc ggtatcattg cagcactggg gccagatggt aagccctccc   5700
gtatcgtagt tatctacacg acggggagtc aggcaactat ggatgaacga atagacaga    5760 tcgctgagat aggtgcctca ctgattaagc attggtaact gtcagaccaa gtttactcat   5820
atatacttta gattgattta aaacttcatt tttaatttaa aaggatctag gtgaagatcc   5880
tttttgataa tctcatgacc aaaatccctt aacgtgagtt ttcgttccac tgagcgtcag   5940
accccgtaga aaagatcaaa ggatcttctt gagatccttt ttttctgcgc gtaatctgct   6000
gcttgcaaac aaaaaaacca ccgctaccag cggtggtttg tttgccggat caagagctac   6060
caactctttt tccgaaggta actggcttca gcagagcgca gataccaaat actgttcttc   6120
tagtgtagcc gtagttaggc caccacttca agaactctgt agcaccgcct acatacctcg   6180
ctctgctaat cctgttacca gtggctgctg ccagtggcga taagtcgtgt cttaccgggt   6240
tggactcaag acgatagtta ccggataagg cgcagcggtc gggctgaacg gggggttcgt   6300
gcacacagcc cagcttggag cgaacgacct acaccgaact gagatacta cagcgtgagc    6360
```

-continued

| | |
|---|---|
| tatgagaaag cgccacgctt cccgaaggga gaaaggcgga caggtatccg gtaagcggca | 6420 |
| gggtcggaac aggagagcgc acgagggagc ttccaggggg aaacgcctgg tatctttata | 6480 |
| gtcctgtcgg gtttcgccac ctctgacttg agcgtcgatt tttgtgatgc tcgtcagggg | 6540 |
| ggcggagcct atggaaaaac gccagcaacg cggccttttt acggttcctg gccttttgct | 6600 |
| ggccttttgc tcacatggct cgacagatct | 6630 |

<210> SEQ ID NO 52
<211> LENGTH: 2009
<212> TYPE: DNA
<213> ORGANISM: Homo sapiens

<400> SEQUENCE: 52

| | |
|---|---|
| atgtggctca cataaattca gaaagtatga tagcagtgta ggtggttagc agcacctcat | 60 |
| aaggtccttc ctagcaaggc aaagggatgc taatgactag ccaatgctct aggaagacat | 120 |
| tgagaccagc caacttcttg ccttgataac tactgaagag acattgggtg ctggattttt | 180 |
| gaaagcagac ttctggttat aggtgatgca acttgaaaaa caatcctgaa acatgaaaca | 240 |
| agaataataa tatttaaatg taacttaatc attataccct tttatccatc aaagtgaatt | 300 |
| cattccattc ccttttcatct gtgctcatac tttgcatcag atattgggta aaccaaagtg | 360 |
| tgtaggaaga aataaatgtt ttcatagtca ttactcttta caatgggagt gctaaaattc | 420 |
| aagcacatct ttttcagaag ctttgttaaa tcaagtggag tatcccagat agttttcacc | 480 |
| ttccttctga ttccatgttg cttgactctg aatttcagag cacctcctgt tattccaaat | 540 |
| gtgcctttcc tctgggcctg gaatgcccca agtgaatttt gtcttggaaa atttgatgag | 600 |
| ccactagata tgagcctctt ctcttttcata ggaagccccc gaataaacgc caccgggcaa | 660 |
| ggtgttacaa tattttatgt tgatagactt ggctactatc cttacataga ttcaatcaca | 720 |
| ggagtaactg tgaatggagg aatccccccag aagatttcct tacaagacca tctggacaaa | 780 |
| gctaagaaag acattacatt ttatatgcca gtagacaatt tgggaatggc tgttattgac | 840 |
| tgggaagaat ggagacccac ttgggcaaga aactggaaac ctaaagatgt ttacaagaat | 900 |
| aggtctattg aattggttca gcaacaaaat gtacaactta gtctcacaga ggccactgag | 960 |
| aaagcaaaac aagaatttga aaaggcaggg aaggatttcc tggtagagac tataaaattg | 1020 |
| ggaaaattac ttcggccaaa tcacttgtgg ggttattatc ttttttccgga ttgttacaac | 1080 |
| catcactata agaaacccgg ttacaatgga agttgcttca atgtagaaat aaaaagaaat | 1140 |
| gatgatctca gctggttgtg gaatgaaagc actgctcttt acccatccat ttatttgaac | 1200 |
| actcagcagt ctcctgtagc tgctacactc tatgtgcgca atcgagttcg ggaagccatc | 1260 |
| agagtttcca aaatacctga tgcaaaaagt ccacttccgg ttttttgcata tacccgcata | 1320 |
| gttttttactg atcaagtttt gaaattcctt tctcaagatg aacttgtgta tacatttggc | 1380 |
| gaaactgttg ctctgggtgc ttctggaatt gtaatatggg gaaccctcag tataatgcga | 1440 |
| agtatgaaat cttgcttgct cctagacaat tacatggaga ctatactgaa tccttacata | 1500 |
| atcaacgtca cactagcagc caaaatgtgt agccaagtgc tttgccagga gcaaggagtg | 1560 |
| tgtataagga aaactggaa ttcaagtgac tatcttcacc tcaacccaga taattttgct | 1620 |
| attcaacttg agaaaggtgg aaagttcaca gtacgtggaa aaccgacact tgaagacctg | 1680 |
| gagcaatttt ctgaaaaatt ttattgcagc tgttatagca ccctgagttg taggagaaa | 1740 |
| gctgatgtaa aagacactga tgctgttgat gtgtgtattg ctgatggtgt ctgtatagat | 1800 |
| gcttttctaa aacctcccat ggagacagaa gaacctcaaa ttttctacaa tgcttcaccc | 1860 |

| | | |
|---|---|---|
| tccacactat ctgccacaat gttcattgtt agtattttgt ttcttatcat ttcttctgta | 1920 | |
| gcgagtttgt aattgcgcag gttagctgaa atgaacaata tgtccatctt aaagtgtgct | 1980 | |
| ttttcgacta attaaatctt tgaaaagaa | 2009 | |

<210> SEQ ID NO 53
<211> LENGTH: 2395
<212> TYPE: DNA
<213> ORGANISM: Homo sapiens

<400> SEQUENCE: 53

| | |
|---|---|
| atgtggctca cataaattca gaaagtatga tagcagtgta ggtggttagc agcacctcat | 60 |
| aaggtccttc ctagcaaggg atgctaatga ctagccaatg ctctaggaag acattgagac | 120 |
| cagccaactt cttgccttga taactactga agagacattg ggtggctgga ttttgaaagc | 180 |
| agacttctgg ttataggtga tgcaacttga aaaacaatcc tgaaacatga acaagaata | 240 |
| ataatattta aatgtaactt aatcattata cctctttatc catcaaagtg aattcattcc | 300 |
| attccctttc atctgtgctc atactttgca tcagatattg ggtaaaccaa agtgtgtagg | 360 |
| aagaaataaa tgttttcata gtcattactc tttacaatgg gagtgctaaa attcaagcac | 420 |
| atcttttca gaagctttgt taaatcaagt ggagtatccc agatagtttt caccttcctt | 480 |
| ctgattccat gttgcttgac tctgaatttc agagcacctc ctgttattcc aaatgtgcct | 540 |
| ttcctctggg cctggaatgc cccaagtgaa ttttgtcttg gaaaatttga tgagccacta | 600 |
| gatatgagcc tcttctcttt cataggaagc ccccgaataa acgccaccgg gcaaggtgtt | 660 |
| acaatatttt atgttgatag acttggctac tatccttaca tagattcaat cacaggagta | 720 |
| actgtgaatg gaggaatccc ccagaagatt tccttacaag accatctgga caaagctaag | 780 |
| aaagacatta cattttatat gccagtagac aatttgggaa tggctgttat tgactgggaa | 840 |
| gaatggagac ccacttgggc aagaaactgg aaacctaaag atgtttacaa gaataggtct | 900 |
| attgaattgg ttcagcaaca aaatgtacaa cttagtctca cagaggccac tgagaaagca | 960 |
| aaacaagaat ttgaaaaggc agggaaggat ttcctggtag agactataaa attgggaaaa | 1020 |
| ttacttcggc caaatcactt gtggggttat tatctttttc cggattgtta caaccatcac | 1080 |
| tataagaaac ccggttacaa tggaagttgc ttcaatgtag aaataaaaag aaatgatgat | 1140 |
| ctcagctggt tgtggaatga aagcactgct ctttacccat ccatttattt gaacactcag | 1200 |
| cagtctcctg tagctgctac actctatgtg cgcaatcgag ttcgggaagc catcagagtt | 1260 |
| tccaaaatac ctgatgcaaa aagtccactt ccggttttg catatacccg catagttttt | 1320 |
| actgatcaag ttttgaaatt cctttctcaa gatgaacttg tgtatacatt ggcgaaact | 1380 |
| gttgctctgg gtgcttctgg aattgtaata tggggaaccc tcagtataat gcgaagtatg | 1440 |
| aaatcttgct tgctcctaga caattacatg gagactatac tgaatcctta cataatcaac | 1500 |
| gtcacactag cagccaaaat gtgtagccaa gtgctttgcc aggagcaagg agtgtgtata | 1560 |
| aggaaaaact ggaattcaag tgactatctt cacctcaacc cagataattt tgctattcaa | 1620 |
| cttgagaaag gtgaaagtt cacagtacgt ggaaaaccga cacttgaaga cctggagcaa | 1680 |
| ttttctgaaa aattttattg cagctgttat agcaccttga gttgtaagga gaaagctgat | 1740 |
| gtaaaagaca ctgatgctgt tgatgtgtgt attgctgatg gtgtctgtat agatgctttt | 1800 |
| ctaaaacctc ccatggagac agaagaacct caaattttct acaatgcttc accctccaca | 1860 |
| ctatctgcca caatgttcat ttggaggctg gaagtctggg atcaaggtat tagcagaatt | 1920 |
| ggtttcttct gagagtcatg agggaaaaat gtgtttcagg cctcttccct tggcttacag | 1980 |

-continued

```
gaaatgaaaa aaccatgact atcatcacca acatccttgg gtattaagtg cagtcactct    2040
cctagatgct gtggggagaa ggcaagttac aaagatagac cttccctcaa gataatcaga    2100
ttttcatggt attatcctta accttttga catcatggag gctttgggaa tctgatgaag    2160
cctatcaatt ttcttccaga agatatttat ataagattat aagaaaaatt atgtacacag    2220
cttattttat tgcattggat caaaatgcca tttataaaga attatgcctt ttccatcaat    2280
tttagcatgg aaaaataatt tcaggcaata tgcttaaaaa ttgggggaag acaaaagaaa    2340
tccatatcgt gtaaataaaa ataaattttg gttttgctca aaaaaaaaaa aaaaa         2395
```